US009279017B2

(12) United States Patent
Raum et al.

(10) Patent No.: US 9,279,017 B2
(45) **Date of Patent: *Mar. 8, 2016**

(54) PREPARATION OF SCFV ANTIBODY FRAGMENTS

(75) Inventors: Tobias Raum, Munich (DE); Julia Henckel, Munich (DE); Eva Krinner, Munich (DE); Silke Mittelstrass, Munich (DE); Andreas Wolf, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 589 days.

This patent is subject to a terminal disclaimer.

(21) Appl. No.: 13/588,678

(22) Filed: Aug. 17, 2012

(65) Prior Publication Data

US 2013/0171165 A1 Jul. 4, 2013

Related U.S. Application Data

(63) Continuation of application No. 11/568,685, filed as application No. PCT/EP2005/004893 on May 4, 2005, now Pat. No. 8,247,194.

(30) Foreign Application Priority Data

May 5, 2004 (EP) .................................... 04010702

(51) Int. Cl.

*C12P 21/08* (2006.01)
*A61K 39/00* (2006.01)
*C07K 16/24* (2006.01)
*C07K 16/00* (2006.01)

(52) U.S. Cl.

CPC ............. *C07K 16/243* (2013.01); *C07K 16/005* (2013.01); *C07K 2317/622* (2013.01); *C07K 2317/73* (2013.01)

(58) Field of Classification Search

None

See application file for complete search history.

(56) References Cited

U.S. PATENT DOCUMENTS

| | | | | |
|---|---|---|---|---|
| 6,265,150 | B1 | 7/2001 | Terstappen et al. | 435/5 |
| 2013/0171165 | A1* | 7/2013 | Raum | C07K 16/005<br>424/158.1 |

OTHER PUBLICATIONS

Clacksou et al., "Making Antibody Fragment Using Phage Display Libraries," *Nature*, 352:624-628, 1991.

Holt et al., "Domain Antibodies: Proteins for Therapy," *Trends in Biotechnology*, 21(11):484-490, 2003.

Lee et al., "Bivalent Antibody Phage Display Mimics Natural Immunoglobin," *Journal of Immunological Methods*, 284:119-132, 2004.

Neri et al.,"Targeting by Affinity-Matured Recombinant Antibody Fragments of an Angiogenesis Associated Fibronectin Isoform," *Nature Biotechnology*, 15(12):1271-1275, 1997.

Pack et al., "Improved Bivalent Miniantibodies, with Identical Avidity as Whole Antibodies, Produced by High Cell Density Fermentation of *Escherichia coli," BIO/Technology*, 11(11):1271-1277, 1993.

Pack et al., "Miniantibodies: Use of Amphipathic Helices to Produce Functional, Flexibly Linked Dimeric FV Fragments with High Avidity in *Escherichia coli," Biochemistry*, 31(6):1579-1584, 1992.

Pack et al., "Tetravalent Miniantibodies with High Avidity Assembling in *Escherichia coli," Journal of Molecular Biology*, 246(1):28-34, 1995.

Sblattero et al., "Exploiting Recombination in Single Bacteria to Make Large Phage Antibody Libraries," *Nature Biotechnology*, 18(1):75-80, 2000.

* cited by examiner

*Primary Examiner* — Michael Burkhart

(74) *Attorney, Agent, or Firm* — Marshall, Gerstein & Borun LLP

(57) ABSTRACT

The invention relates to methods of preparing antibody fragments. The invention further relates to antibody fragments prepared by these methods. The invention further relates to antibody variable regions comprised in antibody fragments producible by these methods.

21 Claims, 38 Drawing Sheets

Response Difference (RU)
1000
800
600
400
200
0
-200
-400
Time (s)
0
600
1200
1800
2400
3000
3600
4200
4800
5400
6000
6600
7200
7800
8400
9000

```
       E  L  Q  L  V   E  Q  S  G  A   A  L  V  K  P   G  D  S  V  K
  1    GAGCTGCAGCTGGTC GAGCAGTCTGGAGCT GCACTGGTGAAGCCT GGGGACTCTGTGAAG
       CTCGACGTCGACCAG CTCGTCAGACCTCGA CGTGACCACTTCGGA CCCCTGAGACACTTC

       M  S  C  K  A   S  G  Y  P  F   T  D  Y  I  V   H  W  V  K  Q
 61    ATGTCTTGCAAAGCT TCTGGTTATCCATTC ACTGACTATATTGTA CACTGGGTGAAGCAG
       TACAGAACGTTTCGA AGACCAATAGGTAAG TGACTGATATAACAT GTGACCCACTTCGTC

       S  H  G  K  S   L  D  W  I  G   Y  I  N  P  Y   S  G  D  T  K
121    AGTCATGGAAAGAGC CTTGACTGGATTGGT TATATTAATCCTTAC AGTGGTGATACTAAG
       TCAGTACCTTTCTCG GAACTGACCTAACCA ATATAATTAGGAATG TCACCACTATGATTC

       F  N  E  K  F   K  S  K  A  T   L  T  V  D  K   S  S  S  T  A
181    TTCAATGAAAAGTTC AAGAGTAAGGCCACG TTGACTGTTGACAAG TCCAGCAGCACAGCC
       AAGTTACTTTTCAAG TTCTCATTCCGGTGC AACTGACAACTGTTC AGGTCGTCGTGTCGG

       Y  M  E  F  S   R  L  T  S  E   D  S  A  I  Y   Y  C  A  R  S
241    TATATGGAGTTTAGC CGATTGACATCTGAG GATTCTGCAATCTAT TACTGTGCAAGATCG
       ATATACCTCAAATCG GCTAACTGTAGACTC CTAAGACGTTAGATA ATGACACGTTCTAGC

       G  L  I  A  V   Y  F  D  Y  W   G  Q  G  T  T   V  T  V  S  S
301    GGTCTGATAGCAGTC TACTTTGATTACTGG GGCCAAGGGACCACG GTCACCGTCTCCTCA
       CCAGACTATCGTCAG ATGAAACTAATGACC CCGGTTCCCTGGTGC CAGTGGCAGAGGAGT

       G  G  G  G  S   G  G  G  G  S   G  G  G  G  S   E  L  Q  M  T
361    GGTGGTGGTGGTTCT GGCGGCGGCGGCTCC GGTGGTGGTGGTTCT GAGCTCCAGATGACC
       CCACCACCACCAAGA CCGCCGCCGCCGAGG CCACCACCACCAAGA CTCGAGGTCTACTGG

       Q  S  P  S  S   L  S  A  S  V   G  D  R  V  T   I  T  C  R  T
421    CAGTCTCCATCCTCC CTGTCTGCATCTGTA GGAGACAGAGTCACC ATCACTTGCCGGACA
       GTCAGAGGTAGGAGG GACAGACGTAGACAT CCTCTGTCTCAGTGG TAGTGAACGGCCTGT

       S  Q  T  I  S   S  L  L  N  W   Y  Q  Q  K  P   G  K  A  P  K
481    AGTCAGACCATTAGC AGTCTTTTAAATTGG TATCAGCAGAAACCA GGGAAAGCCCCTAAG
       TCAGTCTGGTAATCG TCAGAAAATTTAACC ATAGTCGTCTTTGGT CCCTTTCGGGGATTC

       L  L  I  Y  A   A  S  N  L  Q   S  G  V  P  S   R  F  S  G  S
541    CTCCTGATCTATGCT GCATCCAATTTGCAA AGTGGGGTCCCATCA AGGTTCAGTGGCAGT
       GAGGACTAGATACGA CGTAGGTTAAACGTT TCACCCCAGGGTAGT TCCAAGTCACCGTCA

       G  S  G  T  D   F  T  L  T  I   S  G  L  Q  P   E  D  F  S  T
601    GGATCTGGGACAGAT TTCACTCTCACCATC AGCGGTCTGCAACCT GAAGATTTTTCAACT
       CCTAGACCCTGTCTA AAGTGAGAGTGGTAG TCGCCAGACGTTGGA CTTCTAAAAAGTTGA

       Y  F  C  Q  Q   S  Y  S  F  P   R  T  F  G  Q   G  T  K  V  D
661    TACTTCTGTCAACAG AGTTACAGTTTCCCT CGAACGTTCGGCCAA GGGACCAAAGTGGAT
       ATGAAGACAGTTGTC TCAATGTCAAAGGGA GCTTGCAAGCCGGTT CCCTGGTTTCACCTA

       I  K
721    ATCAAA
       TAGTTT
```

```
     E  L  Q  L  V   E  Q  S  G  A   A  L  V  K  P   G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  M  T
361  GGTGGTGGTGGTTCT GGCGGCGGCGGCTCC GGTGGTGGTGGTTCT GAGCTCGTGATGACG
     CCACCACCACCAAGA CCGCCGCCGCCGAGG CCACCACCACCAAGA CTCGAGCACTACTGC

     Q  S  P  A  T   L  S  L  S  P   G  E  R  A  T   L  S  C  R  A
421  CAGTCTCCAGCCACC CTGTCTTTGTCTCCA GGGGAAAGAGCCACC CTCTCCTGCAGGGCC
     GTCAGAGGTCGGTGG GACAGAAACAGAGGT CCCCTTTCTCGGTGG GAGAGGACGTCCCGG

     S  Q  S  V  R   T  Y  L  A  W   Y  Q  Q  K  P   G  Q  A  P  R
481  AGTCAGAGTGTTAGG ACCTACTTAGCCTGG TACCAACAGAAACCT GGCCAGGCTCCCAGG
     TCAGTCTCACAATCC TGGATGAATCGGACC ATGGTTGTCTTTGGA CCGGTCCGAGGGTCC

     L  L  I  Y  A   A  S  H  R  A   T  G  I  P  A   R  F  S  G  S
541  CTCCTCATCTATGCT GCATCCCACAGGGCC ACTGGCATCCCAGCC AGGTTCAGTGGCAGT
     GAGGAGTAGATACGA CGTAGGGTGTCCCGG TGACCGTAGGGTCGG TCCAAGTCACCGTCA

     G  S  G  T  D   F  T  L  T  I   S  R  L  E  P   E  D  F  A  V
601  GGGTCTGGGACAGAC TTCACTCTCACCATC AGCAGACTGGAGCCT GAAGATTTTGCAGTG
     CCCAGACCCTGTCTG AAGTGAGAGTGGTAG TCGTCTGACCTCGGA CTTCTAAAACGTCAC

     Y  Y  C  Q  Q   Y  G  S  S  P   P  T  F  G  Q   G  T  K  V  E
661  TATTACTGTCAGCAG TATGGTAGCTCACCT CCGACGTTCGGCCAA GGGACCAAGGTAGAG
     ATAATGACAGTCGTC ATACCATCGAGTGGA GGCTGCAAGCCGGTT CCCTGGTTCCATCTC

     I  K
721  ATCAAA
     TAGTTT
```

```
     E  L  Q  L  V    E  Q  S  G  A    A  L  V  K  P    G  D  S  V  K
1    GAGCTGCAGCTGGTC  GAGCAGTCTGGAGCT  GCACTGGTGAAGCCT  GGGGACTCTGTGAAG
     CTCGACGTCGACCAG  CTCGTCAGACCTCGA  CGTGACCACTTCGGA  CCCCTGAGACACTTC

     M  S  C  K  A    S  G  Y  P  F    T  D  Y  I  V    H  W  V  K  Q
61   ATGTCTTGCAAAGCT  TCTGGTTATCCATTC  ACTGACTATATTGTA  CACTGGGTGAAGCAG
     TACAGAACGTTTCGA  AGACCAATAGGTAAG  TGACTGATATAACAT  GTGACCCACTTCGTC

     S  H  G  K  S    L  D  W  I  G    Y  I  N  P  Y    S  G  D  T  K
121  AGTCATGGAAAGAGC  CTTGACTGGATTGGT  TATATTAATCCTTAC  AGTGGTGATACTAAG
     TCAGTACCTTTCTCG  GAACTGACCTAACCA  ATATAATTAGGAATG  TCACCACTATGATTC

     F  N  E  K  F    K  S  K  A  T    L  T  V  D  K    S  S  S  T  A
181  TTCAATGAAAAGTTC  AAGAGTAAGGCCACG  TTGACTGTTGACAAG  TCCAGCAGCACAGCC
     AAGTTACTTTTCAAG  TTCTCATTCCGGTGC  AACTGACAACTGTTC  AGGTCGTCGTGTCGG

     Y  M  E  F  S    R  L  T  S  E    D  S  A  I  Y    Y  C  A  R  S
241  TATATGGAGTTTAGC  CGATTGACATCTGAG  GATTCTGCAATCTAT  TACTGTGCAAGATCG
     ATATACCTCAAATCG  GCTAACTGTAGACTC  CTAAGACGTTAGATA  ATGACACGTTCTAGC

     G  L  I  A  V    Y  F  D  Y  W    G  Q  G  T  T    V  T  V  S  S
301  GGTCTGATAGCAGTC  TACTTTGATTACTGG  GGCCAAGGGACCACG  GTCACCGTCTCCTCA
     CCAGACTATCGTCAG  ATGAAACTAATGACC  CCGGTTCCCTGGTGC  CAGTGGCAGAGGAGT

     G  G  G  G  S    G  G  G  G  S    G  G  G  G  S    E  L  V  L  T
361  GGTGGTGGTGGTTCT  GGCGGCGGCGGCTCC  GGTGGTGGTGGTTCT  GAGCTCGTGCTGACT
     CCACCACCACCAAGA  CCGCCGCCGCCGAGG  CCACCACCACCAAGA  CTCGAGCACGACTGA

     Q  S  P  D  F    Q  S  V  T  P    K  E  K  V  T    I  T  C  R  A
421  CAGTCTCCGGACTTT  CAGTCTGTGACTCCA  AAGGAGAAAGTCACC  ATCACCTGCCGGGCC
     GTCAGAGGCCTGAAA  GTCAGACACTGAGGT  TTCCTCTTTCAGTGG  TAGTGGACGGCCCGG

     S  Q  S  I  G    S  S  L  H  W    Y  Q  Q  K  P    D  Q  P  P  K
481  AGTCAGAGCATTGGT  AGTAGCTTACACTGG  TACCAGCAGAAACCA  GATCAGCCTCCAAAG
     TCAGTCTCGTAACCA  TCATCGAATGTGACC  ATGGTCGTCTTTGGT  CTAGTCGGAGGTTTC

     L  L  I  K  F    A  S  Q  S  I    S  R  V  P  S    R  F  S  G  T
541  CTCCTCATCAAATTT  GCTTCCCAGTCCATC  TCAAGGGTCCCCTCG  AGGTTCAGTGGCACT
     GAGGAGTAGTTTAAA  CGAAGGGTCAGGTAG  AGTTCCCAGGGGAGC  TCCAAGTCACCGTGA

     G  S  G  T  D    F  T  L  T  I    N  S  L  E  A    E  D  A  A  T
601  GGATCTGGGACAGAT  TTCACCCTCACCATC  AATAGCCTGGAAGCT  GAAGATGCTGCAACG
     CCTAGACCCTGTCTA  AAGTGGGAGTGGTAG  TTATCGGACCTTCGA  CTTCTACGACGTTGC

     Y  Y  C  Q  Q    S  F  S  F  P    Y  T  F  G  Q    G  T  K  L  E
661  TATTACTGTCAGCAG  AGCTTTAGTTTCCCG  TACACTTTTGGCCAG  GGGACCAAGCTGGAG
     ATAATGACAGTCGTC  TCGAAATCAAAGGGC  ATGTGAAAACCGGTC  CCCTGGTTCGACCTC

     I  K
721  ATCAAA
     TAGTTT
```

```
      E  L  Q  L  V    E  Q  S  G  A    A  L  V  K  P    G  D  S  V  K
1     GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

      M  S  C  K  A    S  G  Y  P  F    T  D  Y  I  V    H  W  V  K  Q
61    ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

      S  H  G  K  S    L  D  W  I  G    Y  I  N  P  Y    S  G  D  T  K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

      F  N  E  K  F    K  S  K  A  T    L  T  V  D  K    S  S  S  T  A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

      Y  M  E  F  S    R  L  T  S  E    D  S  A  I  Y    Y  C  A  R  S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

      G  L  I  A  V    Y  F  D  Y  W    G  Q  G  T  T    V  T  V  S  S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

      G  G  G  G  S    G  G  G  G  S    G  G  G  G  S    E  L  V  M  T
361   GGTGGTGGTGGTTCT  GGCGGCGGCGGCTCC  GGTGGTGGTGGTTCT  GAGCTCGTGATGACC
      CCACCACCACCAAGA  CCGCCGCCGCCGAGG  CCACCACCACCAAGA  CTCGAGCACTACTGG

      Q  S  P  S  S    V  S  A  S  V    G  D  R  V  T    I  A  C  R  A
421   CAGTCTCCATCTTCC  GTGTCTGCATCTGTA  GGAGACAGAGTCACC  ATCGCTTGTCGGGCG
      GTCAGAGGTAGAAGG  CACAGACGTAGACAT  CCTCTGTCTCAGTGG  TAGCGAACAGCCCGC

      S  Q  N  I  R    N  I  L  N  W    Y  Q  Q  R  P    G  K  A  P  Q
481   AGTCAGAACATTAGA  AACATTTTAAATTGG  TATCAACAGAGACCA  GGGAAGGCCCCTCAA
      TCAGTCTTGTAATCT  TTGTAAAATTTAACC  ATAGTTGTCTCTGGT  CCCTTCCGGGGAGTT

      L  L  I  Y  A    A  S  N  L  Q    S  G  V  P  S    R  F  S  G  S
541   CTCCTGATCTATGCT  GCCTCCAATTTACAA  AGTGGCGTCCCATCA  AGGTTCAGTGGCAGT
      GAGGACTAGATACGA  CGGAGGTTAAATGTT  TCACCGCAGGGTAGT  TCCAAGTCACCGTCA

      G  S  G  T  D    F  T  L  T  I    N  S  L  Q  P    E  D  F  A  T
601   GGATCTGGGACAGAT  TTCACTCTCACCATC  AACAGTCTGCAACCT  GAAGATTTTGCAACT
      CCTAGACCCTGTCTA  AAGTGAGAGTGGTAG  TTGTCAGACGTTGGA  CTTCTAAAACGTTGA

      Y  Y  C  Q  Q    S  Y  S  M  P    R  T  F  G  G    G  T  K  V  E
661   TACTACTGTCAACAG  AGTTACAGTATGCCT  CGAACTTTCGGCGGA  GGGACCAAGGTGGAA
      ATGATGACAGTTGTC  TCAATGTCATACGGA  GCTTGAAAGCCGCCT  CCCTGGTTCCACCTT

      I  K
721   ATCAAA
      TAGTTT
```

```
      E  L  Q  L  V    E  Q  S  G  A    A  L  V  K  P    G  D  S  V  K
1     GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

      M  S  C  K  A    S  G  Y  P  F    T  D  Y  I  V    H  W  V  K  Q
61    ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

      S  H  G  K  S    L  D  W  I  G    Y  I  N  P  Y    S  G  D  T  K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

      F  N  E  K  F    K  S  K  A  T    L  T  V  D  K    S  S  S  T  A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

      Y  M  E  F  S    R  L  T  S  E    D  S  A  I  Y    Y  C  A  R  S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

      G  L  I  A  V    Y  F  D  Y  W    G  Q  G  T  T    V  T  V  S  S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

      G  G  G  G  S    G  G  G  G  S    G  G  G  G  S    E  L  V  L  T
361   GGTGGTGGTGGTTCT  GGCGGCGGCGGCTCC  GGTGGTGGTGGTTCT  GAGCTCGTGCTGACT
      CCACCACCACCAAGA  CCGCCGCCGCCGAGG  CCACCACCACCAAGA  CTCGAGCACGACTGA

      Q  S  P  G  F    Q  S  V  T  P    K  E  K  V  T    I  T  C  R  A
421   CAGTCTCCAGGCTTT  CAGTCTGTGACTCCA  AAGGAGAAAGTCACC  ATCACCTGCCGGGCC
      GTCAGAGGTCCGAAA  GTCAGACACTGAGGT  TTCCTCTTTCAGTGG  TAGTGGACGGCCCGG

      S  Q  S  I  G    S  S  L  H  W    Y  Q  Q  K  P    D  Q  P  P  K
481   AGTCAGAGCATTGGT  AGTAGCTTACACTGG  TACCAGCAGAAACCA  GATCAGCCTCCAAAG
      TCAGTCTCGTAACCA  TCATCGAATGTGACC  ATGGTCGTCTTTGGT  CTAGTCGGAGGTTTC

      L  L  I  K  F    A  S  Q  S  I    S  G  V  P  S    R  F  S  G  S
541   CTCCTCATCAAATTT  GCTTCCCAGTCCATC  TCAGGGGTCCCCTCG  AGGTTCAGTGGCAGT
      GAGGAGTAGTTTAAA  CGAAGGGTCAGGTAG  AGTCCCCAGGGGAGC  TCCAAGTCACCGTCA

      G  S  G  T  N    F  T  L  T  I    N  S  L  E  A    E  D  A  A  T
601   GGATCTGGGACAAAT  TTCACCCTCACCATC  AATAGCCTGGAAGCT  GAAGATGCTGCAACC
      CCTAGACCCTGTTTA  AAGTGGGAGTGGTAG  TTATCGGACCTTCGA  CTTCTACGACGTTGG

      Y  Y  C  Q  Q    S  S  T  L  P    P  T  F  G  Q    G  T  K  V  E
661   TATTACTGTCAGCAG  AGTAGTACTTTACCT  CCCACTTTTGGCCAG  GGGACCAAGGTGGAG
      ATAATGACAGTCGTC  TCATCATGAAATGGA  GGGTGAAAACCGGTC  CCCTGGTTCCACCTC

      I  K
721   ATCAAA
      TAGTTT
```

```
    E  L  Q  L  V  E  Q  S  G  A  A  L  V  K  P  G  D  S  V  K
1   GAGCTGCAGCTGGTC GAGCAGTCTGGAGCT GCACTGGTGAAGCCT GGGGACTCTGTGAAG
    CTCGACGTCGACCAG CTCGTCAGACCTCGA CGTGACCACTTCGGA CCCCTGAGACACTTC

    M  S  C  K  A  S  G  Y  P  F  T  D  Y  I  V  H  W  V  K  Q
61  ATGTCTTGCAAAGCT TCTGGTTATCCATTC ACTGACTATATTGTA CACTGGGTGAAGCAG
    TACAGAACGTTTCGA AGACCAATAGGTAAG TGACTGATATAACAT GTGACCCACTTCGTC

    S  H  G  K  S  L  D  W  I  G  Y  I  N  P  Y  S  G  D  T  K
121 AGTCATGGAAAGAGC CTTGACTGGATTGGT TATATTAATCCTTAC AGTGGTGATACTAAG
    TCAGTACCTTTCTCG GAACTGACCTAACCA ATATAATTAGGAATG TCACCACTATGATTC

    F  N  E  K  F  K  S  K  A  T  L  T  V  D  K  S  S  S  T  A
181 TTCAATGAAAAGTTC AAGAGTAAGGCCACG TTGACTGTTGACAAG TCCAGCAGCACAGCC
    AAGTTACTTTTCAAG TTCTCATTCCGGTGC AACTGACAACTGTTC AGGTCGTCGTGTCGG

    Y  M  E  F  S  R  L  T  S  E  D  S  A  I  Y  Y  C  A  R  S
241 TATATGGAGTTTAGC CGATTGACATCTGAG GATTCTGCAATCTAT TACTGTGCAAGATCG
    ATATACCTCAAATCG GCTAACTGTAGACTC CTAAGACGTTAGATA ATGACACGTTCTAGC

    G  L  I  A  V  Y  F  D  Y  W  G  Q  G  T  T  V  T  V  S  S
301 GGTCTGATAGCAGTC TACTTTGATTACTGG GGCCAAGGGACCACG GTCACCGTCTCCTCA
    CCAGACTATCGTCAG ATGAAACTAATGACC CCGGTTCCCTGGTGC CAGTGGCAGAGGAGT

    G  G  G  G  S  G  G  G  G  S  G  G  G  G  S  E  L  V  L  T
361 GGTGGTGGTGGTTCT GGCGGCGGCGGCTCC GGTGGTGGTGGTTCT GAGCTCGTGCTGACT
    CCACCACCACCAAGA CCGCCGCCGCCGAGG CCACCACCACCAAGA CTCGAGCACGACTGA

    Q  S  P  D  F  Q  S  V  T  P  K  E  K  V  T  I  T  C  R  A
421 CAGTCTCCAGACTTT CAGTCTGTGACTCCA AAGGAGAAAGTCACC ATCACCTGCCGGGCC
    GTCAGAGGTCTGAAA GTCAGACACTGAGGT TTCCTCTTTCAGTGG TAGTGGACGGCCCGG

    S  Q  S  I  G  S  S  L  H  W  Y  Q  Q  K  P  D  Q  S  P  K
481 AGTCAGAGCATTGGT AGTAGCTTACACTGG TACCAGCAGAAACCA GATCAGTCTCCAAAG
    TCAGTCTCGTAACCA TCATCGAATGTGACC ATGGTCGTCTTTGGT CTAGTCAGAGGTTTC

    L  L  I  K  F  A  S  Q  S  L  S  G  V  P  S  R  F  S  G  S
541 CTCCTCATCAAGTTT GCTTCCCAGTCCCTC TCAGGGGTCCCCTCG AGGTTCAGTGGCAGT
    GAGGAGTAGTTCAAA CGAAGGGTCAGGGAG AGTCCCCAGGGGAGC TCCAAGTCACCGTCA

    G  S  G  T  D  F  T  L  T  I  S  S  L  Q  P  E  D  F  A  T
601 GGATCTGGGACAGAT TTCACTCTCACCATC AGCAGTCTACAACCT GAAGATTTTGCAACT
    CCTAGACCCTGTCTA AAGTGAGAGTGGTAG TCGTCAGATGTTGGA CTTCTAAAACGTTGA

    Y  Y  C  Q  Q  S  Y  T  T  P  P  T  F  G  G  G  T  K  V  E
661 TACTACTGTCAACAG AGTTACACTACCCCC CCCACTTTCGGCGGA GGGACCAAGGTGGAA
    ATGATGACAGTTGTC TCAATGTGATGGGGG GGGTGAAAGCCGCCT CCCTGGTTCCACCTT

    I  K
721 ATCAAA
    TAGTTT
```

```
         E  L  Q  L  V   E  Q  S  G  A   A  L  V  K  P   G  D  S  V  K
  1     GAGCTGCAGCTGGTC GAGCAGTCTGGAGCT GCACTGGTGAAGCCT GGGGACTCTGTGAAG
        CTCGACGTCGACCAG CTCGTCAGACCTCGA CGTGACCACTTCGGA CCCCTGAGACACTTC

         M  S  C  K  A   S  G  Y  P  F   T  D  Y  I  V   H  W  V  K  Q
 61     ATGTCTTGCAAAGCT TCTGGTTATCCATTC ACTGACTATATTGTA CACTGGGTGAAGCAG
        TACAGAACGTTTCGA AGACCAATAGGTAAG TGACTGATATAACAT GTGACCCACTTCGTC

         S  H  G  K  S   L  D  W  I  G   Y  I  N  P  Y   S  G  D  T  K
121     AGTCATGGAAAGAGC CTTGACTGGATTGGT TATATTAATCCTTAC AGTGGTGATACTAAG
        TCAGTACCTTTCTCG GAACTGACCTAACCA ATATAATTAGGAATG TCACCACTATGATTC

         F  N  E  K  F   K  S  K  A  T   L  T  V  D  K   S  S  S  T  A
181     TTCAATGAAAAGTTC AAGAGTAAGGCCACG TTGACTGTTGACAAG TCCAGCAGCACAGCC
        AAGTTACTTTTCAAG TTCTCATTCCGGTGC AACTGACAACTGTTC AGGTCGTCGTGTCGG

         Y  M  E  F  S   R  L  T  S  E   D  S  A  I  Y   Y  C  A  R  S
241     TATATGGAGTTTAGC CGATTGACATCTGAG GATTCTGCAATCTAT TACTGTGCAAGATCG
        ATATACCTCAAATCG GCTAACTGTAGACTC CTAAGACGTTAGATA ATGACACGTTCTAGC

         G  L  I  A  V   Y  F  D  Y  W   G  Q  G  T  T   V  T  V  S  S
301     GGTCTGATAGCAGTC TACTTTGATTACTGG GGCCAAGGGACCACG GTCACCGTCTCCTCA
        CCAGACTATCGTCAG ATGAAACTAATGACC CCGGTTCCCTGGTGC CAGTGGCAGAGGAGT

         G  G  G  G  S   G  G  G  G  S   G  G  G  G  S   E  L  V  L  T
361     GGTGGTGGTGGTTCT GGCGGCGGCGGCTCC GGTGGTGGTGGTTCT GAGCTCGTGCTGACT
        CCACCACCACCAAGA CCGCCGCCGCCGAGG CCACCACCACCAAGA CTCGAGCACGACTGA

         Q  S  P  G  F   Q  S  V  T  P   K  E  K  V  T   I  T  C  R  A
421     CAGTCTCCCGGCTTT CAGTCTGTGACTCCA AAGGAGAAAGTCACC ATCACCTGCCGGGCC
        GTCAGAGGGCCGAAA GTCAGACACTGAGGT TTCCTCTTTCAGTGG TAGTGGACGGCCCGG

         S  Q  S  I  G   S  S  L  H  W   Y  Q  Q  K  P   D  Q  S  P  K
481     AGTCAGAGCATTGGT AGTAGCTTACACTGG TACCAGCAGAAACCA GATCAGTCTCCAAAG
        TCAGTCTCGTAACCA TCATCGAATGTGACC ATGGTCGTCTTTGGT CTAGTCAGAGGTTTC

         L  L  I  K  F   A  S  Q  S  I   S  G  V  P  S   R  F  T  G  S
541     CTCCTCATCAAATTT GCTTCCCAGTCCATC TCAGGGGTCCCCTCG AGGTTCACTGGCAGT
        GAGGAGTAGTTTAAA CGAAGGGTCAGGTAG AGTCCCCAGGGGAGC TCCAAGTGACCGTCA

         G  S  G  T  D   F  T  L  T  I   S  S  L  Q  P   E  D  I  A  T
601     GGATCTGGGACAGAT TTCACTCTCACCATC AGCAGTCTGCAACCT GAAGATATTGCAACT
        CCTAGACCCTGTCTA AAGTGAGAGTGGTAG TCGTCAGACGTTGGA CTTCTATAACGTTGA

         Y  Y  C  Q  Q   S  Y  S  T  P   W  T  F  G  Q   G  T  K  L  E
661     TACTACTGTCAACAG AGTTACAGTACCCCT TGGACGTTCGGCCAA GGGACCAAGCTGGAG
        ATGATGACAGTTGTC TCAATGTCATGGGGA ACCTGCAAGCCGGTT CCCTGGTTCGACCTC

         I  K
721     ATCAAA
        TAGTTT
```

```
     E  L  Q  L  V    E  Q  S  G  A    A  L  V  K  P    G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A    S  G  Y  P  F    T  D  Y  I  V    H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S    L  D  W  I  G    Y  I  N  P  Y    S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F    K  S  K  A  T    L  T  V  D  K    S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S    R  L  T  S  E    D  S  A  I  Y    Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V    Y  F  D  Y  W    G  Q  G  T  T    V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S    G  G  G  G  S    G  G  G  G  S    E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  G  F    Q  S  V  T  P    K  E  K  V  T    I  T  C  R  A
421  CAGTCTCCCGGCTTT CAGTCTGTGACTCCA AAGGAGAAAGTCACC ATCACCTGCCGGGCC
     GTCAGAGGGCCGAAA GTCAGACACTGAGGT TTCCTCTTTCAGTGG TAGTGGACGGCCCGG

     S  Q  S  I  G    S  S  L  H  W    Y  Q  Q  K  P    D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F    A  S  Q  S  I    S  G  V  P  S    R  F  S  G  T
541  CTCCTCATCAAATTT GCTTCCCAGTCCATC TCAGGGGTCCCCTCG AGGTTCAGTGGCACT
     GAGGAGTAGTTTAAA CGAAGGGTCAGGTAG AGTCCCCAGGGGAGC TCCAAGTCACCGTGA

     G  S  G  T  D    F  T  L  T  I    S  S  L  Q  P    E  D  I  A  T
601  GGATCTGGGACAGAT TTCACTCTCACCATC AGCAGTCTGCAACCT GAAGATATTGCAACT
     CCTAGACCCTGTCTA AAGTGAGAGTGGTAG TCGTCAGACGTTGGA CTTCTATAACGTTGA

     Y  Y  C  Q  Q    S  Y  S  T  P    W  T  F  G  Q    G  T  K  L  E
661  TACTACTGTCAACAG AGTTACAGTACCCCT TGGACGTTCGGCCAA GGGACCAAGCTGGAG
     ATGATGACAGTTGTC TCAATGTCATGGGGA ACCTGCAAGCCGGTT CCCTGGTTCGACCTC

     I  K
721  ATCAAA
     TAGTTT
```

```
         E  L  Q  L  V    E  Q  S  G  A    A  L  V  K  P    G  D  S  V  K
  1     GAGCTGCAGCTGGTC GAGCAGTCTGGAGCT GCACTGGTGAAGCCT GGGGACTCTGTGAAG
        CTCGACGTCGACCAG CTCGTCAGACCTCGA CGTGACCACTTCGGA CCCCTGAGACACTTC

         M  S  C  K  A    S  G  Y  P  F    T  D  Y  I  V    H  W  V  K  Q
 61     ATGTCTTGCAAAGCT TCTGGTTATCCATTC ACTGACTATATTGTA CACTGGGTGAAGCAG
        TACAGAACGTTTCGA AGACCAATAGGTAAG TGACTGATATAACAT GTGACCCACTTCGTC

         S  H  G  K  S    L  D  W  I  G    Y  I  N  P  Y    S  G  D  T  K
121     AGTCATGGAAAGAGC CTTGACTGGATTGGT TATATTAATCCTTAC AGTGGTGATACTAAG
        TCAGTACCTTTCTCG GAACTGACCTAACCA ATATAATTAGGAATG TCACCACTATGATTC

         F  N  E  K  F    K  S  K  A  T    L  T  V  D  K    S  S  S  T  A
181     TTCAATGAAAAGTTC AAGAGTAAGGCCACG TTGACTGTTGACAAG TCCAGCAGCACAGCC
        AAGTTACTTTTCAAG TTCTCATTCCGGTGC AACTGACAACTGTTC AGGTCGTCGTGTCGG

         Y  M  E  F  S    R  L  T  S  E    D  S  A  I  Y    Y  C  A  R  S
241     TATATGGAGTTTAGC CGATTGACATCTGAG GATTCTGCAATCTAT TACTGTGCAAGATCG
        ATATACCTCAAATCG GCTAACTGTAGACTC CTAAGACGTTAGATA ATGACACGTTCTAGC

         G  L  I  A  V    Y  F  D  Y  W    G  Q  G  T  T    V  T  V  S  S
301     GGTCTGATAGCAGTC TACTTTGATTACTGG GGCCAAGGGACCACG GTCACCGTCTCCTCA
        CCAGACTATCGTCAG ATGAAACTAATGACC CCGGTTCCCTGGTGC CAGTGGCAGAGGAGT

         G  G  G  G  S    G  G  G  G  S    G  G  G  G  S    E  L  V  L  T
361     GGTGGTGGTGGTTCT GGCGGCGGCGGCTCC GGTGGTGGTGGTTCT GAGCTCGTGCTGACT
        CCACCACCACCAAGA CCGCCGCCGCCGAGG CCACCACCACCAAGA CTCGAGCACGACTGA

         Q  S  P  D  F    Q  S  V  T  P    K  E  K  V  T    I  T  C  R  A
421     CAGTCTCCAGACTTT CAGTCTGTGACTCCA AAGGAGAAAGTCACC ATCACCTGCCGGGCC
        GTCAGAGGTCTGAAA GTCAGACACTGAGGT TTCCTCTTTCAGTGG TAGTGGACGGCCCGG

         S  Q  S  I  G    S  S  L  H  W    Y  Q  Q  K  P    D  Q  S  P  K
481     AGTCAGAGCATTGGT AGTAGCTTACACTGG TACCAGCAGAAACCA GATCAGTCTCCAAAG
        TCAGTCTCGTAACCA TCATCGAATGTGACC ATGGTCGTCTTTGGT CTAGTCAGAGGTTTC

         L  L  I  K  F    A  S  Q  S  L    S  G  V  P  S    R  F  S  G  S
541     CTCCTCATCAAGTTT GCTTCCCAGTCCCTC TCAGGGGTCCCCTCG AGGTTCAGTGGCAGT
        GAGGAGTAGTTCAAA CGAAGGGTCAGGGAG AGTCCCCAGGGGAGC TCCAAGTCACCGTCA

         G  S  G  T  D    F  T  L  T  I    N  S  L  E  A    E  D  A  A  T
601     GGATCCGGGACAGAT TTCACCCTCACCATC AATAGCCTGGAAGCT GAAGATGCTGCAACG
        CCTAGGCCCTGTCTA AAGTGGGAGTGGTAG TTATCGGACCTTCGA CTTCTACGACGTTGC

         Y  Y  C  Q  Q    S  Y  S  T  P    W  T  F  G  Q    G  T  K  L  E
661     TATTACTGTCAACAG AGTTACAGTACCCCG TGGACGTTCGGCCAA GGGACCAAGCTGGAG
        ATAATGACAGTTGTC TCAATGTCATGGGGC ACCTGCAAGCCGGTT CCCTGGTTCGACCTC

         I  K
721     ATCAAA
        TAGTTT
```

```
      E  L  Q  L  V  E  Q  S  G  A  A  L  V  K  P  G  D  S  V  K
1     GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

      M  S  C  K  A  S  G  Y  P  F  T  D  Y  I  V  H  W  V  K  Q
61    ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

      S  H  G  K  S  L  D  W  I  G  Y  I  N  P  Y  S  G  D  T  K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

      F  N  E  K  F  K  S  K  A  T  L  T  V  D  K  S  S  S  T  A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

      Y  M  E  F  S  R  L  T  S  E  D  S  A  I  Y  Y  C  A  R  S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

      G  L  I  A  V  Y  F  D  Y  W  G  Q  G  T  T  V  T  V  S  S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

      G  G  G  G  S  G  G  G  G  S  G  G  G  G  S  E  L  V  L  T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

      Q  S  P  D  F  Q  S  V  T  P  K  E  K  V  T  I  T  C  R  A
421   CAGTCTCCAGACTTT CAGTCTGTGACTCCA AAGGAGAAAGTCACC ATCACCTGCCGGGCC
      GTCAGAGGTCTGAAA GTCAGACACTGAGGT TTCCTCTTTCAGTGG TAGTGGACGGCCCGG

      S  Q  S  I  G  S  S  L  H  W  Y  Q  Q  K  P  D  Q  S  P  K
481   AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

      L  L  I  K  F  A  S  Q  S  F  S  G  V  P  S  R  F  S  G  S
541   CTCCTCATCAAGTTT GCTTCCCAGTCCTTC TCAGGGGTCCCCTCG AGGTTCAGTGGCAGT
      GAGGAGTAGTTCAAA CGAAGGGTCAGGAAG AGTCCCCAGGGGAGC TCCAAGTCACCGTCA

      G  S  G  T  D  F  T  L  T  I  N  S  L  E  A  E  D  A  A  T
601   GGATCTGGGACAGAT TTCACCCTCACCATC AATAGCCTGGAAGCT GAAGATGCTGCAACG
      CCTAGACCCTGTCTA AAGTGGGAGTGGTAG TTATCGGACCTTCGA CTTCTACGACGTTGC

      Y  Y  C  Q  Q  S  Y  S  T  P  P  T  F  G  Q  G  T  K  V  E
661   TATTACTGTCAACAG AGTTACAGTACCCCT CCGACGTTCGGCCAA GGGACCAAGGTGGAG
      ATAATGACAGTTGTC TCAATGTCATGGGGA GGCTGCAAGCCGGTT CCCTGGTTCCACCTC

      I  K
721   ATCAAA
      TAGTTT
```

```
     E  L  Q  L  V    E  Q  S  G  A    A  L  V  K  P    G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A    S  G  Y  P  F    T  D  Y  I  V    H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S    L  D  W  I  G    Y  I  N  P  Y    S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F    K  S  K  A  T    L  T  V  D  K    S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S    R  L  T  S  E    D  S  A  I  Y    Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V    Y  F  D  Y  W    G  Q  G  T  T    V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S    G  G  G  G  S    G  G  G  G  S    E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  D  F    Q  S  V  T  P    K  E  K  V  T    I  T  C  R  A
421  CAGTCTCCAGACTTT CAGTCTGTGACTCCA AAGGAGAAAGTCACC ATCACCTGCCGGGCC
     GTCAGAGGTCTGAAA GTCAGACACTGAGGT TTCCTCTTTCAGTGG TAGTGGACGGCCCGG

     S  Q  S  I  G    S  S  L  H  W    Y  Q  Q  K  P    D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F    A  S  Q  S  L    S  G  V  P  S    R  F  S  G  S
541  CTCCTCATCAAGTTT GCTTCCCAGTCCCTC TCAGGGGTCCCCTCG AGGTTCAGTGGCAGT
     GAGGAGTAGTTCAAA CGAAGGGTCAGGGAG AGTCCCCAGGGGAGC TCCAAGTCACCGTCA

     G  S  G  T  D    F  T  L  T  I    S  S  L  Q  P    E  D  F  A  T
601  GGATCTGGGACAGAT TTCACTCTCACCATC AGCAGTCTGCAACCT GAAGATTTTGCAACT
     CCTAGACCCTGTCTA AAGTGAGAGTGGTAG TCGTCAGACGTTGGA CTTCTAAAACGTTGA

     Y  Y  C  Q  Q    S  Y  S  T  P    S  T  F  G  P    G  T  K  V  E
661  TACTACTGTCAACAG AGTTACAGTACCCCT AGTACTTTCGGCCCT GGGACCAAGGTGGAG
     ATGATGACAGTTGTC TCAATGTCATGGGGA TCATGAAAGCCGGGA CCCTGGTTCCACCTC

     I  K
721  ATCAAA
     TAGTTT
```

```
      E  L  Q  L  V    E  Q  S  G  A    A  L  V  K  P    G  D  S  V  K
1     GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

      M  S  C  K  A    S  G  Y  P  F    T  D  Y  I  V    H  W  V  K  Q
61    ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

      S  H  G  K  S    L  D  W  I  G    Y  I  N  P  Y    S  G  D  T  K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

      F  N  E  K  F    K  S  K  A  T    L  T  V  D  K    S  S  S  T  A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

      Y  M  E  F  S    R  L  T  S  E    D  S  A  I  Y    Y  C  A  R  S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

      G  L  I  A  V    Y  F  D  Y  W    G  Q  G  T  T    V  T  V  S  S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

      G  G  G  G  S    G  G  G  G  S    G  G  G  G  S    E  L  Q  M  T
361   GGTGGTGGTGGTTCT  GGCGGCGGCGGCTCC  GGTGGTGGTGGTTCT  GAGCTCCAGATGACC
      CCACCACCACCAAGA  CCGCCGCCGCCGAGG  CCACCACCACCAAGA  CTCGAGGTCTACTGG

      Q  S  P  S  S    L  S  A  S  V    G  D  R  V  T    I  T  C  R  A
421   CAGTCTCCATCCTCC  CTGTCTGCATCTGTA  GGAGACAGAGTCACC  ATCACCTGCCGGGCC
      GTCAGAGGTAGGAGG  GACAGACGTAGACAT  CCTCTGTCTCAGTGG  TAGTGGACGGCCCGG

      S  Q  S  I  G    S  S  L  H  W    Y  Q  Q  K  P    D  Q  S  P  K
481   AGTCAGAGCATTGGT  AGTAGCTTACACTGG  TACCAGCAGAAACCA  GATCAGTCTCCAAAG
      TCAGTCTCGTAACCA  TCATCGAATGTGACC  ATGGTCGTCTTTGGT  CTAGTCAGAGGTTTC

      L  L  I  K  F    A  S  Q  S  F    S  G  V  P  S    R  F  G  G  S
541   CTCCTCATCAAGTTT  GCTTCCCAGTCCTTC  TCAGGGGTCCCCTCG  AGGTTCGGTGGCAGT
      GAGGAGTAGTTCAAA  CGAAGGGTCAGGAAG  AGTCCCCAGGGGAGC  TCCAAGCCACCGTCA

      G  S  G  T  N    F  T  L  T  I    N  S  L  E  A    E  D  A  A  T
601   GGATCTGGGACAAAT  TTCACCCTCACCATC  AATAGCCTGGAAGCT  GAAGATGCTGCAACC
      CCTAGACCCTGTTTA  AAGTGGGAGTGGTAG  TTATCGGACCTTCGA  CTTCTACGACGTTGG

      Y  Y  C  Q  Q    S  S  T  L  P    P  T  F  G  Q    G  T  K  L  E
661   TATTACTGTCAGCAG  AGTAGTACTTTACCT  CCCACTTTTGGCCAG  GGGACCAAGCTGGAG
      ATAATGACAGTCGTC  TCATCATGAAATGGA  GGGTGAAAACCGGTC  CCCTGGTTCGACCTC

      I  K
721   ATCAAA
      TAGTTT
```

```
    E  L  Q  L  V  E  Q  S  G  A  A  L  V  K  P  G  D  S  V  K
1   GAGCTGCAGCTGGTC GAGCAGTCTGGAGCT GCACTGGTGAAGCCT GGGGACTCTGTGAAG
    CTCGACGTCGACCAG CTCGTCAGACCTCGA CGTGACCACTTCGGA CCCCTGAGACACTTC

    M  S  C  K  A  S  G  Y  P  F  T  D  Y  I  V  H  W  V  K  Q
61  ATGTCTTGCAAAGCT TCTGGTTATCCATTC ACTGACTATATTGTA CACTGGGTGAAGCAG
    TACAGAACGTTTCGA AGACCAATAGGTAAG TGACTGATATAACAT GTGACCCACTTCGTC

    S  H  G  K  S  L  D  W  I  G  Y  I  N  P  Y  S  G  D  T  K
121 AGTCATGGAAAGAGC CTTGACTGGATTGGT TATATTAATCCTTAC AGTGGTGATACTAAG
    TCAGTACCTTTCTCG GAACTGACCTAACCA ATATAATTAGGAATG TCACCACTATGATTC

    F  N  E  K  F  K  S  K  A  T  L  T  V  D  K  S  S  S  T  A
181 TTCAATGAAAAGTTC AAGAGTAAGGCCACG TTGACTGTTGACAAG TCCAGCAGCACAGCC
    AAGTTACTTTTCAAG TTCTCATTCCGGTGC AACTGACAACTGTTC AGGTCGTCGTGTCGG

    Y  M  E  F  S  R  L  T  S  E  D  S  A  I  Y  Y  C  A  R  S
241 TATATGGAGTTTAGC CGATTGACATCTGAG GATTCTGCAATCTAT TACTGTGCAAGATCG
    ATATACCTCAAATCG GCTAACTGTAGACTC CTAAGACGTTAGATA ATGACACGTTCTAGC

    G  L  I  A  V  Y  F  D  Y  W  G  Q  G  T  T  V  T  V  S  S
301 GGTCTGATAGCAGTC TACTTTGATTACTGG GGCCAAGGGACCACG GTCACCGTCTCCTCA
    CCAGACTATCGTCAG ATGAAACTAATGACC CCGGTTCCCTGGTGC CAGTGGCAGAGGAGT

    G  G  G  G  S  G  G  G  G  S  G  G  G  G  S  E  L  V  L  T
361 GGTGGTGGTGGTTCT GGCGGCGGCGGCTCC GGTGGTGGTGGTTCT GAGCTCGTGCTGACT
    CCACCACCACCAAGA CCGCCGCCGCCGAGG CCACCACCACCAAGA CTCGAGCACGACTGA

    Q  S  P  D  F  Q  S  V  T  P  K  E  K  V  T  I  T  C  R  A
421 CAGTCTCCAGACTTT CAGTCTGTGACTCCA AAGGAGAAAGTCACC ATCACCTGCCGGGCC
    GTCAGAGGTCTGAAA GTCAGACACTGAGGT TTCCTCTTTCAGTGG TAGTGGACGGCCCGG

    S  Q  S  I  G  S  N  L  H  W  Y  Q  Q  K  P  D  Q  S  P  K
481 AGTCAGAGCATTGGT AGTAACTTACACTGG TACCAGCAGAAACCA GATCAGTCTCCAAAG
    TCAGTCTCGTAACCA TCATTGAATGTGACC ATGGTCGTCTTTGGT CTAGTCAGAGGTTTC

    L  L  I  K  F  A  S  Q  S  F  S  G  V  P  S  R  F  S  G  S
541 CTCCTCATCAAGTTT GCTTCCCAGTCCTTC TCAGGGGTCCCCTCG AGGTTCAGTGGCAGT
    GAGGAGTAGTTCAAA CGAAGGGTCAGGAAG AGTCCCCAGGGGAGC TCCAAGTCACCGTCA

    G  S  G  T  D  F  S  L  T  I  N  S  L  E  A  E  D  A  A  T
601 GGATCTGGGACAGAT TTCAGCCTCACCATC AATAGCCTGGAAGCT GAAGATGCTGCAACT
    CCTAGACCCTGTCTA AAGTCGGAGTGGTAG TTATCGGACCTTCGA CTTCTACGACGTTGA

    Y  Y  C  Q  Q  S  Y  S  T  P  P  T  F  G  Q  G  T  R  L  E
661 TACTACTGTCAACAG AGTTACAGTACCCCT CCCACCTTCGGCCAA GGGACACGACTGGAG
    ATGATGACAGTTGTC TCAATGTCATGGGGA GGGTGGAAGCCGGTT CCCTGTGCTGACCTC

    I  K
721 ATTAAA
    TAATTT
```

```
     E  L  Q  L  V   E  Q  S  G  A   A  L  V  K  P   G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  D  F   Q  S  V  T  P   K  E  K  V  T   I  T  C  R  A
421  CAGTCTCCAGACTTT CAGTCTGTGACTCCA AAGGAGAAAGTCACC ATCACCTGCCGGGCC
     GTCAGAGGTCTGAAA GTCAGACACTGAGGT TTCCTCTTTCAGTGG TAGTGGACGGCCCGG

     S  Q  S  I  G   S  S  L  H  W   Y  Q  Q  K  P   D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F   A  S  Q  S  I   S  G  V  P  S   R  F  S  G  S
541  CTCCTCATCAAGTTT GCTTCCCAGTCCATC TCAGGGGTCCCATCG AGGTTCAGTGGCAGT
     GAGGAGTAGTTCAAA CGAAGGGTCAGGTAG AGTCCCCAGGGTAGC TCCAAGTCACCGTCA

     G  S  G  T  D   F  T  L  T  I   S  S  L  Q  P   E  D  F  A  T
601  GGATCTGGGACAGAT TTCACTCTCACCATC AGCAGTCTGCAACCT GAAGATTTTGCAACT
     CCTAGACCCTGTCTA AAGTGAGAGTGGTAG TCGTCAGACGTTGGA CTTCTAAAACGTTGA

     Y  Y  C  Q  Q   S  Y  S  T  P   P  T  F  G  P   G  T  K  L  E
661  TACTACTGTCAACAG AGTTACAGTACCCCT CCCACTTTCGGCCCT GGGACCAAGCTGGAG
     ATGATGACAGTTGTC TCAATGTCATGGGGA GGGTGAAAGCCGGGA CCCTGGTTCGACCTC

     I  K
721  ATCAAA
     TAGTTT
```

```
     E  L  Q  L  V   E  Q  S  G  A   A  L  V  K  P   G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  D  F   Q  S  V  T  P   K  E  K  V  T   I  T  C  R  A
421  CAGTCTCCAGACTTT CAATCTGTGACTCCA AAGGAGAAAGTCACC ATCACCTGCCGGGCC
     GTCAGAGGTCTGAAA GTTAGACACTGAGGT TTCCTCTTTCAGTGG TAGTGGACGGCCCGG

     S  Q  S  I  G   T  G  L  H  W   Y  Q  Q  K  P   D  Q  S  P  K
481  AGTCAGAGCATTGGT ACTGGCTTACACTGG TACCAGCAGAAACCG GATCAGTCTCCAAAG
     TCAGTCTCGTAACCA TGACCGAATGTGACC ATGGTCGTCTTTGGC CTAGTCAGAGGTTTC

     L  L  I  K  F   A  S  Q  S  F   S  G  V  P  S   R  F  S  G  S
541  CTCCTCATCAAATTT GCTTCCCAGTCCTTC TCAGGGGTCCCCTCG AGGTTCAGTGGCAGT
     GAGGAGTAGTTTAAA CGAAGGGTCAGGAAG AGTCCCCAGGGGAGC TCCAAGTCACCGTCA

     G  S  G  T  D   F  T  L  T  I   N  G  L  E  A   E  D  A  A  T
601  GGATCTGGGACAGAT TTCACCCTCACCATC AATGGCCTGGAAGCT GAAGATGCTGCAACG
     CCTAGACCCTGTCTA AAGTGGGAGTGGTAG TTACCGGACCTTCGA CTTCTACGACGTTGC

     Y  Y  C  Q  Q   S  S  T  L  P   P  T  F  G  Q   G  T  K  L  E
661  TATTACTGTCAGCAG AGTAGTACTTTACCT CCCACTTTTGGCCAG GGGACCAAGCTGGAG
     ATAATGACAGTCGTC TCATCATGAAATGGA GGGTGAAAACCGGTC CCCTGGTTCGACCTC

     I  K
721  ATCAAA
     TAGTTT
```

```
     E  L  Q  L  V   E  Q  S  G  A   A  L  V  K  P   G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  G  F   Q  S  V  T  P   K  E  K  V  T   I  T  C  R  A
421  CAGTCTCCAGGCTTT CAGTCTGTGACTCCA AAGGAGAAAGTCACC ATCACCTGCCGGGCC
     GTCAGAGGTCCGAAA GTCAGACACTGAGGT TTCCTCTTTCAGTGG TAGTGGACGGCCCGG

     S  Q  S  I  G   S  S  L  N  W   Y  Q  Q  K  P   D  Q  P  P  K
481  AGTCAGAGCATTGGT AGTAGCTTAAACTGG TACCAGCAGAAACCA GATCAGCCTCCAAAG
     TCAGTCTCGTAACCA TCATCGAATTTGACC ATGGTCGTCTTTGGT CTAGTCGGAGGTTTC

     L  L  I  K  F   A  S  Q  S  I   S  G  V  S  S   R  F  S  G  T
541  CTCCTCATCAAATTC GCTTCGCAGTCCATC TCAGGGGTCTCTTCG AGGTTCAGTGGCACT
     GAGGAGTAGTTTAAG CGAAGCGTCAGGTAG AGTCCCCAGAGAAGC TCCAAGTCACCGTGA

     G  S  G  T  D   F  T  L  T  I   S  S  L  Q  P   E  D  V  A  T
601  GGATCTGGGACAGAT TTCACCCTCACTATC AGCAGCCTGCAGCCT GAAGATGTTGCAACT
     CCTAGACCCTGTCTA AAGTGGGAGTGATAG TCGTCGGACGTCGGA CTTCTACAACGTTGA

     Y  Y  C  Q  Q   S  Y  S  T  P   P  T  F  G  Q   G  T  K  L  E
661  TATTACTGTCAACAG AGTTACAGTACCCCT CCGACGTTCGGCCAA GGGACCAAGCTGGAG
     ATAATGACAGTTGTC TCAATGTCATGGGGA GGCTGCAAGCCGGTT CCCTGGTTCGACCTC

     I  K
721  ATCAAA
     TAGTTT
```

```
     E  L  Q  L  V  E  Q  S  G  A  A  L  V  K  P  G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A  S  G  Y  P  F  T  D  Y  I  V  H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S  L  D  W  I  G  Y  I  N  P  Y  S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F  K  S  K  A  T  L  T  V  D  K  S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S  R  L  T  S  E  D  S  A  I  Y  Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V  Y  F  D  Y  W  G  Q  G  T  T  V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S  G  G  G  G  S  G  G  G  G  S  E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  D  F  Q  S  V  T  P  K  E  K  V  T  I  T  C  R  A
421  CAGTCTCCAGACTTT CAGTCTGTGACTCCA AAGGAGAAAGTCACC ATCACCTGCCGGGCC
     GTCAGAGGTCTGAAA GTCAGACACTGAGGT TTCCTCTTTCAGTGG TAGTGGACGGCCCGG

     S  Q  S  I  G  S  S  L  H  W  Y  Q  Q  K  P  D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F  A  S  Q  S  L  S  G  V  P  S  R  F  S  G  S
541  CTCCTCATCAAGTTT GCTTCCCAGTCCCTC TCAGGGGTCCCCTCG AGGTTCAGTGGCAGT
     GAGGAGTAGTTCAAA CGAAGGGTCAGGGAG AGTCCCCAGGGGAGC TCCAAGTCACCGTCA

     G  S  G  T  D  F  T  L  T  I  N  S  L  E  A  E  D  F  A  T
601  GGATCTGGGACAGAT TTCACCCTCACCATC AATAGCCTGGAAGCT GAAGATTTTGCAACT
     CCTAGACCCTGTCTA AAGTGGGAGTGGTAG TTATCGGACCTTCGA CTTCTAAAACGTTGA

     Y  Y  C  Q  Q  S  Y  S  T  P  S  T  F  G  P  G  T  K  V  E
661  TACTACTGTCAACAG AGTTACAGTACCCCT AGTACTTTCGGCCCT GGGACCAAGGTGGAG
     ATGATGACAGTTGTC TCAATGTCATGGGGA TCATGAAAGCCGGGA CCCTGGTTCCACCTC

     I  K
721  ATCAAA
     TAGTTT
```

```
     E  L  Q  L  V   E  Q  S  G  A   A  L  V  K  P   G  D  S  V  K
  1  GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
 61  ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  G  F   Q  S  V  T  P   K  E  K  V  T   I  T  C  R  A
421  CAGTCTCCCGGCTTT CAGTCTGTGACTCCA AAGGAGAAAGTCACC ATCACCTGCCGGGCC
     GTCAGAGGGCCGAAA GTCAGACACTGAGGT TTCCTCTTTCAGTGG TAGTGGACGGCCCGG

     S  Q  S  I  G   S  S  L  H  W   Y  Q  Q  K  P   D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F   A  S  Q  S  I   S  G  V  P  S   R  F  S  G  T
541  CTCCTCATCAAATTT GCTTCCCAGTCCATC TCAGGGGTCCCCTCG AGGTTCAGTGGCACT
     GAGGAGTAGTTTAAA CGAAGGGTCAGGTAG AGTCCCCAGGGGAGC TCCAAGTCACCGTGA

     G  S  G  T  D   F  T  L  T  I   N  S  L  E  A   E  D  A  A  T
601  GGATCTGGGACAGAT TTCACCCTCACCATC AATAGCCTGGAAGCT GAAGATGCTGCAACC
     CCTAGACCCTGTCTA AAGTGGGAGTGGTAG TTATCGGACCTTCGA CTTCTACGACGTTGG

     Y  Y  C  Q  Q   S  S  T  L  P   P  T  F  G  Q   G  T  K  L  E
661  TATTACTGTCAGCAG AGTAGTACTTTACCT CCCACTTTTGGCCAG GGGACCAAGCTGGAG
     ATAATGACAGTCGTC TCATCATGAAATGGA GGGTGAAAACCGGTC CCCTGGTTCGACCTC

     I  K
721  ATCAAA
     TAGTTT
```

```
      E  L  Q  L  V    E  Q  S  G  A    A  L  V  K  P    G  D  S  V  K
1     GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

      M  S  C  K  A    S  G  Y  P  F    T  D  Y  I  V    H  W  V  K  Q
61    ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

      S  H  G  K  S    L  D  W  I  G    Y  I  N  P  Y    S  G  D  T  K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

      F  N  E  K  F    K  S  K  A  T    L  T  V  D  K    S  S  S  T  A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

      Y  M  E  F  S    R  L  T  S  E    D  S  A  I  Y    Y  C  A  R  S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

      G  L  I  A  V    Y  F  D  Y  W    G  Q  G  T  T    V  T  V  S  S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

      G  G  G  G  S    G  G  G  G  S    G  G  G  G  S    E  L  V  L  T
361   GGTGGTGGTGGTTCT  GGCGGCGGCGGCTCC  GGTGGTGGTGGTTCT  GAGCTCGTGCTGACT
      CCACCACCACCAAGA  CCGCCGCCGCCGAGG  CCACCACCACCAAGA  CTCGAGCACGACTGA

      Q  S  P  D  F    Q  S  V  T  P    K  E  R  V  T    I  T  C  R  A
421   CAGTCTCCAGACTTT  CAGTCTGTGACTCCA  AAGGAGAGAGTCACC  ATCACCTGCCGGGCC
      GTCAGAGGTCTGAAA  GTCAGACACTGAGGT  TTCCTCTCTCAGTGG  TAGTGGACGGCCCGG

      S  Q  T  I  G    N  N  L  H  W    Y  Q  Q  K  P    G  Q  S  P  K
481   AGTCAGACCATTGGT  AATAACTTACACTGG  TACCAGCAGAAACCA  GGTCAGTCTCCAAAG
      TCAGTCTGGTAACCA  TTATTGAATGTGACC  ATGGTCGTCTTTGGT  CCAGTCAGAGGTTTC

      L  L  I  K  F    A  S  Q  S  F    S  G  V  P  S    R  F  S  G  S
541   CTCCTCATCAAGTTT  GCTTCCCAGTCCTTC  TCAGGGGTCCCCTCG  AGGTTCAGTGGCAGT
      GAGGAGTAGTTCAAA  CGAAGGGTCAGGAAG  AGTCCCCAGGGGAGC  TCCAAGTCACCGTCA

      G  S  G  T  D    F  T  L  T  I    N  S  L  E  A    E  D  A  A  T
601   GGATCTGGGACAGAT  TTCACCCTCACCATC  AATAGCCTGGAAGCT  GAAGATGCTGCAACT
      CCTAGACCCTGTCTA  AAGTGGGAGTGGTAG  TTATCGGACCTTCGA  CTTCTACGACGTTGA

      Y  Y  C  Q  Q    S  Y  S  T  P    W  T  F  G  Q    G  T  K  V  E
661   TATTACTGTCAACAG  AGTTACAGTACCCCG  TGGACGTTCGGCCAA  GGGACCAAGGTGGAA
      ATAATGACAGTTGTC  TCAATGTCATGGGGC  ACCTGCAAGCCGGTT  CCCTGGTTCCACCTT

      I  K
721   ATCAAA
      TAGTTT
```

```
    E  L  Q  L  V   E  Q  S  G  A   A  L  V  K  P   G  D  S  V  K
1   GAGCTGCAGCTGGTC GAGCAGTCTGGAGCT GCACTGGTGAAGCCT GGGGACTCTGTGAAG
    CTCGACGTCGACCAG CTCGTCAGACCTCGA CGTGACCACTTCGGA CCCCTGAGACACTTC

    M  S  C  K  A   S  G  Y  P  F   T  D  Y  I  V   H  W  V  K  Q
61  ATGTCTTGCAAAGCT TCTGGTTATCCATTC ACTGACTATATTGTA CACTGGGTGAAGCAG
    TACAGAACGTTTCGA AGACCAATAGGTAAG TGACTGATATAACAT GTGACCCACTTCGTC

    S  H  G  K  S   L  D  W  I  G   Y  I  N  P  Y   S  G  D  T  K
121 AGTCATGGAAAGAGC CTTGACTGGATTGGT TATATTAATCCTTAC AGTGGTGATACTAAG
    TCAGTACCTTTCTCG GAACTGACCTAACCA ATATAATTAGGAATG TCACCACTATGATTC

    F  N  E  K  F   K  S  K  A  T   L  T  V  D  K   S  S  S  T  A
181 TTCAATGAAAAGTTC AAGAGTAAGGCCACG TTGACTGTTGACAAG TCCAGCAGCACAGCC
    AAGTTACTTTTCAAG TTCTCATTCCGGTGC AACTGACAACTGTTC AGGTCGTCGTGTCGG

    Y  M  E  F  S   R  L  T  S  E   D  S  A  I  Y   Y  C  A  R  S
241 TATATGGAGTTTAGC CGATTGACATCTGAG GATTCTGCAATCTAT TACTGTGCAAGATCG
    ATATACCTCAAATCG GCTAACTGTAGACTC CTAAGACGTTAGATA ATGACACGTTCTAGC

    G  L  I  A  V   Y  F  D  Y  W   G  Q  G  T  T   V  T  V  S  S
301 GGTCTGATAGCAGTC TACTTTGATTACTGG GGCCAAGGGACCACG GTCACCGTCTCCTCA
    CCAGACTATCGTCAG ATGAAACTAATGACC CCGGTTCCCTGGTGC CAGTGGCAGAGGAGT

    G  G  G  G  S   G  G  G  G  S   G  G  G  G  S   E  L  V  L  T
361 GGTGGTGGTGGTTCT GGCGGCGGCGGCTCC GGTGGTGGTGGTTCT GAGCTCGTGCTGACT
    CCACCACCACCAAGA CCGCCGCCGCCGAGG CCACCACCACCAAGA CTCGAGCACGACTGA

    Q  S  P  D  F   Q  S  V  T  P   K  E  K  V  T   I  T  C  R  A
421 CAGTCTCCAGACTTT CAGTCTGTGACTCCA AAGGAGAAAGTCACC ATCACCTGCCGGGCC
    GTCAGAGGTCTGAAA GTCAGACACTGAGGT TTCCTCTTTCAGTGG TAGTGGACGGCCCGG

    S  Q  S  I  G   S  S  L  H  W   Y  Q  Q  K  P   D  Q  S  P  K
481 AGTCAGAGTATTGGT AGTAGCTTACACTGG TACCAGCAGAAACCA GATCAGTCTCCAAAG
    TCAGTCTCATAACCA TCATCGAATGTGACC ATGGTCGTCTTTGGT CTAGTCAGAGGTTTC

    L  L  I  K  F   A  S  Q  S  L   S  G  V  P  S   R  F  S  G  S
541 CTCCTCATCAAGTTT GCTTCCCAGTCCCTC TCAGGGGTCCCATCA AGGTTCAGTGGCAGT
    GAGGAGTAGTTCAAA CGAAGGGTCAGGGAG AGTCCCCAGGGTAGT TCCAAGTCACCGTCA

    G  S  G  T  D   F  T  L  T  I   S  S  L  Q  P   E  D  F  A  T
601 GGATCTGGGACAGAT TTCACTCTCACCATC AGCAGTCTGCAACCT GAAGATTTTGCAACT
    CCTAGACCCTGTCTA AAGTGAGAGTGGTAG TCGTCAGACGTTGGA CTTCTAAAACGTTGA

    Y  Y  C  Q  Q   S  Y  S  T  P   P  T  F  G  Q   G  T  K  V  E
661 TACTACTGTCAACAG AGTTACAGTACCCCT CCAACGTTCGGCCAA GGGACCAAGGTGGAA
    ATGATGACAGTTGTC TCAATGTCATGGGGA GGTTGCAAGCCGGTT CCCTGGTTCCACCTT

    I  K
721 ATCAAA
    TAGTTT
```

```
     E  L  Q  L  V   E  Q  S  G  A   A  L  V  K  P   G  D  S  V  K
  1  GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
 61  ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  L  T
361  GGTGGTGGTGGTTCT GGCGGCGGCGGCTCC GGTGGTGGTGGTTCT GAGCTCGTGTTGACG
     CCACCACCACCAAGA CCGCCGCCGCCGAGG CCACCACCACCAAGA CTCGAGCACAACTGC

     Q  S  P  S  S   L  S  A  S  V   G  D  R  V  T   I  T  C  R  A
421  CAGTCTCCATCCTCC CTGTCTGCATCTGTA GGAGACAGAGTCACC ATCACTTGCCGGGCA
     GTCAGAGGTAGGAGG GACAGACGTAGACAT CCTCTGTCTCAGTGG TAGTGAACGGCCCGT

     S  Q  S  I  S   R  Y  L  N  W   Y  Q  Q  K  P   G  K  P  P  K
481  AGTCAGAGCATTAGC AGGTATTTAAATTGG TATCAACAAAAACCA GGGAAACCCCCTAAG
     TCAGTCTCGTAATCG TCCATAAATTTAACC ATAGTTGTTTTTGGT CCCTTTGGGGGATTC

     L  L  I  F  V   A  S  N  L  Q   T  G  V  P  S   R  F  S  G  S
541  CTCCTGATCTTTGTT GCATCCAATTTGCAA ACTGGGGTCCCATCA AGGTTCAGTGGCAGT
     GAGGACTAGAAACAA CGTAGGTTAAACGTT TGACCCCAGGGTAGT TCCAAGTCACCGTCA

     G  S  G  T  D   F  T  L  T  I   S  S  L  E  P   E  D  F  A  V
601  GGATCTGGGACAGAT TTCACTCTCACCATC AGCAGCCTAGAGCCT GAAGATTTTGCAGTT
     CCTAGACCCTGTCTA AAGTGAGAGTGGTAG TCGTCGGATCTCGGA CTTCTAAAACGTCAA

     Y  Y  C  Q  Q   R  S  N  W  P   L  T  F  G  G   G  T  K  V  D
661  TATTACTGTCAGCAG CGTAGCAACTGGCCC CTCACTTTCGGCGGA GGGACCAAAGTGGAT
     ATAATGACAGTCGTC GCATCGTTGACCGGG GAGTGAAAGCCGCCT CCCTGGTTTCACCTA

     I  K
721  ATCAAA
     TAGTTT
```

```
    E  L  Q  L  V  E  Q  S  G  A  A  L  V  K  P  G  D  S  V  K
1   GAGCTGCAGCTGGTC GAGCAGTCTGGAGCT GCACTGGTGAAGCCT GGGGACTCTGTGAAG
    CTCGACGTCGACCAG CTCGTCAGACCTCGA CGTGACCACTTCGGA CCCCTGAGACACTTC

    M  S  C  K  A  S  G  Y  P  F  T  D  Y  I  V  H  W  V  K  Q
61  ATGTCTTGCAAAGCT TCTGGTTATCCATTC ACTGACTATATTGTA CACTGGGTGAAGCAG
    TACAGAACGTTTCGA AGACCAATAGGTAAG TGACTGATATAACAT GTGACCCACTTCGTC

    S  H  G  K  S  L  D  W  I  G  Y  I  N  P  Y  S  G  D  T  K
121 AGTCATGGAAAGAGC CTTGACTGGATTGGT TATATTAATCCTTAC AGTGGTGATACTAAG
    TCAGTACCTTTCTCG GAACTGACCTAACCA ATATAATTAGGAATG TCACCACTATGATTC

    F  N  E  K  F  K  S  K  A  T  L  T  V  D  K  S  S  S  T  A
181 TTCAATGAAAAGTTC AAGAGTAAGGCCACG TTGACTGTTGACAAG TCCAGCAGCACAGCC
    AAGTTACTTTTCAAG TTCTCATTCCGGTGC AACTGACAACTGTTC AGGTCGTCGTGTCGG

    Y  M  E  F  S  R  L  T  S  E  D  S  A  I  Y  Y  C  A  R  S
241 TATATGGAGTTTAGC CGATTGACATCTGAG GATTCTGCAATCTAT TACTGTGCAAGATCG
    ATATACCTCAAATCG GCTAACTGTAGACTC CTAAGACGTTAGATA ATGACACGTTCTAGC

    G  L  I  A  V  Y  F  D  Y  W  G  Q  G  T  T  V  T  V  S  S
301 GGTCTGATAGCAGTC TACTTTGATTACTGG GGCCAAGGGACCACG GTCACCGTCTCCTCA
    CCAGACTATCGTCAG ATGAAACTAATGACC CCGGTTCCCTGGTGC CAGTGGCAGAGGAGT

    G  G  G  G  S  G  G  G  G  S  G  G  G  G  S  E  L  V  L  T
361 GGTGGTGGTGGTTCT GGCGGCGGCGGCTCC GGTGGTGGTGGTTCT GAGCTCGTGCTGACT
    CCACCACCACCAAGA CCGCCGCCGCCGAGG CCACCACCACCAAGA CTCGAGCACGACTGA

    Q  S  P  D  F  Q  S  V  T  P  K  E  K  V  T  I  T  C  R  A
421 CAGTCTCCAGACTTT CAGTCTGTGACTCCA AAGGAGAAAGTCACC ATCACCTGCCGGGCC
    GTCAGAGGTCTGAAA GTCAGACACTGAGGT TTCCTCTTTCAGTGG TAGTGGACGGCCCGG

    S  Q  S  I  G  S  S  L  H  W  Y  Q  Q  K  P  D  Q  S  P  K
481 AGTCAGAGCATTGGT AGTAGCTTACACTGG TACCAGCAGAAACCA GATCAGTCTCCAAAG
    TCAGTCTCGTAACCA TCATCGAATGTGACC ATGGTCGTCTTTGGT CTAGTCAGAGGTTTC

    L  L  I  K  F  A  S  Q  S  L  S  G  V  P  S  R  F  S  G  S
541 CTCCTCATCAAGTTT GCTTCCCAGTCCCTC TCAGGGGTCCCCTCG AGGTTCAGTGGCAGT
    GAGGAGTAGTTCAAA CGAAGGGTCAGGGAG AGTCCCCAGGGGAGC TCCAAGTCACCGTCA

    G  S  G  T  D  F  A  L  T  I  N  S  L  E  A  E  D  A  A  T
601 GGATCTGGGACAGAT TTCGCCCTCACCATC AATAGCCTGGAAGCT GAAGATGCTGCAACC
    CCTAGACCCTGTCTA AAGCGGGAGTGGTAG TTATCGGACCTTCGA CTTCTACGACGTTGG

    Y  Y  C  Q  Q  S  S  T  L  P  P  T  F  G  Q  G  T  K  L  E
661 TATTACTGTCAGCAG AGTAGTACTTTACCT CCCACTTTTGGCCAG GGGACCAAGCTGGAG
    ATAATGACAGTCGTC TCATCATGAAATGGA GGGTGAAAACCGGTC CCCTGGTTCGACCTC

    I  K
721 ATCAAA
    TAGTTT
```

```
     E  L  Q  L  V   E  Q  S  G  A   A  L  V  K  P   G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A   S  G  Y  P  F   T  D  Y  I  V   H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S   L  D  W  I  G   Y  I  N  P  Y   S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F   K  S  K  A  T   L  T  V  D  K   S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S   R  L  T  S  E   D  S  A  I  Y   Y  C  A  R  S
241  TATATGGAGTTTAGC CGATTGACATCTGAG GATTCTGCAATCTAT TACTGTGCAAGATCC
     ATATACCTCAAATCG GCTAACTGTAGACTC CTAAGACGTTAGATA ATGACACGTTCTAGC

     G  L  I  A  V   Y  F  D  Y  W   G  Q  G  T  T   V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S   G  G  G  G  S   G  G  G  G  S   E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  E  F   Q  S  V  A  P   K  E  K  V  T   I  T  C  R  A
421  CAGTCTCCAGAGTTT CAGTCTGTGGCTCCA AAGGAGAAAGTCACC ATCACCTGCCGGGCC
     GTCAGAGGTCTCAAA GTCAGACACCGAGGT TTCCTCTTTCAGTGG TAGTGGACGGCCCGG

     S  Q  S  I  G   S  S  L  H  W   Y  Q  Q  K  P   D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F   A  S  Q  S  F   S  G  V  P  S   R  F  G  G  S
541  CTCCTCATCAAGTTT GCTTCCCAGTCCTTC TCAGGGGTCCCCTCG AGGTTCGGTGGCAGT
     GAGGAGTAGTTCAAA CGAAGGGTCAGGAAG AGTCCCCAGGGGAGC TCCAAGCCACCGTCA

     G  S  G  T  N   F  T  L  T  I   N  S  L  E  A   E  D  A  A  T
601  GGATCTGGGACAAAT TTCACCCTCACCATC AATAGCCTGGAAGCT GAAGATGCTGCAACC
     CCTAGACCCTGTTTA AAGTGGGAGTGGTAG TTATCGGACCTTCGA CTTCTACGACGTTGG

     Y  Y  C  Q  Q   S  S  T  L  P   P  T  F  G  Q   G  T  K  L  E
661  TATTACTGTCAGCAG AGTAGTACCTTACCT CCCACTTTTGGCCAG GGGACCAAGCTGGAG
     ATAATGACAGTCGTC TCATCATGGAATGGA GGGTGAAAACCGGTC CCCTGGTTCGACCTC

     I  K
721  ATCAAA
     TAGTTT
```

```
    E  L  Q  L  V   E  Q  S  G  A   A  L  V  K  P   G  D  S  V  K
1   GAGCTGCAGCTGGTC GAGCAGTCTGGAGCT GCACTGGTGAAGCCT GGGGACTCTGTGAAG
    CTCGACGTCGACCAG CTCGTCAGACCTCGA CGTGACCACTTCGGA CCCCTGAGACACTTC

    M  S  C  K  A   S  G  Y  P  F   T  D  Y  I  V   H  W  V  K  Q
61  ATGTCTTGCAAAGCT TCTGGTTATCCATTC ACTGACTATATTGTA CACTGGGTGAAGCAG
    TACAGAACGTTTCGA AGACCAATAGGTAAG TGACTGATATAACAT GTGACCCACTTCGTC

    S  H  G  K  S   L  D  W  I  G   Y  I  N  P  Y   S  G  D  T  K
121 AGTCATGGAAAGAGC CTTGACTGGATTGGT TATATTAATCCTTAC AGTGGTGATACTAAG
    TCAGTACCTTTCTCG GAACTGACCTAACCA ATATAATTAGGAATG TCACCACTATGATTC

    F  N  E  K  F   K  S  K  A  T   L  T  V  D  K   S  S  S  T  A
181 TTCAATGAAAAGTTC AAGAGTAAGGCCACG TTGACTGTTGACAAG TCCAGCAGCACAGCC
    AAGTTACTTTTCAAG TTCTCATTCCGGTGC AACTGACAACTGTTC AGGTCGTCGTGTCGG

    Y  M  E  F  S   R  L  T  S  E   D  S  A  I  Y   Y  C  A  R  S
241 TATATGGAGTTTAGC CGATTGACATCTGAG GATTCTGCAATCTAT TACTGTGCAAGATCG
    ATATACCTCAAATCG GCTAACTGTAGACTC CTAAGACGTTAGATA ATGACACGTTCTAGC

    G  L  I  A  V   Y  F  D  Y  W   G  Q  G  T  T   V  T  V  S  S
301 GGTCTGATAGCAGTC TACTTTGATTACTGG GGCCAAGGGACCACG GTCACCGTCTCCTCA
    CCAGACTATCGTCAG ATGAAACTAATGACC CCGGTTCCCTGGTGC CAGTGGCAGAGGAGT

    G  G  G  G  S   G  G  G  G  S   G  G  G  G  S   E  L  V  L  T
361 GGTGGTGGTGGTTCT GGCGGCGGCGGCTCC GGTGGTGGTGGTTCT GAGCTCGTGCTGACT
    CCACCACCACCAAGA CCGCCGCCGCCGAGG CCACCACCACCAAGA CTCGAGCACGACTGA

    Q  S  P  D  F   Q  S  V  T  P   K  E  K  V  T   I  T  C  R  A
421 CAGTCTCCAGACTTT CAGTCTGTGACTCCA AAGGAGAAAGTCACC ATCACCTGCCGGGCC
    GTCAGAGGTCTGAAA GTCAGACACTGAGGT TTCCTCTTTCAGTGG TAGTGGACGGCCCGG

    S  Q  S  I  G   S  S  L  H  W   Y  Q  Q  K  P   D  Q  S  P  K
481 AGTCAGAGCATTGGT AGTAGCTTACACTGG TACCAGCAGAAACCA GATCAGTCTCCAAAG
    TCAGTCTCGTAACCA TCATCGAATGTGACC ATGGTCGTCTTTGGT CTAGTCAGAGGTTTC

    L  L  I  K  F   A  S  Q  S  L   S  G  V  P  S   R  F  S  G  S
541 CTCCTCATCAAGTTT GCTTCCCAGTCCCTC TCAGGGGTCCCCTCG AGGTTCAGTGGCAGT
    GAGGAGTAGTTCAAA CGAAGGGTCAGGGAG AGTCCCCAGGGGAGC TCCAAGTCACCGTCA

    G  S  G  T  D   F  T  L  T  I   N  S  L  E  A   E  D  A  A  T
601 GGATCTGGGACAGAT TTCACCCTCACCATC AATAGCCTGGAAGCT GAAGATGCTGCAACT
    CCTAGACCCTGTCTA AAGTGGGAGTGGTAG TTATCGGACCTTCGA CTTCTACGACGTTGA

    Y  Y  C  Q  Q   S  Y  S  T  P   S  T  F  G  P   G  T  K  V  E
661 TACTACTGTCAACAG AGTTACAGTACCCCT AGTACTTTCGGCCCT GGGACCAAGGTGGAG
    ATGATGACAGTTGTC TCAATGTCATGGGGA TCATGAAAGCCGGGA CCCTGGTTCCACCTC

    I  K
721 ATCAAA
    TAGTTT
```

```
     E  L  Q  L  V  E  Q  S  G  A  A  L  V  K  P  G  D  S  V  K
1    GAGCTGCAGCTGGTC GAGCAGTCTGGAGCT GCACTGGTGAAGCCT GGGGACTCTGTGAAG
     CTCGACGTCGACCAG CTCGTCAGACCTCGA CGTGACCACTTCGGA CCCCTGAGACACTTC

     M  S  C  K  A  S  G  Y  P  F  T  D  Y  I  V  H  W  V  K  Q
61   ATGTCTTGCAAAGCT TCTGGTTATCCATTC ACTGACTATATTGTA CACTGGGTGAAGCAG
     TACAGAACGTTTCGA AGACCAATAGGTAAG TGACTGATATAACAT GTGACCCACTTCGTC

     S  H  G  K  S  L  D  W  I  G  Y  I  N  P  Y  S  G  D  T  K
121  AGTCATGGAAAGAGC CTTGACTGGATTGGT TATATTAATCCTTAC AGTGGTGATACTAAG
     TCAGTACCTTTCTCG GAACTGACCTAACCA ATATAATTAGGAATG TCACCACTATGATTC

     F  N  E  K  F  K  S  K  A  T  L  T  V  D  K  S  S  S  T  A
181  TTCAATGAAAAGTTC AAGAGTAAGGCCACG TTGACTGTTGACAAG TCCAGCAGCACAGCC
     AAGTTACTTTTCAAG TTCTCATTCCGGTGC AACTGACAACTGTTC AGGTCGTCGTGTCGG

     Y  M  E  F  S  R  L  T  S  E  D  S  A  I  Y  Y  C  A  R  S
241  TATATGGAGTTTAGC CGATTGACATCTGAG GATTCTGCAATCTAT TACTGTGCAAGATCG
     ATATACCTCAAATCG GCTAACTGTAGACTC CTAAGACGTTAGATA ATGACACGTTCTAGC

     G  L  I  A  V  Y  F  D  Y  W  G  Q  G  T  T  V  T  V  S  S
301  GGTCTGATAGCAGTC TACTTTGATTACTGG GGCCAAGGGACCACG GTCACCGTCTCCTCA
     CCAGACTATCGTCAG ATGAAACTAATGACC CCGGTTCCCTGGTGC CAGTGGCAGAGGAGT

     G  G  G  G  S  G  G  G  G  S  G  G  G  G  S  E  L  V  L  T
361  GGTGGTGGTGGTTCT GGCGGCGGCGGCTCC GGTGGTGGTGGTTCT GAGCTCGTGCTGACT
     CCACCACCACCAAGA CCGCCGCCGCCGAGG CCACCACCACCAAGA CTCGAGCACGACTGA

     Q  S  P  D  F  Q  S  V  T  P  K  E  K  V  T  I  T  C  R  A
421  CAGTCTCCAGACTTT CAGTCTGTGACTCCA AAGGAGAAAGTCACC ATCACCTGCCGGGCC
     GTCAGAGGTCTGAAA GTCAGACACTGAGGT TTCCTCTTTCAGTGG TAGTGGACGGCCCGG

     S  Q  S  I  G  S  S  L  H  W  Y  Q  Q  K  P  D  Q  S  P  K
481  AGTCAGAGCATTGGT AGTAGCTTACACTGG TACCAGCAGAAACCA GATCAGTCTCCAAAG
     TCAGTCTCGTAACCA TCATCGAATGTGACC ATGGTCGTCTTTGGT CTAGTCAGAGGTTTC

     L  L  I  K  F  A  S  Q  S  F  S  G  V  P  S  R  F  S  G  S
541  CTCCTCATCAAGTTT GCTTCCCAGTCCTTC TCAGGGGTCCCCTCG AGGTTCAGTGGCAGT
     GAGGAGTAGTTCAAA CGAAGGGTCAGGAAG AGTCCCCAGGGGAGC TCCAAGTCACCGTCA

     G  S  G  T  D  F  T  L  T  I  N  S  L  E  A  E  D  A  A  T
601  GGATCTGGGACAGAT TTCACCCTCACCATC AATAGCCTGGAAGCT GAAGATGCTGCAACG
     CCTAGACCCTGTCTA AAGTGGGAGTGGTAG TTATCGGACCTTCGA CTTCTACGACGTTGC

     Y  Y  C  Q  Q  S  Y  S  T  P  W  T  F  G  Q  G  T  K  L  E
661  TATTACTGTCAACAG AGTTACAGTACCCCG TGGACGTTCGGCCAA GGGACCAAGCTGGAG
     ATAATGACAGTTGTC TCAATGTCATGGGGC ACCTGCAAGCCGGTT CCCTGGTTCGACCTC

     I  K
721  ATCAAA
     TAGTTT
```

Response Difference (RU)
80
60
40
20
0
-20
Residual
0.9
-0.9
-50
0
50
100
150
200
250
300
Time (s)
Time (s)

PREPARATION OF SCFV ANTIBODY FRAGMENTS

The present application is a continuation of U.S. Ser. No. 11/568,685, filed Dec. 3, 2007, now U.S. Pat. No. 8,247,194, which issued on Aug. 21, 2012, which is a national stage filing under 35 U.S.C. §371 of PCT Application No.: PCT/EP2005/004893, filed on May 4, 2005, which claims priority to EP 04010702.1 filed on May 5, 2004; and all of the disclosures of which are incorporated herein by reference in their entirety.

REFERENCE TO THE SEQUENCE LISTING

The present application is being filed along with a Sequence Listing in electronic format. The Sequence Listing is provided as a file entitled MCMT P0011US.txt, created May 17, 2010, which is 87 KB in size. The information in the electronic format of the Sequence Listing is incorporated herein by reference in its entirety.

The invention relates to methods of preparing antibody fragments. Further, the invention relates to antibody fragments prepared by said methods. Further, the invention relates to antibody variable regions comprised in antibody fragments producible by said methods.

Antibody fragments offer many advantages over full immunoglobulin molecules when used as an active agent in a therapeutic regimen. For example, being of smaller size than their full size immunoglobulin counterparts, antibody fragments can achieve higher levels of tissue penetration when administered to a patient in need thereof, and therefore higher therapeutic efficacy than a larger immunoglobulin molecule of comparable antigen specificity. Further, due to this smaller size, antibody fragments are often more easily and economically producible than their full immunoglobulin counterparts of comparable antigen specificity. This is especially the case where the antibody is a single chain antibody fragment. A single chain antibody fragment is an antibody fragment which unifies at least one each of a variable region from the antibody heavy chain ("VH") and a variable region from the antibody light chain ("VL") into a single polypeptide chain, the respective VH and VL regions being separated by a peptide linker chosen so as to allow formation of a unified antigen binding site by complementarity determining regions ("CDRs") of the VH and VL domains. Finally, the modular construction of antibody fragments, comprising at least one VH and VL region, allows for a greater degree of flexibility in the design and construction of such fragments than possible for full immunoglobulin molecules, production of the latter often requiring the use of special cell lines to achieve the complex folding and, often, glycosylation patterns necessary for a desired biological activity.

The researcher seeking to develop antibody fragments useful in therapy will often already have access to a full immunoglobulin molecule of the desired specificity, either directly or via a suitable hybridoma cell line. Starting from such an immunoglobulin, he may make a corresponding antibody fragment comprising both the VH and VL regions of the "parent" immunoglobulin molecule. Such a corresponding antibody fragment may for example take the form of a Fab fragment, a (Fab)2 fragment, an scFv fragment (i.e. a single chain antibody ("SCA") unifying both VH and VL as part of a single polypeptide chain, as described above) or even a bivalent single chain antibody comprising two scFv fragments on a single polypeptide chain. In the latter case, the bivalent single chain antibody may comprise one scFv derived from the parent immunoglobulin molecule (bivalent bispecific single chain antibody), or two such scFvs (bivalent monospecific single chain antibody, or diabody).

However, it is often the case that direct conversion of a parent immunoglobulin molecule into an antibody fragment, that is to say, recombinant incorporation of the VH and VL regions comprised in one binding arm of the parent immunoglobulin molecule into a corresponding antibody fragment intended to have the same antigen binding specificity as the parent immunoglobulin molecule, leads to an antibody fragment which is not, or is not sufficiently expressible in soluble form. This problem is especially common when the corresponding antibody fragment is intended to be an scFv, regardless of whether this scFv is intended to be produced in monovalent form, or as part of a larger construct in bivalent form.

The inability to recombinantly express or sufficiently express such a corresponding antibody fragment in soluble form makes it impossible or, in the best case, much less feasible to exploit the advantages outlined above for antibody fragments in a contemplated regimen of therapy. In such a situation, the researcher seeking to develop antibody fragments useful in therapy is often left with the choice of either using the parent immunoglobulin antibody in full form or direct cleavage products thereof (e.g. Fab) as an active therapeutic agent, or finding or developing another full immunoglobulin with the desired specificity to use as a starting point for the construction of another corresponding antibody fragment which, he hopes, will not suffer the same problems as the first antibody fragment. The first scenario is unsatisfactory, since it implies accepting certain disadvantages associated with full immunoglobulin molecules which may not be in standing with the particular therapeutic regimen contemplated. The second scenario is unsatisfactory for several reasons. First, another immunoglobulin suitable for use as a new starting point for a new corresponding antibody fragment is not always available. Second, development of a new immunoglobulin with the desired antigen binding specificity can take a long time, and is in any case a costly undertaking, typically involving as it does the use of research animals from which a new hybridoma may be derived. Finally, even if another suitable immunoglobulin is already available, or another suitable immunoglobulin is developed, significant risk still remains that a corresponding antibody fragment resulting from such a new immunoglobulin will suffer the same problems of recombinant expressibility as experienced for the corresponding antibody fragment derived from the first immunoglobulin. In the case that no other immunoglobulin was available, and a new immunoglobulin had to be developed, such risk is especially acute, since the time and resources devoted to such development stand to be rendered worthless in retrospect.

There therefore exists a need for a method of preparing an antibody fragment from an immunoglobulin in cases where attempts at direct conversion of this immunoglobulin into an antibody fragment have failed. The aim of the invention is therefore to provide a method allowing such preparation.

Accordingly, a first aspect of the invention provides a method of preparing an antibody fragment of a source immunoglobulin, which source immunoglobulin specifically binds to an antigen of interest, a corresponding antibody fragment of which source immunoglobulin exhibits insufficient soluble recombinant expression, comprising:

(a) providing a nucleic acid molecule encoding a first antibody variable region or fragment thereof comprised in the source immunoglobulin, wherein the first antibody variable region or fragment thereof is a heavy chain variable region (VH) or a light chain variable region (VL), or a fragment of either of these;

(b) respectively combining (i) the nucleic acid molecule encoding the first antibody VH or VL region or fragment of either with (ii) a plurality of nucleic acid molecules encoding a diverse population of a second antibody variable region or fragment thereof, wherein the second antibody variable region or fragment thereof is a light chain variable region (VL) or a heavy chain variable region (VH), or a fragment of either of these, whereby a first population of combined nucleic acid molecules is obtained;

(c) introducing the first population of combined nucleic acid molecules into a display system chosen from a phage display system, a prokaryotic display system, a eukaryotic display system, or an mRNA display system;

(d) selecting at least one first antibody fragment displayed in step (c) and comprising the VH and VL region, or a fragment of either or both of these, which specifically binds to the antigen of interest; and (e) isolating the at least one first antibody fragment selected in step (d);

characterized in that the nucleic acid molecule encoding the first antibody variable region or fragment thereof or the nucleic acid molecule encoding the second antibody variable region or fragment thereof is operably linked to a nucleic acid molecule encoding an N-terminal, cis-acting amphipathic polypeptide moiety such that said N-terminal, cis-acting amphipathic polypeptide moiety, when translated, is linked to the N-terminal end of the first or second antibody variable region.

According to a preferred embodiment of the present invention, the nucleic acid molecule encoding the first antibody variable region or fragment thereof is obtained by PCR amplification of at least one polynucleotide comprised in a hybridoma cell or B cell which produces the source immunoglobulin; or peptide sequencing of at least one portion of the source immunoglobulin to determine the primary amino acid sequence of the at least one portion of the source immunoglobulin, followed by synthesis of a corresponding nucleic acid molecule capable of encoding the at least one portion of the source immunoglobulin sequenced.

According to another preferred embodiment of the present invention, the method of preparing an antibody fragment of a source immunoglobulin further comprises the following steps:

(a) respectively combining (i) the nucleic acid molecule encoding the second antibody variable region or fragment thereof with (ii) a plurality of nucleic acid molecules encoding a diverse population of a third antibody variable region or fragment thereof, wherein the third antibody variable region or fragment thereof is a heavy chain variable region (VH) or a light chain variable region (VL), or a fragment of either of these, whereby a second population of combined nucleic acid molecules is obtained;

(b) introducing the second population of combined nucleic acid molecules into a display system chosen from a phage display system, a prokaryotic display system, a eukaryotic display system, or an mRNA display system;

(c) selecting at least one second antibody fragment displayed in step (c) and comprising the VH and VL region, or a fragment of either or both of these, which specifically binds to the antigen of interest; and (d) isolating the at least one second antibody fragment selected in step (d);

characterized in that the nucleic acid molecule encoding the second antibody variable region or fragment thereof or the nucleic acid molecule encoding the third antibody variable region or fragment thereof is operably linked to a nucleic acid molecule encoding an N-terminal, cis-acting amphipathic polypeptide moiety such that said N-terminal, cis-acting amphipathic polypeptide moiety, when translated, is linked to the N-terminal end of the second or third antibody variable region.

Further preferred embodiments of the present invention are set out in the accompanying claims 3 and 5 to 15.

As used in the context of the present invention, the expressions "soluble expression" or "expressed in soluble form" or "expression in soluble form" or "solubly expressed" or other comparable expressions refer to a scenario in which an antibody fragment is expressed and/or secreted in a form allowing it to specifically bind to a desired antigen. One of skill in the art understands such a scenario as implying a native state of said antibody fragment in which the polypeptide chain/s of the antibody fragment is/are folded so as to allow the CDRs comprised within the VH and VL regions to spatially interact to form a single unified antigen binding site. Such folding is understood within the present invention as being stable enough such that the unified antigen binding site created by the mutual interaction of the CDRs persists under normal physiological conditions, i.e. the VH and VL regions do not continuously part and re-associate, but rather a single stable structure in which the VH and VL regions remain associated is formed. "Soluble expression" and other like terms such as those indicated above exclude the scenario in which the antibody fragment is expressed as inclusion bodies; such inclusion bodies are insoluble, and would require laborious refolding in order to render the antibody fragment capable of specifically binding to a desired antigen.

In the context of the present invention, the term "recombinant" encompasses all processes involving genetic sequences which are present in a form derived from, but not per se present in nature. For example, the incorporation of two genetic sequences encoding two discrete polypeptides individually found in nature into a new genetic sequence encoding a single protein not found in nature, said protein comprising each of these two discrete polypeptides, would be a "recombinant" process in the sense of the present invention. By the same token, the resulting protein comprising each of the two polypeptides mentioned above would be a "recombinant" protein, and its expression in a suitable host system, be it prokaryotic or eukaryotic, would be considered to be recombinant expression in the sense of the present invention.

As used in the context of the present invention, the terms "insufficient", "not sufficient" or other comparable terms refer in the context of soluble recombinant expression to the fact that said soluble recombinant expression (see above) being either absent or of such a low level as to render the conversion of a source immunoglobulin into a corresponding antibody fragment practically and/or economically unfeasible. Here it is noted that where soluble expression of a corresponding antibody fragment is unfeasible or of limited feasibility, such expression will generally also be of limited economic feasibility.

As used in the context of the present invention, the term "amphipathic polypeptide moiety" denotes a polypeptide having both hydrophobic and hydrophilic regions, each region being spatially defined and distinct from the other. One example of an "amphipathic polypeptide moiety" as used herein is a polypeptide comprising both hydrophilic and hydrophobic amino acids and in which, when the polypeptide forms a stable alpha-helix, the hydrophilic residues are spatially disposed on one side of the alpha helix, while the hydrophobic residues are spatially disposed on the other side of the alpha helix. Imagining such an alpha helix as an extended tube, then, the cross-section of this tube at any point would yield a circle, one hemisphere of which presents predominantly hydrophilic amino acid side chains to the outer environment, and the other hemisphere of which presents predominantly hydrophobic amino acid side chains to the outer environment. Another example of an "amphipathic polypeptide moiety" as used herein is a polypeptide beta sheet or even a globular polypeptide, one face of which presents predominantly hydrophilic amino acid side chains to the outer environment, and the other hemisphere of which presents predominantly hydrophobic amino acid side chains to the outer environment. An amphipathic polypeptide moiety may comprise one or more hydrophilic and/or hydrophobic regions, as described above.

As used in the context of the present invention, the term "operably associated" refers to a joining such that, upon translation of, e.g., a first and/or second antibody fragment, e.g., the amphipathic polypeptide moiety is also co-translated as part of the same polypeptide chain as, e.g., the first and/or second antibody variable region. Such joining should allow sufficient spatial degrees of freedom of the, e.g., amphipathic polypeptide moiety with respect to the, e.g., antibody fragment so as to allow spatial interaction between the former and the latter. Practically, this may be accomplished by interposing a polypeptide chain of sufficient length between the, e.g., amphipathic polypeptide moiety and, e.g., an antibody variable region to which it is attached such that the, e.g., amphipathic polypeptide moiety may "fold back" on the, e.g., antibody variable region and spatially interact with it.

The amphipathic polypeptide moiety is "N-terminal", meaning that it is located at the amino-terminus of the translated polypeptide. Since the amphipathic polypeptide moiety is located, N-terminally, on the same polypeptide chain as the first and second or, as the case may be, as the second and third antibody variable regions, it is able to interact with the variable region which is first translated in the translating step ("cis-acting"), in order to stabilize this region until the variable region which is second translated can complex with the first translated region, thereby possibly displacing the amphipathic polypeptide moiety, and forming a complex between the two antibody variable regions which remains stable and soluble even in the absence of the amphipathic polypeptide moiety.

As used in the context of the present invention, the expression "corresponding antibody fragment" refers to an antibody fragment which has been produced without the inventive method. As such, a "corresponding antibody fragment" will be the result of transferring, usually by recombinant technology, the VH and VL regions of the source immunoglobulin into a desired antibody fragment format. It is immaterial for the meaning of the expression "corresponding antibody fragment" as used according to the present invention what the format of the antibody fragment is; as long as the antibody fragment comprises both the VH and VL regions as they are each present in the source immunoglobulin, it is to be considered a "corresponding antibody fragment".

As used in the context of the present invention, the expression "source immunoglobulin" refers to any immunoglobulin molecule in full form, i.e. including Fc portion, but not necessarily including glycosylation decoration, which, when used as the starting point in making a corresponding antibody fragment, produces a corresponding antibody fragment which exhibits insufficient soluble recombinant expression (in the sense explained above). It follows, then, that an immunoglobulin used as a starting point in making a corresponding antibody fragment which does exhibit sufficient soluble expression (in the sense explained above) is not to be regarded as a "source immunoglobulin" within the sense of this term.

As used in the context of the present invention, the expression "antigen binding properties" refers to any parameter of an antibody fragment which is descriptive of the interaction of this antibody fragment with the antigen of interest. Such "antigen binding properties" may for example include, but are not limited to, the specificity of binding with respect to an antigen of choice and the strength of binding, i.e. binding affinity, with respect to this antigen.

As used in the context of the present invention, the term "complementary" refers to a state of mutual spatial and/or electrostatic compatibility between two antibody variable regions, for example between a VH and VL region, which allows and/or fosters stable formation of a complex between these two regions. As such, "complementary" antibody variable regions fit together in a spatial, three-dimensional sense, and this fitting may be promoted by specific and/or non-specific electrostatic interactions between the amino acid side chains of one antibody variable region with those of the other antibody variable region. The term "complementary" also encompasses the scenario in which the proper (i.e. naïve) three-dimensional folding of one respective antibody variable domain depends on the presence of another antibody variable domain, and vice-versa. This latter scenario is one in which the two antibody variable domains are "complementary," at least in part due to a mutual induction of fit.

Within the meaning of the invention, an antibody fragment is "selectable" when, after having been translated into a polypeptide from a corresponding nucleic acid molecule, the antibody fragment is rendered accessible from outside the system allowing correlation between genotype and phenotype such that the antigen binding properties of the antibody fragment can be ascertained in a qualitative or quantitative sense. If an antibody fragment is selectable, it has obviously been translated and recombinantly expressed in soluble form. As such, the requirement that the antibody fragment be "selectable" aims at determining which antibody fragment/s of the larger pool of antibody fragments which were recombinantly expressible in soluble form also bind to the antigen of interest, i.e. the antigen bound by the source immunoglobulin.

The method according to the invention provides an efficient and reliable way of recovering, in an antibody fragment, desired antigen binding properties hitherto observed in a source immunoglobulin, when standard efforts to convert this source immunoglobulin to a corresponding antibody fragment have failed. As such, the method according to the invention eliminates the dependency on full immunoglobulin molecules as active binding agents, e.g. of medicaments, where the use of antibody fragments of identical or comparable antigen specificity would be either desirable or necessary for a particular therapeutic application. By facilitating the production of alternate antibody-based binding agents, the method of the invention significantly expands the palette of antibody-based therapeutic agents open for use when treating a particular disease.

It has surprisingly been observed that by providing the amphipathic polypeptide moiety as defined above, the soluble recombinant expression of new combinations of antibody variable regions is promoted. A lack of recombinant solubility may arise for any number of reasons. For example, the polypeptide being expressed may contain predominantly hydrophobic amino acids, or at least bear such hydrophobic amino acids to the external hydrophilic environment. In another possible scenario, the charges of charged amino acids in contact with the aqueous (hydrophilic) environment may be neutralized by counterions in solution such that the charged amino acids are no longer able to interact hydrophilically with their environment, thereby leading to a decrease in overall polypeptide solubility (i.e. isoelectric precipitation). Without being bound by theory, the inventors believe that the amphipathic polypeptide moiety non-covalently associates with, say, a predominantly hydrophobic partner protein or with a predominantly hydrophobic region of a partner protein. Such association in effect "converts" the hydrophobic nature of the partner protein to a hydrophilic nature since, seen from the standpoint of the solution in the aqueous environment, the hydrophobic amino acid side chains of the partner protein have been replaced by the hydrophilic amino acid side chains in the amphipathic polypeptide moiety. In this way the aqueous solubility of a partner protein, for example a first or second antibody fragment as in the present method, is greatly enhanced by an effective chaperoning provided by the amphipathic polypeptide moiety. A similar effect of interaction between the amphipathic polypeptide moiety and regions of the partner protein/polypeptide is conceivable in the phenomenon of isoelectric precipitation mentioned above. In such a scenario, the amphipathic polypeptide moiety would likely displace any charge-neutralizing moieties from the outer surface of the partner polypeptide, thereby increasing the latter's solubility.

The inventors believe that such chaperoning may be important in the translation step of the present inventive method. Here, a translated first antibody variable region which alone may not be sufficiently recombinantly expressible in soluble form is kept—by virtue of the amphipathic polypeptide moiety—soluble long enough to form a complex with a complementary second antibody variable region. A complex of first and second complementary antibody variable regions then likely has sufficient solubility to exist in stably folded form in the absence of the amphipathic polypeptide moiety. In effect, then, the amphipathic polypeptide moiety chaperones an otherwise insoluble first antibody variable region to a second antibody variable region such that a complex of first and second antibody variable regions is formed which is also soluble in the absence of the amphipathic polypeptide moiety. In the absence of the amphipathic polypeptide moiety, such a complex would not likely have formed at all, and certainly would not have formed in the time available before the selecting step, since the first antibody variable region would not have sufficient solubility in aqueous solution to form a complex with the second antibody variable region.

Analogous reasoning may also be applied to chaperoning of an otherwise insoluble second antibody variable region prior to the latter's forming a complex with a first antibody variable region.

After a sufficiently soluble first and/or second antibody fragment has/ve been identified in the selection step of the inventive method, the amphipathic polypeptide moiety and any additional polypeptide linking the amphipathic polypeptide moiety to an antibody variable region may be removed, either at the polypeptide level (e.g. by incorporating a suitable protease cleavage site just outside the antibody variable region), or at the nucleotide level (e.g. by omitting the nucleic acid molecule encoding the amphipathic polypeptide moiety and any linking polypeptide in a nucleic acid molecule to be incorporated into a vector for separate recombinant expression).

According to an embodiment of the present method, amphipathic polypeptide moieties suitable for this purpose may be chosen from the pro regions of any of the following polypeptides: papain, cruzain, thermolysin, cathepsin B, cathepsin L, protease A, protease B, IgA protease and carboxypeptidase Y; the N2 domain of filamentous phage (e.g. M13); or any polypeptide moiety which comprises an amphipathic region as determined by the publicly available internet program at www.dkfz-heidelberg.de/tbi/bioinfo/Individual/HelicalWheel/.

It should be noted that the provision of a nucleic acid molecule encoding the first antibody variable region may be effected by any number of methods. In principle, any method which allows conversion of the primary amino acid sequence of the first antibody variable region into a base sequence of a nucleic acid molecule which, when translated, will result in the primary amino acid sequence of the first antibody variable domain, is acceptable and within the scope of the invention as a way of "providing a nucleic acid molecule encoding a first antibody variable domain". One way of providing a nucleic acid molecule encoding a first antibody variable region may be by PCR amplification of at least one polynucleotide comprised in an immortalized hybridoma cell which produces the source immunoglobulin, for example PCR amplification of an mRNA molecule encoding a first antibody variable region. Another way may be by PCR amplification of at least one polynucleotide comprised in a non-immortalized lymphocyte in or isolated from a blood sample, said lymphocyte producing the source immunoglobulin.

Another way of "providing a nucleic acid molecule encoding a first antibody variable domain" is by direct peptide sequencing of at least a portion of the source immunoglobulin to determine a primary amino acid sequence. From this primary amino acid sequence, it is possible to construct at least one nucleic acid molecule which, when translated, results in the amino acid sequence of the first antibody variable domain. This way of providing a nucleic acid molecule encoding a first antibody variable domain has the advantage of great flexibility in construction of a nucleic acid molecule. Due to the degeneracy of the genetic code, there will exist a large number of possible nucleic acid molecules which, when translated, will lead to the primary sequence of the first antibody variable domain. For each amino acid in the first antibody variable region for which there exists more than one codon, there also exists the possibility of optimizing the codon chosen. For example, it may be that of several potential codons, one is known to be most the common codon for the amino acid in question in the particular expression system to be used later in the inventive method. Choosing at this position this most commonly used codon, and then repeating the same process for each of the degenerate codons encountered in the sequence of the first antibody variable region therefore leads to a nucleic acid molecule which, when translated in the system of choice later in the method, is likely to lead to the highest expression levels. In this way, an optimization of expression profile in the system of choice is achieved.

Alternatively, a slowing down of the translation process may be desirable in some circumstances, for example to allow the emerging protein or polypeptide chain time to properly fold. Here, it is within the ambit of the invention to choose codons such that the speed of translation is reduced to allow this effect. One of ordinary skill in the art understands how to manipulate codon usage to achieve such effects.

The above method of direct peptide sequencing followed by construction of a suitable nucleic acid molecule would lead to a polypeptide which is identical to the first antibody variable region. It should also be appreciated, however, that the nucleic acid molecule obtained in this manner need not necessarily lead to a polypeptide exhibiting a sequence which is identical to that of the first antibody variable region comprised in the source immunoglobulin. It is also possible to effect changes in the individual codons of the resulting nucleotide acid sequence such that the polypeptide is more suitable for use as a therapeutic agent. For example, the primary amino acid sequence of the first antibody variable region may be evaluated by known methods for determining the presence of potential T cell epitopes (for example as described in WO 92/10755, WO 00/34317, WO 98/52976, WO 02/079415, WO 02/012899 and WO 02/069232) which, if left unchanged in the first antibody variable region, would likely trigger an immunogenic response in the body of a patient to whom the resulting antibody fragment has been administered. Should T cell epitopes be found to exist, amino acid mutations may be performed at the nucleic acid level to eliminate or at least reduce the presence of such T cell epitopes in the finally translated polypeptide molecule. Such mutations will likely be of a conservative nature, i.e. will be of the sort which retains to as great an extent as possible the chemical characteristics (e.g. molecular weight, molecular shape, electronegativity, electrostatic charge, etc.) of the amino acid side chain, so as to perturb the folding of the first antibody variable region as little as possible in the final antibody fragment (i.e. in the "first antibody fragment").

In general, then, de novo amino acid sequencing may allow the researcher a great deal of freedom to tailor the nucleic acid molecule at the most fundamental level so as to fulfil the various requirements set upon the antibody fragment finally obtained.

As stated above, the inventive method may advantageously be used to render expressible an antibody fragment derived from a source immunoglobulin, where the corresponding antibody fragment derived directly from the source immunoglobulin was previously not at all recombinantly expressible in soluble form (i.e. expression which is under the detection limit using standard detection methods, for example ELISA). However, the teaching of the inventive method can also be employed to enhance the soluble recombinant expressibility of an antibody fragment derived from a source immunoglobulin in the event that the corresponding antibody fragment derived directly from the source immunoglobulin was previously recombinantly expressible in soluble form, but only poorly so.

Accordingly, one embodiment of the invention provides the additional steps of evaluating the ability of the isolated first antibody fragment to be recombinantly expressed in soluble form, and isolating at least one first antibody fragment, the soluble recombinant expression properties of which have been improved relative to those of said corresponding antibody fragment. As such, the method of the invention as described above allows an improvement in the recombinant expressibility of an antibody fragment derived from a source immunoglobulin (i.e. non-expressible antibody fragment rendered expressible, or poorly expressible antibody fragment rendered more expressible).

One of ordinary skill in the art understands how to evaluate the soluble recombinant expressibility of polypeptides such as the isolated first antibody fragment, the primary indicator of recombinant expressibility being the yield of said first antibody fragment in a recombinant expression system identical to that used to express a corresponding antibody fragment directly derived from the source immunoglobulin. Comparative yields may be measured by known methods, for example SDS-PAGE, Western blot, antigen binding ELISA, BIAcore and/or spectroscopic methods ($OD_{280}$). Alternatively, a functional readout may be used in evaluating the soluble recombinant expressibility of a first antibody fragment as compared to that of a corresponding antibody fragment. Such functional readouts may for example be antibody fragment binding (e.g. ELISA, immunoblot, BIAcore, FACS analysis, isothermal titration calorimetry (ITC), fluorescent correlation spectroscopy (FCS) and/or Scatchard analysis), neutralization (e.g. competitive binding assays, inhibition of cell proliferation or inhibition of signal transduction) and/or FACS analysis.

Whether or not the isolated first antibody fragment represents a qualitative or a quantitative improvement in the soluble recombinant expressibility of a corresponding antibody fragment, this first antibody fragment comprises a first antibody variable region identical to or, in the event that mutations have been made at the nucleic acid level following peptide sequencing of at least a portion of the source immunoglobulin as described above, derived from a variable region of the source immunoglobulin as well as a complementary second antibody variable region originating from the plurality of nucleic acid molecules. So one variable region comprised in the first antibody fragment originates from the source immunoglobulin, while the other variable region originates from elsewhere, i.e. from a source of the researcher's choice. Ideally, this source may be a diverse library of different antibody variable domains obtained, for example, from blood cells, for example human blood cells.

A further embodiment of the method according to the invention entails an iterative application of the method. In a first round (described above) the first antibody variable region is held constant while being randomly combined, at the nucleic acid level, with many different potential nucleic acid molecules encoding a second antibody variable region. The present embodiment provides a second round in which now the second antibody variable region present in the first antibody fragment (the first antibody fragment being derived in the first iterative round) is held constant and is randomly combined, at the nucleic acid level, with many different potential nucleic acid molecules encoding a third antibody variable region complementary to the second antibody variable region. The plurality of nucleic acid molecules encoding a third antibody variable region may be for example a diverse library of different antibody variable domains obtained, for example, from blood cells, for example human blood cells.

As such, the second antibody fragment isolated after the second iterative round described according to the present embodiment will not comprise a first antibody variable region from the source immunoglobulin, since the first antibody variable region will have been replaced in the second iterative round of the method by the third antibody variable region. This embodiment has the advantage that the natures (i.e. origins) of the second and third antibody variable chains comprised in the second antibody fragment may be tuned as desired by choosing the natures (i.e. origins) of the plurality of nucleic acid molecules encoding diverse populations of second and third antibody variable regions used in the first and second iterative rounds, respectively. In this way, the present embodiment of the inventive method may be used to optimize the immunogenic potential of a second antibody fragment intended for use in a particular patient species. Specifically, in the event that the second antibody fragment is intended for eventual use in a human patient, the pluralities of nucleic acid molecules encoding diverse populations of second and third antibody variable regions used in, respectively, the first and second iterative rounds of the method may each be of human origin. In this way, the second antibody fragment obtained is not only one in which the soluble recombinant expressibility of the second antibody fragment has been made possible or enhanced, but also one which comprises only sequences which will be least likely to elicit an unwanted host immune response when administered to a human patient. Similar considerations may be applied to the preparation of second antibody fragments intended for use in veterinary applications, for example as therapeutic agents for primate, feline, canine, equine, fish, bird, or tylopod subjects.

A further embodiment of the method of the invention provides the additional steps of evaluating the ability of the isolated second antibody fragment to be recombinantly expressed in soluble form, and isolating at least one second antibody fragment, the expression and general properties (physical, biophysical, chemical properties) of which have been improved relative to those of a corresponding antibody fragment or relative to the isolated first antibody fragment. This embodiment is analogous to the embodiment discussed above as optionally following a first iterative round of the inventive method and has the advantage that it is possible to achieve a quantitative enhancement of the soluble recombinant expressibility of the isolated second antibody fragment relative to the isolated first antibody fragment and/or the corresponding antibody fragment produced directly from the source immunoglobulin.

According to a further embodiment of the method of the invention, the nucleic acid molecules encoding the first and the second antibody variable regions or fragments thereof making up the first population of combined nucleic acid molecules; and/or the nucleic acid molecules encoding the second and the third antibody variable regions or fragments thereof making up the second population of combined nucleic acid molecules are introduced into said system as a single continuous nucleic acid molecule or as two discrete nucleic acid molecules. Introduction of said sequences into said system as a single contiguous nucleic acid molecule will result, when this single contiguous nucleic acid molecule is translated, in a single polypeptide chain. This single polypeptide chain may comprise both a VH and VL region, i.e. may be a single chain antibody in which the VH and VL regions are disposed, for example via a suitable polypeptide linker, so as to allow association between complementary VH and VL polypeptides. Introduction of said molecules into said system as two discrete nucleic acid molecules will result, when these molecules are translated, in two discrete polypeptide chains. In this latter case, the nature of the system allowing correlation between the genotype of a member of the first or second population of combined nucleic acid molecules with the phenotype of a respective first or second antibody fragment must be such as to allow covalent or non-covalent association of the first with the second antibody variable region or, as the case may be, of the second with the third antibody variable region.

This embodiment of the method of the invention has the advantage that in rendering an antibody fragment recombinantly expressible in soluble form (or enhancing its recombinant expressibility in soluble form), the researcher is not limited to a specific antibody format. Starting from a source immunoglobulin, the researcher might choose to create both the first and second antibody fragments in the form of a single chain antibody, or he might choose first to create a Fab-like construct (i.e. a Fab or (Fab')2 fragment) as the first antibody fragment before converting it to a single chain (i.e. scFv format) in the second antibody fragment. The researcher is also free to perform only the first iteration of the method, in which case he might choose to convert a source immunoglobulin into either a solubly expressible scFv or Fab format.

In an especially preferred embodiment of the method of the invention, the first or first and second antibody fragments are prepared as scFv antibody fragments. According to this especially preferred embodiment, then, soluble recombinant expressibility of an antibody fragment derived from a source immunoglobulin is made possible or enhanced in the form of an scFv antibody fragment.

According to a further embodiment of the inventive method, the system allowing correlation of the genotype of the first or second population of combined nucleic acid molecules with the phenotype of, respectively, a first or second antibody fragment may be a phage display system, a ribosome display system, a display system involving eukaryotic cells, a display system involving prokaryotic cells, a system for intracellular selection, covalent display, puromycin display, Cys-display or mRNA display. Of these systems, a phage display system is especially preferred due to its established nature and ease of performance for the skilled practitioner. According to a further embodiment, the display system involving prokaryotic cells is a *E. coli* display method. The skilled person is well acquainted with the above display systems and thus knows that an mRNA display system is unsuitable for use in the event that an antibody fragment comprising two or more distinct polypeptide chains is to be produced. This renders any kind of mRNA display unsuitable for use in the present invention for production of i.a. a Fab antibody fragment or a (Fab)2 antibody fragment.

The system should be employed, and the first or second population of combined nucleic acid molecules incorporated into this system such that the first or first and second antibody fragment, when translated within the system, become/s selectable. Selection occurs according to two criteria: (a) the antibody fragment must have been recombinantly expressed in soluble form and (b) the antibody fragment must bind to the antigen of interest. If criterion (b) is fulfilled, then criterion (a) is necessarily present as well; an antibody fragment which is selectable has also been recombinantly expressed in soluble form. For the purposes of the present embodiment of the invention, it is advantageous to fashion the first population or first and second populations of nucleic acid molecules such that, when translated in said system, the portion of the resulting antibody fragment responsible for specifically binding to an antigen of interest, i.e. the CDRs of the first and second antibody variable regions or of the second and third antibody variable regions, are accessible from outside said system, e.g. by an antigen of interest outside the system. For example, in the event that a phage display system is employed, it is advantageous to fashion the point of connection of the antibody fragment to be selected to the outer coat protein of the phage particle such that the CDRs of the first and second antibody variable regions or, as the case may be, of the second and third antibody variable regions are directed away from the phage particle. This may for example be achieved when introducing the first or second population of combined nucleic acid molecules by covalently anchoring the antibody fragment to a phage coat protein, for example cpIII or cpVIII of a filamentous phage particle, for example via a peptidic linkage located in the antibody fragment at a position distal to the CDRs. In this way, the antibody fragment remains anchored to its phage particle, without the point of anchoring interfering with the ability of the antibody fragment to specifically bind to an antigen of interest. So once such an antibody fragment has been translated and recombinantly expressed in soluble form, it will also remain selectable with respect to its ability to specifically bind to an antigen of interest.

According to a further embodiment, the nucleic acid molecules encoding the first, second and/or third antibody variable regions or fragments thereof are derived from the same or different species. The benefits of varying the species of origin of the antibody variable regions or fragments thereof in terms of the nature of the final antibody fragment product obtained have been explained above. In particular, it should be noted that the ability to independently vary the origin of the antibody variable regions obtained allows the researcher to align the species of origin of these antibody variable regions with the species for which treatment of a disease is contemplated using an antibody fragment prepared by methods described herein. In this way, decoupling the origin of the final antibody fragment obtained from the origin of the source immunoglobulin allows alignment of the origin of the antibody fragment with the species intended for treatment so as to minimize any potential unwanted immunogenic side effects following administration.

According to an especially preferred embodiment, the source immunoglobulin and the nucleic acid molecule encoding the first antibody variable region or fragment thereof may be of non-human origin, and the nucleic acid molecule encoding the second and/or third antibody variable region or fragment thereof may be of human origin, or at least 85%, 90% or 95% of the nucleic acid molecule are of human origin. Preferably, one CDR such as CDR1, CDR2, or CDR3, the latter being especially preferred, is of non-human origin, the remainder of the CDRs being human. An important advantage of this embodiment is that immunoglobulin molecules of non-human origin for which, up to now, conversion into a corresponding antibody fragment has been impossible or unfeasible may now be converted into corresponding antibody fragments. At the same time, the resulting antibody fragments may be optimized for administration to a human subject. In this way, the researcher now has access to the formidable diversity of available, non-human immunoglobulin molecules as antibody fragments in therapeutically relevant form.

In a further particularly preferred embodiment, the source immunoglobulin and the nucleic acid molecule encoding the first antibody variable region or fragment thereof are of rodent origin, preferably of murine or rat origin. This is advantageous since the majority of immunoglobulin molecules or hybridoma cell lines available are of rodent, especially of murine or rat origin. This opens significant avenues for the preparation of antibody fragments of partly or completely human origin starting from any of the multitude of commercially available immunoglobulin molecules or hybridoma cell lines of rodent (e.g. murine or rat) origin.

According to a further embodiment of the invention, the first, second and third antibody variable regions or fragments thereof may independently be a VH region or a fragment thereof, or a VL region or a fragment thereof. It is therefore irrelevant whether the first antibody variable region derived from the source immunoglobulin is a VH or a VL region. Given the high degree of mutual compatibility between VH and VL regions, two scenarios immediately arise in this context. In the first scenario, the first antibody variable region or fragment thereof is a VH region or fragment thereof. In this case, an antibody variable region complementary for the first antibody variable region will most likely be a VL region and, if a further iterative round of the method is performed as described above, a third antibody variable region complementary to the second antibody variable region will be a VH region. In the second, converse scenario, if the first antibody variable region or fragment thereof is a VL region or fragment thereof, the second antibody variable region or fragment thereof will likely be a VH region and any third antibody variable region or fragment thereof will likely be a VL region. Generally, therefore, given that a VH region will most likely pair with a complementary VL region and a VL region will most likely pair with a complementary VH region, the choice of the first antibody variable region as a VH or VL region is very likely to be sufficient to determine the identity of the second antibody variable region and any third antibody variable region in the final antibody fragment product(s).

It should be noted, however, that it is within the ambit of this embodiment of the invention that a VH region may be complementary to another VH region, or that a VL region may be complementary to another VL region. In this case, the choice of the first antibody variable region as VH or VL region need not determine the identity of the second and third antibody variable regions. As a result, it is not excluded from the ambit of this embodiment of the invention that the first or first and second antibody fragments obtained as products of the methods described herein comprise two VH regions or two VL regions, the main criteria for selection of such antibody fragments being that the antibody fragment product is both recombinantly expressible, or sufficiently recombinantly expressible in soluble form and specifically binds to the antigen of interest, the antigen of interest being the same antigen as that bound by the source immunoglobulin.

A further aspect of the invention provides a first antibody fragment obtainable by the methods described in the foregoing. This first antibody fragment may advantageously be in the form of an scFv fragment or a Fab fragment. The first antibody fragment has the advantage that it is expressible in soluble form and specifically binds the same antigen as the source immunoglobulin, whereas a corresponding antibody fragment, i.e. an antibody fragment converted directly from the source immunoglobulin without first performing the inventive method, would not have been obtainable, either at all or in sufficient amount in soluble form. Seen this way, the first antibody fragment represents a molecular species in which the antigen binding properties of the source immunoglobulin have been "rescued" in the form of an antibody fragment.

As described above, the first antibody fragment will comprise the first antibody variable region derived from the source immunoglobulin. According to one embodiment of this aspect of the invention, the first antibody variable region comprised in the first antibody fragment is present in modified form as compared to the form in which it is comprised in the source immunoglobulin. Modification may advantageously take place at the nucleotide level, for example prior to combination of the nucleic acid molecule encoding the first antibody variable region with a plurality of nucleic acid molecules encoding a diverse population of a second antibody variable region complementary to the first antibody variable region. According to an especially preferred embodiment, the first antibody variable region is modified so as to render it less likely to elicit a host immune response when administered to a subject as a therapeutic agent. Such modifications may for example include humanization (i.e. CDR-grafting or modification to correspond to a close human germline sequence, for example as described in WO 91/09968 and U.S. Pat. No. 6,407,213) and/or deimmunization of the first antibody variable region (for example as described in WO 92/10755, WO 00/34317, WO 98/52976, WO 02/079415, WO 02/012899 and WO 02/069232). When the second antibody variable region comprised in the first antibody fragment is chosen to be of human origin, but the source immunoglobulin—and hence the first antibody variable region—is of non-human origin, humanization and/or deimmunization (the latter taking into account known human T cell epitopes) of the first antibody variable region results in a first antibody fragment which is very unlikely to elicit an immunogenic response when introduced into a human patient.

According to another exemplary embodiment of this aspect of the invention, the first antibody fragment comprises a region exhibiting the amino acid sequence as set out in SEQ ID NO: 1, or a modified version of SEQ ID NO: 1 ("modified" is to be understood as within the meaning as set out in the preceding paragraph). SEQ ID NO: 1 represents the VH of a hybridoma-derived immunoglobulin which specifically binds to human granulocyte macrophage colony stimulating factor (GM-CSF). As a full immunoglobulin molecule with an Fc portion, this may not be suitable for implementation as a therapeutic agent. However, direct incorporation of the VH and VL regions of this immunoglobulin into, for example, a corresponding scFv fragment yields a molecular species which is not expressible in soluble form (i.e. the immunoglobulin qualifies as a "source immunoglobulin" as defined hereinabove). Only by performing at least one round of the method as described hereinabove is an scFv obtainable in soluble form which also demonstrated the same binding characteristics (i.e. anti-GM-CSF) as the source immunoglobulin. As such, the method as disclosed hereinabove allows the "rescue" of the antigen binding properties of the anti-GM-CSF source immunoglobulin in the form of an scFv comprising the VH of the source immunoglobulin, said scFv being more suitable for use for many kinds of therapy than the source immunoglobulin. As indicated above, the skilled person will readily recognize that the source immunoglobulin and the antibody fragments having anti GM-CSF specificity, which are described in great detail in the examples, represent just one antibody (specificity) and that the method of the present invention is likewise useful for the preparation of any other antibody fragments of specificity other than for (human) GM-CSF, regardless of what this other binding specificity might be. As such, the inventive method represents a method of general applicability for converting any source immunoglobulin (specific for any antigen) to an antibody fragment having the same specificity as said source immunoglobulin, where previous attempts at such conversion by simple transfer of e.g. the variable regions of said source immunoglobulin into a desired antibody fragment have resulted in an antibody fragment which is not recombinantly, solubly expressible. The GM-CSF antigen as described in the appended examples is thus merely illustrative of the method's functionality, and is not to be interpreted as in any way restrictive to the term "antigen of interest".

Modification of SEQ ID NO: 1 within the first antibody fragment as outlined above in order to render the molecule less likely to elicit an immune response when introduced into a subject, especially a human subject, is within the ambit of this embodiment.

A further aspect of the invention provides a first or second antibody variable region or fragment thereof, as derived from the first antibody fragment obtained by the methodology described hereinabove. In a preferred embodiment, the second antibody variable region is a VL, especially preferred a VL comprising a region exhibiting any VL amino acid sequence as shown in any of FIGS. 11-35.

Further aspects of the invention in this context provide a polypeptide comprising the VL region as shown in any of FIGS. 11-35, any nucleic acid molecule encoding such a polypeptide, and any nucleic acid molecules hybridizing with the nucleic acid molecule encoding such a polypeptide under stringent conditions (for example as described in Sambrook, Cold Spring Harbor Laboratory Press 1989, Second Edition).

A further aspect of the invention provides a second antibody fragment obtainable by the methods described in the foregoing. This second antibody fragment may advantageously be in the form of an scFv fragment or a Fab fragment. The second antibody fragment has the advantage that it is recombinantly expressible in soluble form and specifically binds the same antigen as both the source immunoglobulin and the first antibody fragment, whereas a corresponding antibody fragment, i.e. an antibody fragment converted directly from the source immunoglobulin without first performing the inventive method, would not have been obtainable, either at all or in sufficient amount in soluble form. Seen this way, the second antibody fragment represents a molecular species in which the antigen binding properties of both the source immunoglobulin and the first antibody fragment have been "rescued" in the form of an antibody fragment.

While modification of sequences comprised in the second antibody fragment to lessen the propensity of the second antibody fragment to elicit an immunogenic response from a host subject into which the second antibody fragment is introduced is possible in an analogous sense as already described above for modification of the first antibody variable region, such modification will generally not be necessary. This is because it will be possible to construct the combinations between first and second antibody variable regions on the one hand, and between second and third antibody variable regions on the other hand such that second and third antibody variable regions each stem from libraries which have been developed using the same species as the species to which the second antibody is to be administered as a therapeutic agent. It is more often practical to modulate the immunogenic properties of the second antibody fragment in this manner than it would be to derive, say, a third antibody variable region from a species other than that to which the second antibody fragment is to be administered, and then subsequently humanize and/or deimmunize said third antibody variable region.

A further aspect of the invention provides a second or a third antibody variable region derived from the second antibody fragment. In a preferred embodiment, the third antibody variable region is a VH.

Further aspects of the invention in this context provide a polypeptide comprising said VH, any nucleic acid molecule encoding such a polypeptide, and any nucleic acid molecules hybridizing with the nucleic acid molecule encoding such a polypeptide.

A further aspect of the invention provides a composition comprising a first and/or second antibody fragment as set out hereinabove. In a preferred embodiment, the composition comprises a first, second and/or third antibody variable region as set out herein above. In an especially preferred embodiment the composition comprises a VL exhibiting an amino acid sequence corresponding to the amino acid sequence of the VL region in any of FIGS. 11-35.

A further aspect of the invention provides a use of a composition as set out above for the preparation of a medicament. According to a preferred embodiment, the medicament is suitable for administration to a subject for the treatment of autoimmune diseases or inflammatory conditions. According to an especially preferred embodiment of the invention, such autoimmune dieases may be chosen from one or more of the following diseases or conditions: rheumatoid arthritis, chronic obstructive pulmonary disease (COPD), asthma, multiple sclerosis (MS), and psoriasis. According to another especially preferred embodiment of the invention, such inflammatory conditions include chronic inflammatory conditions and/or airway inflammation.

Further details and advantages of the invention will be explained in light of the following non-limiting figures and examples.

ELISA experiments were carried out by coating the rhGM-CSF on wells of 96-well plastic plates (Nunc, maxisorb) typically at 4° C. overnight. The antigen was then removed, wells washed once with PBS/0.05% Tween 20 and subsequently blocked with PBS/3% BSA for at least one hour. After removal of the blocking solution, refolded maternal SCA and SCA controls were added to the wells and typically incubated for one hour at room temperature. The wells were then washed three times with PBS/0.05% Tween 20. Detection of SCA and control antibodies bound to immobilized antigen was carried out using a monoclonal murine anti-His6 antibody (Qiagen anti-PentaHis typically at a final concentration of 1 μg/ml PBS) detected with a peroxidase-labeled polyclonal goat anti-(mouse Fab-fragment) antibody (Dianova, 1 μg/ml PBS). The signal was developed by adding ABTS substrate solution and measured at a wavelength of 405 nm. Background reaction of an unrelated sample SCA with the coated antigen was determined (neg. control) as well as specific binding of an SCA known to interact with high specificity with the rhGM-CSF (pos. control). The refolded maternal SCA shows a clear binding signal to the antigen rhGM-CSF.

Figure 5:
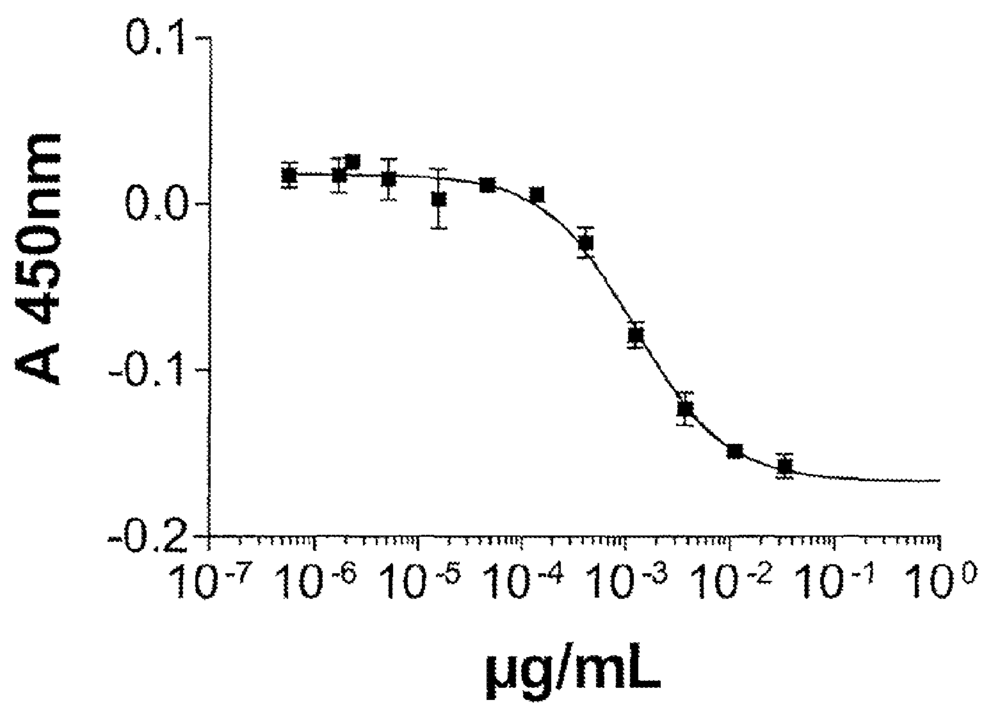

FIG. 5: Inhibition of rhGM-CSF dependent proliferation of TF-1 cells by maternal mAb. TF-1 cells were cultivated at a final concentration of 1×10exp5 cells/mL in RPMI 1640, 10% FCS and 90 μL cell suspension per well are used (0.9×10exp4 cells/well). A final concentration of 0.3 ng/mL rhGM-CSF was used to stimulate the proliferation of the TF-1 cells. For neutralization of GM-CSF dependent proliferation maternal mAb in 1×PBS was added in a dilution series with final protein concentrations ranging from 30 ng/mL to 1 pg/mL. TF-1 cells were incubated at 37° C. at 5% $CO_2$ in the presence of GM-CSF and maternal mAb for 72 h. 10 μL WST-1 (Roche) was added and the absorption at 450 nm (A 450 nm) was determined and plotted against the protein concentration. The data were fitted for half maximal inhibition of proliferation (IC50) using the non-linear regression curve fit of the Prism software. The maternal mAb inhibits the rhGM-CSF induced proliferation of the TF-1 cells with an $IC_{50}$ of 1.2 ng/mL (80 pM).

Figure 6:
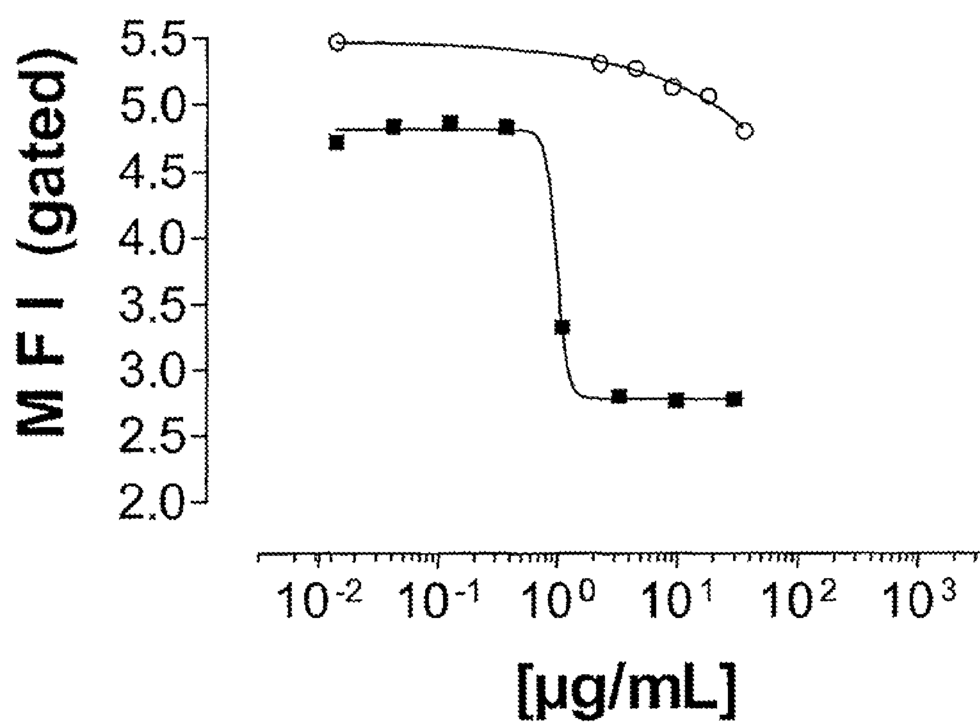

FIG. 6: Inhibition of binding of hGM-CSF-FITC to TF-1 cells by maternal mAb and maternal SCA.

For the flow cytometry based assay a final concentration of 0.4 μg/mL hGM-CSF-FITC conjugate in PBS were incubated with maternal mAb (filled squares) in concentrations ranging from 30 μg/mL to 0.014 μg/mL or the refolded maternal SCA (open circles). The protein samples were left to equilibrate at 25° C. for 1 h prior to addition of TF-1 cell suspension. The TF-1 were cultivated in RPMI 1640 medium GIBCO (L-glutamine, phenol-red free), 10% heat inactivated FCS in the absence of rhGM-CSF overnight. A final concentration of 2×10exp6 cells/mL and 150 μl of cell suspension was used per sample. The cells were harvested by centrifugation at 500 G at 4° C. for 3 min and washed twice with FACS buffer. The washed cells were resuspended in 100 μL of pre-equilibrated protein sample containing the hGM-CSF-FITC and maternal mAb or maternal SCA respectively. The samples were incubated at 4° C. for 60 min. After two further washes the cells were resuspended in 150 μL ice cold FACS buffer and subsequently analysed by flow cytometry. The mean fluorescence intensity (MFI) was plotted against the concentration of the used maternal mAb and maternal SCA. A clear concentration dependent loss of fluorescence intensity of the TF-1 cells was observed with the maternal mAb. The refolded maternal SCA induced some residual concentration dependent decrease in fluorescence intensity of the hGM-CSF-FITC labelled TF-1 cells, indicating its activity.

Figure 7:
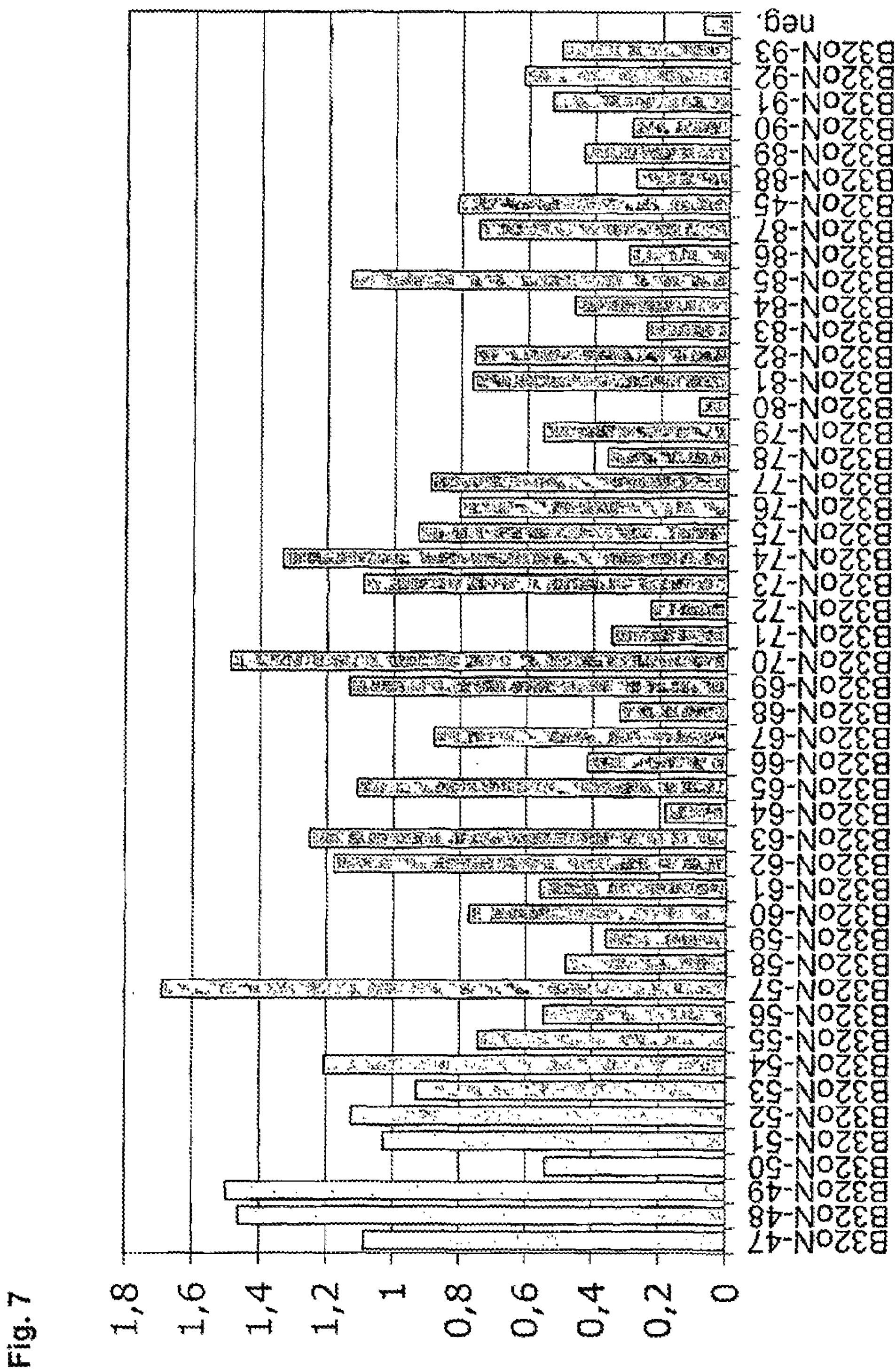

FIG. 7: Recombinant human GM-CSF-specific ELISA-analysis of periplasmic preparations containing SCA fragments derived from the method of the invention. Preparations of soluble SCA protein fragments were added to wells of an ELISA-plate which had been coated with a soluble recombinant human GM-CSF antigen (Leukine). Detection of SCA-fragments bound to immobilized recombinant human GM-CSF antigen (Leukine) was carried out using a biotinylated anti-flag M2 (1 μg/mL PBS/1% BSA) detected with horseradish peroxidase-conjugated goat anti mouse Fab2 specific polyclonal antibody (Dianova, 1 μg/mL PBS/1% BSA). The signal was developed by adding ABTS (2,2'-Azino-di[3-ethylbenzthiazoline sulfonate (6)] diammonium salt) substrate solution and detected at a wavelength of 405 nm. The OD-values (y axis) were measured at 405 nm by an ELISA reader. Clone numbers are presented on the x axis, where the first number of the clone number indicates the round of panning in which the respective clone was obtained (32=fifth round, 33=sixth round; B and C indicating the series of selection), while the second number indicates the respective clone of this round.

Figure 8:
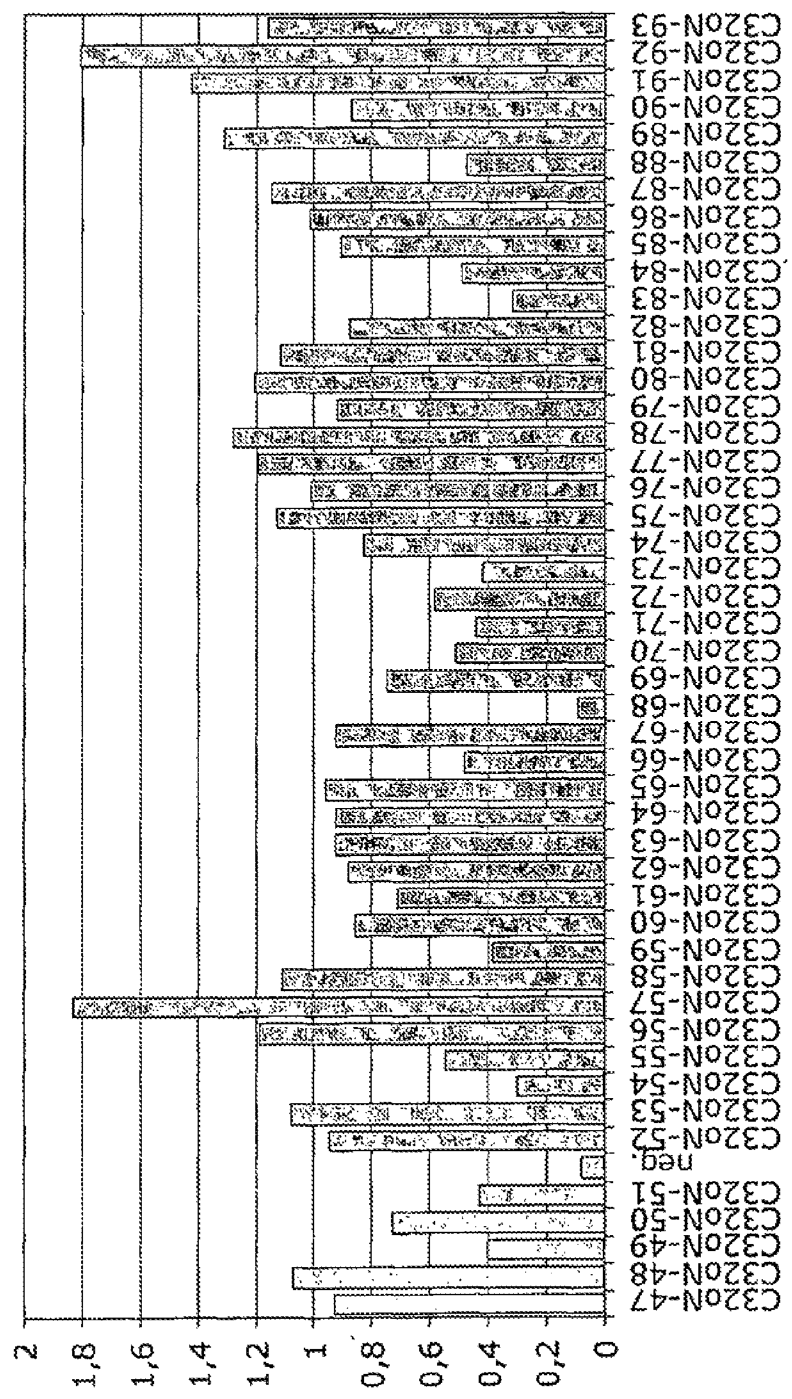

FIG. 8: Recombinant human GM-CSF-specific ELISA-analysis of periplasmic preparations containing SCA protein fragments derived from the method of the invention. Preparations of soluble SCA protein fragments were added to wells of an ELISA-plate, which had been coated with a soluble recombinant human GM-CSF antigen (Leukine). Detection of SCA-fragments bound to immobilized recombinant human GM-CSF antigen (Leukine) was carried out using a biotinylated anti-flag M2 (1 μg/mL PBS/1% BSA) detected with horseradish peroxidase-conjugated goat anti mouse Fab2 specific polyclonal antibody (Dianova, 1 μg/mL PBS/1% BSA). The signal was developed by adding ABTS (2,2'-Azino-di[3-ethylbenzthiazoline sulfonate (6)] diammonium salt) substrate solution and detected at a wavelength of 405 nm. The OD-values (y axis) were measured at 405 nm by an ELISA reader. Clone numbers are presented on the x axis, where the first number of the clone number indicates the round of panning in which the respective clone was obtained (32=fifth round, 33=sixth round; B and C indicating the series of selection), while the second number indicates the respective clone of this round.

Figure 4:
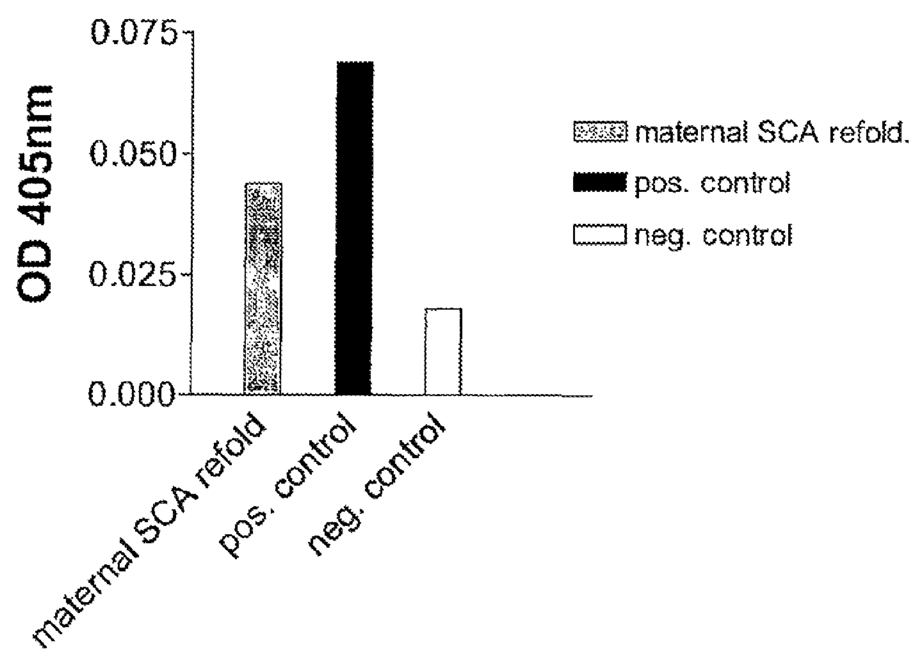
FIG. 4: Binding to rhGM-CSF of maternal SCA determined by ELISA.
Figure 9:
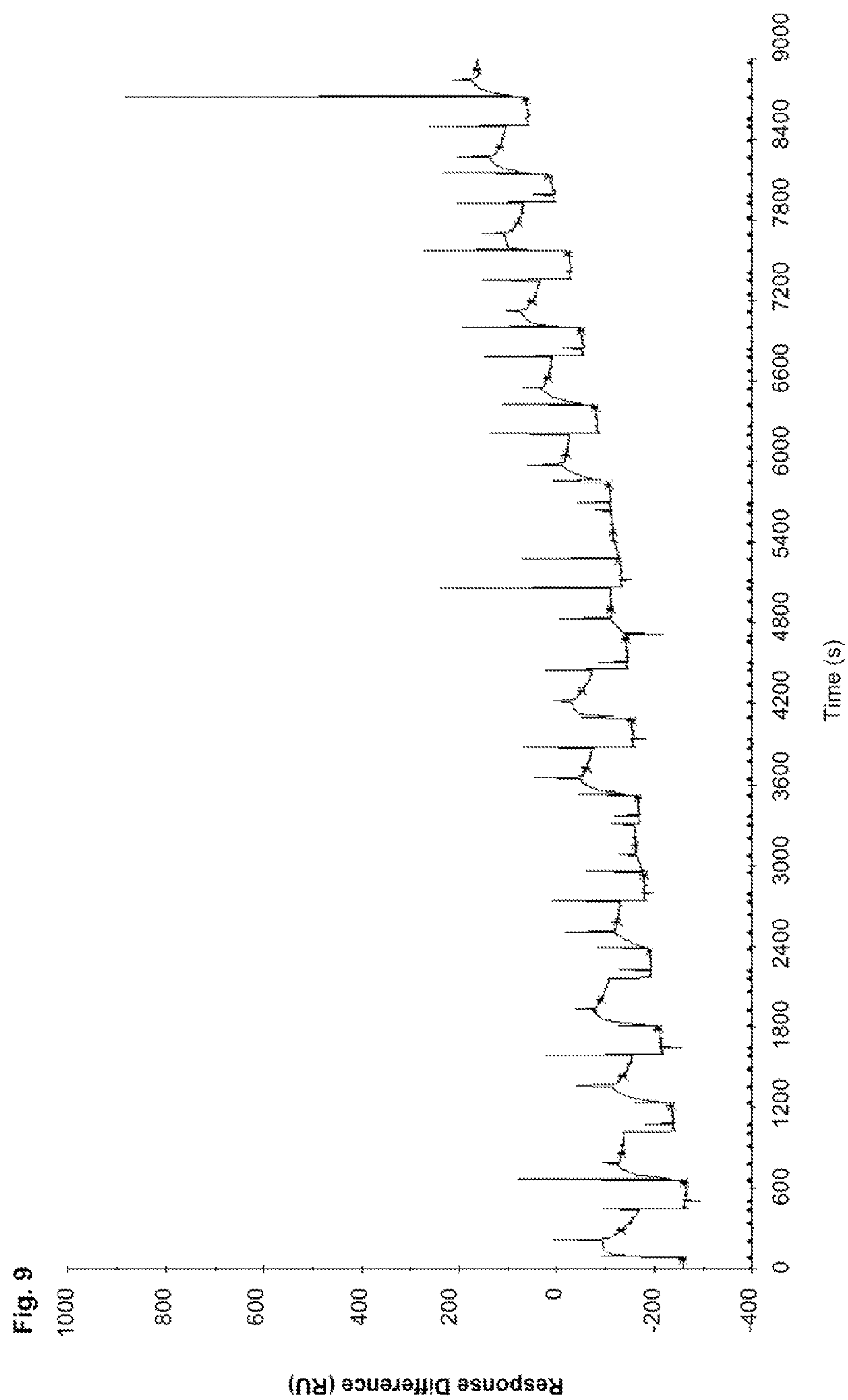

FIG. 9: Binding analysis (kinetic off rate) of SCA hits derived from the method of the invention, as determined by SPR. Binding kinetics of the SCA hits were measured injecting 10 μL of purified periplasmic preparation ("PPP") protein solution with a flow rate of 5 μL/min at 25° C. onto the sensor chip. The data were monitored in all four flow cells. Background association with the unmodified CM5 chip surface (FC1) was substracted from the binding to the immobilised rhGM-CSF (FC2) allowing analysis of the specific binding signal (FC2-FC1 response difference). The dissociation rate was monitored for 100 sec (FIG. 4). The amplitude of the binding peak (RUmax) directly correlates to the protein concentration in the injected sample. The kinetic association rate constant (ka) is concentration dependent and can—due to varying concentrations of the PPP protein solution—not be used for the qualitative ranking of the purified PPP SCA material. The kinetic dissociation rate constant (kd) is protein concentration independent and characteristic for the binding strength of the respective SCA hit. The SCA hits with the best apparent off rate were identified.

Figure 10:
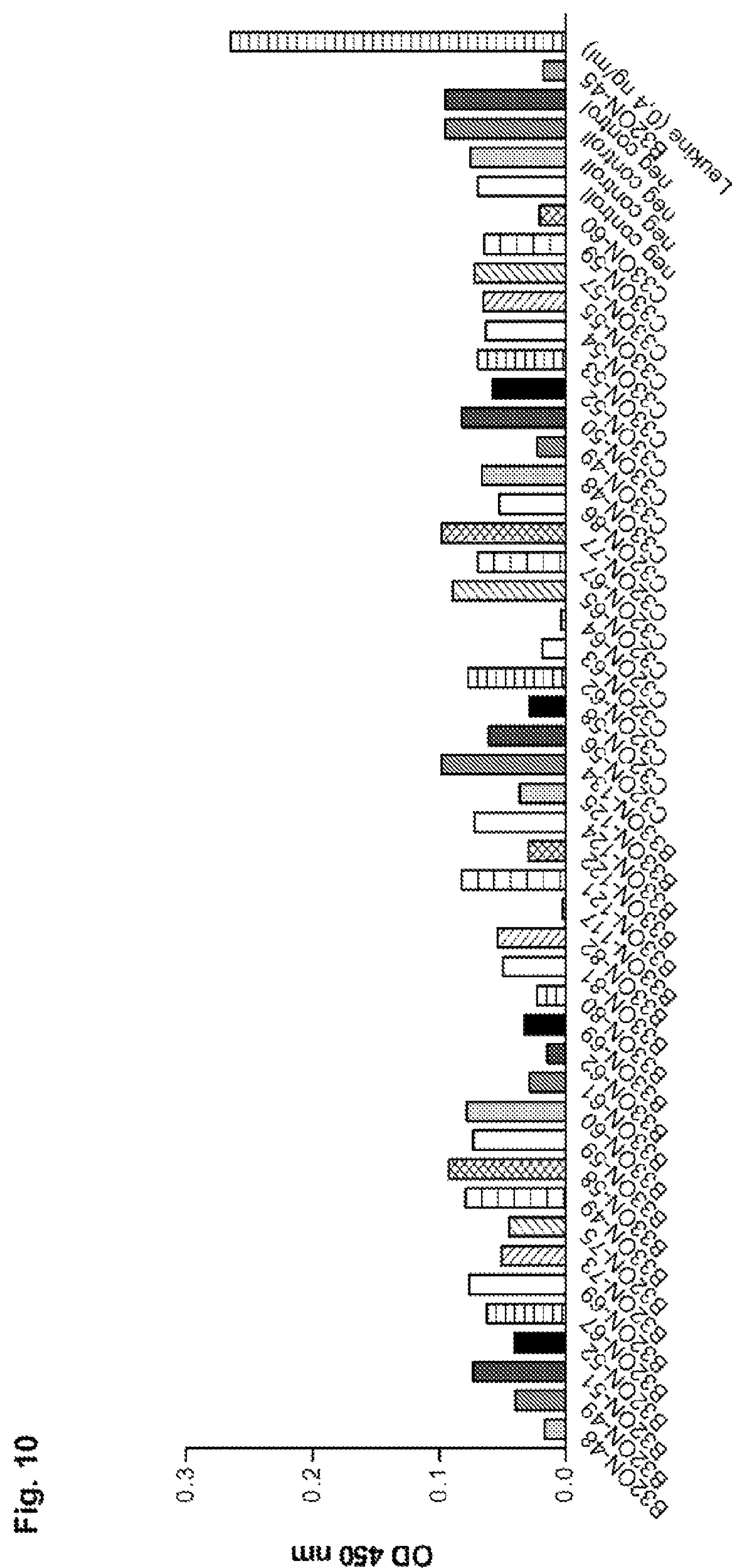

FIG. 10: Inhibition of rhGM-CSF-dependent proliferation of TF-1 cells by SCA hits. Cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF dependent proliferation purified PPP of the SCA hits were dialyzed against 1×PBS at 25° C. for 2 h. 10 μL of dialyzed and sterile filtered protein solution (0.22 μm filter) were added to 100 μL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm. The inhibition of the rhGM-CSF dependent proliferation of the TF-1 cells by the SCA constructs is of varying strength. Some SCA constructs do not inhibit the proliferation to a large degree—this can be due to a lack of stable complex formation of the SCA constructs and the rhGM-CSF over the period of 72 h at 37° C.

FIG. 11: Nucleotide and amino acid sequences of the nucleic acid molecule encoding half-human SCA B32oN-10 and of half-human SCA B32oN-10, respectively (SEQ ID NOS: 2 and 3). Numbers indicate the nucleotide (nt) positions, amino acids (aa) are presented in single letter code. The region of the DNA coding for the V-region of the heavy chain starts at nt 1 and ends at nt 360 of SEQ ID NO: 2, followed by a $(G_4S_1)_3$-linker starting at nt 361 and ending at nt 405 of SEQ ID NO: 2. The region of the DNA coding for the V-region of the kappa (light) chain starts at nt 406 and ends at nt 726 of SEQ ID NO: 2. Respectively, the protein coding region for the V-region of the heavy chain starts at amino acid 1 and ends at amino acid 120 of SEQ ID NO: 3 and corresponds to SEQ ID NO: 90. The $(G_4S_1)_3$ linker starts at amino acids 121 and ends at amino acid 135 of SEQ ID NO: 3. The protein coding region for the V-region of kappa (light) chain starts at amino acid 136 and ends at amino acid 242 of SEQ ID NO: 3 and corresponds to SEQ ID NO: 94. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 89); H-CDR1 polypeptide sequence (SEQ ID NO: 91); H-CDR2 polypeptide sequence (SEQ ID NO: 92); H-CDR3 polypeptide sequence (SEQ ID NO: 93); L-CDR1 polypeptide sequence (SEQ ID NO: 95); L-CDR2 polypeptide sequence (SEQ ID NO: 96); and L-CDR3 polypeptide sequence (SEQ ID NO: 97).

FIG. 12: Nucleotide and amino acid sequences of the nucleic acid molecule encoding half-human SCA B32oN-33 and of half-human SCA B32oN-33, respectively (SEQ ID NOS: 4 and 5). Numbers indicate the nucleotide (nt) positions, amino acids (aa) are presented in single letter code. The region of the DNA coding for the V-region of the heavy chain starts at nt 1 and ends at nt 360 of SEQ ID NO: 4, followed by a $(G_4S_1)_3$-linker starting at nt 361 and ending at nt 405 of SEQ ID NO: 4. The region of the DNA coding for the V-region of the kappa (light) chain starts at nt 406 and ends at nt 726 of SEQ ID NO: 4Respectively, the protein coding region for the V-region of the heavy chain starts at amino acid 1 and ends at amino acid 120 of SEQ ID NO: 5 and corresponds to SEQ ID NO: 99. The $(G_4S_1)_3$ linker starts at amino acids 121 and ends at amino acid 135 of SEQ ID NO: 5. The protein coding region for the V-region of kappa (light) chain starts at amino acid 136 and ends at amino acid 242 of SEQ ID NO: 5 and corresponds to SEQ ID NO: 103. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 98); H-CDR1 polypeptide sequence (SEQ ID NO: 100); H-CDR2 polypeptide sequence (SEQ ID NO: 101); H-CDR3 polypeptide sequence (SEQ ID NO: 102); L-CDR1 ypeptide sequence (SEQ ID NO: 104); L-CDR2 polypeptide sequence (SEQ ID NO: 105); and L-CDR3 polypeptide sequence (SEQ ID NO: 106).

FIG. 13: Nucleotide and amino acid sequences of the nucleic acid molecule encoding half-human SCA B32oN-44 and of half-human SCA B32oN-44, respectively (SEQ ID NOS: 6 and 7). Numbers indicate the nucleotide (nt) positions, amino acids (aa) are presented in single letter code. The region of the DNA coding for the V-region of the heavy chain starts at nt 1 and ends at nt 360 of SEQ ID NO: 6, followed by a $(G_4S_1)_3$-linker starting at nt 361 and ending at nt 405 of SEQ ID NO: 6. The region of the DNA coding for the V-region of the kappa (light) chain starts at nt 406 and ends at nt 726 of SEQ ID NO: 6. Respectively, the protein coding region for the V-region of the heavy chain starts at amino acid 1 and ends at amino acid 120 of SEQ ID NO: 7 and corresponds to SEQ ID NO: 108. The $(G_4S_1)_3$ linker starts at amino acids 121 and ends at amino acid 135 of SEQ ID NO: 7. The protein coding region for the V-region of kappa (light) chain starts at amino acid 136 and ends at amino acid 242 of SEQ ID NO: 7 and corresponds to SEQ ID NO: 112. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 107); H-CDR1 polypeptide sequence (SEQ ID NO: 109); H-CDR2 polypeptide sequence (SEQ ID NO: 110); H-CDR3 polypeptide sequence (SEQ ID NO: 111); L-CDR1 polypeptide sequence (SEQ ID NO: 113); L-CDR2 polypeptide sequence (SEQ ID NO: 114); and L-CDR3 polypeptide sequence (SEQ ID NO: 115).

FIG. 14: Nucleotide and amino acid sequences of the nucleic acid molecule encoding half-human SCA B32oN-45 and of half-human SCA B32oN-45, respectively (SEQ ID NOS: 8 and 9). Numbers indicate the nucleotide (nt) positions, amino acids (aa) are presented in single letter code. The region of the DNA coding for the V-region of the heavy chain starts at nt 1 and ends at nt 360 of SEQ ID NO: 8, followed by a $(G_4S_1)_3$-linker starting at nt 361 and ending at nt 405 of SEQ ID NO: 8. The region of the DNA coding for the V-region of the kappa (light) chain starts at nt 406 and ends at nt 726 of SEQ ID NO: 8. Respectively, the protein coding region for the V-region of the heavy chain starts at amino acid 1 and ends at amino acid 120 of SEQ ID NO: 9 and corresponds to SEQ ID NO: 117. The $(G_4S_1)_3$ linker starts at amino acids 121 and ends at amino acid 135 of SEQ ID NO: 9. The protein coding region for the V-region of kappa (light) chain starts at amino acid 136 and ends at amino acid 242 of SEQ ID NO: 9 and corresponds to SEQ ID NO: 121. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 116); H-CDR1 polypeptide sequence (SEQ ID NO: 118); H-CDR2 polypeptide sequence (SEQ ID NO: 119); H-CDR3 polypeptide sequence (SEQ ID NO: 120); L-CDR1 polypeptide sequence (SEQ ID NO: 122); L-CDR2 polypeptide sequence (SEQ ID NO: 123); and L-CDR3 polypeptide sequence (SEQ ID NO: 124).

FIG. 15: Nucleotide and amino acid sequences of the nucleic acid molecule encoding half-human SCA B32oN-48 and of half-human SCA B32oN-48, respectively (SEQ ID NOS: 10 and 11). Numbers indicate the nucleotide (nt) positions, amino acids (aa) are presented in single letter code. The region of the DNA coding for the V-region of the heavy chain starts at nt 1 and ends at nt 360 of SEQ ID NO: 10, followed by a $(G_4S_1)_3$-linker starting at nt 361 and ending at nt 405 of SEQ ID NO: 10. The region of the DNA coding for the V-region of the kappa (light) chain starts at nt 406 and ends at nt 726 of SEQ ID NO: 10. Respectively, the protein coding region for the V-region of the heavy chain starts at amino acid 1 and ends at amino acid 120 of SEQ ID NO: 11 and corresponds to SEQ ID NO: 126. The $(G_4S_1)_3$ linker starts at amino acids 121 and ends at amino acid 135 of SEQ ID NO: 11. The protein coding region for the V-region of kappa (light) chain starts at amino acid 136 and ends at amino acid 242 of SEQ ID NO: 11 and corresponds to SEQ ID NO: 130. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 125); H-CDR1 polypeptide sequence (SEQ ID NO: 127); H-CDR2 polypeptide sequence (SEQ ID NO: 128); H-CDR3 polypeptide sequence (SEQ ID NO: 129); L-CDR1 polypeptide sequence (SEQ ID NO: 131); L-CDR2 polypeptide sequence (SEQ ID NO: 132); and L-CDR3 polypeptide sequence (SEQ ID NO: 133).

FIG. 16: Nucleotide and amino acid sequences of the nucleic acid molecule encoding half-human SCA B32oN-49 and of half-human SCA B32oN-49, respectively (SEQ ID NOS: 12 and 13). Numbers indicate the nucleotide (nt) positions, amino acids (aa) are presented in single letter code. The region of the DNA coding for the V-region of the heavy chain starts at nt 1 and ends at nt 360 of SEQ ID NO: 12, followed by a $(G_4S_1)_3$-linker starting at nt 361 and ending at nt 405 of SEQ ID NO: 12. The region of the DNA coding for the V-region of the kappa (light) chain starts at nt 406 and ends at nt 726 of SEQ ID NO: 12.Respectively, the protein coding region for the V-region of the heavy chain starts at amino acid 1 and ends at amino acid 120 of SEQ ID NO: 13 and corresponds to SEQ ID NO: 135. The $(G_4S_1)_3$ linker starts at amino acids 121 and ends at amino acid 135 of SEQ ID NO: 13. The protein coding region for the V-region of kappa (light) chain starts at amino acid 136 and ends at amino acid 242 of SEQ ID NO: 13 and corresponds to SEQ ID NO: 139. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 134); H-CDR1 polypeptide sequence (SEQ ID NO: 136); H-CDR2 polypeptide sequence (SEQ ID NO: 137); H-CDR3 polypeptide sequence (SEQ ID NO: 138); L-CDR1 polypeptide sequence (SEQ ID NO: 140); L-CDR2 polypeptide sequence (SEQ ID NO: 141); and L-CDR3 polypeptide sequence (SEQ ID NO: 142).

FIG. 17: Nucleotide and amino acid sequences of the nucleic acid molecule encoding half-human SCA B32oN-67 and of half-human SCA B32oN-67, respectively (SEQ ID NOS: 14 and 15). Numbers indicate the nucleotide (nt) positions, amino acids (aa) are presented in single letter code. The region of the DNA coding for the V-region of the heavy chain starts at nt 1 and ends at nt 360 of SEQ ID NO: 14, followed by a $(G_4S_1)_3$-linker starting at nt 361and ending at nt 405 of SEQ ID NO: 14. The region of the DNA coding for the V-region of the kappa (light) chain starts at nt 406 and ends at nt 726 of SEQ ID NO: 14. Respectively, the protein coding region for the V-region of the heavy chain starts at amino acid 1 and ends at amino acid 120 of SEQ ID NO: 15 and corresponds to SEQ ID NO: 144. The $(G_4S_1)_3$ linker starts at amino acids 121 and ends at amino acid 135 of SEQ ID NO: 15. The protein coding region for the V-region of kappa (light) chain starts at amino acid 136 and ends at amino acid 242 of SEQ ID NO: 15 and corresponds to SEQ ID NO: 148. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 143); H-CDR1 polypeptide sequence (SEQ ID NO: 145); H-CDR2 polypeptide sequence (SEQ ID NO: 146); H-CDR3 polypeptide sequence (SEQ ID NO: 147); L-CDR1 polypeptide sequence (SEQ ID NO: 149); L-CDR2 polypeptide sequence (SEQ ID NO: 150); and L-CDR3 polypeptide sequence (SEQ ID NO: 151).

FIG. 18: Nucleotide and amino acid sequences of the nucleic acid molecule encoding half-human SCA B32oN-73 and of half-human SCA B32oN-73, respectively (SEQ ID NOS: 16 and 17). Numbers indicate the nucleotide (nt) positions, amino acids (aa) are presented in single letter code. The region of the DNA coding for the V-region of the heavy chain starts at nt 1 and ends at nt 360 of SEQ ID NO: 16, followed by a $(G_4S_1)_3$-linker starting at nt 361 and ending at nt 405 of SEQ ID NO: 16. The region of the DNA coding for the V-region of the kappa (light) chain starts at nt 406 and ends at nt 726 of SEQ ID NO: 16. Respectively, the protein coding region for the V-region of the heavy chain starts at amino acid 1 and ends at amino acid 120 of SEQ ID NO: 17 and corresponds to SEQ ID NO: 153. The $(G_4S_1)_3$ linker starts at amino acids 121 and ends at amino acid 135 of SEQ ID NO: 17. The protein coding region for the V-region of kappa (light) chain starts at amino acid 136 and ends at amino acid 242 of SEQ ID NO: 17 and corresponds to SEQ ID NO: 157. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 152); H-CDR1 polypeptide sequence (SEQ ID NO: 154); H-CDR2 polypeptide sequence (SEQ ID NO: 155); H-CDR3 polypeptide sequence (SEQ ID NO: 156); L-CDR1 polypeptide sequence (SEQ ID NO: 158); L-CDR2 polypeptide sequence (SEQ ID NO: 159); and L-CDR3 polypeptide sequence (SEQ ID NO: 160).

FIG. 19: Nucleotide and amino acid sequences of the nucleic acid molecule encoding half-human SCA B33oN-21 and of half-human SCA B33oN-21, respectively (SEQ ID NOS: 20 and 21). Numbers indicate the nucleotide (nt) positions, amino acids (aa) are presented in single letter code. The region of the DNA coding for the V-region of the heavy chain starts at nt 1 and ends at nt 360 of SEQ ID NO: 20, followed by a $(G_4S_1)_3$-linker starting at nt 361 and ending at nt 405 of SEQ ID NO: 20. The region of the DNA coding for the V-region of the kappa (light) chain starts at nt 406 and ends at nt 726 of SEQ ID NO: 20. Respectively, the protein coding region for the V-region of the heavy chain starts at amino acid 1 and ends at amino acid 120 of SEQ ID NO: 21 and corresponds to SEQ ID NO: 162. The $(G_4S_1)_3$ linker starts at amino acids 121 and ends at amino acid 135 of SEQ ID NO: 21. The protein coding region for the V-region of kappa (light) chain starts at amino acid 136 and ends at amino acid 242 of SEQ ID NO: 21 and corresponds to SEQ ID NO: 166. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 161); H-CDR1 polypeptide sequence (SEQ ID NO: 163); H-CDR2 polypeptide sequence (SEQ ID NO: 164); H-CDR3 polypeptide sequence (SEQ ID NO: 165); L-CDR1 polypeptide sequence (SEQ ID NO: 167); L-CDR2 polypeptide sequence (SEQ ID NO: 168); and L-CDR3 polypeptide sequence (SEQ ID NO: 169).

FIG. 20: Nucleotide and amino acid sequences of the nucleic acid molecule encoding half-human SCA B33oN-22 and of half-human SCA B33oN-22, respectively (SEQ ID NOS: 22 and 23). Numbers indicate the nucleotide (nt) positions, amino acids (aa) are presented in single letter code. The region of the DNA coding for the V-region of the heavy chain starts at nt 1 and ends at nt 360 of SEQ ID NO: 22, followed by a $(G_4S_1)_3$-linker starting at nt 361 and ending at nt 405 of SEQ ID NO: 22. The region of the DNA coding for the V-region of the kappa (light) chain starts at nt 406 and ends at nt 726 of SEQ ID NO: 22. Respectively, the protein coding region for the V-region of the heavy chain starts at amino acid 1 and ends at amino acid 120 of SEQ ID NO: 23 and corresponds to SEQ ID NO: 171. The $(G_4S_1)_3$ linker starts at amino acids 121 and ends at amino acid 135 of SEQ ID NO: 23. The protein coding region for the V-region of kappa (light) chain starts at amino acid 136 and ends at amino acid 242 of SEQ ID NO: 23 and corresponds to SEQ ID NO: 175. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 170); H-CDR1 polypeptide sequence (SEQ ID NO: 172); H-CDR2 polypeptide sequence (SEQ ID NO: 173); H-CDR3 polypeptide sequence (SEQ ID NO: 174); L-CDR1 polypeptide sequence (SEQ ID NO: 176); L-CDR2 polypeptide sequence (SEQ ID NO: 177); and L-CDR3 polypeptide sequence (SEQ ID NO: 178).

FIG. 21: Nucleotide and amino acid sequences of the nucleic acid molecule encoding half-human SCA B33oN-115 and of half-human SCA B33oN-115, respectively (SEQ ID NOS: 32 and 33). Numbers indicate the nucleotide (nt) positions, amino acids (aa) are presented in single letter code. The region of the DNA coding for the V-region of the heavy chain starts at nt 1 and ends at nt 360 of SEQ ID NO: 32, followed by a $(G_4S_1)_3$-linker starting at nt 361 and ending at nt 405 of SEQ ID NO: 32. The region of the DNA coding for the V-region of the kappa (light) chain starts at nt 406 and ends at nt 726 of SEQ ID NO: 32. Respectively, the protein coding region for the V-region of the heavy chain starts at amino acid 1 and ends at amino acid 120 of SEQ ID NO: 33 and corresponds to SEQ ID NO: 180. The $(G_4S_1)_3$ linker starts at amino acids 121 and ends at amino acid 135 of SEQ ID NO: 33. The protein coding region for the V-region of kappa (light) chain starts at amino acid 136 and ends at amino acid 242 of SEQ ID NO: 33 and corresponds to SEQ ID NO: 184. Complementarity determining regions (CDRs) are indicated by boxes surrounding the relevant nt and aa positions (according to the Kabat definition for CDRs). Additional sequences exemplified in this Figure are set forth as follows: complementary nucleotide sequence SEQ ID NO: 179H-CDR1 polypeptide sequence (SEQ ID NO: 181); H-CDR2 polypeptide sequence (SEQ ID NO: 182); H-CDR3 polypeptide sequence (SEQ ID NO: 183); L-CDR1 polypeptide sequence (SEQ ID NO: 185); L-CDR2 polypeptide sequence (SEQ ID NO: 186); and L-CDR3 polypeptide sequence (SEQ ID NO: 187).

FIG. 22: Nucleotide and amino acid sequences of the nucleic acid molecule encoding half-human SCA B33oN-35 and of half-human SCA B33oN-35, respectively (SEQ ID NOS: 24 and 25). Numbers indicate the nucleotide (nt) positions, amino acids (aa) are presented in single letter code. The region of the DNA coding for the V-region of the heavy chain starts at nt 1 and ends at nt 360 of SEQ ID NO: 24, followed by a $(G_4S_1)_3$-linker starting at nt 361 and ending at nt 405 of SEQ ID NO: 24. The region of the DNA coding for the V-region of the kappa (light) chain starts at nt 406 and ends at nt 726 of SEQ ID NO: 24. Respectively, the protein coding region for the V-region of the heavy chain starts at amino acid 1 and ends at amino acid 120 of SEQ ID NO: 25 and corresponds to SEQ ID NO: 189. The $(G_4S_1)_3$linker starts at amino acids 121 and ends at amino acid 135 of SEQ ID NO: 25. The protein coding region for the V-region of kappa (light) chain starts at amino acid 136 and ends at amino acid 242 of SEQ ID NO: 25 and corresponds to SEQ ID NO: 193. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 188); H-CDR1 polypeptide sequence (SEQ ID NO: 190); H-CDR2 polypeptide sequence (SEQ ID NO: 191); H-CDR3 polypeptide sequence (SEQ ID NO: 192); L-CDR1 polypeptide sequence (SEQ ID NO: 194); L-CDR2 polypeptide sequence (SEQ ID NO: 195); and L-CDR3 polypeptide sequence (SEQ ID NO: 196).

FIG. 23: Nucleotide and amino acid sequences of the nucleic acid molecule encoding half-human SCA B33oN-66 and of half-human SCA B33oN-66, respectively (SEQ ID NOS: 26 and 27). Numbers indicate the nucleotide (nt) positions, amino acids (aa) are presented in single letter code. The region of the DNA coding for the V-region of the heavy chain starts at nt 1 and ends at nt 360 of SEQ ID NO: 26, followed by a $(G_4S_1)_3$-linker starting at nt 361 and ending at nt 405 of SEQ ID NO: 26. The region of the DNA coding for the V-region of the kappa (light) chain starts at nt 406 and ends at nt 726 of SEQ ID NO: 26. Respectively, the protein coding region for the V-region of the heavy chain starts at amino acid 1 and ends at amino acid 120 of SEQ ID NO: 27 and corresponds to SEQ ID NO: 198. The $(G_4S_1)_3$ linker starts at amino acids 121 and ends at amino acid 135 of SEQ ID NO: 27. The protein coding region for the V-region of kappa (light) chain starts at amino acid 136 and ends at amino acid 242 of SEQ ID NO: 27 and corresponds to SEQ ID NO: 202. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 197); H-CDR1 polypeptide sequence (SEQ ID NO: 199); H-CDR2 polypeptide sequence (SEQ ID NO: 200); H-CDR3 polypeptide sequence (SEQ ID NO: 201); L-CDR1 polypeptide sequence (SEQ ID NO: 203); L-CDR2 polypeptide sequence (SEQ ID NO: 204); and L-CDR3 polypeptide sequence (SEQ ID NO: 205).

FIG. 24: Nucleotide and amino acid sequences of the nucleic acid molecule encoding half-human SCA B33oN-67 and of half-human SCA B33oN-67, respectively (SEQ ID NOS: 27 and 28). Numbers indicate the nucleotide (nt) positions, amino acids (aa) are presented in single letter code. The region of the DNA coding for the V-region of the heavy chain starts at nt 1 and ends at nt 360 of SEQ ID NO: 27, followed by a $(G_4S_1)_3$-linker starting at nt 361 and ending at nt 405 of SEQ ID NO: 27. The region of the DNA coding for the V-region of the kappa (light) chain starts at nt 406 and ends at nt 726 of SEQ ID NO: 27. Respectively, the protein coding region for the V-region of the heavy chain starts at amino acid 1 and ends at amino acid 120 of SEQ ID NO: 28 and corresponds to SEQ ID NO: 207. The $(G_4S_1)_3$ linker starts at amino acids 121 and ends at amino acid 135 of SEQ ID NO: 28. The protein coding region for the V-region of kappa (light) chain starts at amino acid 136 and ends at amino acid 242 of SEQ ID NO: 28 and corresponds to SEQ ID NO: 211. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 206); H-CDR1 polypeptide sequence (SEQ ID NO: 208); H-CDR2 polypeptide sequence (SEQ ID NO: 209); H-CDR3 polypeptide sequence (SEQ ID NO: 210); L-CDR1 polypeptide sequence (SEQ ID NO: 212); L-CDR2 polypeptide sequence (SEQ ID NO: 213); and L-CDR3 polypeptide sequence (SEQ ID NO: 214).

FIG. 25: Nucleotide and amino acid sequences of the nucleic acid molecule encoding half-human SCA B33oN-69 and of half-human SCA B33oN-69, respectively (SEQ ID NOS: 30 and 31). Numbers indicate the nucleotide (nt) positions, amino acids (aa) are presented in single letter code. The region of the DNA coding for the V-region of the heavy chain starts at nt 1 and ends at nt 360 of SEQ ID NO: 30, followed by a $(G_4S_1)_3$-linker starting at nt 361 and ending at nt 405 of SEQ ID NO: 30. The region of the DNA coding for the V-region of the kappa (light) chain starts at nt 406 and ends at nt 726 of SEQ ID NO: 30. Respectively, the protein coding region for the V-region of the heavy chain starts at amino acid 1 and ends at amino acid 120 of SEQ ID NO: 31 and corresponds to SEQ ID NO: 216. The $(G_4S_1)_3$ linker starts at amino acids 121 and ends at amino acid 135 of SEQ ID NO: 31. The protein coding region for the V-region of kappa (light) chain starts at amino acid 136 and ends at amino acid 242 of SEQ ID NO: 31 and corresponds to SEQ ID NO: 220. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 215); H-CDR1 polypeptide sequence (SEQ ID NO: 217); H-CDR2 polypeptide sequence (SEQ ID NO: 218); H-CDR3 polypeptide sequence (SEQ ID NO: 219); L-CDR1 polypeptide sequence (SEQ ID NO: 221); L-CDR2 polypeptide sequence (SEQ ID NO: 222); and L-CDR3 polypeptide sequence (SEQ ID NO: 223).

FIG. 26: Nucleotide and amino acid sequences of the nucleic acid molecule encoding half-human SCA B33oN-8 and of half-human SCA B33oN-8, respectively (SEQ ID NOS: 18 and 19). Numbers indicate the nucleotide (nt) positions, amino acids (aa) are presented in single letter code. The region of the DNA coding for the V-region of the heavy chain starts at nt 1 and ends at nt 360 of SEQ ID NO: 18, followed by a $(G_4S_1)_3$-linker starting at nt 361 and ending at nt 405 of SEQ ID NO: 18. The region of the DNA coding for the V-region of the kappa (light) chain starts at nt 406 and ends at nt 726 of SEQ ID NO: 18. Respectively, the protein coding region for the V-region of the heavy chain starts at amino acid 1 and ends at amino acid 120 of SEQ ID NO: 19 and corresponds to SEQ ID NO: 225. The $(G_4S_1)_3$linker starts at amino acids 121 and ends at amino acid 135 of SEQ ID NO: 19. The protein coding region for the V-region of kappa (light) chain starts at amino acid 136 and ends at amino acid 242 of SEQ ID NO: 19 and corresponds to SEQ ID NO: 229. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 224); H-CDR1 polypeptide sequence (SEQ ID NO: 226); H-CDR2 polypeptide sequence (SEQ ID NO: 227); H-CDR3 polypeptide sequence (SEQ ID NO: 228); L-CDR1 polypeptide sequence (SEQ ID NO: 230); L-CDR2 polypeptide sequence (SEQ ID NO: 231); and L-CDR3 polypeptide sequence (SEQ ID NO: 232).

FIG. 27: Nucleotide and amino acid sequences of the nucleic acid molecule encoding half-human SCA C32oN-10 and of half-human SCA C32oN-10, respectively (SEQ ID NOS: 34 and 35). Numbers indicate the nucleotide (nt) positions, amino acids (aa) are presented in single letter code. The region of the DNA coding for the V-region of the heavy chain starts at nt 1 and ends at nt 360 of SEQ ID NO: 34, followed by a $(G_4S_1)_3$-linker starting at nt 361 and ending at nt 405 of SEQ ID NO: 34. The region of the DNA coding for the V-region of the kappa (light) chain starts at nt 406 and ends at nt 726 of SEQ ID NO: 34. Respectively, the protein coding region for the V-region of the heavy chain starts at amino acid 1 and ends at amino acid 120 of SEQ ID NO: 35 and corresponds to SEQ ID NO: 234. The $(G_4S_1)_3$ linker starts at amino acids 121 and ends at amino acid 135 of SEQ ID NO: 35. The protein coding region for the V-region of kappa (light) chain starts at amino acid 136 and ends at amino acid 242 of SEQ ID NO: 35 and corresponds to SEQ ID NO: 238. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 233); H-CDR1 polypeptide sequence (SEQ ID NO: 235); H-CDR2 polypeptide sequence (SEQ ID NO:236); H-CDR3 polypeptide sequence (SEQ ID NO: 237); L-CDR1 polypeptide sequence (SEQ ID NO: 239); L-CDR2 polypeptide sequence (SEQ ID NO: 240); and L-CDR3 polypeptide sequence (SEQ ID NO: 241).

FIG. 28: Nucleotide and amino acid sequences of the nucleic acid molecule encoding half-human SCA C32oN-21 and of half-human SCA C32oN-21, respectively (SEQ ID NOS: 36 and 37). Numbers indicate the nucleotide (nt) positions, amino acids (aa) are presented in single letter code. The region of the DNA coding for the V-region of the heavy chain starts at nt 1 and ends at nt 360 of SEQ ID NO: 36, followed by a $(G_4S_1)_3$-linker starting at nt 361 and ending at nt 405 of SEQ ID NO: 36. The region of the DNA coding for the V-region of the kappa (light) chain starts at nt 406 and ends at nt 726 of SEQ ID NO: 36. Respectively, the protein coding region for the V-region of the heavy chain starts at amino acid 1 and ends at amino acid 120 of SEQ ID NO: 37 and corresponds to SEQ ID NO: 243. The $(G_4S_1)_3$ linker starts at amino acids 121 and ends at amino acid 135 of SEQ ID NO: 37. The protein coding region for the V-region of kappa (light) chain starts at amino acid 136 and ends at amino acid 242 of SEQ ID NO: 37 and corresponds to SEQ ID NO: 247. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 242); H-CDR1 polypeptide sequence (SEQ ID NO: 244); H-CDR2 polypeptide sequence (SEQ ID NO: 245); H-CDR3 polypeptide sequence (SEQ ID NO: 246); L-CDR1 polypeptide sequence (SEQ ID NO: 248); L-CDR2 polypeptide sequence (SEQ ID NO: 249); and L-CDR3 polypeptide sequence (SEQ ID NO: 250).

FIG. 29: Nucleotide and amino acid sequences of the nucleic acid molecule encoding half-human SCA C32oN-34 and of half-human SCA C32oN-34, respectively (SEQ ID NOS: 38 and 39). Numbers indicate the nucleotide (nt) positions, amino acids (aa) are presented in single letter code. The region of the DNA coding for the V-region of the heavy chain starts at nt 1 and ends at nt 360 of SEQ ID NO: 28, followed by a $(G_4S_1)_3$-linker starting at nt 361 and ending at nt 405 of SEQ ID NO: 28. The region of the DNA coding for the V-region of the kappa (light) chain starts at nt 406 and ends at nt 726 of SEQ ID NO: 28. Respectively, the protein coding region for the V-region of the heavy chain starts at amino acid 1 and ends at amino acid 120 of SEQ ID NO: 39 and corresponds to SEQ ID NO: 252. The $(G_4S_1)_3$ linker starts at amino acids 121 and ends at amino acid 135 of SEQ ID NO: 39. The protein coding region for the V-region of kappa (light) chain starts at amino acid 136 and ends at amino acid 242 of SEQ ID NO: 39 and corresponds to SEQ ID NO: 256. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 251); H-CDR1 polypeptide sequence (SEQ ID NO: 253); H-CDR2 polypeptide sequence (SEQ ID NO: 254); H-CDR3 polypeptide sequence (SEQ ID NO: 255); L-CDR1 polypeptide sequence (SEQ ID NO: 257); L-CDR2 polypeptide sequence (SEQ ID NO: 258); and L-CDR3 polypeptide sequence (SEQ ID NO: 259).

FIG. 30: Nucleotide and amino acid sequences of the nucleic acid molecule encoding half-human SCA C32oN-46 and of half-human SCA C32oN-46, respectively (SEQ ID NOS: 40 and 41). Numbers indicate the nucleotide (nt) positions, amino acids (aa) are presented in single letter code. The region of the DNA coding for the V-region of the heavy chain starts at nt 1 and ends at nt 360 of SEQ ID NO: 40, followed by a $(G_4S_1)_3$-linker starting at nt 361 and ending at nt 405 of SEQ ID NO: 40. The region of the DNA coding for the V-region of the kappa (light) chain starts at nt 406 and ends at nt 726 of SEQ ID NO: 40. Respectively, the protein coding region for the V-region of the heavy chain starts at amino acid 1 and ends at amino acid 120 of SEQ ID NO: 41 and corresponds to SEQ ID NO: 261. The $(G_4S_1)_3$ linker starts at amino acids 121 and ends at amino acid 135 of SEQ ID NO: 41. The protein coding region for the V-region of kappa (light) chain starts at amino acid 136 and ends at amino acid 242 of SEQ ID NO: 41 and corresponds to SEQ ID NO: 265. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 260); H-CDR1 polypeptide sequence (SEQ ID NO: 262); H-CDR2 polypeptide sequence (SEQ ID NO: 263); H-CDR3 polypeptide sequence (SEQ ID NO: 264); L-CDR1 polypeptide sequence (SEQ ID NO: 266); L-CDR2 polypeptide sequence (SEQ ID NO: 267); and L-CDR3 polypeptide sequence (SEQ ID NO: 268).

FIG. 31: Nucleotide and amino acid sequences of the nucleic acid molecule encoding half-human SCA C32oN-89 and of half-human SCA C32oN-89, respectively (SEQ ID NOS: 42 and 43). Numbers indicate the nucleotide (nt) positions, amino acids (aa) are presented in single letter code. The region of the DNA coding for the V-region of the heavy chain starts at nt 1 and ends at nt 360 of SEQ ID NO: 42, followed by a $(G_4S_1)_3$-linker starting at nt 361 and ending at nt 405 of SEQ ID NO: 42. The region of the DNA coding for the V-region of the kappa (light) chain starts at nt 406 and ends at nt 726 of SEQ ID NO: 42. Respectively, the protein coding region for the V-region of the heavy chain starts at amino acid 1 and ends at amino acid 120 of SEQ ID NO: 43 and corresponds to SEQ ID NO: 270. The $(G_4S_1)_3$ linker starts at amino acids 121 and ends at amino acid 135 of SEQ ID NO: 43. The protein coding region for the V-region of kappa (light) chain starts at amino acid 136 and ends at amino acid 242 of SEQ ID NO: 43 and corresponds to SEQ ID NO: 274. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 269); H-CDR1 polypeptide sequence (SEQ ID NO: 271); H-CDR2 polypeptide sequence (SEQ ID NO: 272); H-CDR3 polypeptide sequence (SEQ ID NO: 273); L-CDR1 polypeptide sequence (SEQ ID NO: 275); L-CDR2 polypeptide sequence (SEQ ID NO: 276); and L-CDR3 polypeptide sequence (SEQ ID NO: 277).

FIG. 32: Nucleotide and amino acid sequences of the nucleic acid molecule encoding half-human SCA C32oN-92 and of half-human SCA C32oN-92, respectively (SEQ ID NOS: 44 and 45). Numbers indicate the nucleotide (nt) positions, amino acids (aa) are presented in single letter code. The region of the DNA coding for the V-region of the heavy chain starts at nt 1 and ends at nt 360 of SEQ ID NO: 44, followed by a $(G_4S_1)_3$-linker starting at nt 361 and ending at nt 405 of SEQ ID NO: 44. The region of the DNA coding for the V-region of the kappa (light) chain starts at nt 406 and ends at nt 726 of SEQ ID NO: 44. Respectively, the protein coding region for the V-region of the heavy chain starts at amino acid 1 and ends at amino acid 120 of SEQ ID NO: 45 and corresponds to SEQ ID NO: 279. The $(G_4S_1)_3$linker starts at amino acids 121 and ends at amino acid 135 of SEQ ID NO: 45. The protein coding region for the V-region of kappa (light) chain starts at amino acid 136 and ends at amino acid 242 of SEQ ID NO: 45 and corresponds to SEQ ID NO: 283. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 278); H-CDR1 polypeptide sequence (SEQ ID NO: 280); H-CDR2 polypeptide sequence (SEQ ID NO: 281); H-CDR3 polypeptide sequence (SEQ ID NO: 282); L-CDR1 polypeptide sequence (SEQ ID NO: 284); L-CDR2 polypeptide sequence (SEQ ID NO: 285); and L-CDR3 polypeptide sequence (SEQ ID NO: 286).

FIG. 33: Nucleotide and amino acid sequences of the nucleic acid molecule encoding half-human SCA C33oN-32 and of half-human SCA C33oN-32, respectively (SEQ ID NOS: 46 and 47). Numbers indicate the nucleotide (nt) positions, amino acids (aa) are presented in single letter code. The region of the DNA coding for the V-region of the heavy chain starts at nt 1 and ends at nt of SEQ ID NO: 46, followed by a $(G_4S_1)_3$-linker starting at nt 361and ending at nt 405 of SEQ ID NO: 46. The region of the DNA coding for the V-region of the kappa (light) chain starts at nt 406 and ends at nt 726 of SEQ ID NO: 46. Respectively, the protein coding region for the V-region of the heavy chain starts at amino acid 1 and ends at amino acid 120 of SEQ ID NO: 47 and corresponds to SEQ ID NO: 288. The $(G_4S_1)_3$ linker starts at amino acids 121 and ends at amino acid 135 of SEQ ID NO: 47. The protein coding region for the V-region of kappa (light) chain starts at amino acid 136 and ends at amino acid 242 of SEQ ID NO: 47 and corresponds to SEQ ID NO: 292. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 287); H-CDR1 polypeptide sequence (SEQ ID NO: 289); H-CDR2 polypeptide sequence (SEQ ID NO: 290); H-CDR3 polypeptide sequence (SEQ ID NO: 291); L-CDR1 polypeptide sequence (SEQ ID NO: 293); L-CDR2 polypeptide sequence (SEQ ID NO: 294); and L-CDR3 polypeptide sequence (SEQ ID NO: 295).

FIG. 34: Nucleotide and amino acid sequences of the nucleic acid molecule encoding half-human SCA C33oN-33 and of half-human SCA C33oN-33, respectively (SEQ ID NOS: 48 and 49). Numbers indicate the nucleotide (nt) positions, amino acids (aa) are presented in single letter code. The region of the DNA coding for the V-region of the heavy chain starts at nt 1 and ends at nt 360 of SEQ ID NO: 48, followed by a $(G_4S_1)_3$-linker starting at nt 361 and ending at nt 405 of SEQ ID NO: 48. The region of the DNA coding for the V-region of the kappa (light) chain starts at nt 406 and ends at nt 726 of SEQ ID NO: 48. Respectively, the protein coding region for the V-region of the heavy chain starts at amino acid 1 and ends at amino acid 120 of SEQ ID NO: 49 and corresponds to SEQ ID NO: 297. The $(G_4S_1)_3$ linker starts at amino acids 121 and ends at amino acid 135 of SEQ ID NO: 49. The protein coding region for the V-region of kappa (light) chain starts at amino acid 136 and ends at amino acid 242 of SEQ ID NO: 49 and corresponds to SEQ ID NO: 301. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 296); H-CDR1 polypeptide sequence (SEQ ID NO: 298); H-CDR2 polypeptide sequence (SEQ ID NO: 299); H-CDR3 polypeptide sequence (SEQ ID NO: 300); L-CDR1 polypeptide sequence (SEQ ID NO: 302); L-CDR2 polypeptide sequence (SEQ ID NO: 303); and L-CDR3 polypeptide sequence (SEQ ID NO: 304).

FIG. 35: Nucleotide and amino acid sequences of the nucleic acid molecule encoding half-human SCA C33oN-49 and of half-human SCA C33oN-49, respectively (SEQ ID NOS: 50 and 51). Numbers indicate the nucleotide (nt) positions, amino acids (aa) are presented in single letter code. The region of the DNA coding for the V-region of the heavy chain starts at nt 1 and ends at nt 360 of SEQ ID NO: 50, followed by a $(G_4S_1)_3$-linker starting at nt 361 and ending at nt 405 of SEQ ID NO: 50. The region of the DNA coding for the V-region of the kappa (light) chain starts at nt 406 and ends at nt 726 of SEQ ID NO: 50. Respectively, the protein coding region for the V-region of the heavy chain starts at amino acid 1 and ends at amino acid 120 of SEQ ID NO: 51 and corresponds to SEQ ID NO: 306. The $(G_4S_1)_3$ linker starts at amino acids 121 and ends at amino acid 135 of SEQ ID NO: 51. The protein coding region for the V-region of kappa (light) chain starts at amino acid 136 and ends at amino acid 242 of SEQ ID NO: 51 and corresponds to SEQ ID NO: 310. Complementarity determining regions (CDRs) are indicated by boxes surrounding the relevant nt and aa positions (according to the Kabat definition for CDRs). Additional sequences exemplified in this Figure are set forth as follows: complementary nucleotide sequence (SEQ ID NO: 305); H-CDR1 polypeptide sequence (SEQ ID NO: 307); H-CDR2 polypeptide sequence (SEQ ID NO: 308); H-CDR3 polypeptide sequence (SEQ ID NO: 309); L-CDR1 polypeptide sequence (SEQ ID NO: 311); L-CDR2 polypeptide sequence (SEQ ID NO: 312); and L-CDR3 polypeptide sequence (SEQ ID NO: 313).

Figure 36:
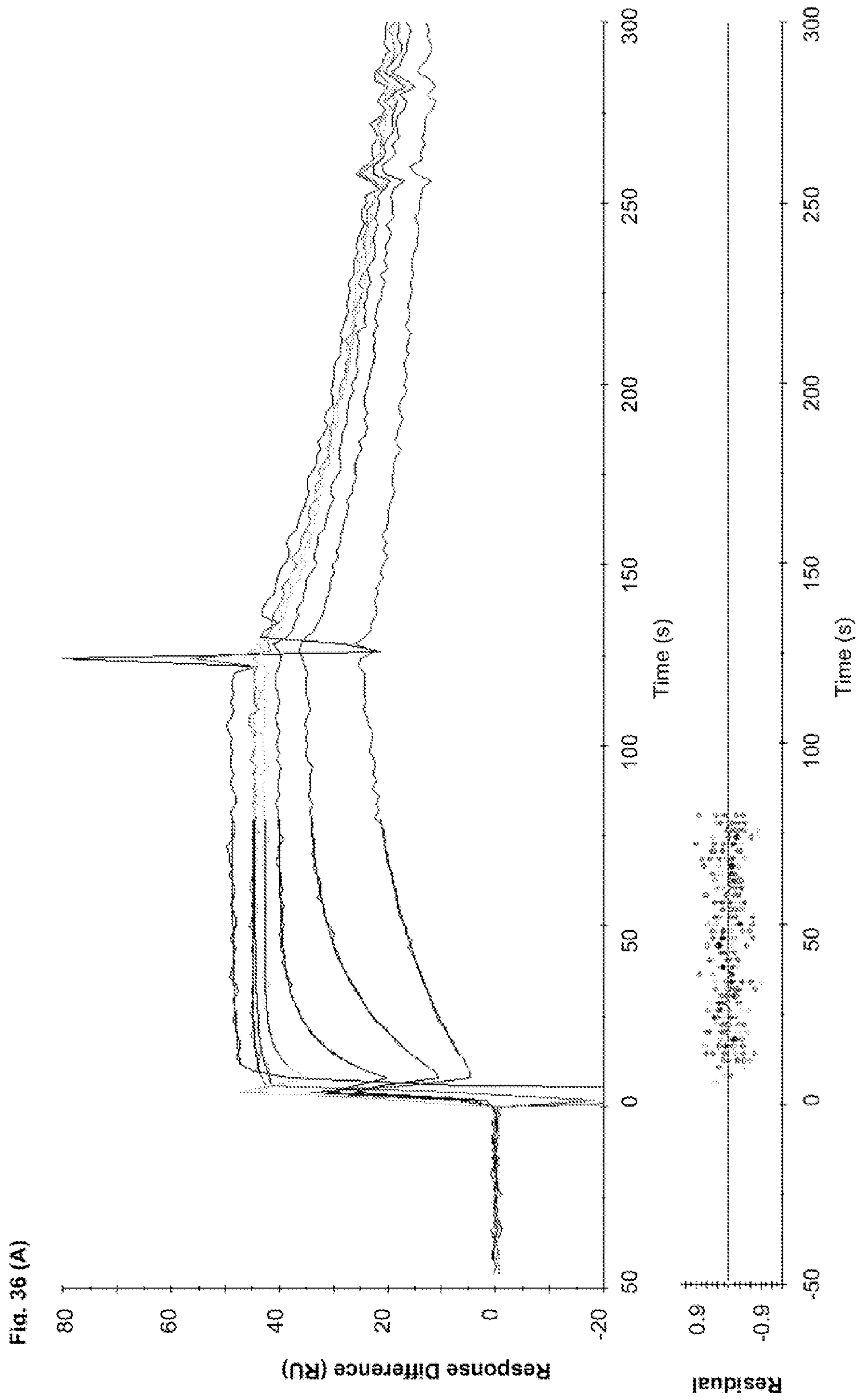
Figure 36:
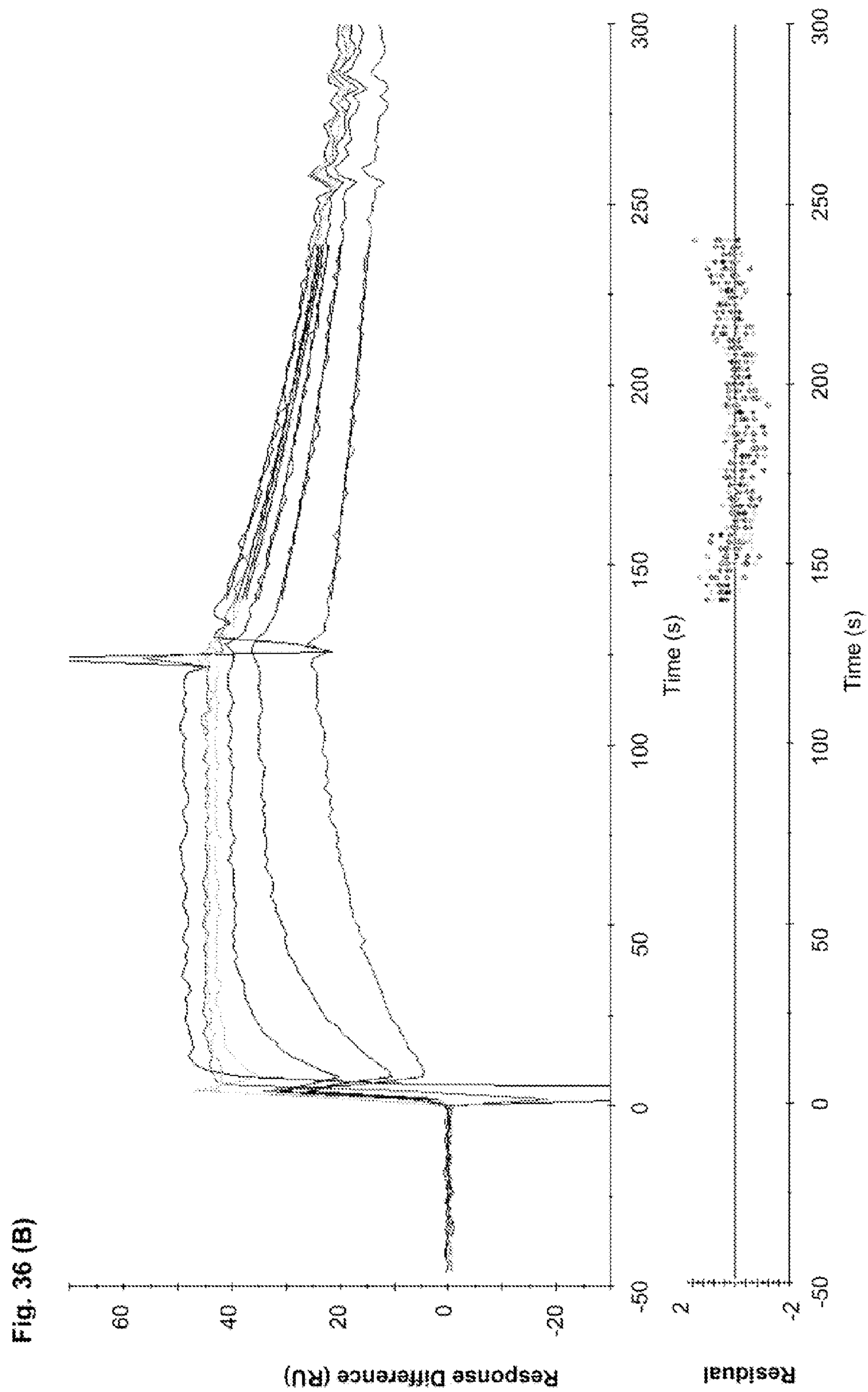

FIG. 36 A, B: Kinetic binding analysis of SCA leads derived from the method of the invention, as determined by SPR. Binding kinetics (kd and ka) of the SCA leads were measured injecting 10 μL of purified protein in dilution series ranging from 10 μg/mL to 1 pg/mL purified SCA onto a rhGM-CSF coated sensor chip surface. The dissociation was monitored at 25° C. for 100 sec. Data were fitted using BIAevalution™ software determining the rate constant for dissociation (FIG. 36B) and association (FIG. 36A) kinetics. The results are summarized in Table 1. The residuals corresponding to the fitted data monitoring the deviation from the raw data indicated no systematic deviation for the fit.

Figure 37:
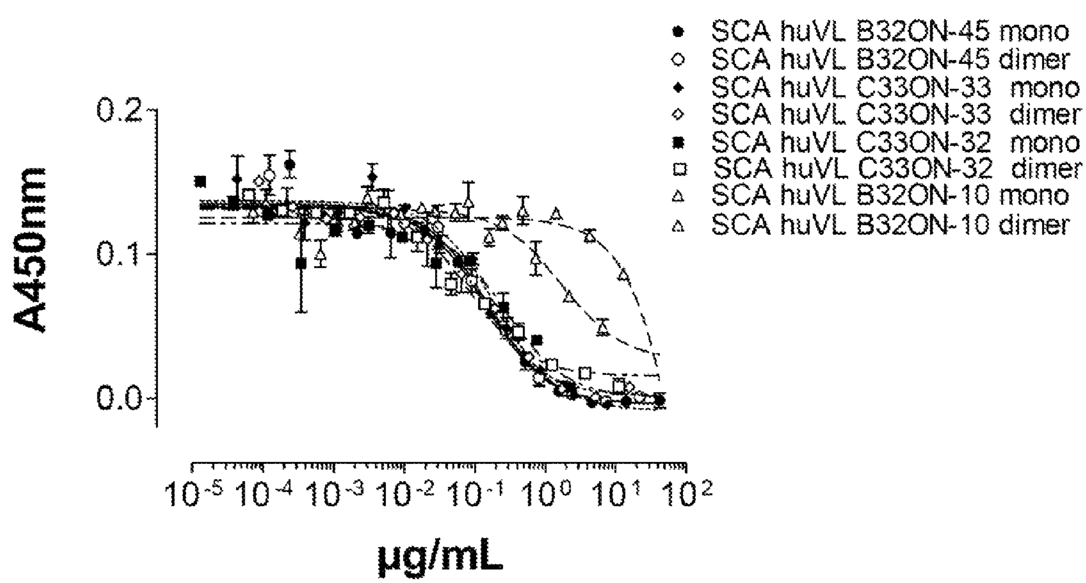

FIG. 37: Inhibition of rhGM-CSF dependent proliferation of TF-1 cells by SCA constructs. TF-1 cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF dependent proliferation purified SCA in 1×PBS was added in a dilution series with final protein concentrations ranging from 100 μg/mL to 10 pg/mL. 10 μL of dialyzed and sterile filtered protein solution (0.22 μm filter) was added to 100 μL TF-1 and rhGM-CSF solution. The samples were incubated at 37° C. at 5%

$CO_2$ for 72 h. After 72 h the proliferative status of the TF-1 cells was determined adding WST-1 and monitoring the colorimetric change with an ELISA reader at 450 nm.

EXAMPLES

Example 1

Procurement of the Recombinant Human GM-CSF Antigen 1.1 Cloning, Expression and Purification of the Human GM-CSF Antigen:

The gene encoding for the human GM-CSF antigen was subcloned into the pET22b(+) (Novagene, USA) from the expression vector pORF-hGM-CSF (Novagen, USA) via the PCR-introduced restriction enzyme recognition sites NdeI and XhoI. The hGM-CSF encoding gene in pET22b(+) is fused to the pelB leader sequence and is suitable for expression in *E. coli* periplasm.

Protein production and purification was performed as described by the manufacturer. In brief, *E. coli* BL21DE3 were transformed with the expression plasmid and grown at 37° C. in selective medium to an optical density at 600 nm of 0.5-0.8. Protein production was induced by addition of IPTG to 1 mM and reduction of temperature to 25° C. A periplasmic preparation was done via osmotic shock using 20% sucrose solution to selectively destroy the cell wall maintaining an intact cell membrane. The native hGM-CSF contains two formed disulfide bridges and expression in the oxidative periplasm of *E. coli* allows for formation of these functionally important disulfide bridges.

Recombinant human GM-CSF ("hGM-CSF") was purified in a two step purification process via immobilized metal affinity chromatography (IMAC) and gel filtration. An Äkta® FPLC System (Pharmacia) and Unicorn® Software were used for chromatography. All chemicals were of research grade and purchased from Sigma (Deisenhofen) or Merck (Darmstadt).

IMAC was performed using a Qiagen Ni-NTA Superflow column according to the protocol provided by the manufacturer. The column was equilibrated with buffer A2 (20 mM sodium phosphate pH 7.2, 0.4 M NaCl) and the periplasmic preparation (PPP) (100 mL) was applied to the column (2 mL) at a flow rate of 2 mL/min. The column was washed with 5 column volumes 5% buffer B2 (20 mM sodium phosphate pH 7.2, 0.4 M NaCl, 0.5 M Imidazol) to remove unbound sample. Bound protein was eluted using 100% buffer B2 in 5 column volumes. Eluted protein fractions were pooled for further purification.

Gel filtration chromatography was performed on a Superdex 200 Prep Grade column (Pharmacia) equilibrated with PBS (Gibco). Eluted protein samples (flow rate 1 mL/min) were subjected to standard SDS-PAGE and Western Blot for detection. Prior to purification, the column was calibrated for molecular weight determination (molecular weight marker kit, Sigma MW GF-200). Protein concentrations were determined measuring OD 280 nm and calculated using the sequence specific molecular extinction coefficient.

1.2 Biotinylation of the Recombinant Human GM-CSF Antigen

For phage library selection recombinant human GM-CSF antigen A) Leukine (Leukine Liquid, Immunex) and B) recombinant human GM-CSF produced in *E. coli* (see 1.1) were biotinylated. Biotinylation was accomplished in PBS containing 5% DMSO (Sigma) with a five-fold molar excess of EZ-Link Sulfo NHS-LC-LC-Biotin (Pierce) for 1 hour at room temperature in a sample mixer (Dynal). For the separation of free Biotin and biotinylated human GM-CSF antigen, anion exchange chromatography (Resource Q, Amersham Biosciences) was carried out according to standard protocols. The chromatography resulted in both approaches (A and B) in two elution peaks. In case A the primary eluted peak was fractionated again via a second anion exchange chromatography step (same conditions as above) into two elution peaks. Afterwards the obtained fractions were serially diluted (dilutions 1:2; start concentration 6 μg/mL determined from the peak height) coated to 96 wells ELISA plates and detected. The detection was carried out using A) an anti human GM-CSF antibody M500-A (Sigma, 2.5 μg/mL in PBS/1% BSA) detected with horseradish peroxidase-conjugated goat anti-mouse Fab2 specific polyclonal antibody (Dianova, 1 μg/mL PBS/1% BSA) and B) the maternal antibody (1 μg/mL PBS/1% BSA) detected with horseradish peroxidase-conjugated goat anti-rat polyclonal antibody (Dianova, 1 μg/mL PBS/1% BSA). The successful biotinylation was demonstrated by a similar ELISA experiment that was carried out using horseradish peroxide-conjugated streptavidin (Dako, 1 μg/mL PBS/1% BSA). The signal was developed by adding OPD substrate solution (Sigma) and detected at a wavelength of 492 nm (reference wavelength 620 nm). To estimate the degree of biotinylation the above mentioned ELISA was carried out using the anion exchange fractions directly or after an incubation step with 6.7×10exp7 streptavidine magnetic beads (Dynabeads M-280-Streptavidine, Dynal) with gentle agitation for 30 minutes. The resulting supernatant was coated onto the wells of 96-well ELISA plates and detected as described above. The ELISA results showed that the second eluted peak contained the biotinylated human GM-CSF and that A) about 95% and B) about 50% of the eluted human GM-CSF was conjugated. Concentrations were estimated using the original material (A and B) as a standard and resulted in A) 100 μg/mL and B) 20 μg/mL.

The retained bioactivity of the biotin-labeled human GM-CSF was confirmed in TF-1 proliferation assays according to protocols described in the characterization of the single chain antibodies (SCAs).

1.3 Fluorescein Labeling of the Recombinant Human GM-CSF Antigen

For binding studies on TF-1 cells recombinant human GM-CSF antigen produced in *E. coli* (see 1.2.) was conjugated with fluorescein-5(6)-carboxamidocaproic acid N-succinimidyl ester (Fluka, fluorescein-NHS). The conjugation step was performed in borate buffer (0.05 M boric acid, 0.1 M NaCl, pH 8.5) containing 17.5% DMSO with a five fold molar excess of fluorescein-NHS for 1 hour at room temperature in a sample mixer. Afterwards a gel filtration (Sephadex G25 medium, Amersham Biosciences) was carried out to dissociate fluorescein-labeled human GM-CSF antigen from free fluorescein-NHS. The gel filtration resulted in two peaks measured at a wavelength of 485 nm (reference wavelength 535 nm), whereas the primary peak represents the FITC-labeled human GM-CSF. The degree of labeling was determined by defining the F/P ratio of the conjugate ($[mg/mL]=(A_{280}-0.35\times A_{493})\times 1.08$; $F/P=(A_{493}/73.000)\times(15.000/([mg/mL]))$). The determined concentration was 0.041 mg/mL with an F/P ratio of 1.2.

Example 2

Cloning, Expression and Characterization of the Maternal Anti-Human GM-CSF SCA 2.1. Cloning of the Maternal V-Regions from Hybridoma HB-9569

As used throughout the foregoing examples, a "maternal" V-region denotes that the V-region in question originates from a full immunoglobulin molecule. A "maternal" SCA refers to the SCA resulting from direct incorporation of the maternal V-regions into SCA format without performing the inventive method as described hereinabove. In the event that the "maternal SCA" exhibits insufficient soluble recombinant expression, such a "maternal SCA" therefore represents a "corresponding antibody fragment" of a "source immunoglobulin", as this term is used hereinbove.

As used throughout the foregoing examples, a "hit" denotes a molecule which is known to bind an antigen of interest, but which binding has not been quantitatively evaluated. A "hit" is a molecule in an early stage of characterization for which small-scale production might have already been performed. Such a molecule is in the validation stage of characterization.

As used throughout the foregoing examples, a "lead" molecule denotes a molecule the binding and neutralization potentials of which has been quantified. Production of a "lead" molecule has already taken place on a large scale.

The aim of this experiment is the isolation and sub-cloning of the genes encoding the VH and VL regions in the maternal mAb produced by the hybridoma cell line HB-9569. The hybridoma HB-9569 was obtained from ATCC (USA). Hybridoma cells were cultivated in ATCC complete growth medium: RPMI 1640 medium with 2 mM L-glutamine adjusted to contain 1.5 g/L sodium bicarbonate, 4.5 g/L glucose, 10 mM HEPES, and 1.0 mM sodium pyruvate and supplemented with 0.05 mM 2-mercaptoethanol, fetal bovine serum 10% at 37° C. with 5% $CO_2$. For total RNA preparation, 1×10exp7 cells were used and RNA was prepared as described in the product manual of the Qiagen Omni-Skript Kit (Qiagen, Germany). cDNA was synthesized according to standard methods (Sambrook, Cold Spring Harbor Laboratory Press 1989, Second Edition).

For the isolation of light chain V-region DNA, RT-PCR was carried out using 5E1-kSalI-AS: TTT GCG GCC GCG TCG ACT AAC ACT CAT TCC TGT TG (SEQ ID NO:52) and MLALT3.RV: GCC GAA TTC CAC CAT GRA GTC ACA KAC YCA GGT CTT YRT A (SEQ ID NO:53) primer set. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

For the isolation of heavy chain V-region DNA, RT-PCR was carried out using MHALT1R.V: GCC GAA TTC CAC CAT GGR ATG SAG CTG KGT MAT SCT CTT (SEQ ID NO:54) and Race GSP rIgG2a/b: CAC ACC GCT GGA CAG GGC TCC AGA GTT CC (SEQ ID NO:55) primer set. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Heavy chain DNA V-fragments were then isolated according to standard protocols.

For further subcloning the necessary restriction enzyme recognition sites had to be introduced via PCR. For the light chain V-region DNA the primer pair: maternal mAb vLSacI-S:TGG GAG CTC TGA CAT CGT GCT GAC TCA GTC (SEQ ID NO:56) and maternal mAb vL-Not-AS: ATT GCG GCC GCT TTC AGT TCC AGC TTG GTC C (SEQ ID NO:57) were used. The heavy chain V-region DNA was amplified by PCR introducing the required restriction enzyme recognition sites via the primer pair: maternal mAb vH Sal I: AAA GTC GAC AAA CTG CTG CAG TCT GGG (SEQ ID NO:58) and maternal mAb vH BspEI-AS: ATT TCC GGA TGA GGA GAC TGT GAC CAT G (SEQ ID NO:59).

2.2. Cloning of the Maternal Sca into the Phagemid Vector pComb3H5BHis and Protein Expression Cloning of the VH: For cloning of the maternal VH into the phagemid vector pComb3H5BHis a PCR amplification from the Vector PCR script-CAM containing the maternal VH (see Example 2.1.) was carried out. Amplification was performed according to standard procedures using the 5'-primer MVH8 (5'-GAG GTT CAG CTC GAG CAG TCT GGA GCT-3' (SEQ ID NO:60)) and the 3'-primer 3'-MuVHBstEII (5'-TGA GGA GAC GGT GAC CGT GGT CCC TTG GCC CCA G-3' (SEQ ID NO:61)). The approx 350 bp fragment was identified by agarose gel electrophoresis, purified from the gel and cut with the restriction enzymes BstEII and XhoI. The phagemid pComb3H5BHis (vector described in thesis dissertation of Dr. Ralf Lutterbüse) was digested with the restriction enzymes SalI and BstEII and the large fragment was ligated with the above mentioned VH fragment via compatible SalI and XhoI nucleotide-overhangs. After transformation into *E. coli* XL1 blue, a single clone was cultivated in 5 mL LB medium (containing 50 μg/mL Carbenicilline) and the plasmid prepared according to standard protocols (designated as: pComb3H5BHis/maternal VH w/o N2). The successful cloning was confirmed by sequencing the insert (Sequiserve, Munich).

Cloning of the VL: For cloning of the maternal VL into the phagemid vector pComb3H5BHis PCR amplification was performed from the Vector PCR script-CAM containing the maternal VL (see Example 2.1). Amplification was performed according to standard procedures using the 5'-primer MuVK3 (5'-CCA GTT CCG AGC TCG TGC TCA CCC AGT CTC CA-3' (SEQ ID NO:62) and the 3'-primer 3'-MuVHK-HindIII-BsiWI (5'-TGG TGC ACT AGT CGT ACG TTT GAT CTC AAG CTT GGT CCC-3' (SEQ ID NO:63)). The approx 350 bp fragment was identified by agarose gel electrophoresis, purified from the gel and cut with the restriction enzymes SacI and SpeI. The phagemid pComb3H5BHis (vector described in thesis dissertation of Dr. Ralf Lutterbüse) was digested with the restriction enzymes SacI and NheI and the large fragment ligated with the above mentioned VL fragment via compatible SpeI and NheI nucleotide-overhangs. After transformation into *E. coli* XL1 blue, a single clone was cultivated in 5 mL LB medium (containing 50 μg/mL Carbenicilline) and the plasmid prepared according to standard protocols (designated as: pComb3H5BHis/maternal VL w/o gene III). The successful cloning was confirmed by sequencing the insert (Sequiserve, Munich).

Cloning of the SCA: For cloning of the maternal VL into the phagemid vector pComb3H5BHis/maternal VH w/o N2 (as mentioned above), both plasmids (pComb3H5BHis/maternal VH w/o N2 and pComb3H5BHis/maternal VL w/o gene III) were cut with the restriction enzymes SacI and NotI.

The large VH-containing vector band from the VH-plasmid and the small VL-containing fragment band from the VL plasmid were isolated and ligated.

After ligation the plasmid DNA was transformed into 100 μL heat shock competent *E. coli* XL1 Blue and plated on Carbenicillin LB-Agar. Single colonies were grown in 5 mL LB-Carbenicillin-cultures/20 mM $MgCl_2$ and expression of SCA was induced after six hours by adding Isopropyl-β-D-thiogalactoside (IPTG) to a final concentration of 1 mM followed by incubation at 30° C.

These cells were harvested after 20 hours by centrifugation and typically resuspended in 500 μL PBS. Through four rounds of freezing at −70° C. and thawing at 37° C. the outer membrane of the bacteria was destroyed by temperature shock so that the soluble periplasmic proteins including the SCA fusion-proteins were released into the liquid. After elimination of intact cells and cell-debris by centrifugation, the supernatant was evaluated by ELISA.

In a first ELISA assay the periplasmic extracts were tested for binding to immobilized recombinant human GM-CSF (Leukomax, Novartis, *E. coli* material).

50 μL of a 1 μg recombinant human GM-CSF/mL PBS solution was coated onto the wells of a 96-well ELISA plate. Coating was typically performed over night at 4° C. After washing the wells once with PBS/0.05% Tween, the wells were blocked with 200 μL PBS/3% BSA per well for 1 h at room temperature. Then, 50 μL of the respective periplasmic preparations or of the murine anti-human GM-CSF antibody 7A6 (0.5 μg/mL PBS) as a positive control were added to the wells and incubated for another hour at room temperature.

Detection of SCA-fragments bound to immobilized recombinant human GM-CSF antigen was carried out using a Penta-His antibody (Qiagen, 1 μg/mL PBS) detected with horseradish peroxidase-conjugated goat anti-mouse IgG Fab2 (Jackson, 1 ng/mL PBS). The signal was developed by adding ABTS substrate solution and detected at a wavelength of 405 nm.

Figure 1:
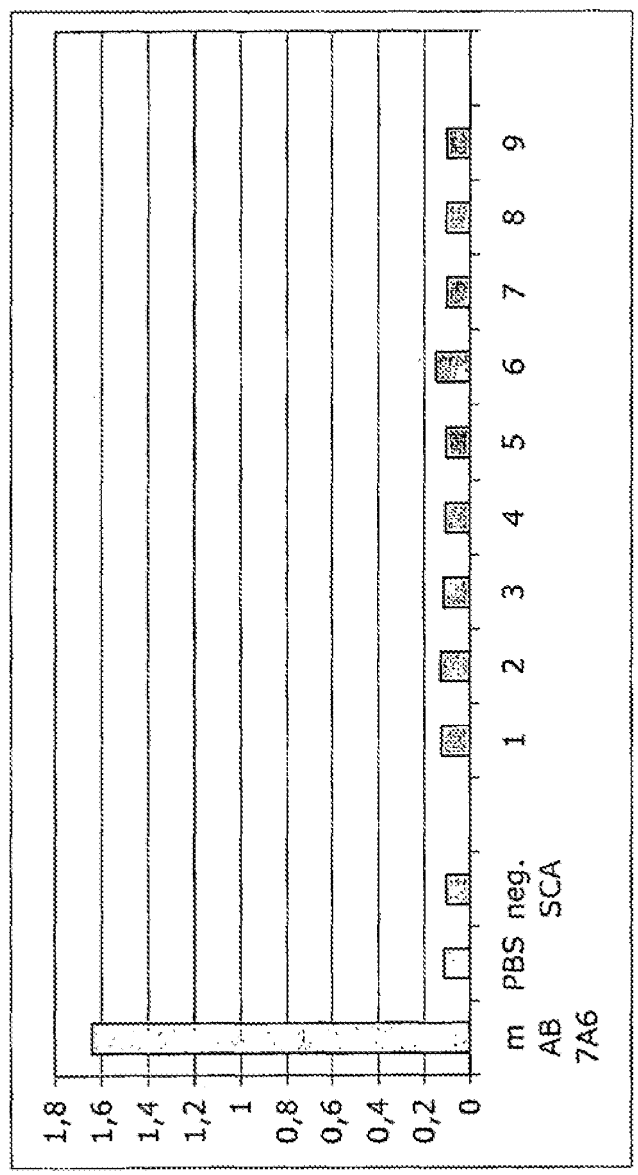
FIG. 1: Recombinant human GM-CSF-specific ELISA-analysis of periplasmic preparations of nine clones containing SCA fragments of the maternal anti-human GM-CSF antibody (i.e. the "corresponding antibody fragment" derived from direct conversion of the "source immunoglobulin" into SCA format). Preparations of soluble SCA fragments were added to wells of an ELISA-plate which had been coated with a soluble recombinant human GM-CSF antigen (*E. coli* material). Detection of SCA-fragments bound to immobilized recombinant human GM-CSF antigen was carried out using a Penta-His antibody (Qiagen, 1 μg/mL PBS) detected with horseradish peroxidase-conjugated goat anti-mouse IgG Fab2 specific polyclonal antibody (Jackson, 1 μg/mL PBS). The signal was developed by adding ABTS (2,2'-Azino-di[3-ethylbenzthiazoline sulfonate (6)] diammonium sal5t) substrate solution and detected at a wavelength of 405 nm. The OD-values (y axis) were measured at 405 nm by an ELISA reader. Clone numbers are presented on the x axis, the murine anti human-GM-CSF antibody 7A6 was used as a positive control, an irrelevant SCA containing periplasmic preparation was used as a negative control.

In contrast to the strong signal of the positive control murine mAB 7A6, none of the periplasmic preparations potentially containing the maternal SCA showed a binding signal (FIG. 1). The detected signals were only in the range of PBS and an irrelevant SCA as negative controls.

To determine whether there was any SCA protein at all in the periplasmic extracts, 50 μL of the crude periplasmic extracts were coated directly onto the wells of a 96-well ELISA plate at 4° C. overnight. As described above, the wells were washed, blocked and positive binding detected.

Figure 2:
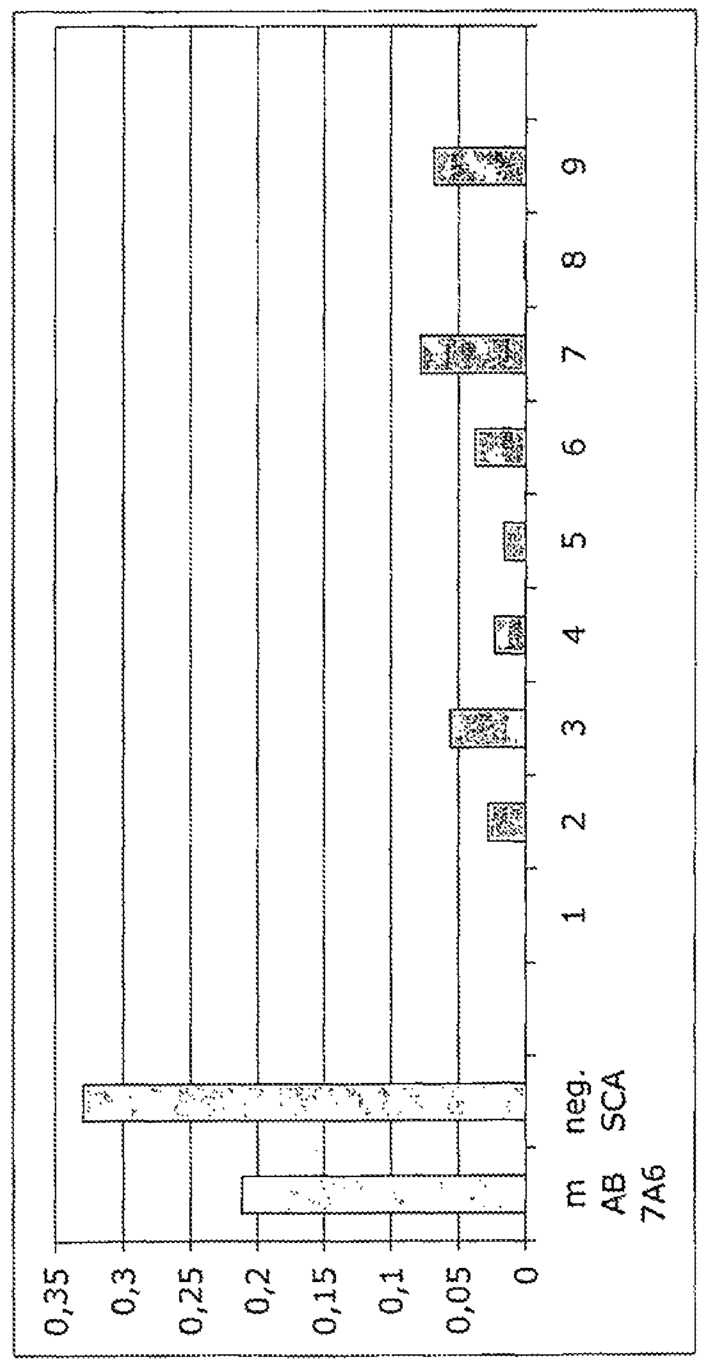
FIG. 2: Recombinant human GM-CSF-specific ELISA-analysis of periplasmic preparations of nine clones containing SCA fragments of the maternal anti-human GM-CSF antibody (i.e. the "corresponding antibody fragment" derived resulting from direct conversion of the "source immunoglobulin" into SCA format). Preparations of soluble SCA fragments were added to wells of an ELISA-plate which had been coated with a soluble recombinant human GM-CSF antigen (*E. coli* material). Detection of SCA-fragments bound to immobilized recombinant human GM-CSF antigen was carried out using a Penta-His antibody (Qiagen, 1 μg/mL PBS) detected with horseradish peroxidase-conjugated goat anti mouse IgG Fab2 specific polyclonal antibody (Jackson, 1 μg/mL PBS). The signal was developed by adding ABTS (2,2'-Azino-di[3-ethylbenzthiazoline sulfonate (6)] diammonium salt) substrate solution and detected at a wavelength of 405 nm. The OD-values (y axis) were measured at 405 nm by an ELISA reader. Clone numbers are presented on the x axis, the murine anti human-GM-CSF antibody 7A6 and an irrelevant SCA-containing periplasmic preparation was used as a positive control.

In contrast to the positive control murine mAb 7A6 and the periplasmic preparation containing an irrelevant SCA ("neg. SCA"), some of the periplasmic preparations containing the maternal SCA showed some positivity, indicating the presence of the His-tagged SCA (as depicted in FIG. 2). All values were normalized against a PBS control. Although there is an indication of periplasmically produced maternal SCA, the detected signals could also be due to a contamination with cracked cytoplasmic contents including misfolded SCA in inclusion bodies.

To rule out the possibility that the missing binding activity of the maternal SCAs expressed in *E. coli* periplasm is due to a non-functional nucleic acid molecule derived from a cloning artefact, the clone 8 was used for plasmid preparation. Clone 8 was chosen because of its poor ELISA signal and, therefore, its assumed potential of not having a correct SCA sequence. The respective DNA sequence of the maternal SCA clone was confirmed by sequencing and did not show any indication of incorrect cloning or nonfunctional expression due to DNA aberrations.

2.3. Cloning of the Maternal SCA into the Vector pBAD-HisA for Cytoplasmic Expression and Inclusion Body Production For the expression of the maternal SCA in the insoluble inclusion body fraction of *E. coli*, the gene coding for the maternal SCA was subcloned into the pBAD expression plasmid. The maternal SCA gene was cut using the restriction enzymes NcoI and NotI and was cloned into the vector pBAD-H isA which had been precut using NcoI and NotI, thereby resulting in the expression plasmid pBAD-maternal SCA-HisA.

2.4. Refolding of Maternal SCA from Inclusion Bodies

The aim of this experiment is the production of insoluble protein in inclusion bodies in *E. coli* and the refolding of said insoluble protein from inclusion bodies.

For the production of inclusion bodies of the maternal SCA, BL21 DE3 (Novagen, USA) were transformed with the expression plasmid pBAD-maternal SCA-H isA. Single colonies were used for inoculation of 60 mL of selective medium overnight. For the production culture, 500 mL of selective medium were inoculated with a 1:50 dilution of the cell culture grown overnight. Cells were grown shaking at 37° C. to reach an optical density at 600 nm of 0.75. Induction of protein production was initiated by addition of 0.2% L-arabinose to the cell culture. After four hours of induction of protein production at 37° C. the cells were harvested by centrifugation and the cell pellet was used for the inclusion body purification.

For the purification of the inclusion bodies the cell pellet was resuspended in 10 mL of lysis buffer containing 50 mM Tris-HCl, pH 8.0, 2 mM EDTA and 100 μg/mL lysozyme. The resuspended cells were exposed to three freeze (−80° C.)-thaw (37° C.) cycles. After the third thaw, DNAse and $MgSO_4$ were added to final concentrations of 20 μg/mL, and the culture was subsequently incubated at 37° C. for 30 min. The samples were spun at approximately 20000 g for 30 min to separate inclusion body material from the soluble cellular proteins. The protein was then solubilized in 5 mL solubilization buffer (6 M GuHCl, 200 mM NaCl, 100 mM Tris-HCl and 1 mM EDTA, pH 8.3). Ten mM beta-mercaptoethanol was added to the solubilized inclusion bodies and the solution was incubated overnight at 4° C. The sample was spun at approximately 25000 g for 30 min to remove any insoluble material.

The refolding of the inclusion bodies was performed as previously described (Sinacola, J. R.; Robinson, A. S., Protein Expression and Purification 26 (2002) 301-8) using the controlled dilution/filtration (CDF) method. Five mL of solubilized and reduced SCA was transferred to a standard 200 mL ultrafiltration stirred cell (Amicon) containing a water-washed polyethersulfone membrane with a nominal molecular weight limit of 10 kDa (Millipore). Cycles of solubilization buffer addition (equal to sample volume) followed by filtration at 25-30 psig to the original sample volume (5 mL) were repeated at room temperature until the reducing agent concentration was reduced 1000-fold, requiring approximately 45 min. The stirred cell was transferred to a 4° C. room and connected to a HPLC pump. Cold buffer containing 200 mM NaCl, 100 mM Tris-HCl and 1 mM EDTA at pH 8.3 (salt buffer) was slowly pumped into the stirred cell to reduce the denaturant concentration by dilution in a controlled manner. The guanidine hydrochloride concentration was reduced to 2 M by a constant rate of salt buffer addition over 100 min. Addition of buffer containing 800 mM L-arginine, 200 mM NaCl, 100 mM Tris-HCl, 1 mM EDTA and 750 μM GSSG at pH 8.3 at a constant rate over 1 h was used to transition the sample from 2 to 1 M guanidine hydrochloride. The guanidine hydrochloride concentration was then reduced to 0.25 M over a 90 min period by a constant rate of addition of the original buffer lacking the folding additives. The sample was then concentrated via ultrafiltration to its original volume in an ice water bath. Cycles of salt buffer addition (equal to sample volume) followed by filtration to the original volume were repeated approximately every 5 min to reduce the guanidine hydrochloride concentration to less than 1 mM. After the final filtration step, the sample was allowed to stir in the ice water for several minutes before removal from the stirred cell. The sample was briefly stored at 4° C., prior to analysis.

2.5. Characterization of Functionality of Maternal mAb and Maternal SCA 2.5.1 Binding to Recombinant Human GM-CSF (rhGM-CSF) as Determined by Surface Plasmon Resonance (SPR)

The aim of this experiment is the functional characterization of the maternal mAb and the derived maternal SCA with respect to their binding properties to the native antigen hGM-CSF. Equilibrium and kinetic binding experiments were performed using surface plasmon resonance on the BIAcore™ 2000, Biacore AB (Uppsala, Sweden) with a flow rate of 5 μL/min and HBS-EP (0.01 M HEPES, pH 7.4, 0.15 M NaCl, 3 mM EDTA, 0.005% surfactant P20) as running buffer at 25° C. rhGM-CSF produced in *E. coli* was immobilized onto flow cells 2-4 on a CM5 sensor chip. The chip surface was activated injecting 80 μL of 0.1 M sodium-hydroxysuccinimid, 0.4 M N-ethyl-N'(3-dimethylaminepropyl)-carbodiimid (NHS/EDC). The antigen was coupled by manual injection of 10 μg/mL rhGM-CSF in 0.01 M sodium-acetate, pH 4.7. Different densities of antigen were immobilized on flow cells 2-4 adjusting the amount of manual injection times. Flow cell 1 was left unmodified while flow cell 2 was coated with the highest density of rhGM-CSF (800 RU). Flow cell 3 was coated with 50% of the amount of antigen immobilized on flow cell 2 and flow cell 4 was coated with lowest density of rhGM-CSF (typically 10%). The activated surface of the sensor chip was blocked injecting 85 μL of 1 M ethanolamine and the chip was left to equilibrate overnight with a constant flow of 5 μL/min of HBS-EP.

Figure 3:
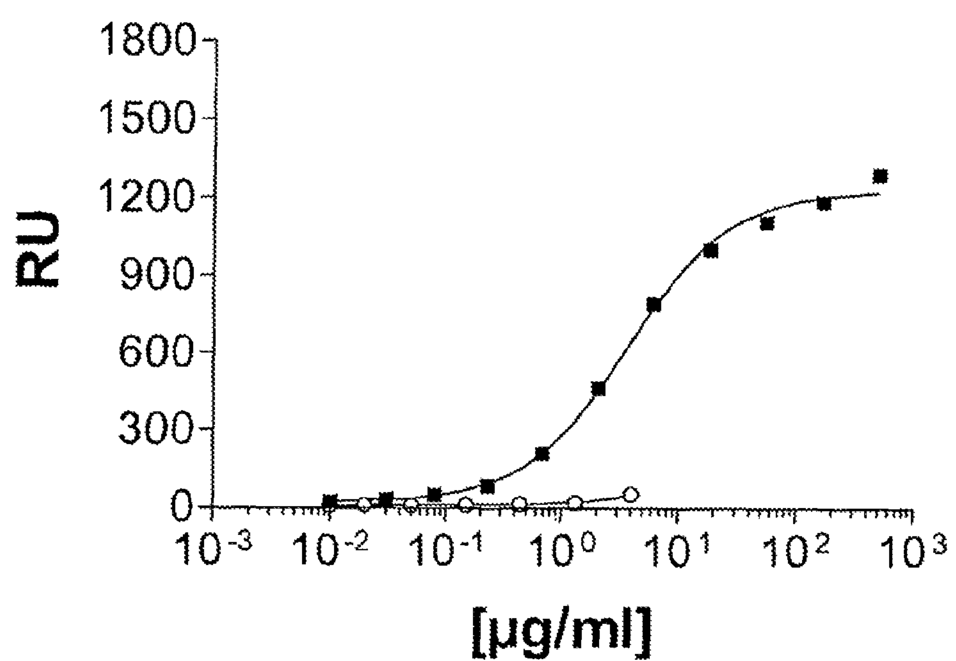
FIG. 3: Binding of maternal mAb and refolded maternal SCA to recombinant human GM-CSF (rhGM-CSF) immobilized on BIAcore sensor chip by surface plasmon resonance. Equilibrium binding of the maternal mAb (filled squares) and refolded maternal SCA (open circles) were measured injecting 10 μL of protein solution at concentrations ranging from 1 mg/mL to 6 ng/mL and monitoring the dissociation for 100 sec. Protein was buffered in HBS-EP. The relative response signal was determined at 100 sec of dissociation and plotted against the respective protein concentration. The data were fitted for half maximal binding at equilibrium (KD) using the Prism software program. The maternal mAb binds to the immobilized rhGM-CSF with an apparent equilibrium binding constant KD of 5 μg/mL (30 nM).

Equilibrium binding of the maternal mAb and refolded maternal SCA protein was measured by injecting 10 μL of protein solution at concentrations ranging from 1 mg/mL to 6 ng/mL and monitoring the dissociation at 25° C. for 100 sec. Protein was buffered in HBS-EP. The non-specific background adsorption of protein to the unmodified sensor chip surface (FC1) was subtracted from the response signal in the rhGM-CSF immobilized flow cells (FC2, FC3, FC4). The relative response signal (FC2-1, FC3-1, FC4-1) was determined after 100 sec of dissociation and plotted against the respective protein concentration. The data were fitted for half maximal binding at equilibrium (KD) using the Prism software (FIG. 3).

The maternal mAb binds to the immobilized rhGM-CSF with an apparent equilibrium binding constant KD of 5 μg/mL (30 nM). The binding of the mAb derived maternal SCA could not be determined with sufficient accuracy. The quality of the available soluble material expressed in the periplasm as well as refolded from inclusion bodies of *E. coli* did not suffice for reliable equilibrium. Nor could kinetic affinity measurements by SPR be made.

2.5.2 Binding to rhGM-CSF by Maternal, Refolded SCA Determined by ELISA

The aim of this experiment was to show with the very limited amount of protein that was available from refolding experiments that the maternal SCA exhibits some residual binding properties of the parent maternal mAb. The sensitivity of the binding experiment via ELISA is higher as compared to the SPR measurements due to the signal amplification that is intrinsic to the ELISA setup.

ELISA experiments were carried out by coating the rhGM-CSF onto wells of 96-well plastic plates (Nunc, maxisorb) typically at 4° C. overnight. The antigen was then removed, wells washed once with PBS/0.05% Tween 20 and subsequently blocked with PBS/3% BSA for at least one hour. After removal of the blocking solution, refolded maternal SCA and SCA controls were added to the wells and incubated for typically one hour at room temperature. The wells were then washed three times with PBS/0.05% Tween 20. Detection of SCA and control antibodies bound to immobilized antigen was carried out using a monoclonal murine anti-His6 antibody (Qiagen anti-PentaHis typically at a final concentration of 1 μg/mL PBS) detected with a peroxidase-labeled polyclonal goat anti-(mouse Fab-fragment) antibody (Dianova, 1 μg/mL PBS). The signal was developed by adding ABTS substrate solution and measured at a wavelength of 405 nm. Background reaction of an unrelated sample SCA with the coated antigen was determined (neg. control) as well as specific binding of an SCA known to interact with high specificity with the rhGM-CSF (pos. control) (FIG. 4). The refolded maternal SCA shows a clear binding signal to the antigen rhGM-CSF.

2.5.3 Inhibition of rhGM-CSF Dependent Proliferation of TF-1 Cells by Maternal mAb and Maternal SCA The aim of this experiment is the characterization of the maternal mAb and maternal SCA neutralization activity with the hGM-CSF dependant cell line TF-1 (DSMZ ACC 334). TF-1 cells were cultivated in RPMI 1640 medium GIBCO (L-glutamine, phenol-red free), 10% heat inactivated FCS in the presence of 2.5 ng/mL rhGM-CSF as described by the distributor (Deutsche Sammlung von Mikroorganismen and Zellkulturen GmbH, Braunschweig, Germany) Cells were grown to a cell density of 0.5×10exp6 cells/mL. For the proliferation assay TF-1 cells were harvested by centrifugation at 180×g for 4 min. and washed with 1×PBS (Dulbecco's, GIBCO). Cells were resuspended at a final concentration of 1×10exp5 cells/mL in RPMI 1640, 10% FCS and 90 μL cell suspension per Microtest flat bottom cell culture plate well were used (0.9×10exp4 cells/well). A final concentration of 0.3 ng/mL rhGM-CSF was used to stimulate the proliferation of the TF-1 cells. For neutralization of GM-CSF dependent proliferation maternal mAb in 1×PBS was added in a dilution series with final protein concentrations ranging from 30 ng/mL to 1 pg/mL. TF-1 cells were incubated at 37° C. at 5% $CO_2$ for 72 h. After 72 h the proliferative status of the TF-1 cells was determined with a colorimetric assay based on the cleavage of tetrazolium salts (WST-1, Roche) by mitochondrial dehydrogenase in viable cells. The formazan dye formed by metabolically active cells was quantitated by measuring its absorbance with an ELISA reader at 450 nm. The absorption (A) at 450 nm was plotted against the determined protein concentration. The data were fitted for half maximal inhibition of proliferation ($IC_{50}$) using the non-linear regression curve fit of the Prism software (FIG. 5).

The maternal mAb inhibits the rhGM-CSF induced proliferation of the TF-1 cells with an $IC_{50}$ of 1.2 ng/mL (80 pM). The neutralization of the mAb-derived maternal SCA could not be determined with sufficient accuracy. The quality of the available soluble material expressed in the periplasm as well as refolded from inclusion bodies of *E. coli* did not suffice for reliable data on inhibition of GM-CSF dependent TF-1 proliferation. The lack of inhibition of the maternal SCA derived from refolding experiments might be due to an intrinsic instability of the protein that is more exposed to unfolding conditions in the 72 h lasting TF-1 proliferation inhibition experiment at 37° C. that in the ELISA binding experiment where the sample is incubated for less than two hours at 25° C.

2.5.4 Inhibition of Binding of hGM-CSF-FITC to TF-1 Cells by Maternal, Refolded mAb and Maternal SCA The aim of this experiment is to show that the maternal mAb and the derived maternal SCA are capable of inhibiting biding of hGM-CSF to TF-1 cell surface displayed GM-CSF receptor complex. The neutralizing antibody constructs compete for the receptor-binding epitope on the hGM-CSF molecule. The hGM-CSF is no longer able to bind to the TF-1 cell surface displayed hGM-CSF receptor complex. This competitive binding for the same epitope on the antigen is shown by a loss in fluorescence staining of TF-1 cells by fluorescein labelled hGM-CSF (hGM-CSF-FITC) in a flow cytometry-based assay.

For the flow cytometry based assay a final concentration of 0.4 μg/mL hGM-CSF-FITC conjugate in PBS was incubated with maternal mAb in concentrations ranging from 30 μg/mL to 0.014 μg/mL or the refolded maternal SCA. The protein samples were left to equilibrate at 25° C. for 1 h prior to addition of TF-1 cell suspension. The TF-1 were cultivated in RPMI 1640 medium GIBCO (L-glutamine, phenol-red free), 10% heat inactivated FCS in the absence of rhGM-CSF overnight. A final concentration of 2×10exp6 cells/mL and 150 μL of cell suspension was used per sample. The cells were harvested by centrifugation at 500 G at 4° C. for 3 min and washed twice with FACS buffer. The washed cells were resuspended in 100 μL of pre-equilibrated protein sample containing the hGM-CSF-FITC and maternal mAb or maternal SCA respectively. The samples were incubated at 4° C. for 60 min. After two further washes the cells were resuspended in 150 μL ice cold FACS buffer and subsequently analysed by flow cytometry (FIG. 6).

The mean fluorescence intensity (MFI) was plotted against the concentration of the used maternal mAb and maternal SCA. A clear concentration-dependent loss of fluorescence intensity of the TF-1 cells was observed with the maternal mAb. The refolded maternal SCA induced some residual concentration dependent decrease in fluorescence intensity of the hGM-CSF-FITC labelled TF-1 cells, indicating its activity.

The above experiments show that the maternal SCA did in fact have the intended amino acid sequence, since otherwise, no binding signal by ELISA and no competition binding as seen in the TF-1 assay would have been observed for the maternal SCA following refolding. However, the fact that refolding of the maternal SCA from inclusion bodies was necessary before any such behavior could be observed indicates that the maternal SCA as originally expressed in *E. coli* was not recombinantly expressible in soluble form. As such, the maternal mAb represents a "source immunoglobulin" and the maternal SCA represents a "corresponding SCA" in the sense of these terms as used and defined hereinabove.

Example 3

Construction of the Antibody Libraries and Phage Display Selections

3.1 Isolation of RNA from Selected IgD-Positive B-Cells 100 mL blood were taken from five healthy human donors. Peripheral blood mononuclear cells (PBMCs) were isolated by a ficoll-gradient according to standard methods. To select IgD-positive cells, 1 mL anti-mouse IgG-beads (CELLection™ Pan Mouse IgG Kit; DYNAL) were coated with 20 μg mouse anti-human IgD-antibody (PharMingen). Approximately 2.5×10exp7 PBMCs were added to the beads and incubated at 4° C. for 15 minutes. After washing four times with 1 mL RPMI-medium (BioChrom) IgD-positive cells were released from the beads by adding 8 μL release buffer (DNase) and transferred to a fresh tube. By this method 0.9×10exp5 to 3.7×10exp6 IgD-positive cells could be obtained. Total RNA was isolated from IgD-positive cells using the RNeasy® Midi Kit (QIAGEN) following the manufacturer's instructions. cDNA was synthesized according to standard methods (Sambrook, Cold Spring Harbor Laboratory Press 1989, Second Edition).

3.2 PCR-Amplification of Variable Light Chain Regions (VL-Regions)

For the isolation of light chain V-region DNA, RT-PCR was carried out using V-kappa-(5'-huVK1-SacI-2001 (5'-GAGCCGCACG AGCCCGAGCT CCAGATGACC CAGTCTCC-3'(SEQ ID NO:64)), 5'-huVK2/4-SacI-2001 (5'-GAGCCGCACG AGCCCGAGCT CGTGATGACY CAGTCTCC-3' (SEQ ID NO:65)), 5'-huVK3-SacI-2001 (5'-GAGCCGCACG AGCCCGAGCT CGTGWTGACR CAGTCTCC-3' (SEQ ID NO:66)), 5'-huVK5-SacI-2001 (5'-GAGCCGCACG AGCCCGAGCT CACACTCACG CAGTCTCC-3' (SEQ ID NO:67)), 5'-huVK6-SacI-2001 (5'-GAGCCGCACG AGCCCGAGCT CGTGCTGACT CAGTCTCC-3' (SEQ ID NO:68)), 3'-hu-Vk-J1-SpeI-BsiWI (5'-GACGACACTA GTTGCAGCCA CCGTACGTTT GATTTCCACC TTGGTCC-3' (SEQ ID NO:69)), 3'-hu-Vk-J2/4-SpeI-BsiWI (5'-GACGACACTA GTTGCAGCCA CCGTACGTTT GATCTCCASC TTGGTCC-3' (SEQ ID NO:70)), 3'-hu-Vk-J3-SpeI-BsiWI (5'-GACGACACTA GTTGCAGCCA CCGTACGTTT GATATCCACT TTGGTCC-3' (SEQ ID NO:71)), 3'-hu-Vk-J5-SpeI-BsiWI (5'-GACGACACTA GTTGCAGCCA CCGTACGTTT AATCTCCAGT CGTGTCC-3' (SEQ ID NO:72)) primer sets. RNA from IgD-positive B-cells was transcribed into cDNA (as described above) and used as template DNA in PCR reactions. Per PCR reaction, one 5'-primer was combined with one 3'-primer. The number of different PCR reactions was determined by the number of possible combinations of 5'- and 3'-primers.

The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

3.3 Library Construction—Cloning of the Human VL Pool

A phage display library was generally constructed based on standard procedures, as for example disclosed in "Phage Display: A Laboratory Manual"; Ed. Barbas, Burton, Scott & Silverman; Cold Spring Harbor Laboratory Press, 2001. The primers chosen for PCR amplification gave rise to 5'-SacI and 3'-SpeI recognition sites for the light chain V-fragments. Two ligation reactions were set up, each consisting of 400 ng of the kappa light chain fragments (SacI-SpeI digested) and 1400 ng of the plasmid pBluescript KS+ (SacI-SpeI digested; large fragment). The two resulting antibody V-light chain pools were then each transformed into 300 μL of electrocompetent *Escherichia coli* XL1 Blue by electroporation (2.5 kV, 0.2 cm gap cuvette, 25 Microfaraday, 200 Ohm, Biorad gene-pulser) resulting in a library size of 5.8×10exp8 independent clones in total.

Kappa (light chain) DNA-fragments from the different PCR amplifications were weighted for each ligation as follows: Each 5'-primer defines a specific group. Within these groups the 3'-primers define the subgroups. The subgroups were weighted 1:2:1:1 corresponding to the primers 3'-hu-Vk-J1-SpeI-BsiWI: 3'-hu-Vk-J2/4-SpeI-BsiWI: 3'-hu-Vk-J3-SpeI-BsiWI: 3'-hu-Vk-J5-SpeI-BsiWI. The groups were weighted according to their germline distribution 1:1:1:0.2:0.2 corresponding to the primers 5'-huVK1-Sac-2001: 5'-huVK3-Sac-2001: 5'-huVK2/4-Sac-2001: 5'-huVK5-Sac-2001: 5'-huVK6-Sac-2001.

After electroporation the assay was incubated in SOC broth (Fluka) for phenotype expression. The cultures were then incubated each in 500 mL of SB selection medium containing 50 ng/mL Carbenicillin and 2% w/v Glucose overnight. The next day, cells of the cultures were harvested by centrifugation and plasmid preparation carried out using a commercially available plasmid preparation kit (Qiagen).

3.4 Construction of the Antibody Library—Human VL—Maternal VH

A PCR was carried out to amplify the maternal VH from the vector containing the maternal VH for SCA expression described above in example 2. For amplification a PCR protocol was carried out according to standard procedures using the 5'-primer MVH8 (5'-GAG GTT CAG CTC GAG CAG TCT GGA GCT-3' (SEQ ID NO:73)) and the 3'-primer 3'-MuVHBstEII (5'-TGA GGA GAC GGT GAC CGT GGT CCC TTG GCC CCA G-3' (SEQ ID NO:74)).

After purification of the approximately 350 bp amplification product from an analytical agarose gel, the DNA fragment was cut with the restriction enzymes BstEII and XhoI. The phagemid pComb3H5BHis (vector described in thesis dissertation of Dr. Ralf Lutterbüse) was digested accordingly and the large fragment ligated with the above mentioned fragment. After transformation into *E. coli* XL1 blue, a single clone was cultivated in 100 mL SB medium (containing 50 μg/mL Carbenicilline) and the plasmid was prepared according to standard protocols. The successful cloning was confirmed by sequencing the insert (Sequiserve, Munich). This vector pComb3H5BHis/maternalVH was restricted with the restriction enzymes SacI and SpeI. The large vector fragment was isolated. Plasmid-DNA containing the VK-library from example 3.3 was restricted with the restriction enzymes SacI and SpeI. The small VK fragment band (approx 350 bp) was isolated.

1200 ng of the vector fragment were ligated with 400 ng of the VK fragments and transformed into 300 μL of electrocompetent *E. coli* XL1 Blue by electroporation (2.5 kV, 0.2 cm gap cuvette, 25 MICROFD, 200 Ohm) resulting in a total SCA library size of 2.8×10exp8 independent clones.

After phenotype expression and slow adaptation to Carbenicillin, the antibody library was transferred into SB-Carbenicillin (50 μg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a half human SCA-fragment and displayed the corresponding SCA-protein as a translational fusion to phage coat protein III.

3.5 Phage Display Selection of a Human VL

The phage library carrying the cloned SCA-repertoire was harvested from the culture supernatant by PEG8000/NaCl precipitation and centrifugation. Then approximately 1×10exp11 to 1×10exp12 SCA phage particles were resuspended in 0.4 mL of PBS/0.1% BSA and incubated with recombinant biotinylated soluble human GM-CSF (produced in *E. coli* as described above in example 1) for 2 h with gentle agitation in a total volume of 0.5 mL (Concentrations. Then 6.7×10exp7 streptavidine magnetic beads (Dynabeads M-280-Streptavidine, Dynal) were added and further incubated under gentle agitation for 30 minutes.

SCA phage that did not specifically bind to the target antigen were eliminated by washing steps with PBS/0.1% BSA. For that purpose the biotinylated antigen—streptavidin bead complexes (with the potential SCA binders) were collected with a magnet and resuspended in 1 mL of the washing solution (one washing step). This washing procedure was repeated up to four times in further rounds.

After washing, binding entities were eluted by using HCl-Glycine pH 2.2. Following neutralization with 2 M Tris pH 12, the eluate was used for infection of a fresh uninfected *E. coli* XL1 Blue culture. To elute remaining high binding entities this step was repeated using HC1-Glycine pH 1.0. This second eluate was again neutralized and used for infection of a fresh uninfected *E. coli* XL1 Blue culture. Both infected *E. coli* cultures were then mixed and cells that were successfully transduced with a phagemid copy, encoding a human SCA-fragment, were again selected for Carbenicillin resistance and subsequently infected with VCMS13 helper phage to start the second round of antibody display and in vitro selection.

After three rounds of production and selection for antigen-binding SCA-displaying phage the culture supernatant were harvested. Later, 5 mL of a fresh *E. coli* XL1 blue culture (OD>1) was infected with the SCA phages from 2 mL of the above mentioned SCA phage containing culture supernatants (after the third round of phage display selection).

After phenotype expression and slow adaptation to Carbenicillin the reinfected antibody library was transferred into SB-Carbenicillin (50 μg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a half human SCA-fragment and displayed the corresponding SCA-protein as a translational fusion to phage coat protein III. The phage library carrying the cloned SCA-repertoire was harvested from the culture supernatant by PEG8000/NaCl precipitation and centrifugation.

Then approximately 1×10exp11 to 1×10exp12 SCA phages were resuspended in 1.5 mL of PBS/0.1% BSA and split into three equal aliquots (A, B and C).

Fourth round (=first round on Leukine material): A and B were incubated with 10 nM recombinant biotinylated soluble human GM-CSF (Leukine, as described in example 1) for 1 h under gentle agitation in a total volume of 0.5 mL. Then 6.7×10exp7 streptavidine magnetic beads (Dynabeads M-280-Streptavidine, Dynal) were added and further incubated under gentle agitation for 30 minutes. C was incubated with 1 nM recombinant biotinylated soluble human GM-CSF (Leukine, as described in example 1) for 1 h under gentle agitation in a total volume of 0.5 mL. Then 6.7×10exp7 streptavidine magnetic beads (Dynabeads M-280-Streptavidine, Dynal) were added and further incubated under gentle agitation for 30 minutes.

For A, B and C, SCA phage that did not specifically bind to the target antigen were eliminated by washing steps with PBS/0.1% BSA. For that purpose the biotinylated antigen—streptavidine bead complexes (with the potential SCA binders) were collected using a magnet and resuspended in 1 mL of the washing solution (one washing step). This washing procedure was repeated four to ten times.

After washing, binding entities were eluted a) by using HCl-Glycine pH 2.2 and after neutralization with 2 M Tris pH 12, the eluate was used for infection of a fresh uninfected *E. coli* XL1 Blue culture and, subsequently, b) by adding 200 μL of a fresh *E. coli* XL1 Blue directly to the antigen bead complexes for 10 minutes. Both cultures a) and b) were then mixed and cells that successfully transduced with a phagemid copy, encoding a human SCA-fragment, were again selected for Carbenicillin resistance and subsequently infected with VCMS13 helper phage to start the second round of antibody display and in vitro selection.

Two further rounds of selections were carried out for the three antibody libraries A, B and C. Antigen concentrations were decreased during selection to the final concentrations as follows:

Library A: fifth round (=second round on Leukine material) 10 nM, sixth round (=third round on Leukine material) 1 nM.

Library B: fifth round (=second round on Leukine material) 1 nM, sixth round (=third round on Leukine material) 0.1 nM.

Library C: fifth round (=second round on Leukine material) 0.1 nM, sixth round (=third round on Leukine material) 0.1 nM.

Plasmid DNA corresponding to 4, 5 and 6 rounds of panning was isolated from *E. coli* cultures. For the production of soluble SCA-protein, VL-DNA fragments were excised from the plasmids (SacI-SpeI), and cloned via the same restriction sites in the plasmid pComb3H5BFlag/His with the maternal VH differing from the initial pComb3H5BHis/maternal VH in that it adds to the expression construct (e.g. SCA) a Flag-tag (TGDYKDDDDK (SEQ ID NO:75)) between the SCA and the His6-tag and having the phage gene III and the N2 domain deleted.

After ligation each pool (different rounds of panning) of plasmid DNA was transformed into 100 μL heat shock competent *E. coli* TG1 and plated on Carbenicillin LB-Agar. Single colonies were picked into 120 μL of LB carb (50 μg/mL) 1% glucose in 96-well plates (Greiner). The wells were sealed with a semipermeable membrane (Greiner) and the plates were incubated in a shaking incubator overnight at 37° C. (master plate).

Then, 10 μL of the master plate cultures were transferred into a second 96-well plate (working plate) containing 90 μL LB carb (50 μg/mL) 0.1% glucose per well. After incubation for 4 h in a 37° C. shaking incubator, SCA production was induced by adding 20 μL LB carb 6 mM IPTG to each well. After another incubation step overnight at 30° C. under shaking, cell were lysed in a 1 h room temperature incubation with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 2500 rpm (Hettich). The SCA-containing supernatants were then tested for binding in ELISA assays.

Detection of SCA-fragments bound to immobilized recombinant human GM-CSF antigen (Leukine) was carried out using a biotinylated anti-flag M2 (1 μg/mL PBS/1% BSA) detected with horseradish peroxidase-conjugated goat anti mouse Fab2 specific polyclonal antibody (Dianova, 1 μg/mL PBS/1% BSA). The signal was developed by adding ABTS substrate solution and detected at a wavelength of 405 nm.

From approximately 500 clones tested, most lysates showed strong ELISA signals in contrast to PBS as negative control on the recombinant antigen. The first 96 lysates were tested in a parallel experiment for unspecific binding to the blocking agent and no GM-CSF antigen. No significant detectable signal could be observed, indicating the specificity of the binding to the recombinant human GM-CSF. FIGS. 7 & 8 are illustrative of typical ELISA results.

The fact that SCAs were obtained that specifically bind to the human GM-CSF antigen clearly demonstrates that such SCAs produced using the method of the present invention were recombinantly solubly expressible. This is in stark contrast to the maternal SCA (i.e. the "corresponding antibody fragment" as defined hereinabove) which, after direct conversion from the source immunoglobulin but prior to performing the method of the invention, was not recombinantly solubly expressible. As such, the present results show that a "corresponding antibody fragment" which was originally not recombinantly solubly expressible was rendered so by employing the method of the invention.

3.6 Isolation of RNA from Peripheric Blood Mononuclear Cells (PBMCs)

100 mL blood were taken from five healthy human donors. Peripheral blood mononuclear cells (PBMCs) were isolated by a ficoll-gradient according to standard methods. Total RNA was isolated from PBMCs using the RNeasy® Midi Kit (QIAGEN) following the manufacturer's instructions. cDNA was synthesized according to standard methods (Sambrook, Cold Spring Harbor Laboratory Press 1989, Second Edition).

3.7 PCR-Amplification of Variable Heavy Chain Regions (VH-Regions)

3.7.1 Amplification of Human VH Fragments

For the isolation of human VH-regions, RT-PCR was carried out using a 5'-VH-specific primer set (5'-huVH1,3,5-XhoI-2001 (5'-AGG TGC AGC TGC TCG AGT CTG G-3' (SEQ ID NO:76)), 5'-huVH2-XhoI-2001 (5'-CAG RTC ACC TTG CTC GAG TCT GG-3' (SEQ ID NO:77)), 5'-huVH4-XhoI-2001 (5'-CAG GTG CAG CTG CTC GAG TCG GG-3' (SEQ ID NO:78)), 5'-huVH4B-XhoI-2001 (5'-CAG GTG CAG CTA CTC GAG TGG GG-3' (SEQ ID NO:79)), 5'-huVH6-XhoI-2001 (5'-CAG GTA CAG CTG CTC GAG TCA GG-3' (SEQ ID NO:80)) and a set of two 3'-VH-specific primers (3'-hu-VH-BstEII-2001 (5'-CTG AGG AGA CGG TGA CC-3' (SEQ ID NO:81)), 3'-hu-VH-J3-BstEII-2001 (5'-CTG AAG AGA CGG TGA CC-3' (SEQ ID NO:82)). Per PCR reaction, one 5'-primer was combined with one 3'-primer; the number of different PCR reactions was determined by the number of possible combinations of 5'- and 3'-primers. The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes.

3.7.2 Amplification of Human Lib134-VH Fragments

The second VH library was constructed and named Lib 134-VH. This VH-library consists of the human repertoire of FR1-CDR2-FR2-CDR2-FR3 from the PCR amplified VH-regions of the above described PBMC pool, linked operatively to the VH CDR3 of the maternal antibody followed by a human FR4 germline sequence.

For the isolation of human template VH-regions, RT-PCR was carried out using a 5'-VH-specific primer set (5'-huVH1, 3,5-XhoI-2001 (5'-AGG TGC AGC TGC TCG AGT CTG G-3'(SEQ ID NO:76)), 5'-huVH4-XhoI-2001 (5'-CAG GTG CAG CTG CTC GAG TCG GG-3' (SEQ ID NO:78)), 5'-huVH4B-XhoI-2001 (5'-CAG GTG CAG CTA CTC GAG TGG GG-3' (SEQ ID NO:79)) and a set of two 3'-VH-specific primers (3'-hu-VH-BstEII-2001 (5'-CTG AGG AGA CGG TGA CC-3' (SEQ ID NO:81)), 3'-hu-VH-J3-BstEII-2001 (5'-CTG AAG AGA CGG TGA CC-3' (SEQ ID NO:82)). Per PCR reaction, one 5'-primer was combined with one 3'-primer; the number of different PCR reactions was determined by the number of possible combinations of 5'- and 3'-primers. The PBMC cDNA (as described above of four donors only was used as a source of VH-genes). The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes. The amplificates with a size of approximately 350 bp were isolated according to standard methods.

For the isolation of Lib 134-VH-regions, RT-PCR was carried out in two steps. First, the human heavy chain VH-segments (FR1-CDR2-FR2-CDR2-FR3) were PCR-amplified from the isolated template VH fragments using the same 5'-VH-specific primer set as described above (5'-huVH1,3,5-XhoI-2001, 5'-huVH4-XhoI-2001, 5'-huVH4B-XhoI-2001) and a 3'-specific primer set (3'-Lib 134-VH-1A-MH3 (5'-GTA ATC AAA GTA GAC TGC TAT CAG ACC CGA TCT YGC ACA GTA ATA CAC GGC-3' (SEQ ID NO:83)), 3'-Lib 134-VH-1B-MH3 (5'-GTA ATC AAA GTA GAC TGC TAT CAG ACC CGA TCT YGC ACA GTA ATA CAY RGC-3' (SEQ ID NO:84)), 3'-Lib 134-VH-3A-MH3 (5'-GTA ATC AAA GTA GAC TGC TAT CAG ACC CGA TCT NGY ACA GTA ATA CAC RGC-3' (SEQ ID NO:85)), 3'-Lib 134-VH-3B-MH3 (5'-GTA ATC AAA GTA GAC TGC TAT CAG ACC CGA TCT NGC ACA GTA ATA CAA RGC-3' (SEQ ID NO:86)), 3'-Lib 134-VH-4-MH3 (5'-GTA ATC AAA GTA GAC TGC TAT CAG ACC CGA TCT SGC ACA GTA ATA CAC RGC-3' (SEQ ID NO:87)) for the human VH subfamilies 1, 3 and 4 matching in the very terminal region of FR3.

The following primer combinations were used:

a) 5'-huVH1,3,5-XhoI-2001×3'-Lib 134-VH-1A-MH3
b) 5'-huVH1,3,5-XhoI-2001×3'-Lib 134-VH-1B-MH3
c) 5'-huVH1,3,5-XhoI-2001×3'-Lib 134-VH-3A-MH3
d) 5'-huVH1,3,5-XhoI-2001×3'-Lib 134-VH-3B-MH3
e) 5'-huVH4-XhoI-2001×3'-Lib 134-VH-4-MH3
f) 5'-huVH4B-XhoI-2001×3'-Lib 134-VH-4-MH3

Per PCR reaction, one 5'-primer was combined with the 3'-primer; the number of different PCR reactions was determined by the number of possible combinations of 5'- and the 3'-primer. The following PCR-program was used for amplification: Denaturation at 94° C. for 15 seconds, primer annealing at 52° C. for 50 seconds and primer extension at 72° C. for 90 seconds was performed over 40 cycles, followed by final extension at 72° C. for 10 minutes. Through this PCR step and the respective 3'-primer sequence, the human VH segments are prolonged for a part of the maternal VH CDR3, which then in turn is the priming site for the second step PCR 3'-primer.

These VH-(FR1-CDR2-FR2-CDR2-FR3) DNA-fragments were then used as templates in this second PCR reaction using again the respective 5'VH-specific primer and an universal 3' primer matching to the universal 3'-terminus of the amplified DNA-fragments (3'-Lib 134-JH3-BstE2, 5'-AGA GAC GGT GAC CAT TGT CCC TTG GCC CCA GTA ATC AAA GTA GAC TGC-3' (SEQ ID NO:88)).

The following PCR-program was used for amplification:

Denaturation at 94° C. for 15 seconds, primer annealing at 52° C. for 50 seconds and primer extension at 72° C. for 60 seconds were performed over 40 cycles, followed by final extension at 72° C. for 10 minutes. The DNA V-fragments were isolated according to standard protocols.

3.8 Library Construction—Cloning of the Human VH Pool

In a second round of the foregoing method, one VL identified in the first, previous round was chosen, and subsequently combined with a library of human VH fragments with the aim of generating a "second antibody fragment". A phage display library was generally constructed based on standard procedures, as for example disclosed in "Phage Display: A Laboratory Manual"; Ed. Barbas, Burton, Scott & Silverman; Cold Spring Harbor laboratory Press, 2001.

3.8.1 Cloning of Human VH Fragments

Heavy chain DNA fragments were first subcloned into pBluescript KS vector (Stratagene). To this end, 400 ng of VH fragments (XhoI-BstEII digested) were each ligated with 1200 ng pBluescript KS (XhoI-BstEII digested) and transformed into electrocompetent *E. coli* XL1 Blue by electroporation (as described for the light chains) resulting in a library of 3.4×10exp8 independent clones in total.

Heavy chain DNA-fragments from the different PCR amplifications were weighted for each ligation as follows: Each 5'-primer defines a specific group. Within these groups the 3'-primers define the subgroups. The subgroups were weighted 3:1 corresponding to the primers 3'-hu-VH-BstEII-2001: 3'-hu-VH-J3-BstEII. The groups were weighted according to their germline distribution 7:1:1:1:0.3 corresponding to the primers 5'-huVH1,3,5-XhoI-2001: 5'-huVH2-XhoI-2001: 5'-huVH4-XhoI-2001: 5'-huVH4B-XhoI-2001: 5'-huVH6-XhoI-2001.

One ligation reaction was set up, consisting of 400 ng of human VH fragment pool (from the pBluescript/VH as mentioned above, XhoI-BstEII digested) and 1200 ng of the plasmid pComb3H5BHis/B32oN-45VL ((the B32oN-45VL nucleic acid molecule was cloned via the restriction sites SacI and SpeI into pComb3H5BHis according to standard procedures) XhoI-BstE2 digested; large fragment). The resulting antibody human VH pool was then transformed into 300 μL of electrocompetent *Escherichia coli* XL1 Blue by electroporation (2.5 kV, 0.2 cm gap cuvette, 25 microFD, 200 Ohm, Biorad gene-pulser) resulting in a library size of 1.1×10exp9 independent clones in total.

After electroporation the assay was incubated in SOC for phenotype expression. The cultures were then incubated each in 500 mL of SB selection medium containing 50 μg/mL Carbenicillin and 2% v/v Glucose overnight. The next day, cells of the cultures were harvested by centrifugation and plasmid preparation carried out using a commercially available plasmid preparation kit (Qiagen) to preserve the DNA library.

1.5 μg of this plasmid pool encoding the respective SCA pool were then electroporated into *E. coli* XL1blue (2.5 kV, 0.2 cm gap cuvette, 25 microFD, 200 Ohm, Biorad gene-pulser) resulting in a library size of 2.0×10exp9 independent clones in total.

After phenotype expression and slow adaption to Carbenicillin the antibody library was transferred into SB-Carbenicillin (50 μg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a human SCA-fragment and displayed the corresponding SCA-protein as a translational fusion to phage coat protein III.

3.8.2 Cloning of Human Lib134-VH Fragments

Heavy chain DNA-fragments from the different PCR amplifications were weighted for each ligation as follows: a:b:c:d:e:f=3:1:3:1:1:1, wherein a-f have the following meanings:

a) 5'-huVH1,3,5-XhoI-2001×3'-Lib 134-VH-1A-MH3×3'-Lib 134-JH3-BstE2
b) 5'-huVH1,3,5-XhoI-2001×3'-Lib 134-VH-1B-MH3×3'-Lib 134-JH3-BstE2
c) 5'-huVH1,3,5-XhoI-2001×3'-Lib 134-VH-3A-MH3×3'-Lib 134-JH3-BstE2
d) 5'-huVH1,3,5-XhoI-2001×3'-Lib 134-VH-3B-MH3×3'-Lib 134-JH3-BstE2
e) 5'-huVH4-XhoI-2001×3'-Lib 134-VH-4-MH3×3'-Lib 134-JH3-BstE2
f) 5'-huVH4B-XhoI-2001×3'-Lib 134-VH-4-MH3×3'-Lib 134-JH3-BstE2

One ligation reaction was set up consisting of 400 ng of human Lib 134-VH fragment pool (XhoI-BstE2I digested) and 1200 ng of the plasmid pComb3H5BHis/B32oN-45VL ((the B32oN-45VL nucleic acid molecule was cloned via the restriction sites SacI and SpeI into pComb3H5BHis according to standard procedures) XhoI-BstE2 digested; large fragment). The resulting antibody human VH pool was then transformed into 300 μL of electrocompetent *Escherichia coli* XL1 Blue by electroporation (2.5 kV, 0.2 cm gap cuvette, 25 Microfaraday, 200 Ohm, Biorad gene-pulser) resulting in a library size of 1.6×10exp8 Lib independent clones in total.

After electroporation the assay was incubated in SOC broth (Fluka) for phenotype expression. The cultures were then incubated each in 500 mL of SB selection medium containing 50 μg/mL Carbenicillin and 2% v/v Glucose overnight. The next day, cells of the cultures were harvested by centrifugation and plasmid preparation carried out using a commercially available plasmid preparation kit (Qiagen) to preserve the DNA library.

1.5 μg of this plasmid pool encoding the respective SCA pool were then electroporated into *E. coli* XLlblue (2.5 kV, 0.2 cm gap cuvette, 25 microFD, 200 Ohm, Biorad gene-pulser) resulting in a library size of 2.4×10exp9 independent clones in total. After phenotype expression and slow adaption to Carbenicillin the antibody library was transferred into SB-Carbenicillin (50 μg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a (mostly) human SCA-fragment and displayed the corresponding SCA-protein as a translational fusion to phage coat protein III.

3.9 Phage Display Selection for a Human VH

The phage libraries from 3.8.1 and 3.8.2 carrying the cloned SCA-repertoire was harvested from the culture supernatant by PEG8000/NaCl precipitation and centrifugation.

The same protocol was carried out for both libraries:

Approximately 1×10exp11 to 1×10exp12 SCA phages were resuspended in 0.4 mL of PBS/0.1% BSA and incubated with a) recombinant biotinylated soluble human GM-CSF (*E. coli* material, as described in example 1) and b) recombinant biotinylated soluble human GM-CSF (Leukine, as described in example 1) for 1 h under gentle agitation in a total volume of 0.5 mL. Then 6.7×10exp7 streptavidine magnetic beads (Dynabeads M-280-Streptavidine, Dynal) were added and further incubated under gentle agitation for 30 minutes.

SCA phage that did not specifically bind to the target antigen were eliminated by washing steps with PBS/0.1% BSA. For that purpose the biotinylated antigen—streptavidine bead complexes (with the potential SCA binders) were collected via a magnet and resuspended in 1 mL of the washing solution (one washing step). This washing procedure was repeated up to four times. After washing, binding entities were eluted by using HCl-Glycine pH 2.2 and after neutralization with 2 M Tris pH 12, the eluate was used for infection of a fresh uninfected *E. coli* XL1 Blue culture.

To elute remaining high binding entities the beads were resuspended directly in 200 μL of a fresh *E. coli* XL1 blue culture (OD600≥0.5) and incubated for 10 minutes under gentle agitation. Both cultures were then mixed and cells successfully transduced with a phagemid copy, encoding a human SCA-fragment, were again selected for Carbenicillin resistance and subsequently infected with VCMS13 helper phage to start the second round of antibody display and in vitro selection.

A total of 4 rounds of selections were carried out for the two antibodies. Antigen concentrations were decreased during selection to the final concentrations as follows:

| | |
|---|---|
| 1. round | 100 nM |
| 2. round | 10 nM |
| 3. round | 10 nM |
| 4. round | 10 nM |

Plasmid DNA from *E. coli* cultures was isolated corresponding to 3 and 4 rounds of panning.

For the production of soluble SCA-protein the VH-VL-DNA fragments were excised from the plasmids (Xho-SpeI), and cloned via the same restriction sites in the plasmid pComb3H$_5$BFlag/His (w/o N2 domain). After ligation each pool (different rounds of panning) of plasmid DNA was transformed into 100 μL heat shock competent *E. coli* TG1 and plated on Carbenicillin LB-Agar. Single colonies were picked and inoculated into 120 μL of LB carb (50 μg/mL) 1% glucose in 96-well plates (Greiner). The wells were sealed with a semipermeable membrane (Greiner) and the plates incubated overnight at 37° C. in a shaking incubator (master plate). Then, 10 μL of the master plate cultures were transferred into a second 96 well plate (working plate) containing 90 μL LB carb (50 μg/mL) 0.1% glucose per well. After incubation for 4 h in a 37° C. shaking incubator, SCA production was induced by adding 20 μL LB carb 6 mM IPTG to each well. After another incubation step overnight at 30° C. with shaking, cell were lysed in a 1 h room temperature incubation with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 2500 rpm (Hettich).

The SCA containing supernatants were then tested for binding in ELISA assays.

Detection of SCA-fragments bound to immobilized recombinant human GM-CSF antigen (Leukine) was carried out using a biotinylated anti-flag M2 (1 μg/mL PBS/1% BSA) detected with horseradish peroxidase-conjugated goat anti mouse Fab2 specific polyclonal antibody (Dianova, 1 μg/mL PBS/1% BSA). The signal was developed by adding ABTS substrate solution and detected at a wavelength of 405 nm.

From approximately 200 clones tested, at least 1/3 of the lysates showed strong ELISA signals as compared to PBS as a negative control on the recombinant antigen. The lysates were tested in a parallel experiment for unspecific binding to the blocking agent and no GM-CSF antigen. No significant detectable signal could be observed, indicating the specificity of the binding to the recombinant human GM-CSF.

The DNA sequences of more than 20 ELISA-positive SCA clones were determined and most of the clones corresponded to a human VH FR1-CDR1-FR2-CDR2-FR3 polypeptide combined with the maternal VH CDR3 indicating their origin from the Lib 134. Some ELISA-positive clones corresponded to a human polypeptide over the whole VH molecule indicating their origin from the human VH library.

Example 4

Characterization of SCA Hit and Lead Constructs 4.1 Characterisation of SCA Hit Constructs Derived from the Method of Section 3 as Applied to Maternal huVL 4.1.1 Small-Scale Expression and Purification of Sca Hits (Derived as Described Above) in *E. coli*

As previously mentioned, *E. coli* TG1 transformed with pComb3H5BFlag/His containing a VL- and VH-segment can produce soluble SCA in sufficient amounts after induction with 1 mM IPTG. The SCA-chain is exported into the periplasm where it folds into a functional conformation. The SCA hits derived as described above were screened for their newly acquired propensity to yield sufficient amounts of soluble, folded, functional, active SCA protein.

For periplasmic preparations the cells were grown in SB-medium supplemented with 20 mM $MgCl_2$ and carbenicillin 50 μg/mL and redissolved in 1 mL PBS after harvesting. By four rounds of freezing at −70° C. and thawing at 37° C., the outer membrane of the bacteria was destroyed by temperature shock and the soluble periplasmic proteins including the SCAs were released into the supernatant. After elimination of intact cells and cell-debris by centrifugation, the supernatant containing the SCAs was collected and used for further examination. These crude supernatants containing SCA will be further termed PPP.

For further purification, 25 μL 20 mM $NaH_2PO_4$, 400 mM NaCl, 250 mM Imidazol, pH 7.0 was added to the PPP. The PPP were purified via Ni-NTA Spin Columns (Qiagen) as recommended in the manual. In brief, the PPP solution was added to the pre-equilibrated column to bind to the resin. The Spin Columns were washed twice with 20 mM $NaH_2PO_4$, 400 mM NaCl, 20 mM Imidazol, pH 7.0. The bound protein was eluted twice in 200 μL 20 mM $NaH_2PO_4$, 400 mM NaCl, 250 mM Imidazol, pH 7.0. The purified SCA proteins were further analysed for binding strength (kinetic off rate) and neutralization capabilities (inhibition of GM-CSF dependent TF-1 proliferation). Though not separating and distinguishing between the different possible conformations of the SCA, this crude purification of PPP yields 80% pure SCA protein as judged by Western-blot analysis (data not shown).

4.1.2 Kinetic Binding Analysis of SCA Hits Derived from the Above Method as Determined by SPR The aim of this experiment is to establish a qualitative ranking of the ELISA-positive and expressible SCA hits derived from the method as described above in section 3. The SPR experiment was performed as described in detail in section 2.5.1. Prior to the experiment eluted protein solutions of the PPP were dialyzed against PBS at 25° C. for 2 h and diluted 1:1 in HBS-EP. Binding kinetics of the SCA hits were measured injecting 10 μL of purified PPP protein solution as described in section 4.1.1 at 25° C. over the sensor chip. The non-specific background adsorption of protein to the unmodified sensor chip surface (FC1) was subtracted from the response signal in the rhGM-CSF immobilized flow cells (FC2, FC3, FC4). The relative response signal (FC2-1, FC3-1, FC4-1) was determined and the specific dissociation rate was monitored for 100 sec (FIG. 9).

The amplitude of the binding peak (RUmax) directly correlates to the protein concentration in the injected sample. The kinetic on rate (ka) is concentration dependent and cannot be used for the qualitative ranking of the purified PPP SCA material due to varying concentrations of the PPP protein. The kinetic off rate (kd) is protein concentration independent and characteristic for the binding strength of a respective SCA hit. Almost all expressed and identified SCA hits derived from the method as described above in section 3 show some degree of specific binding to the immobilized rhGM-CSF. The SCA hits with the best apparent off rate were identified and, after further correlation of the SPR data with the inhibition data as described in 4.1.3, submitted for sequencing.

4.1.3 Inhibition of rhGM-CSF-Dependent Proliferation of TF-1 Cells by SCA Hits

The aim of this experiment is to establish a qualitative ranking of the ELISA-positive, expressible and off rate-characterized SCA hits derived from the method in section 3 above for their proliferation-inhibition activity. TF-1 proliferation-inhibition experiments were performed as described in detail in section 2.5.2. Cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF-dependent proliferation, purified PPP of the SCA hits were dialyzed against 1×PBS at 25° C. for 2 h. 10 μL of dialyzed and sterile filtered protein solution (0.22 μm filter) was added to 100 μL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm (FIG. 10).

The inhibition of the rhGM-CSF dependent proliferation of the TF-1 cells by the SCA constructs is of varying strength. Some SCA constructs do not inhibit the proliferation to a large degree—this can be due to a lack of stable complex formation of the SCA constructs and the rhGM-CSF over the period of 72 h at 37° C. The SCA hits displaying the strongest inhibition of TF-1 proliferation were identified and after correlation of with the SPR data (see section 4.1.2, above) submitted for sequencing.

4.1.4 Sequencing of Identified Neutralizing SCA Hits

Sequencing was carried out at Sequiserve (Munich).

The following different human VL-region sequences were identified (FIGS. 11-35):

| | | |
|---|---|---|
| B32oN-10 (FIG. 11) | B32oN-33 (FIG. 12) | B32oN-44 (FIG.13) |
| B32oN-45 (FIG. 14) | B32oN-48 (FIG. 15) | B32oN-49 (FIG. 16) |
| B32oN-67 (FIG. 17) | B32oN-73 (FIG. 18) | B33oN-115 (FIG. 21) |
| B33oN-8 (FIG. 26) | B33oN-21 (FIG. 19) | B33oN-22 (FIG. 20) |
| B33oN-35 (FIG. 22) | B33oN-66 (FIG. 23) | B33oN-67 (FIG. 24) |
| B33oN-69 (FIG. 25) | C32oN-10 (FIG. 27) | C32oN-34 (FIG. 29) |
| C32oN-21 (FIG. 28) | C32oN-46 (FIG. 30) | C32oN-89 (FIG. 31) |
| C32oN-92 (FIG. 32) | C33oN-32 (FIG. 33) | C33oN-33 (FIG. 34) |
| C33oN-49 (FIG. 35) | | |

4.2 Characterisation of SCA Lead Constructs Combining a huVL with the VH of the Maternal SCA 4.2.1 Large Scale Production and Purification of SCA Leads Constructs Produced by the Method Described in Example 3

The SCA leads were isolated in a two-step purification process of immobilized metal affinity chromatography (IMAC) and gel filtration. All leads were purified according to this method. Äkta® FPLC System (Pharmacia) and Unicorn® Software were used for chromatography. All chemicals were of research grade and purchased from Sigma (Deisenhofen) or Merck (Darmstadt). IMAC was performed using a Quiagen Ni-NTA Superflow column according to the protocol provided by the manufacturer. The column was equilibrated with buffer A2 (20 mM sodium phosphate pH 7.2, 0.4 M NaCl) and the PPP (100 mL) was applied to the column (2 mL) at a flow rate of 2 mL/min. The column was washed with 5 column volumes 5% buffer B2 (20 mM sodium phosphate pH 7.2, 0.4 M NaCl, 0.5 M Imidazol) to remove unbound sample. Bound protein was eluted using 100% buffer B2 in 5 column volumes. Eluted protein fractions were pooled for further purification.

Gel filtration chromatography was performed on a HiLoad™ 16/60 Superdex 75 Prep Grade column (Pharmacia) equilibrated with PBS (Gibco). Eluted protein samples (flow rate 1 mL/min) were subjected to standard SDS-PAGE and Western Blot for detection. Prior to purification, the column was calibrated for molecular weight determination (molecular weight marker kit, Sigma MW GF-200). The size dependent separation on the Superdex 75 Prep Grade column resulted in clearly distinguishable monomer and associative dimer peak fractions of the SCA leads. Protein concentrations were determined measuring OD at 280 nm and calculated using the sequence specific molecular extinction coefficient of the respective SCA leads.

4.2.2 Kinetic Binding Analysis of SCA Leads by SPR

The aim of the experiment is the in-depth characterisation of the SCA leads selected with focus on the preserved functionality in comparison to the parent maternal mAb. Binding to the naive antigen—here rhGM-CSF—is one of the attributes the maternal mAb-derived SCA leads.

Binding kinetics (kd and ka) of the SCA leads were measured injecting 10 μL of purified protein in dilution series ranging from 10 μg/mL to 1 pg/mL purified SCA and monitoring the dissociation at 25° C. for 100 sec. Protein was buffered in HBS-EP. The data were fitted using BIAevaluation™ software determining the rate constant for dissociation and association kinetics with a 1:1 Langmuir binding equation (1, 2), where A is the concentration of injected analyte and B is the concentration of the ligand.

$$dB/dt=-(ka*[A]*[B]-kd*[AB]) \quad (1)$$

$$dAB/dt=-(ka*[A]*[B]-kd*[AB]) \quad (2)$$

Kinetic binding curves were determined using up to 8 concentrations of each SCA lead analyzed. The independent fitting of the raw data resulted in dissociation and association rate constants that were used to calculate the equilibrium dissociation constant (KD) (FIGS. 36A, 36B). The data of the maternal SCA B32oN-45 represent a typical sensogram and results are summarized in Table 1. The maternal SCA B32oN-45, derived from the method as described above, demonstrates specific binding to rhGM-CSF with an apparent KD of 50 nM. The binding specificity of the parent maternal mAb with a KD of 30 nM has been preserved in this SCA lead.

4.2.3 Inhibition of rhGM-CSF Dependent Proliferation of TF-1 Cells by SCA Leads

After confirming that the strength of specific binding was preserved in the SCA leads described in section 4.2.2, the aim of this experiment was to assess the specificity of the interaction of the SCA lead with the antigen hGM-CSF. The inhibition of the biological function of the antigen hGM-CSF by binding of the SCA was characterized in a TF-1 proliferation-inhibition experiment.

TF-1 proliferation-inhibition experiments were performed as described above in section 2.5.3. Cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF dependent proliferation purified SCA in 1×PBS was added in a dilution series with final protein concentrations ranging from 100 μg/mL to 10 pg/mL. 10 μL of dialyzed and sterile filtered protein solution (0.22 μm filter) was added to 100 μL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm (FIG. 37).

The half maximal inhibition constant ($IC_{50}$) of the maternal SCA B32oN-45, generated by the method described above, is 6 nM. The $IC_{50}$s of the characterized SCA leads are in the same nanomolar inhibition range, implying the potential of the methodology as described in Example 3. The selected and characterized SCAs all preserve the binding specificity (KD determined by SPR as described in section 4.2.2) and neutralization potential of the parent maternal mAb (i.e. the "source immunoglobulin"). In addition to preservation of the original functional specificities of the parent maternal mAb the SCA leads produced via the method of Example 3 show satisfying expression and folding properties that were not observed in the original maternal SCA (i.e. the "corresponding antibody fragment").

TABLE 1

| | ka (1/Ms) | kd (1/s) | Conc of analyte (nM) | KA (1/M) | KD (M) |
|---|---|---|---|---|---|
| SCA B32ON-45 | 5.43exp4 | 5.14exp-3 | 3120 | 1.06exp7 | 9.46exp-8 |
| SCA B32ON-45 | 8.71exp4 | 4.6exp-3 | 1040 | 1.89exp7 | 5.28exp-8 |
| SCA B32ON-45 | 4.4exp5 | 4.77exp-3 | 347 | 9.22exp7 | 1.08exp-8 |
| SCA B32ON-45 | 7.72exp5 | 4.64exp-3 | 116 | 1.66exp8 | 6.01exp-9 |
| SCA B32ON-45 | 9.75exp5 | 4.44exp-3 | 38.5 | 2.2exp8 | 4.55exp-9 |
| SCA B32ON-45 | 1.25exp6 | 3.84exp-3 | 12.8 | 3.25exp8 | 3.07exp-9 |

The invention claimed is:

1. An antibody fragment obtainable by a method comprising:

a) providing a nucleic acid molecule encoding a first antibody variable region or fragment thereof comprising the complementarity determining regions (CDRs) of the first antibody variable region in a source immunoglobulin, wherein the first antibody variable region or fragment thereof is a heavy chain variable region (VH) or a light chain variable region (VL), or a fragment of either of these;

b) respectively combining (i) the nucleic acid molecule encoding the first antibody VH or VL region or fragment of either with (ii) a plurality of nucleic acid molecules encoding a diverse population of a second antibody variable region or fragment thereof comprising the CDRs of the second antibody variable region, wherein the second antibody variable region or fragment thereof is a light chain variable region (VL) or a heavy chain variable region (VH), or a fragment of either of these, whereby a population of combined nucleic acid molecules is obtained;

c) introducing the population of combined nucleic acid molecules into a display system chosen from a phage display system, a prokaryotic display system, a eukaryotic display system, or an mRNA display system;

d) selecting at least one antibody fragment displayed in any one of the display systems of (c) and comprising the VH and VL regions, or a fragment of either or both of these, which specifically binds to an antigen of interest; and e) isolating the at least one antibody fragment selected in (d);

wherein the nucleic acid molecule encoding the first antibody variable region or fragment thereof or the nucleic acid molecule encoding the second antibody variable region or fragment thereof is operably linked to a nucleic acid molecule encoding an N-terminal, cis-acting amphipathic polypeptide moiety such that said N-terminal, cis-acting amphipathic polypeptide moiety, when translated, is linked to the N-terminal end of the first or second antibody variable region;

wherein the amphipathic polypeptide moiety is chosen from the pro region of any of the following polypeptides: papain, cruzain, thermolysin, cathepsin B, cathepsin L, protease A, protease B, IgA protease, carboxypeptidase Y, or the N2 domain of a filamentous phage; and wherein the source immunoglobulin specifically binds to an antigen of interest, a corresponding antibody fragment of which source immunoglobulin exhibits insufficient soluble recombinant expression.

2. The antibody fragment of claim 1, wherein the second antibody variable region comprised in the antibody fragment is of human origin.

3. The antibody fragment of claim 1, wherein the antigen of interest is GM-CSF.

4. The antibody fragment of claim 1, wherein the first antibody variable region comprised in the antibody fragment is present in modified form as compared to the form in which it is comprised in the source immunoglobulin.

5. The antibody fragment of claim 4, wherein the first antibody variable region has been modified so as to render it less likely to elicit a host immune response when administered to a subject as a therapeutic agent.

6. The antibody fragment of claim 5, wherein the first antibody variable region has been humanized and/or deimmunized.

7. The antibody fragment of claim 6, wherein the first antibody variable region has an amino acid sequence as set out in SEQ ID NO: 1.

8. The antibody fragment of claim 1, wherein the second antibody variable region or fragment thereof is a light chain variable region (VL) or fragment thereof.

9. The antibody fragment of claim 8, wherein the light chain variable region (VL) comprises an amino acid sequence corresponding to a VL sequence selected from the group consisting of SEQ ID NO: 94, 103, 112, 121, 130, 139, 148, 157, 166, 175, 184, 193, 202, 211, 220, 229, 238, 247, 256, 265, 274, 283, 292, 301, and 310.

10. An antibody fragment obtainable by a method comprising:

a) providing a nucleic acid molecule encoding a first antibody variable region or fragment thereof comprising the complementarity determining regions (CDRs) of the first antibody variable region in a source immunoglobulin, wherein the first antibody variable region or fragment thereof is a heavy chain variable region (VH) or a light chain variable region (VL), or a fragment of either of these;

b) respectively combining (i) the nucleic acid molecule encoding the first antibody VH or VL region or fragment of either with (ii) a plurality of nucleic acid molecules encoding a diverse population of a second antibody variable region or fragment thereof comprising the CDRs of the second antibody variable region, wherein the second antibody variable region or fragment thereof is a light chain variable region (VL) or a heavy chain variable region (VH), or a fragment of either of these, whereby a first population of combined nucleic acid molecules is obtained;

c) introducing the first population of combined nucleic acid molecules into a display system chosen from a phage display system, a prokaryotic display system, a eukaryotic display system, or an mRNA display system;

d) selecting at least one first antibody fragment displayed in any one of the display systems of (c) and comprising the VH and VL regions, or a fragment of either or both of these, which specifically binds to an antigen of interest;

e) respectively combining (i) the nucleic acid molecule encoding the second antibody variable region or fragment thereof with (ii) a plurality of nucleic acid molecules encoding a diverse population of a third antibody variable region or fragment thereof comprising the CDRs of the third antibody variable region, wherein the third antibody variable region or fragment thereof is a heavy chain variable region (VH) or a light chain variable region (VL), or a fragment of either of these, whereby a second population of combined nucleic acid molecules is obtained;

f) introducing the second population of combined nucleic acid molecules into a display system chosen from a phage display system, a prokaryotic display system, a eukaryotic display system, or an mRNA display system;

g) selecting at least one second antibody fragment displayed in any one of the display systems of (f) and comprising the VH and VL regions, or a fragment of either or both of these, which specifically binds to the antigen of interest; and h) isolating the at least one antibody fragment selected in (g);

wherein the nucleic acid molecule encoding the first antibody variable region or fragment thereof or the nucleic acid molecule encoding the second antibody variable region or fragment thereof of (b) is operably linked to a nucleic acid molecule encoding an N-terminal, cis-acting amphipathic polypeptide moiety such that said N-terminal, cis-acting amphipathic polypeptide moiety, when translated, is linked to the N-terminal end of the first or second antibody variable region;

wherein the amphipathic polypeptide moiety is chosen from the pro region of any of the following polypeptides: papain, cruzain, thermolysin, cathepsin B, cathepsin L, protease A, protease B, IgA protease, carboxypeptidase Y, or the N2 domain of a filamentous phage; and wherein the nucleic acid molecule encoding the second antibody variable region or fragment thereof or the nucleic acid molecule encoding the third antibody variable region or fragment thereof of (e) is operably linked to a nucleic acid molecule encoding an N-terminal, cis-acting amphipathic polypeptide moiety such that said N-terminal, cis-acting amphipathic polypepetide moiety, when translated, is linked to the N-terminal end of the second or third antibody variable region;

wherein the amphipathic polypeptide moiety is chosen from the pro region of any of the following polypeptides: papain, cruzain, thermolysin, cathepsin B, cathepsin L, protease A, protease B, IgA protease, carboxypeptidase Y, or the N2 domain of a filamentous phage; and wherein the source immunoglobulin specifically binds to an antigen of interest, a corresponding antibody fragment of which source immunoglobulin exhibits insufficient soluble recombinant expression.

11. The antibody fragment of claim 10, wherein the first antibody variable region is replaced by the third antibody variable region.

12. The antibody fragment of claim 11, wherein the pluralities of nucleic acid molecules encoding diverse populations of second and third antibody variable regions are each of human origin.

13. The antibody fragment of claim 10, wherein the third antibody variable region or fragment thereof is a heavy chain variable region (VH) or fragment thereof.

14. A composition comprising an antibody fragment of claim 1, and optionally a carrier or an excipient.

15. A composition comprising an antibody fragment of claim 10, and optionally a carrier or an excipient.

16. The antibody fragment of claim 1, wherein the second antibody variable region or fragment thereof is a heavy chain variable region (VH) or fragment thereof.

17. The antibody fragment of claim 10, wherein the third antibody variable region or fragment thereof is a light chain variable region (VL) or fragment thereof.

18. The antibody fragment of claim 8, wherein CDR1, CDR2, and CDR3 of the light chain variable region (VL) are set out as shown in any of FIGS. 11-35.

19. The antibody fragment of claim 1 comprising in its light chain variable region a CDR1 comprising an amino acid sequence as set out in SEQ ID NO: 122, a CDR2 comprising an amino acid sequence as set out in SEQ ID NO: 123, and a CDR3 comprising an amino acid sequence as set out in SEQ ID NO: 124.

20. The antibody fragment of claim 1 comprising in its heavy chain variable region a CDR1 comprising an amino acid sequence as set out in SEQ ID NO: 118, a CDR2 comprising an amino acid sequence as set out in SEQ ID NO: 119, and a CDR3 comprising an amino acid sequence as set out in SEQ ID NO: 120.

21. The antibody fragment of claim 1 comprising the amino acid sequence set forth in SEQ ID NO: 9.

* * * * *

SEQUENCE LISTING

```
<160> NUMBER OF SEQ ID NOS: 313

<210> SEQ ID NO 1
<211> LENGTH: 120
<212> TYPE: PRT
<213> ORGANISM: artificial sequence
<220> FEATURE:
<223> OTHER INFORMATION: VH of anti-GM-CSF immunoglobulin

<400> SEQUENCE: 1

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
```

```
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 2
<211> LENGTH: 726
<212> TYPE: DNA
<213> ORGANISM: artificial sequence
<220> FEATURE:
<223> OTHER INFORMATION: B32oN-10 (nuc)

<400> SEQUENCE: 2

gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct ccagatgacc    420

cagtctccat cctccctgtc tgcatctgta ggagacagag tcaccatcac ttgccggaca    480

agtcagacca ttagcagtct tttaaattgg tatcagcaga aaccagggaa agcccctaag    540

ctcctgatct atgctgcatc caatttgcaa agtggggtcc catcaaggtt cagtggcagt    600

ggatctggga cagatttcac tctcaccatc agcggtctgc aacctgaaga tttttcaact    660

tacttctgtc aacagagtta cagtttccct cgaacgttcg gccaagggac caaagtggat    720

atcaaa                                                                726


<210> SEQ ID NO 3
<211> LENGTH: 242
<212> TYPE: PRT
<213> ORGANISM: artificial sequence
<220> FEATURE:
<223> OTHER INFORMATION: B32oN-10 (prot)

<400> SEQUENCE: 3

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
```

```
        115                 120                 125

Gly Ser Gly Gly Gly Gly Ser Glu Leu Gln Met Thr Gln Ser Pro Ser
    130                 135                 140

Ser Leu Ser Ala Ser Val Gly Asp Arg Val Thr Ile Thr Cys Arg Thr
145                 150                 155                 160

Ser Gln Thr Ile Ser Ser Leu Leu Asn Trp Tyr Gln Gln Lys Pro Gly
                165                 170                 175

Lys Ala Pro Lys Leu Leu Ile Tyr Ala Ala Ser Asn Leu Gln Ser Gly
            180                 185                 190

Val Pro Ser Arg Phe Ser Gly Ser Gly Ser Gly Thr Asp Phe Thr Leu
        195                 200                 205

Thr Ile Ser Gly Leu Gln Pro Glu Asp Phe Ser Thr Tyr Phe Cys Gln
    210                 215                 220

Gln Ser Tyr Ser Phe Pro Arg Thr Phe Gly Gln Gly Thr Lys Val Asp
225                 230                 235                 240

Ile Lys


<210> SEQ ID NO 4
<211> LENGTH: 726
<212> TYPE: DNA
<213> ORGANISM: artificial sequence
<220> FEATURE:
<223> OTHER INFORMATION: B32oN-33 (nuc)

<400> SEQUENCE: 4

gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgatgacg    420

cagtctccag ccaccctgtc tttgtctcca ggggaaagag ccaccctctc ctgcagggcc    480

agtcagagtg ttaggaccta cttagcctgg taccaacaga aacctggcca ggctcccagg    540

ctcctcatct atgctgcatc ccacagggcc actggcatcc cagccaggtt cagtggcagt    600

gggtctggga cagacttcac tctcaccatc agcagactgg agcctgaaga ttttgcagtg    660

tattactgtc agcagtatgg tagctcacct ccgacgttcg gccaagggac caaggtagag    720

atcaaa                                                               726


<210> SEQ ID NO 5
<211> LENGTH: 242
<212> TYPE: PRT
<213> ORGANISM: artificial sequence
<220> FEATURE:
<223> OTHER INFORMATION: B32oN-33 (prot)

<400> SEQUENCE: 5

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45
```

```
Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Ser Val Arg Thr Tyr Leu Ala Trp Tyr Gln Gln Lys Pro Gly
                165                 170                 175

Gln Ala Pro Arg Leu Leu Ile Tyr Ala Ala Ser His Arg Ala Thr Gly
            180                 185                 190

Ile Pro Ala Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

Gln Tyr Gly Ser Ser Pro Pro Thr Phe Gly Gln Gly Thr Lys Val Glu
225                 230                 235                 240

Ile Lys
```

<210> SEQ ID NO 6
<211> LENGTH: 726
<212> TYPE: DNA
<213> ORGANISM: artificial sequence
<220> FEATURE:
<223> OTHER INFORMATION: B32oN-44 (nuc)

<400> SEQUENCE: 6

```
gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccgg actttcagtc tgtgactcca aaggagaaag tcaccatcac ctgccgggcc     480

agtcagagca ttggtagtag cttacactgg taccagcaga aaccagatca gcctccaaag     540

ctcctcatca aatttgcttc ccagtccatc tcaagggtcc cctcgaggtt cagtggcact     600

ggatctggga cagatttcac cctcaccatc aatagcctgg aagctgaaga tgctgcaacg     660

tattactgtc agcagagctt tagtttcccg tacacttttg gccaggggac caagctggag     720

atcaaa                                                                726
```

<210> SEQ ID NO 7
<211> LENGTH: 242
<212> TYPE: PRT

<213> ORGANISM: artificial sequence
<220> FEATURE:
<223> OTHER INFORMATION: B32oN-44 (prot)

<400> SEQUENCE: 7

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Pro Pro Lys Leu Leu Ile Lys Phe Ala Ser Gln Ser Ile Ser Arg
            180                 185                 190

Val Pro Ser Arg Phe Ser Gly Thr Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Phe Ser Phe Pro Tyr Thr Phe Gly Gln Gly Thr Lys Leu Glu
225                 230                 235                 240

Ile Lys
```

<210> SEQ ID NO 8
<211> LENGTH: 726
<212> TYPE: DNA
<213> ORGANISM: artificial sequence
<220> FEATURE:
<223> OTHER INFORMATION: B32oN-45 (nuc)

<400> SEQUENCE: 8

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgatgacc    420

cagtctccat cttccgtgtc tgcatctgta ggagacagag tcaccatcgc ttgtcgggcg    480
```

```
agtcagaaca ttagaaacat tttaaattgg tatcaacaga gaccagggaa ggcccctcaa    540

ctcctgatct atgctgcctc caatttacaa agtggcgtcc catcaaggtt cagtggcagt    600

ggatctggga cagatttcac tctcaccatc aacagtctgc aacctgaaga ttttgcaact    660

tactactgtc aacagagtta cagtatgcct cgaactttcg gcggagggac caaggtggaa    720

atcaaa                                                                726
```

<210> SEQ ID NO 9
<211> LENGTH: 242
<212> TYPE: PRT
<213> ORGANISM: artificial sequence
<220> FEATURE:
<223> OTHER INFORMATION: B32oN-45 (prot)

<400> SEQUENCE: 9

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Met Thr Gln Ser Pro Ser
    130                 135                 140

Ser Val Ser Ala Ser Val Gly Asp Arg Val Thr Ile Ala Cys Arg Ala
145                 150                 155                 160

Ser Gln Asn Ile Arg Asn Ile Leu Asn Trp Tyr Gln Gln Arg Pro Gly
                165                 170                 175

Lys Ala Pro Gln Leu Leu Ile Tyr Ala Ala Ser Asn Leu Gln Ser Gly
            180                 185                 190

Val Pro Ser Arg Phe Ser Gly Ser Gly Ser Gly Thr Asp Phe Thr Leu
        195                 200                 205

Thr Ile Asn Ser Leu Gln Pro Glu Asp Phe Ala Thr Tyr Tyr Cys Gln
    210                 215                 220

Gln Ser Tyr Ser Met Pro Arg Thr Phe Gly Gly Gly Thr Lys Val Glu
225                 230                 235                 240

Ile Lys
```

<210> SEQ ID NO 10
<211> LENGTH: 726
<212> TYPE: DNA
<213> ORGANISM: artificial sequence
<220> FEATURE:
<223> OTHER INFORMATION: B32oN-48 (nuc)

<400> SEQUENCE: 10

```
gagctgcagc tggtcgagca gtctggagct gcactggtga agcctgggga ctctgtgaag     60
```

```
atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag gctttcagtc tgtgactcca aaggagaaag tcaccatcac ctgccgggcc    480

agtcagagca ttggtagtag cttacactgg taccagcaga aaccagatca gcctccaaag    540

ctcctcatca aatttgcttc ccagtccatc tcaggggtcc cctcgaggtt cagtggcagt    600

ggatctggga caaatttcac cctcaccatc aatagcctgg aagctgaaga tgctgcaacc    660

tattactgtc agcagagtag tactttacct cccacttttg gccaggggac caaggtggag    720

atcaaa                                                               726
```

```
<210> SEQ ID NO 11
<211> LENGTH: 242
<212> TYPE: PRT
<213> ORGANISM: artificial sequence
<220> FEATURE:
<223> OTHER INFORMATION: B32oN-48 (prot)

<400> SEQUENCE: 11

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Pro Pro Lys Leu Leu Ile Lys Phe Ala Ser Gln Ser Ile Ser Gly
            180                 185                 190

Val Pro Ser Arg Phe Ser Gly Ser Gly Ser Gly Thr Asn Phe Thr Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Val Glu
225                 230                 235                 240
```

Ile Lys

<210> SEQ ID NO 12
<211> LENGTH: 726
<212> TYPE: DNA
<213> ORGANISM: artificial sequence
<220> FEATURE:
<223> OTHER INFORMATION: B32oN-49 (nuc)

<400> SEQUENCE: 12

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag actttcagtc tgtgactcca aaggagaaag tcaccatcac ctgccgggcc    480

agtcagagca ttggtagtag cttacactgg taccagcaga aaccagatca gtctccaaag    540

ctcctcatca agtttgcttc ccagtccctc tcaggggtcc cctcgaggtt cagtggcagt    600

ggatctggga cagatttcac tctcaccatc agcagtctac aacctgaaga ttttgcaact    660

tactactgtc aacagagtta cactaccccc cccactttcg gcggagggac caaggtggaa    720

atcaaa                                                               726
```

<210> SEQ ID NO 13
<211> LENGTH: 242
<212> TYPE: PRT
<213> ORGANISM: artificial sequence
<220> FEATURE:
<223> OTHER INFORMATION: B32oN-49 (prot)

<400> SEQUENCE: 13

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
```

```
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Thr Thr Pro Pro Thr Phe Gly Gly Gly Thr Lys Val Glu
225                 230                 235                 240

Ile Lys


<210> SEQ ID NO 14
<211> LENGTH: 726
<212> TYPE: DNA
<213> ORGANISM: artificial sequence
<220> FEATURE:
<223> OTHER INFORMATION: B32oN-67 (nuc)

<400> SEQUENCE: 14

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctcccg gctttcagtc tgtgactcca aaggagaaag tcaccatcac ctgccgggcc     480

agtcagagca ttggtagtag cttacactgg taccagcaga aaccagatca gtctccaaag     540

ctcctcatca aatttgcttc ccagtccatc tcaggggtcc cctcgaggtt cactggcagt     600

ggatctggga cagatttcac tctcaccatc agcagtctgc aacctgaaga tattgcaact     660

tactactgtc aacagagtta cagtacccct tggacgttcg gccaagggac caagctggag     720

atcaaa                                                                726


<210> SEQ ID NO 15
<211> LENGTH: 242
<212> TYPE: PRT
<213> ORGANISM: artificial sequence
<220> FEATURE:
<223> OTHER INFORMATION: B32oN-67 (prot)

<400> SEQUENCE: 15

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95
```

```
Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Thr Gly Ser Gly Ser Gly Thr Asp Phe Thr Leu
        195                 200                 205

Thr Ile Ser Ser Leu Gln Pro Glu Asp Ile Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys


<210> SEQ ID NO 16
<211> LENGTH: 726
<212> TYPE: DNA
<213> ORGANISM: artificial sequence
<220> FEATURE:
<223> OTHER INFORMATION: B32oN-73 (nuc)

<400> SEQUENCE: 16

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctcccg gctttcagtc tgtgactcca aaggagaaag tcaccatcac ctgccgggcc     480

agtcagagca ttggtagtag cttacactgg taccagcaga aaccagatca gtctccaaag     540

ctcctcatca aatttgcttc ccagtccatc tcaggggtcc cctcgaggtt cagtggcact     600

ggatctggga cagatttcac tctcaccatc agcagtctgc aacctgaaga tattgcaact     660

tactactgtc aacagagtta cagtacccct tggacgttcg gccaagggac caagctggag     720

atcaaa                                                                726


<210> SEQ ID NO 17
<211> LENGTH: 242
<212> TYPE: PRT
<213> ORGANISM: artificial sequence
<220> FEATURE:
<223> OTHER INFORMATION: B32oN-73 (prot)

<400> SEQUENCE: 17

Glu Leu Gln Leu Val Glu Gln Ser Gly Ala Ala Leu Val Lys Pro Gly
1               5                   10                  15
```

```
Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Ser Gly Thr Gly Ser Gly Thr Asp Phe Thr Leu
        195                 200                 205

Thr Ile Ser Ser Leu Gln Pro Glu Asp Ile Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys
```

```
<210> SEQ ID NO 18
<211> LENGTH: 726
<212> TYPE: DNA
<213> ORGANISM: artificial sequence
<220> FEATURE:
<223> OTHER INFORMATION: B33oN-8 (nuc)

<400> SEQUENCE: 18

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag gctttcagtc tgtgactcca aaggagaaag tcaccatcac ctgccgggcc     480

agtcagagca ttggtagtag cttaaactgg taccagcaga aaccagatca gcctccaaag     540

ctcctcatca aattcgcttc gcagtccatc tcaggggtct cttcgaggtt cagtggcact     600

ggatctggga cagatttcac cctcactatc agcagcctgc agcctgaaga tgttgcaact     660

tattactgtc aacagagtta cagtacccct ccgacgttcg gccaagggac caagctggag     720

atcaaa                                                                726
```

<210> SEQ ID NO 19
<211> LENGTH: 242
<212> TYPE: PRT
<213> ORGANISM: artificial sequence
<220> FEATURE:
<223> OTHER INFORMATION: B33oN-8 (prot)

<400> SEQUENCE: 19

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu Asn Trp Tyr Gln Gln Lys Pro Asp
                165                 170                 175

Gln Pro Pro Lys Leu Leu Ile Lys Phe Ala Ser Gln Ser Ile Ser Gly
            180                 185                 190

Val Ser Ser Arg Phe Ser Gly Thr Gly Ser Gly Thr Asp Phe Thr Leu
        195                 200                 205

Thr Ile Ser Ser Leu Gln Pro Glu Asp Val Ala Thr Tyr Tyr Cys Gln
    210                 215                 220

Gln Ser Tyr Ser Thr Pro Pro Thr Phe Gly Gln Gly Thr Lys Leu Glu
225                 230                 235                 240

Ile Lys
```

<210> SEQ ID NO 20
<211> LENGTH: 726
<212> TYPE: DNA
<213> ORGANISM: artificial sequence
<220> FEATURE:
<223> OTHER INFORMATION: B33oN-21 (nuc)

<400> SEQUENCE: 20

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360
```

```
ggtggtggtg gttctggcgg cggcggctcc ggtggtggtg gttctgagct cgtgctgact    420

cagtctccag actttcagtc tgtgactcca aaggagaaag tcaccatcac ctgccgggcc    480

agtcagagca ttggtagtag cttacactgg taccagcaga aaccagatca gtctccaaag    540

ctcctcatca agtttgcttc ccagtccctc tcaggggtcc cctcgaggtt cagtggcagt    600

ggatccggga cagatttcac cctcaccatc aatagcctgg aagctgaaga tgctgcaacg    660

tattactgtc aacagagtta cagtaccccg tggacgttcg gccaagggac caagctggag    720

atcaaa                                                               726
```

```
<210> SEQ ID NO 21
<211> LENGTH: 242
<212> TYPE: PRT
<213> ORGANISM: artificial sequence
<220> FEATURE:
<223> OTHER INFORMATION: B33oN-21 (prot)

<400> SEQUENCE: 21

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys
```

```
<210> SEQ ID NO 22
<211> LENGTH: 726
<212> TYPE: DNA
<213> ORGANISM: artificial sequence
<220> FEATURE:
<223> OTHER INFORMATION: B33oN-22 (nuc)
```

<400> SEQUENCE: 22

```
gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag actttcagtc tgtgactcca aaggagaaag tcaccatcac ctgccgggcc     480

agtcagagca ttggtagtag cttacactgg taccagcaga aaccagatca gtctccaaag     540

ctcctcatca agtttgcttc ccagtccttc tcaggggtcc cctcgaggtt cagtggcagt     600

ggatctggga cagatttcac cctcaccatc aatagcctgg aagctgaaga tgctgcaacg     660

tattactgtc aacagagtta cagtacccct ccgacgttcg gccaagggac caaggtggag     720

atcaaa                                                                726
```

<210> SEQ ID NO 23
<211> LENGTH: 242
<212> TYPE: PRT
<213> ORGANISM: artificial sequence
<220> FEATURE:
<223> OTHER INFORMATION: B33oN-22 (prot)

<400> SEQUENCE: 23

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
```

```
    210                 215                 220

Gln Ser Tyr Ser Thr Pro Pro Thr Phe Gly Gln Gly Thr Lys Val Glu
225                 230                 235                 240

Ile Lys
```

<210> SEQ ID NO 24
<211> LENGTH: 726
<212> TYPE: DNA
<213> ORGANISM: artificial sequence
<220> FEATURE:
<223> OTHER INFORMATION: B33oN-35 (nuc)

<400> SEQUENCE: 24

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct ccagatgacc    420

cagtctccat cctccctgtc tgcatctgta ggagacagag tcaccatcac ctgccgggcc    480

agtcagagca ttggtagtag cttacactgg taccagcaga aaccagatca gtctccaaag    540

ctcctcatca agtttgcttc ccagtccttc tcaggggtcc cctcgaggtt cggtggcagt    600

ggatctggga caaatttcac cctcaccatc aatagcctgg aagctgaaga tgctgcaacc    660

tattactgtc agcagagtag tactttacct cccacttttg gccaggggac caagctggag    720

atcaaa                                                               726
```

<210> SEQ ID NO 25
<211> LENGTH: 242
<212> TYPE: PRT
<213> ORGANISM: artificial sequence
<220> FEATURE:
<223> OTHER INFORMATION: B33oN-35 (prot)

<400> SEQUENCE: 25

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Gln Met Thr Gln Ser Pro Ser
    130                 135                 140
```

```
Ser Leu Ser Ala Ser Val Gly Asp Arg Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Gly Gly Ser Gly Ser Gly Thr Asn Phe Thr Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240

Ile Lys
```

<210> SEQ ID NO 26
<211> LENGTH: 727
<212> TYPE: DNA
<213> ORGANISM: artificial sequence
<220> FEATURE:
<223> OTHER INFORMATION: B33oN-66 (nuc)

<400> SEQUENCE: 26

```
bgagctgcag ctggtcgagc agtctggagc tgcactggtg aagcctgggg actctgtgaa     60

gatgtcttgc aaagcttctg gttatccatt cactgactat attgtacact gggtgaagca    120

gagtcatgga aagagccttg actggattgg ttatattaat ccttacagtg gtgatactaa    180

gttcaatgaa aagttcaaga gtaaggccac gttgactgtt gacaagtcca gcagcacagc    240

ctatatggag tttagccgat tgacatctga ggattctgca atctattact gtgcaagatc    300

gggtctgata gcagtctact ttgattactg gggccaaggg accacggtca ccgtctcctc    360

aggtggtggt ggttctggcg gcggcggctc cggtggtggt ggttctgagc tcgtgctgac    420

tcagtctcca gactttcagt ctgtgactcc aaaggagaaa gtcaccatca cctgccgggc    480

cagtcagagc attggtagta acttacactg gtaccagcag aaaccagatc agtctccaaa    540

gctcctcatc aagtttgctt cccagtcctt ctcaggggtc cctcgaggt tcagtggcag    600

tggatctggg acagatttca gcctcaccat caatagcctg gaagctgaag atgctgcaac    660

ttactactgt caacagagtt acagtacccc tcccaccttc ggccaaggga cacgactgga    720

gattaaa                                                               727
```

<210> SEQ ID NO 27
<211> LENGTH: 242
<212> TYPE: PRT
<213> ORGANISM: artificial sequence
<220> FEATURE:
<223> OTHER INFORMATION: B33oN-66 (prot)

<400> SEQUENCE: 27

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60
```

```
Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Asn Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Ser Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Pro Thr Phe Gly Gln Gly Thr Arg Leu Glu
225                 230                 235                 240

Ile Lys
```

<210> SEQ ID NO 28
<211> LENGTH: 726
<212> TYPE: DNA
<213> ORGANISM: artificial sequence
<220> FEATURE:
<223> OTHER INFORMATION: B33oN-67 (nuc)

<400> SEQUENCE: 28

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag actttcagtc tgtgactcca aaggagaaag tcaccatcac ctgccgggcc    480

agtcagagca ttggtagtag cttacactgg taccagcaga aaccagatca gtctccaaag    540

ctcctcatca aatttgcttc ccagtccatc tcaggggtcc catcgaggtt cagtggcagt    600

ggatctggga cagatttcac tctcaccatc agcagtctgc aacctgaaga ttttgcaact    660

tactactgtc aacagagtta cagtacccct cccactttcg gccctgggac caagctggag    720

atcaaa                                                               726
```

<210> SEQ ID NO 29
<211> LENGTH: 242
<212> TYPE: PRT
<213> ORGANISM: artificial sequence
<220> FEATURE:
<223> OTHER INFORMATION: B33oN-67 (prot)

<400> SEQUENCE: 29

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Pro Thr Phe Gly Pro Gly Thr Lys Leu Glu
225                 230                 235                 240

Ile Lys
```

<210> SEQ ID NO 30
<211> LENGTH: 726
<212> TYPE: DNA
<213> ORGANISM: artificial sequence
<220> FEATURE:
<223> OTHER INFORMATION: B33oN-69 (nuc)

<400> SEQUENCE: 30

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag actttcaatc tgtgactcca aaggagaaag tcaccatcac ctgccgggcc    480

agtcagagca ttggtactgg cttacactgg taccagcaga aaccggatca gtctccaaag    540

ctcctcatca aatttgcttc ccagtccttc tcaggggtcc cctcgaggtt cagtggcagt    600
```

```
ggatctggga cagatttcac cctcaccatc aatggcctgg aagctgaaga tgctgcaacg    660

tattactgtc agcagagtag tactttacct cccacttttg gccaggggac caagctggag    720

atcaaa                                                               726
```

<210> SEQ ID NO 31
<211> LENGTH: 242
<212> TYPE: PRT
<213> ORGANISM: artificial sequence
<220> FEATURE:
<223> OTHER INFORMATION: B33oN-69 (prot)

<400> SEQUENCE: 31

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Thr Gly Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Thr Leu
        195                 200                 205

Thr Ile Asn Gly Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240

Ile Lys
```

<210> SEQ ID NO 32
<211> LENGTH: 726
<212> TYPE: DNA
<213> ORGANISM: artificial sequence
<220> FEATURE:
<223> OTHER INFORMATION: B33oN-115 (nuc)

<400> SEQUENCE: 32

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180
```

```
ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag actttcagtc tgtgactcca aaggagaaag tcaccatcac ctgccgggcc    480

agtcagagca ttggtagtag cttacactgg taccagcaga aaccagatca gtctccaaag    540

ctcctcatca agtttgcttc ccagtccctc tcaggggtcc cctcgaggtt cagtggcagt    600

ggatctggga cagatttcac tctcaccatc agcagtctgc aacctgaaga ttttgcaact    660

tactactgtc aacagagtta cagtacccct agtactttcg gccctgggac caaggtggag    720

atcaaa                                                               726


<210> SEQ ID NO 33
<211> LENGTH: 242
<212> TYPE: PRT
<213> ORGANISM: artificial sequence
<220> FEATURE:
<223> OTHER INFORMATION: B33oN-115 (prot)

<400> SEQUENCE: 33

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Ser Thr Phe Gly Pro Gly Thr Lys Val Glu
225                 230                 235                 240

Ile Lys


<210> SEQ ID NO 34
```

<211> LENGTH: 726
<212> TYPE: DNA
<213> ORGANISM: artificial sequence
<220> FEATURE:
<223> OTHER INFORMATION: C32oN-10 (nuc)

<400> SEQUENCE: 34

```
gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag actttcagtc tgtgactcca aaggagaaag tcaccatcac ctgccgggcc     480

agtcagagca ttggtagtag cttacactgg taccagcaga aaccagatca gtctccaaag     540

ctcctcatca agtttgcttc ccagtccctc tcaggggtcc cctcgaggtt cagtggcagt     600

ggatctggga cagatttcac cctcaccatc aatagcctgg aagctgaaga ttttgcaact     660

tactactgtc aacagagtta cagtacccct agtactttcg gccctgggac caaggtggag     720

atcaaa                                                                726
```

<210> SEQ ID NO 35
<211> LENGTH: 242
<212> TYPE: PRT
<213> ORGANISM: artificial sequence
<220> FEATURE:
<223> OTHER INFORMATION: C32oN-10 (prot)

<400> SEQUENCE: 35

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190
```

```
Val Pro Ser Arg Phe Ser Gly Ser Gly Ser Gly Thr Asp Phe Thr Leu
        195                 200                 205

Thr Ile Asn Ser Leu Glu Ala Glu Asp Phe Ala Thr Tyr Tyr Cys Gln
    210                 215                 220

Gln Ser Tyr Ser Thr Pro Ser Thr Phe Gly Pro Gly Thr Lys Val Glu
225                 230                 235                 240

Ile Lys


<210> SEQ ID NO 36
<211> LENGTH: 726
<212> TYPE: DNA
<213> ORGANISM: artificial sequence
<220> FEATURE:
<223> OTHER INFORMATION: C32oN-21 (nuc)

<400> SEQUENCE: 36

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctcccg gctttcagtc tgtgactcca aaggagaaag tcaccatcac ctgccgggcc     480

agtcagagca ttggtagtag cttacactgg taccagcaga aaccagatca gtctccaaag     540

ctcctcatca aatttgcttc ccagtccatc tcaggggtcc cctcgaggtt cagtggcact     600

ggatctggga cagatttcac cctcaccatc aatagcctgg aagctgaaga tgctgcaacc     660

tattactgtc agcagagtag tactttacct cccacttttg gccaggggac caagctggag     720

atcaaa                                                                726


<210> SEQ ID NO 37
<211> LENGTH: 242
<212> TYPE: PRT
<213> ORGANISM: artificial sequence
<220> FEATURE:
<223> OTHER INFORMATION: C32oN-21 (prot)

<400> SEQUENCE: 37

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110
```

```
Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Ser Gly Thr Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240

Ile Lys


<210> SEQ ID NO 38
<211> LENGTH: 726
<212> TYPE: DNA
<213> ORGANISM: artificial sequence
<220> FEATURE:
<223> OTHER INFORMATION: C32oN-34 (nuc)

<400> SEQUENCE: 38

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag actttcagtc tgtgactcca aaggagagag tcaccatcac ctgccgggcc     480

agtcagacca ttggtaataa cttacactgg taccagcaga aaccaggtca gtctccaaag     540

ctcctcatca agtttgcttc ccagtccttc tcaggggtcc cctcgaggtt cagtggcagt     600

ggatctggga cagatttcac cctcaccatc aatagcctgg aagctgaaga tgctgcaact     660

tattactgtc aacagagtta cagtaccccg tggacgttcg gccaagggac caaggtggaa     720

atcaaa                                                                726


<210> SEQ ID NO 39
<211> LENGTH: 242
<212> TYPE: PRT
<213> ORGANISM: artificial sequence
<220> FEATURE:
<223> OTHER INFORMATION: C32oN-34 (prot)

<400> SEQUENCE: 39

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
```

```
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Arg Val Thr Ile Thr Cys Arg Ala
145                 150                 155                 160

Ser Gln Thr Ile Gly Asn Asn Leu His Trp Tyr Gln Gln Lys Pro Gly
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Trp Thr Phe Gly Gln Gly Thr Lys Val Glu
225                 230                 235                 240

Ile Lys

<210> SEQ ID NO 40
<211> LENGTH: 726
<212> TYPE: DNA
<213> ORGANISM: artificial sequence
<220> FEATURE:
<223> OTHER INFORMATION: C32oN-46 (nuc)

<400> SEQUENCE: 40

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag actttcagtc tgtgactcca aaggagaaag tcaccatcac ctgccgggcc     480

agtcagagta ttggtagtag cttacactgg taccagcaga aaccagatca gtctccaaag     540

ctcctcatca agtttgcttc ccagtccctc tcaggggtcc catcaaggtt cagtggcagt     600

ggatctggga cagatttcac tctcaccatc agcagtctgc aacctgaaga ttttgcaact     660

tactactgtc aacagagtta cagtacccct ccaacgttcg gccaagggac caaggtggaa     720

atcaaa                                                                726

<210> SEQ ID NO 41
<211> LENGTH: 242
```

```
<212> TYPE: PRT
<213> ORGANISM: artificial sequence
<220> FEATURE:
<223> OTHER INFORMATION: C32oN-46 (prot)

<400> SEQUENCE: 41

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Pro Thr Phe Gly Gln Gly Thr Lys Val Glu
225                 230                 235                 240

Ile Lys


<210> SEQ ID NO 42
<211> LENGTH: 726
<212> TYPE: DNA
<213> ORGANISM: artificial sequence
<220> FEATURE:
<223> OTHER INFORMATION: C32oN-89 (nuc)

<400> SEQUENCE: 42

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgttgacg     420

cagtctccat cctccctgtc tgcatctgta ggagacagag tcaccatcac ttgccgggca     480
```

```
agtcagagca ttagcaggta tttaaattgg tatcaacaaa aaccagggaa accccctaag    540

ctcctgatct ttgttgcatc caatttgcaa actggggtcc catcaaggtt cagtggcagt    600

ggatctggga cagatttcac tctcaccatc agcagcctag agcctgaaga ttttgcagtt    660

tattactgtc agcagcgtag caactggccc ctcactttcg gcggagggac caaagtggat    720

atcaaa                                                                726
```

<210> SEQ ID NO 43
<211> LENGTH: 242
<212> TYPE: PRT
<213> ORGANISM: artificial sequence
<220> FEATURE:
<223> OTHER INFORMATION: C32oN-89 (prot)

<400> SEQUENCE: 43

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Arg Tyr Leu Asn Trp Tyr Gln Gln Lys Pro Gly
                165                 170                 175

Lys Pro Pro Lys Leu Leu Ile Phe Val Ala Ser Asn Leu Gln Thr Gly
            180                 185                 190

Val Pro Ser Arg Phe Ser Gly Ser Gly Ser Gly Thr Asp Phe Thr Leu
        195                 200                 205

Thr Ile Ser Ser Leu Glu Pro Glu Asp Phe Ala Val Tyr Tyr Cys Gln
    210                 215                 220

Gln Arg Ser Asn Trp Pro Leu Thr Phe Gly Gly Gly Thr Lys Val Asp
225                 230                 235                 240

Ile Lys
```

<210> SEQ ID NO 44
<211> LENGTH: 726
<212> TYPE: DNA
<213> ORGANISM: artificial sequence
<220> FEATURE:
<223> OTHER INFORMATION: C32oN-92 (nuc)

<400> SEQUENCE: 44

```
gagctgcagc tggtcgagca gtctggagct gcactggtga agcctgggga ctctgtgaag     60
```

```
atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag actttcagtc tgtgactcca aaggagaaag tcaccatcac ctgccgggcc    480

agtcagagca ttggtagtag cttacactgg taccagcaga aaccagatca gtctccaaag    540

ctcctcatca agtttgcttc ccagtccctc tcaggggtcc cctcgaggtt cagtggcagt    600

ggatctggga cagatttcgc cctcaccatc aatagcctgg aagctgaaga tgctgcaacc    660

tattactgtc agcagagtag tactttacct cccacttttg gccaggggac caagctggag    720

atcaaa                                                               726
```

```
<210> SEQ ID NO 45
<211> LENGTH: 242
<212> TYPE: PRT
<213> ORGANISM: artificial sequence
<220> FEATURE:
<223> OTHER INFORMATION: C32oN-92 (prot)

<400> SEQUENCE: 45

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Ala Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240
```

Ile Lys

<210> SEQ ID NO 46
<211> LENGTH: 726
<212> TYPE: DNA
<213> ORGANISM: artificial sequence
<220> FEATURE:
<223> OTHER INFORMATION: C33oN-32 (nuc)

<400> SEQUENCE: 46

```
gagctgcagc tggtcgagca gtctggagct gcactggtga agcctgggga ctctgtgaag     60

atgtcttgca aagcttctgg ttatccattc actgactata ttgtacactg ggtgaagcag    120

agtcatggaa agagccttga ctggattggt tatattaatc cttacagtgg tgatactaag    180

ttcaatgaaa agttcaagag taaggccacg ttgactgttg acaagtccag cagcacagcc    240

tatatggagt ttagccgatt gacatctgag gattctgcaa tctattactg tgcaagatcg    300

ggtctgatag cagtctactt tgattactgg ggccaaggga ccacggtcac cgtctcctca    360

ggtggtggtg gttctggcgg cggcggctcc ggtggtggtg gttctgagct cgtgctgact    420

cagtctccag agtttcagtc tgtggctcca aaggagaaag tcaccatcac ctgccgggcc    480

agtcagagca ttggtagtag cttacactgg taccagcaga aaccagatca gtctccaaag    540

ctcctcatca agtttgcttc ccagtccttc tcaggggtcc cctcgaggtt cggtggcagt    600

ggatctggga caaatttcac cctcaccatc aatagcctgg aagctgaaga tgctgcaacc    660

tattactgtc agcagagtag taccttacct cccacttttg gccaggggac caagctggag    720

atcaaa                                                               726
```

<210> SEQ ID NO 47
<211> LENGTH: 242
<212> TYPE: PRT
<213> ORGANISM: artificial sequence
<220> FEATURE:
<223> OTHER INFORMATION: C33oN-32 (prot)

<400> SEQUENCE: 47

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Glu
    130                 135                 140

Phe Gln Ser Val Ala Pro Lys Glu Lys Val Thr Ile Thr Cys Arg Ala
145                 150                 155                 160
```

```
Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Gly Gly Ser Gly Ser Gly Thr Asn Phe Thr Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240

Ile Lys
```

<210> SEQ ID NO 48
<211> LENGTH: 726
<212> TYPE: DNA
<213> ORGANISM: artificial sequence
<220> FEATURE:
<223> OTHER INFORMATION: C33oN-33 (nuc)

<400> SEQUENCE: 48

```
gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag actttcagtc tgtgactcca aaggagaaag tcaccatcac ctgccgggcc     480

agtcagagca ttggtagtag cttacactgg taccagcaga aaccagatca gtctccaaag     540

ctcctcatca agtttgcttc ccagtccctc tcaggggtcc cctcgaggtt cagtggcagt     600

ggatctggga cagatttcac cctcaccatc aatagcctgg aagctgaaga tgctgcaact     660

tactactgtc aacagagtta cagtacccct agtactttcg gccctgggac caaggtggag     720

atcaaa                                                                726
```

<210> SEQ ID NO 49
<211> LENGTH: 242
<212> TYPE: PRT
<213> ORGANISM: artificial sequence
<220> FEATURE:
<223> OTHER INFORMATION: C33oN-33 (prot)

<400> SEQUENCE: 49

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
```

```
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Ser Thr Phe Gly Pro Gly Thr Lys Val Glu
225                 230                 235                 240

Ile Lys


<210> SEQ ID NO 50
<211> LENGTH: 726
<212> TYPE: DNA
<213> ORGANISM: artificial sequence
<220> FEATURE:
<223> OTHER INFORMATION: C33oN-49 (nuc)

<400> SEQUENCE: 50

gagctgcagc tggtcgagca gtctggagct gcactggtga agcctgggga ctctgtgaag      60

atgtcttgca aagcttctgg ttatccattc actgactata ttgtacactg ggtgaagcag     120

agtcatggaa agagccttga ctggattggt tatattaatc cttacagtgg tgatactaag     180

ttcaatgaaa agttcaagag taaggccacg ttgactgttg acaagtccag cagcacagcc     240

tatatggagt ttagccgatt gacatctgag gattctgcaa tctattactg tgcaagatcg     300

ggtctgatag cagtctactt tgattactgg ggccaaggga ccacggtcac cgtctcctca     360

ggtggtggtg gttctggcgg cggcggctcc ggtggtggtg gttctgagct cgtgctgact     420

cagtctccag actttcagtc tgtgactcca aaggagaaag tcaccatcac ctgccgggcc     480

agtcagagca ttggtagtag cttacactgg taccagcaga aaccagatca gtctccaaag     540

ctcctcatca agtttgcttc ccagtccttc tcaggggtcc cctcgaggtt cagtggcagt     600

ggatctggga cagatttcac cctcaccatc aatagcctgg aagctgaaga tgctgcaacg     660

tattactgtc aacagagtta cagtaccccg tggacgttcg gccaagggac caagctggag     720

atcaaa                                                                726


<210> SEQ ID NO 51
<211> LENGTH: 242
<212> TYPE: PRT
<213> ORGANISM: artificial sequence
<220> FEATURE:
<223> OTHER INFORMATION: C33oN-49 (prot)

<400> SEQUENCE: 51

Glu Leu Gln Leu Val Glu Gln Ser Gly Ala Ala Leu Val Lys Pro Gly
1               5                   10                  15
```

```
Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys
```

<210> SEQ ID NO 52
<211> LENGTH: 35
<212> TYPE: DNA
<213> ORGANISM: Artificial Sequence
<220> FEATURE:
<223> OTHER INFORMATION: Synthetic primer

<400> SEQUENCE: 52
tttgcggccg cgtcgactaa cactcattcc tgttg 35

<210> SEQ ID NO 53
<211> LENGTH: 40
<212> TYPE: DNA
<213> ORGANISM: Artificial Sequence
<220> FEATURE:
<223> OTHER INFORMATION: Synthetic primer

<400> SEQUENCE: 53
gccgaattcc accatgragt cacakacyca ggtcttyrta 40

<210> SEQ ID NO 54
<211> LENGTH: 39
<212> TYPE: DNA
<213> ORGANISM: Artificial Sequence
<220> FEATURE:
<223> OTHER INFORMATION: Synthetic primer

<400> SEQUENCE: 54
gccgaattcc accatggrat gsagctgkgt matsctctt 39

<210> SEQ ID NO 55
<211> LENGTH: 29
<212> TYPE: DNA
<213> ORGANISM: Artificial Sequence
<220> FEATURE:
<223> OTHER INFORMATION: Synthetic primer

<400> SEQUENCE: 55
cacaccgctg gacagggctc cagagttcc 29

<210> SEQ ID NO 56
<211> LENGTH: 30
<212> TYPE: DNA
<213> ORGANISM: Artificial Sequence
<220> FEATURE:
<223> OTHER INFORMATION: Synthetic primer

<400> SEQUENCE: 56
tgggagctct gacatcgtgc tgactcagtc 30

<210> SEQ ID NO 57
<211> LENGTH: 31
<212> TYPE: DNA
<213> ORGANISM: Artificial Sequence
<220> FEATURE:
<223> OTHER INFORMATION: Synthetic primer

<400> SEQUENCE: 57
attgcggccg ctttcagttc cagcttggtc c 31

<210> SEQ ID NO 58
<211> LENGTH: 27
<212> TYPE: DNA
<213> ORGANISM: Artificial Sequence
<220> FEATURE:
<223> OTHER INFORMATION: Synthetic primer

<400> SEQUENCE: 58
aaagtcgaca aactgctgca gtctggg 27

<210> SEQ ID NO 59
<211> LENGTH: 28
<212> TYPE: DNA
<213> ORGANISM: Artificial Sequence
<220> FEATURE:
<223> OTHER INFORMATION: Synthetic primer

<400> SEQUENCE: 59
atttccggat gaggagactg tgaccatg 28

<210> SEQ ID NO 60
<211> LENGTH: 27
<212> TYPE: DNA
<213> ORGANISM: Artificial Sequence
<220> FEATURE:
<223> OTHER INFORMATION: Synthetic primer

<400> SEQUENCE: 60
gaggttcagc tcgagcagtc tggagct 27

<210> SEQ ID NO 61
<211> LENGTH: 34
<212> TYPE: DNA
<213> ORGANISM: Artificial Sequence
<220> FEATURE:
<223> OTHER INFORMATION: Synthetic primer

<400> SEQUENCE: 61
tgaggagacg gtgaccgtgg tcccttggcc ccag 34

<210> SEQ ID NO 62
<211> LENGTH: 32
<212> TYPE: DNA
<213> ORGANISM: Artificial Sequence
<220> FEATURE:
<223> OTHER INFORMATION: Synthetic primer

<400> SEQUENCE: 62
ccagttccga gctcgtgctc acccagtctc ca 32

<210> SEQ ID NO 63
<211> LENGTH: 39
<212> TYPE: DNA
<213> ORGANISM: Artificial Sequence
<220> FEATURE:
<223> OTHER INFORMATION: Synthetic primer

<400> SEQUENCE: 63
tggtgcacta gtcgtacgtt tgatctcaag cttggtccc 39

<210> SEQ ID NO 64
<211> LENGTH: 38
<212> TYPE: DNA
<213> ORGANISM: Artificial Sequence
<220> FEATURE:
<223> OTHER INFORMATION: Synthetic primer

<400> SEQUENCE: 64
gagccgcacg agcccgagct ccagatgacc cagtctcc 38

<210> SEQ ID NO 65
<211> LENGTH: 38
<212> TYPE: DNA
<213> ORGANISM: Artificial Sequence
<220> FEATURE:
<223> OTHER INFORMATION: Synthetic primer

<400> SEQUENCE: 65
gagccgcacg agcccgagct cgtgatgacy cagtctcc 38

<210> SEQ ID NO 66
<211> LENGTH: 38
<212> TYPE: DNA
<213> ORGANISM: Artificial Sequence
<220> FEATURE:
<223> OTHER INFORMATION: Synthetic primer

<400> SEQUENCE: 66
gagccgcacg agcccgagct cgtgwtgacr cagtctcc 38

<210> SEQ ID NO 67
<211> LENGTH: 38
<212> TYPE: DNA
<213> ORGANISM: Artificial Sequence
<220> FEATURE:
<223> OTHER INFORMATION: Synthetic primer

<400> SEQUENCE: 67
gagccgcacg agcccgagct cacactcacg cagtctcc 38

<210> SEQ ID NO 68
<211> LENGTH: 38
<212> TYPE: DNA
<213> ORGANISM: Artificial Sequence
<220> FEATURE:
<223> OTHER INFORMATION: Synthetic primer

<400> SEQUENCE: 68
gagccgcacg agcccgagct cgtgctgact cagtctcc 38

<210> SEQ ID NO 69
<211> LENGTH: 47
<212> TYPE: DNA
<213> ORGANISM: Artificial Sequence
<220> FEATURE:
<223> OTHER INFORMATION: Synthetic primer

<400> SEQUENCE: 69
gacgacacta gttgcagcca ccgtacgttt gatttccacc ttggtcc 47

<210> SEQ ID NO 70
<211> LENGTH: 47
<212> TYPE: DNA
<213> ORGANISM: Artificial Sequence
<220> FEATURE:
<223> OTHER INFORMATION: Synthetic primer

<400> SEQUENCE: 70
gacgacacta gttgcagcca ccgtacgttt gatctccasc ttggtcc 47

<210> SEQ ID NO 71
<211> LENGTH: 47
<212> TYPE: DNA
<213> ORGANISM: Artificial Sequence
<220> FEATURE:
<223> OTHER INFORMATION: Synthetic primer

<400> SEQUENCE: 71
gacgacacta gttgcagcca ccgtacgttt gatatccact ttggtcc 47

<210> SEQ ID NO 72
<211> LENGTH: 47
<212> TYPE: DNA
<213> ORGANISM: Artificial Sequence
<220> FEATURE:
<223> OTHER INFORMATION: Synthetic primer

<400> SEQUENCE: 72
gacgacacta gttgcagcca ccgtacgttt aatctccagt cgtgtcc 47

<210> SEQ ID NO 73
<211> LENGTH: 27
<212> TYPE: DNA
<213> ORGANISM: Artificial Sequence
<220> FEATURE:
<223> OTHER INFORMATION: Synthetic primer

<400> SEQUENCE: 73
gaggttcagc tcgagcagtc tggagct 27

<210> SEQ ID NO 74
<211> LENGTH: 34
<212> TYPE: DNA
<213> ORGANISM: Artificial Sequence
<220> FEATURE:
<223> OTHER INFORMATION: Synthetic primer

<400> SEQUENCE: 74
tgaggagacg gtgaccgtgg tcccttggcc ccag 34

<210> SEQ ID NO 75
<211> LENGTH: 10
<212> TYPE: PRT
<213> ORGANISM: Artificial Sequence
<220> FEATURE:
<223> OTHER INFORMATION: Synthetic peptide

<400> SEQUENCE: 75

Thr Gly Asp Tyr Lys Asp Asp Asp Asp Lys
1 5 10

<210> SEQ ID NO 76
<211> LENGTH: 22
<212> TYPE: DNA
<213> ORGANISM: Artificial Sequence
<220> FEATURE:
<223> OTHER INFORMATION: Synthetic primer

<400> SEQUENCE: 76
aggtgcagct gctcgagtct gg 22

<210> SEQ ID NO 77
<211> LENGTH: 23
<212> TYPE: DNA
<213> ORGANISM: Artificial Sequence
<220> FEATURE:
<223> OTHER INFORMATION: Synthetic primer

<400> SEQUENCE: 77
cagrtcacct tgctcgagtc tgg 23

<210> SEQ ID NO 78
<211> LENGTH: 23
<212> TYPE: DNA
<213> ORGANISM: Artificial Sequence
<220> FEATURE:
<223> OTHER INFORMATION: Synthetic primer

<400> SEQUENCE: 78
caggtgcagc tgctcgagtc ggg 23

<210> SEQ ID NO 79
<211> LENGTH: 23
<212> TYPE: DNA
<213> ORGANISM: Artificial Sequence
<220> FEATURE:
<223> OTHER INFORMATION: Synthetic primer

<400> SEQUENCE: 79
caggtgcagc tactcgagtg ggg 23

<210> SEQ ID NO 80
<211> LENGTH: 23
<212> TYPE: DNA
<213> ORGANISM: Artificial Sequence
<220> FEATURE:
<223> OTHER INFORMATION: Synthetic primer

<400> SEQUENCE: 80
caggtacagc tgctcgagtc agg 23

<210> SEQ ID NO 81
<211> LENGTH: 17
<212> TYPE: DNA
<213> ORGANISM: Artificial Sequence
<220> FEATURE:
<223> OTHER INFORMATION: Synthetic primer

<400> SEQUENCE: 81
ctgaggagac ggtgacc 17

<210> SEQ ID NO 82
<211> LENGTH: 17
<212> TYPE: DNA
<213> ORGANISM: Artificial Sequence
<220> FEATURE:
<223> OTHER INFORMATION: Synthetic primer

<400> SEQUENCE: 82
ctgaagagac ggtgacc 17

<210> SEQ ID NO 83
<211> LENGTH: 51
<212> TYPE: DNA
<213> ORGANISM: Artificial Sequence
<220> FEATURE:
<223> OTHER INFORMATION: Synthetic primer

<400> SEQUENCE: 83
gtaatcaaag tagactgcta tcagacccga tctygcacag taatacacgg c 51

<210> SEQ ID NO 84
<211> LENGTH: 51
<212> TYPE: DNA
<213> ORGANISM: Artificial Sequence
<220> FEATURE:
<223> OTHER INFORMATION: Synthetic primer

<400> SEQUENCE: 84
gtaatcaaag tagactgcta tcagacccga tctygcacag taatacayrg c 51

<210> SEQ ID NO 85
<211> LENGTH: 51
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (34)..(34)
<223> OTHER INFORMATION: n is a, c, g, or t

<400> SEQUENCE: 85
gtaatcaaag tagactgcta tcagacccga tctngyacag taatacacrg c 51

<210> SEQ ID NO 86
<211> LENGTH: 51
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (34)..(34)
<223> OTHER INFORMATION: n is a, c, g, or t

<400> SEQUENCE: 86
gtaatcaaag tagactgcta tcagacccga tctngcacag taatacaarg c 51

<210> SEQ ID NO 87
<211> LENGTH: 51
<212> TYPE: DNA
<213> ORGANISM: Artificial Sequence
<220> FEATURE:
<223> OTHER INFORMATION: Synthetic primer

<400> SEQUENCE: 87
gtaatcaaag tagactgcta tcagacccga tctsgcacag taatacacrg c 51

<210> SEQ ID NO 88
<211> LENGTH: 48
<212> TYPE: DNA
<213> ORGANISM: Artificial Sequence
<220> FEATURE:
<223> OTHER INFORMATION: Synthetic primer

<400> SEQUENCE: 88
agagacggtg accattgtcc cttggcccca gtaatcaaag tagactgc 48

<210> SEQ ID NO 89
<211> LENGTH: 726
<212> TYPE: DNA
<213> ORGANISM: Artificial Sequence
<220> FEATURE:
<223> OTHER INFORMATION: B32oN-10 complement n.t. sequence

<400> SEQUENCE: 89
ctcgacgtcg accagctcgt cagacctcga cgtgaccact tcggacccct gagacacttc 60
tacagaacgt ttcgaagacc aataggtaag tgactgatat aacatgtgac ccacttcgtc 120
tcagtacctt tctcggaact gacctaacca atataattag gaatgtcacc actatgattc 180
aagttacttt tcaagttctc attccggtgc aactgacaac tgttcaggtc gtcgtgtcgg 240
atatacctca aatcggctaa ctgtagactc ctaagacgtt agataatgac acgttctagc 300
ccagactatc gtcagatgaa actaatgacc ccggttccct ggtgccagtg gcagaggagt 360
ccaccaccac caagaccgcc gccgccgagg ccaccaccac caagactcga ggtctactgg 420
gtcagaggta ggagggacag acgtagacat cctctgtctc agtggtagtg aacggcctgt 480
tcagtctggt aatcgtcaga aaatttaacc atagtcgtct ttggtccctt tcggggattc 540
gaggactaga tacgacgtag gttaaacgtt tcaccccagg gtagttccaa gtcaccgtca 600
cctagaccct gtctaaagtg agagtggtag tcgccagacg ttggacttct aaaaagttga 660
atgaagacag ttgtctcaat gtcaaaggga gcttgcaagc cggttccctg gtttcaccta 720
tagttt 726

<210> SEQ ID NO 90
<211> LENGTH: 120
<212> TYPE: PRT
<213> ORGANISM: Artificial Sequence
<220> FEATURE:
<223> OTHER INFORMATION: B32oN-10 VH

<400> SEQUENCE: 90

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45
```

```
Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 91
<211> LENGTH: 5
<212> TYPE: PRT
<213> ORGANISM: Artificial Sequence
<220> FEATURE:
<223> OTHER INFORMATION: B32oN-10 H-CDR1

<400> SEQUENCE: 91

Asp Tyr Ile Val His
1               5


<210> SEQ ID NO 92
<211> LENGTH: 17
<212> TYPE: PRT
<213> ORGANISM: Artificial Sequence
<220> FEATURE:
<223> OTHER INFORMATION: B32oN-10 H-CDR2

<400> SEQUENCE: 92

Tyr Ile Asn Pro Tyr Ser Gly Asp Thr Lys Phe Asn Glu Lys Phe Lys
1               5                   10                  15

Ser


<210> SEQ ID NO 93
<211> LENGTH: 10
<212> TYPE: PRT
<213> ORGANISM: Artificial Sequence
<220> FEATURE:
<223> OTHER INFORMATION: B32oN-10 H-CDR3

<400> SEQUENCE: 93

Ser Gly Leu Ile Ala Val Tyr Phe Asp Tyr
1               5                   10


<210> SEQ ID NO 94
<211> LENGTH: 107
<212> TYPE: PRT
<213> ORGANISM: Artificial Sequence
<220> FEATURE:
<223> OTHER INFORMATION: B32oN-10 VL

<400> SEQUENCE: 94

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Thr Ile Ser Ser Leu
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
```

65 70 75 80

Glu Asp Phe Ser Thr Tyr Phe Cys Gln Gln Ser Tyr Ser Phe Pro Arg
85 90 95

Thr Phe Gly Gln Gly Thr Lys Val Asp Ile Lys
100 105

<210> SEQ ID NO 95
<211> LENGTH: 11
<212> TYPE: PRT
<213> ORGANISM: Artificial Sequence
<220> FEATURE:
<223> OTHER INFORMATION: B32oN-10 L-CDR1

<400> SEQUENCE: 95

Arg Thr Ser Gln Thr Ile Ser Ser Leu Leu Asn
1 5 10

<210> SEQ ID NO 96
<211> LENGTH: 7
<212> TYPE: PRT
<213> ORGANISM: Artificial Sequence
<220> FEATURE:
<223> OTHER INFORMATION: B32oN-10 L-CDR2

<400> SEQUENCE: 96

Ala Ala Ser Asn Leu Gln Ser
1 5

<210> SEQ ID NO 97
<211> LENGTH: 9
<212> TYPE: PRT
<213> ORGANISM: Artificial Sequence
<220> FEATURE:
<223> OTHER INFORMATION: B32oN-10 L-CDR3

<400> SEQUENCE: 97

Gln Gln Ser Tyr Ser Phe Pro Arg Thr
1 5

<210> SEQ ID NO 98
<211> LENGTH: 726
<212> TYPE: DNA
<213> ORGANISM: Artificial Sequence
<220> FEATURE:
<223> OTHER INFORMATION: B32oN-33 complement n.t. sequence

<400> SEQUENCE: 98
ctcgacgtcg accagctcgt cagacctcga cgtgaccact tcggacccct gagacacttc 60
tacagaacgt ttcgaagacc aataggtaag tgactgatat aacatgtgac ccacttcgtc 120
tcagtacctt tctcggaact gacctaacca atataattag gaatgtcacc actatgattc 180
aagttacttt tcaagttctc attccggtgc aactgacaac tgttcaggtc gtcgtgtcgg 240
atatacctca aatcggctaa ctgtagactc ctaagacgtt agataatgac acgttctagc 300
ccagactatc gtcagatgaa actaatgacc ccggttccct ggtgccagtg gcagaggagt 360
ccaccaccac caagaccgcc gccgccgagg ccaccaccac caagactcga gcactactgc 420
gtcagaggtc ggtgggacag aaacagaggt cccctttctc ggtgggagag gacgtcccgg 480
tcagtctcac aatcctggat gaatcggacc atggttgtct ttggaccggt ccgagggtcc 540
gaggagtaga tacgacgtag ggtgtcccgg tgaccgtagg gtcggtccaa gtcaccgtca 600
cccagaccct gtctgaagtg agagtggtag tcgtctgacc tcggacttct aaaacgtcac 660

```
ataatgacag tcgtcatacc atcgagtgga ggctgcaagc cggttccctg gttccatctc     720

tagttt                                                                726


<210> SEQ ID NO 99
<211> LENGTH: 120
<212> TYPE: PRT
<213> ORGANISM: Artificial Sequence
<220> FEATURE:
<223> OTHER INFORMATION: B32oN-33 VH

<400> SEQUENCE: 99

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 100
<211> LENGTH: 5
<212> TYPE: PRT
<213> ORGANISM: Artificial Sequence
<220> FEATURE:
<223> OTHER INFORMATION: B32oN-33 H-CDR1

<400> SEQUENCE: 100

Asp Tyr Ile Val His
1               5


<210> SEQ ID NO 101
<211> LENGTH: 17
<212> TYPE: PRT
<213> ORGANISM: Artificial Sequence
<220> FEATURE:
<223> OTHER INFORMATION: B32oN-33 H-CDR2

<400> SEQUENCE: 101

Tyr Ile Asn Pro Tyr Ser Gly Asp Thr Lys Phe Asn Glu Lys Phe Lys
1               5                   10                  15

Ser


<210> SEQ ID NO 102
<211> LENGTH: 10
<212> TYPE: PRT
<213> ORGANISM: Artificial Sequence
<220> FEATURE:
<223> OTHER INFORMATION: B32oN-33 H-CDR3

<400> SEQUENCE: 102

Ser Gly Leu Ile Ala Val Tyr Phe Asp Tyr
1               5                   10
```

<210> SEQ ID NO 103
<211> LENGTH: 107
<212> TYPE: PRT
<213> ORGANISM: Artificial Sequence
<220> FEATURE:
<223> OTHER INFORMATION: B32oN-33 VL

<400> SEQUENCE: 103

```
Glu Leu Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Arg Thr Tyr
            20                  25                  30

Leu Ala Trp Tyr Gln Gln Lys Pro Gly Gln Ala Pro Arg Leu Leu Ile
        35                  40                  45

Tyr Ala Ala Ser His Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Lys Val Glu Ile Lys
            100                 105
```

<210> SEQ ID NO 104
<211> LENGTH: 11
<212> TYPE: PRT
<213> ORGANISM: Artificial Sequence
<220> FEATURE:
<223> OTHER INFORMATION: B32oN-33 L-CDR1

<400> SEQUENCE: 104

```
Arg Ala Ser Gln Ser Val Arg Thr Tyr Leu Ala
1               5                   10
```

<210> SEQ ID NO 105
<211> LENGTH: 7
<212> TYPE: PRT
<213> ORGANISM: Artificial Sequence
<220> FEATURE:
<223> OTHER INFORMATION: B32oN-33 L-CDR2

<400> SEQUENCE: 105

```
Ala Ala Ser His Arg Ala Thr
1               5
```

<210> SEQ ID NO 106
<211> LENGTH: 9
<212> TYPE: PRT
<213> ORGANISM: Artificial Sequence
<220> FEATURE:
<223> OTHER INFORMATION: B32oN-33 L-CDR3

<400> SEQUENCE: 106

```
Gln Gln Tyr Gly Ser Ser Pro Pro Thr
1               5
```

<210> SEQ ID NO 107
<211> LENGTH: 726
<212> TYPE: DNA
<213> ORGANISM: Artificial Sequence
<220> FEATURE:
<223> OTHER INFORMATION: B32oN-44 complement n.t. sequence

<400> SEQUENCE: 107

```
ctcgacgtcg accagctcgt cagacctcga cgtgaccact tcggacccct gagacacttc     60

tacagaacgt ttcgaagacc aataggtaag tgactgatat aacatgtgac ccacttcgtc    120

tcagtacctt tctcggaact gacctaacca atataattag gaatgtcacc actatgattc    180

aagttacttt tcaagttctc attccggtgc aactgacaac tgttcaggtc gtcgtgtcgg    240

atatacctca aatcggctaa ctgtagactc ctaagacgtt agataatgac acgttctagc    300

ccagactatc gtcagatgaa actaatgacc ccggttccct ggtgccagtg gcagaggagt    360

ccaccaccac caagaccgcc gccgccgagg ccaccaccac caagactcga gcacgactga    420

gtcagaggcc tgaaagtcag acactgaggt ttcctctttc agtggtagtg gacggcccgg    480

tcagtctcgt aaccatcatc gaatgtgacc atggtcgtct ttggtctagt cggaggtttc    540

gaggagtagt ttaaacgaag ggtcaggtag agttcccagg ggagctccaa gtcaccgtga    600

cctagaccct gtctaaagtg ggagtggtag ttatcggacc ttcgacttct acgacgttgc    660

ataatgacag tcgtctcgaa atcaaagggc atgtgaaaac cggtcccctg gttcgacctc    720

tagttt                                                               726
```

```
<210> SEQ ID NO 108
<211> LENGTH: 120
<212> TYPE: PRT
<213> ORGANISM: Artificial Sequence
<220> FEATURE:
<223> OTHER INFORMATION: B32oN-44  VH

<400> SEQUENCE: 108

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 109
<211> LENGTH: 5
<212> TYPE: PRT
<213> ORGANISM: Artificial Sequence
<220> FEATURE:
<223> OTHER INFORMATION: B32oN-44 H-CDR1

<400> SEQUENCE: 109

Asp Tyr Ile Val His
1               5


<210> SEQ ID NO 110
<211> LENGTH: 17
<212> TYPE: PRT
<213> ORGANISM: Artificial Sequence
```

```
<220> FEATURE:
<223> OTHER INFORMATION: B32oN-44 H-CDR2

<400> SEQUENCE: 110

Tyr Ile Asn Pro Tyr Ser Gly Asp Thr Lys Phe Asn Glu Lys Phe Lys
1               5                   10                  15

Ser


<210> SEQ ID NO 111
<211> LENGTH: 10
<212> TYPE: PRT
<213> ORGANISM: Artificial Sequence
<220> FEATURE:
<223> OTHER INFORMATION: B32oN-44 H-CDR3

<400> SEQUENCE: 111

Ser Gly Leu Ile Ala Val Tyr Phe Asp Tyr
1               5                   10


<210> SEQ ID NO 112
<211> LENGTH: 107
<212> TYPE: PRT
<213> ORGANISM: Artificial Sequence
<220> FEATURE:
<223> OTHER INFORMATION: B32oN-44  VL

<400> SEQUENCE: 112

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Pro Pro Lys Leu Leu Ile
        35                  40                  45

Lys Phe Ala Ser Gln Ser Ile Ser Arg Val Pro Ser Arg Phe Ser Gly
    50                  55                  60

Thr Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Phe Ser Phe Pro Tyr
                85                  90                  95

Thr Phe Gly Gln Gly Thr Lys Leu Glu Ile Lys
            100                 105


<210> SEQ ID NO 113
<211> LENGTH: 11
<212> TYPE: PRT
<213> ORGANISM: Artificial Sequence
<220> FEATURE:
<223> OTHER INFORMATION: B32oN-44 L-CDR1

<400> SEQUENCE: 113

Arg Ala Ser Gln Ser Ile Gly Ser Ser Leu His
1               5                   10


<210> SEQ ID NO 114
<211> LENGTH: 7
<212> TYPE: PRT
<213> ORGANISM: Artificial Sequence
<220> FEATURE:
<223> OTHER INFORMATION: B32oN-44 L-CDR2

<400> SEQUENCE: 114

Phe Ala Ser Gln Ser Ile Ser
1               5
```

<210> SEQ ID NO 115
<211> LENGTH: 9
<212> TYPE: PRT
<213> ORGANISM: Artificial Sequence
<220> FEATURE:
<223> OTHER INFORMATION: B32oN-44 L-CDR3

<400> SEQUENCE: 115

Gln Gln Ser Phe Ser Phe Pro Tyr Thr
1               5

<210> SEQ ID NO 116
<211> LENGTH: 726
<212> TYPE: DNA
<213> ORGANISM: Artificial Sequence
<220> FEATURE:
<223> OTHER INFORMATION: B32oN-45 complement n.t. sequence

<400> SEQUENCE: 116
ctcgacgtcg accagctcgt cagacctcga cgtgaccact tcggacccct gagacacttc 60
tacagaacgt ttcgaagacc aataggtaag tgactgatat aacatgtgac ccacttcgtc 120
tcagtacctt tctcggaact gacctaacca atataattag gaatgtcacc actatgattc 180
aagttacttt tcaagttctc attccggtgc aactgacaac tgttcaggtc gtcgtgtcgg 240
atatacctca aatcggctaa ctgtagactc ctaagacgtt agataatgac acgttctagc 300
ccagactatc gtcagatgaa actaatgacc ccggttccct ggtgccagtg gcagaggagt 360
ccaccaccac caagaccgcc gccgccgagg ccaccaccac caagactcga gcactactgg 420
gtcagaggta gaaggcacag acgtagacat cctctgtctc agtggtagcg aacagcccgc 480
tcagtcttgt aatctttgta aaatttaacc atagttgtct ctggtccctt ccggggagtt 540
gaggactaga tacgacggag gttaaatgtt tcaccgcagg gtagttccaa gtcaccgtca 600
cctagaccct gtctaaagtg agagtggtag ttgtcagacg ttggacttct aaaacgttga 660
atgatgacag ttgtctcaat gtcatacgga gcttgaaagc cgcctccctg gttccacctt 720
tagttt 726

<210> SEQ ID NO 117
<211> LENGTH: 120
<212> TYPE: PRT
<213> ORGANISM: Artificial Sequence
<220> FEATURE:
<223> OTHER INFORMATION: B32oN-45 VH

<400> SEQUENCE: 117

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln

```
            100                 105                 110

Gly Thr Thr Val Thr Val Ser Ser
        115                 120


<210> SEQ ID NO 118
<211> LENGTH: 5
<212> TYPE: PRT
<213> ORGANISM: Artificial Sequence
<220> FEATURE:
<223> OTHER INFORMATION: B32oN-45 H-CDR1

<400> SEQUENCE: 118

Asp Tyr Ile Val His
1               5


<210> SEQ ID NO 119
<211> LENGTH: 17
<212> TYPE: PRT
<213> ORGANISM: Artificial Sequence
<220> FEATURE:
<223> OTHER INFORMATION: B32oN-45 H-CDR2

<400> SEQUENCE: 119

Tyr Ile Asn Pro Tyr Ser Gly Asp Thr Lys Phe Asn Glu Lys Phe Lys
1               5                   10                  15

Ser


<210> SEQ ID NO 120
<211> LENGTH: 10
<212> TYPE: PRT
<213> ORGANISM: Artificial Sequence
<220> FEATURE:
<223> OTHER INFORMATION: B32oN-45 H-CDR3

<400> SEQUENCE: 120

Ser Gly Leu Ile Ala Val Tyr Phe Asp Tyr
1               5                   10


<210> SEQ ID NO 121
<211> LENGTH: 107
<212> TYPE: PRT
<213> ORGANISM: Artificial Sequence
<220> FEATURE:
<223> OTHER INFORMATION: B32oN-45 VL

<400> SEQUENCE: 121

Glu Leu Val Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105


<210> SEQ ID NO 122
```

<211> LENGTH: 11
<212> TYPE: PRT
<213> ORGANISM: Artificial Sequence
<220> FEATURE:
<223> OTHER INFORMATION: B32oN-45 L-CDR1

<400> SEQUENCE: 122

Arg Ala Ser Gln Asn Ile Arg Asn Ile Leu Asn
1 5 10

<210> SEQ ID NO 123
<211> LENGTH: 7
<212> TYPE: PRT
<213> ORGANISM: Artificial Sequence
<220> FEATURE:
<223> OTHER INFORMATION: B32oN-45 L-CDR2

<400> SEQUENCE: 123

Ala Ala Ser Asn Leu Gln Ser
1 5

<210> SEQ ID NO 124
<211> LENGTH: 9
<212> TYPE: PRT
<213> ORGANISM: Artificial Sequence
<220> FEATURE:
<223> OTHER INFORMATION: B32oN-45 L-CDR3

<400> SEQUENCE: 124

Gln Gln Ser Tyr Ser Met Pro Arg Thr
1 5

<210> SEQ ID NO 125
<211> LENGTH: 726
<212> TYPE: DNA
<213> ORGANISM: Artificial Sequence
<220> FEATURE:
<223> OTHER INFORMATION: B32oN-48 complement n.t. sequence

<400> SEQUENCE: 125
ctcgacgtcg accagctcgt cagacctcga cgtgaccact tcggacccct gagacacttc 60
tacagaacgt ttcgaagacc aataggtaag tgactgatat aacatgtgac ccacttcgtc 120
tcagtacctt tctcggaact gacctaacca atataattag gaatgtcacc actatgattc 180
aagttacttt tcaagttctc attccggtgc aactgacaac tgttcaggtc gtcgtgtcgg 240
atatacctca aatcggctaa ctgtagactc ctaagacgtt agataatgac acgttctagc 300
ccagactatc gtcagatgaa actaatgacc ccggttccct ggtgccagtg gcagaggagt 360
ccaccaccac caagaccgcc gccgccgagg ccaccaccac caagactcga gcacgactga 420
gtcagaggtc cgaaagtcag acactgaggt ttcctctttc agtggtagtg gacggcccgg 480
tcagtctcgt aaccatcatc gaatgtgacc atggtcgtct ttggtctagt cggaggtttc 540
gaggagtagt ttaaacgaag ggtcaggtag agtccccagg ggagctccaa gtcaccgtca 600
cctagaccct gtttaaagtg ggagtggtag ttatcggacc ttcgacttct acgacgttgg 660
ataatgacag tcgtctcatc atgaaatgga gggtgaaaac cggtcccctg gttccacctc 720
tagttt 726

<210> SEQ ID NO 126
<211> LENGTH: 120
<212> TYPE: PRT
<213> ORGANISM: Artificial Sequence
<220> FEATURE:

<223> OTHER INFORMATION: B32oN-48 VH

<400> SEQUENCE: 126

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120
```

<210> SEQ ID NO 127
<211> LENGTH: 5
<212> TYPE: PRT
<213> ORGANISM: Artificial Sequence
<220> FEATURE:
<223> OTHER INFORMATION: B32oN-48 H-CDR1

<400> SEQUENCE: 127

```
Asp Tyr Ile Val His
1               5
```

<210> SEQ ID NO 128
<211> LENGTH: 17
<212> TYPE: PRT
<213> ORGANISM: Artificial Sequence
<220> FEATURE:
<223> OTHER INFORMATION: B32oN-48 H-CDR2

<400> SEQUENCE: 128

```
Tyr Ile Asn Pro Tyr Ser Gly Asp Thr Lys Phe Asn Glu Lys Phe Lys
1               5                   10                  15

Ser
```

<210> SEQ ID NO 129
<211> LENGTH: 10
<212> TYPE: PRT
<213> ORGANISM: Artificial Sequence
<220> FEATURE:
<223> OTHER INFORMATION: B32oN-48 H-CDR3

<400> SEQUENCE: 129

```
Ser Gly Leu Ile Ala Val Tyr Phe Asp Tyr
1               5                   10
```

<210> SEQ ID NO 130
<211> LENGTH: 107
<212> TYPE: PRT
<213> ORGANISM: Artificial Sequence
<220> FEATURE:
<223> OTHER INFORMATION: B32oN-48 VL

<400> SEQUENCE: 130

```
Glu Leu Val Leu Thr Gln Ser Pro Gly Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Pro Pro Lys Leu Leu Ile
        35                  40                  45

Lys Phe Ala Ser Gln Ser Ile Ser Gly Val Pro Ser Arg Phe Ser Gly
    50                  55                  60

Ser Gly Ser Gly Thr Asn Phe Thr Leu Thr Ile Asn Ser Leu Glu Ala
65                  70                  75                  80

Glu Asp Ala Ala Thr Tyr Tyr Cys Gln Gln Ser Ser Thr Leu Pro Pro
                85                  90                  95

Thr Phe Gly Gln Gly Thr Lys Val Glu Ile Lys
            100                 105
```

<210> SEQ ID NO 131
<211> LENGTH: 11
<212> TYPE: PRT
<213> ORGANISM: Artificial Sequence
<220> FEATURE:
<223> OTHER INFORMATION: B32oN-48 L-CDR1

<400> SEQUENCE: 131

```
Arg Ala Ser Gln Ser Ile Gly Ser Ser Leu His
1               5                   10
```

<210> SEQ ID NO 132
<211> LENGTH: 7
<212> TYPE: PRT
<213> ORGANISM: Artificial Sequence
<220> FEATURE:
<223> OTHER INFORMATION: B32oN-48 L-CDR2

<400> SEQUENCE: 132

```
Phe Ala Ser Gln Ser Ile Ser
1               5
```

<210> SEQ ID NO 133
<211> LENGTH: 9
<212> TYPE: PRT
<213> ORGANISM: Artificial Sequence
<220> FEATURE:
<223> OTHER INFORMATION: B32oN-48 L-CDR3

<400> SEQUENCE: 133

```
Gln Gln Ser Ser Thr Leu Pro Pro Thr
1               5
```

<210> SEQ ID NO 134
<211> LENGTH: 726
<212> TYPE: DNA
<213> ORGANISM: Artificial Sequence
<220> FEATURE:
<223> OTHER INFORMATION: B32oN-49 complement n.t. sequence

<400> SEQUENCE: 134

```
ctcgacgtcg accagctcgt cagacctcga cgtgaccact tcggacccct gagacacttc     60

tacagaacgt ttcgaagacc aataggtaag tgactgatat aacatgtgac ccacttcgtc    120

tcagtacctt tctcggaact gacctaacca atataattag gaatgtcacc actatgattc    180

aagttacttt tcaagttctc attccggtgc aactgacaac tgttcaggtc gtcgtgtcgg    240

atatacctca aatcggctaa ctgtagactc ctaagacgtt agataatgac acgttctagc    300
```

```
ccagactatc gtcagatgaa actaatgacc ccggttccct ggtgccagtg gcagaggagt    360

ccaccaccac caagaccgcc gccgccgagg ccaccaccac caagactcga gcacgactga    420

gtcagaggtc tgaaagtcag acactgaggt ttcctctttc agtggtagtg gacggcccgg    480

tcagtctcgt aaccatcatc gaatgtgacc atggtcgtct ttggtctagt cagaggtttc    540

gaggagtagt tcaaacgaag ggtcagggag agtccccagg ggagctccaa gtcaccgtca    600

cctagaccct gtctaaagtg agagtggtag tcgtcagatg ttggacttct aaaacgttga    660

atgatgacag ttgtctcaat gtgatggggg gggtgaaagc cgcctccctg gttccacctt    720

tagttt                                                               726
```

```
<210> SEQ ID NO 135
<211> LENGTH: 120
<212> TYPE: PRT
<213> ORGANISM: Artificial Sequence
<220> FEATURE:
<223> OTHER INFORMATION: B32oN-49 VH

<400> SEQUENCE: 135

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 136
<211> LENGTH: 5
<212> TYPE: PRT
<213> ORGANISM: Artificial Sequence
<220> FEATURE:
<223> OTHER INFORMATION: B32oN-49 H-CDR1

<400> SEQUENCE: 136

Asp Tyr Ile Val His
1               5


<210> SEQ ID NO 137
<211> LENGTH: 17
<212> TYPE: PRT
<213> ORGANISM: Artificial Sequence
<220> FEATURE:
<223> OTHER INFORMATION: B32oN-49 H-CDR2

<400> SEQUENCE: 137

Tyr Ile Asn Pro Tyr Ser Gly Asp Thr Lys Phe Asn Glu Lys Phe Lys
1               5                   10                  15

Ser
```

```
<210> SEQ ID NO 138
<211> LENGTH: 10
<212> TYPE: PRT
<213> ORGANISM: Artificial Sequence
<220> FEATURE:
<223> OTHER INFORMATION: B32oN-49 H-CDR3

<400> SEQUENCE: 138

Ser Gly Leu Ile Ala Val Tyr Phe Asp Tyr
1               5                   10


<210> SEQ ID NO 139
<211> LENGTH: 107
<212> TYPE: PRT
<213> ORGANISM: Artificial Sequence
<220> FEATURE:
<223> OTHER INFORMATION: B32oN-49 VL

<400> SEQUENCE: 139

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gly Gly Thr Lys Val Glu Ile Lys
            100                 105


<210> SEQ ID NO 140
<211> LENGTH: 11
<212> TYPE: PRT
<213> ORGANISM: Artificial Sequence
<220> FEATURE:
<223> OTHER INFORMATION: B32oN-49 L-CDR1

<400> SEQUENCE: 140

Arg Ala Ser Gln Ser Ile Gly Ser Ser Leu His
1               5                   10


<210> SEQ ID NO 141
<211> LENGTH: 7
<212> TYPE: PRT
<213> ORGANISM: Artificial Sequence
<220> FEATURE:
<223> OTHER INFORMATION: B32oN-49 L-CDR2

<400> SEQUENCE: 141

Phe Ala Ser Gln Ser Leu Ser
1               5


<210> SEQ ID NO 142
<211> LENGTH: 9
<212> TYPE: PRT
<213> ORGANISM: Artificial Sequence
<220> FEATURE:
<223> OTHER INFORMATION: B32oN-49 L-CDR3

<400> SEQUENCE: 142
```

```
Gln Gln Ser Tyr Thr Thr Pro Pro Thr
1               5


<210> SEQ ID NO 143
<211> LENGTH: 726
<212> TYPE: DNA
<213> ORGANISM: Artificial Sequence
<220> FEATURE:
<223> OTHER INFORMATION: B32oN-67 complement n.t. sequence

<400> SEQUENCE: 143

ctcgacgtcg accagctcgt cagacctcga cgtgaccact tcggacccct gagacacttc     60

tacagaacgt ttcgaagacc aataggtaag tgactgatat aacatgtgac ccacttcgtc    120

tcagtacctt tctcggaact gacctaacca atataattag gaatgtcacc actatgattc    180

aagttacttt tcaagttctc attccggtgc aactgacaac tgttcaggtc gtcgtgtcgg    240

atatacctca aatcggctaa ctgtagactc ctaagacgtt agataatgac acgttctagc    300

ccagactatc gtcagatgaa actaatgacc ccggttccct ggtgccagtg gcagaggagt    360

ccaccaccac caagaccgcc gccgccgagg ccaccaccac caagactcga gcacgactga    420

gtcagagggc cgaaagtcag acactgaggt ttcctctttc agtggtagtg gacggcccgg    480

tcagtctcgt aaccatcatc gaatgtgacc atggtcgtct ttggtctagt cagaggtttc    540

gaggagtagt ttaaacgaag ggtcaggtag agtccccagg ggagctccaa gtgaccgtca    600

cctagaccct gtctaaagtg agagtggtag tcgtcagacg ttggacttct ataacgttga    660

atgatgacag ttgtctcaat gtcatgggga acctgcaagc cggttccctg gttcgacctc    720

tagttt                                                               726


<210> SEQ ID NO 144
<211> LENGTH: 120
<212> TYPE: PRT
<213> ORGANISM: Artificial Sequence
<220> FEATURE:
<223> OTHER INFORMATION: B32oN-67 VH

<400> SEQUENCE: 144

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 145
<211> LENGTH: 5
<212> TYPE: PRT
<213> ORGANISM: Artificial Sequence
```

<220> FEATURE:
<223> OTHER INFORMATION: B32oN-67 H-CDR1

<400> SEQUENCE: 145

```
Asp Tyr Ile Val His
1               5
```

<210> SEQ ID NO 146
<211> LENGTH: 17
<212> TYPE: PRT
<213> ORGANISM: Artificial Sequence
<220> FEATURE:
<223> OTHER INFORMATION: B32oN-67 H-CDR2

<400> SEQUENCE: 146

```
Tyr Ile Asn Pro Tyr Ser Gly Asp Thr Lys Phe Asn Glu Lys Phe Lys
1               5                   10                  15

Ser
```

<210> SEQ ID NO 147
<211> LENGTH: 10
<212> TYPE: PRT
<213> ORGANISM: Artificial Sequence
<220> FEATURE:
<223> OTHER INFORMATION: B32oN-67 H-CDR3

<400> SEQUENCE: 147

```
Ser Gly Leu Ile Ala Val Tyr Phe Asp Tyr
1               5                   10
```

<210> SEQ ID NO 148
<211> LENGTH: 98
<212> TYPE: PRT
<213> ORGANISM: Artificial Sequence
<220> FEATURE:
<223> OTHER INFORMATION: B32oN-67 VL

<400> SEQUENCE: 148

```
Glu Leu Val Leu Thr Gln Ser Pro Gly Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Phe Gly Gln Gly Thr Lys Leu Glu
                85                  90                  95

Ile Lys
```

<210> SEQ ID NO 149
<211> LENGTH: 11
<212> TYPE: PRT
<213> ORGANISM: Artificial Sequence
<220> FEATURE:
<223> OTHER INFORMATION: B32oN-67 L-CDR1

<400> SEQUENCE: 149

```
Arg Ala Ser Gln Ser Ile Gly Ser Ser Leu His
1               5                   10
```

<210> SEQ ID NO 150
<211> LENGTH: 7
<212> TYPE: PRT
<213> ORGANISM: Artificial Sequence
<220> FEATURE:
<223> OTHER INFORMATION: B32oN-67 L-CDR2

<400> SEQUENCE: 150

Phe Ala Ser Gln Ser Ile Ser
1               5

<210> SEQ ID NO 151
<211> LENGTH: 9
<212> TYPE: PRT
<213> ORGANISM: Artificial Sequence
<220> FEATURE:
<223> OTHER INFORMATION: B32oN-67 L-CDR3

<400> SEQUENCE: 151

Gln Gln Ser Tyr Ser Thr Pro Trp Thr
1               5

<210> SEQ ID NO 152
<211> LENGTH: 726
<212> TYPE: DNA
<213> ORGANISM: Artificial Sequence
<220> FEATURE:
<223> OTHER INFORMATION: B32oN-73 complement n.t. sequence

<400> SEQUENCE: 152
ctcgacgtcg accagctcgt cagacctcga cgtgaccact tcggacccct gagacacttc 60
tacagaacgt ttcgaagacc aataggtaag tgactgatat aacatgtgac ccacttcgtc 120
tcagtacctt tctcggaact gacctaacca atataattag gaatgtcacc actatgattc 180
aagttacttt tcaagttctc attccggtgc aactgacaac tgttcaggtc gtcgtgtcgg 240
atatacctca aatcggctaa ctgtagactc ctaagacgtt agataatgac acgttctagc 300
ccagactatc gtcagatgaa actaatgacc ccggttccct ggtgccagtg gcagaggagt 360
ccaccaccac caagaccgcc gccgccgagg ccaccaccac caagactcga gcacgactga 420
gtcagagggc cgaaagtcag acactgaggt ttcctctttc agtggtagtg gacggcccgg 480
tcagtctcgt aaccatcatc gaatgtgacc atggtcgtct ttggtctagt cagaggtttc 540
gaggagtagt ttaaacgaag ggtcaggtag agtccccagg ggagctccaa gtcaccgtga 600
cctagaccct gtctaaagtg agagtggtag tcgtcagacg ttggacttct ataacgttga 660
atgatgacag ttgtctcaat gtcatgggga acctgcaagc cggttccctg gttcgacctc 720
tagttt 726

<210> SEQ ID NO 153
<211> LENGTH: 120
<212> TYPE: PRT
<213> ORGANISM: Artificial Sequence
<220> FEATURE:
<223> OTHER INFORMATION: B32oN-73 VH

<400> SEQUENCE: 153

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp

```
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 154
<211> LENGTH: 5
<212> TYPE: PRT
<213> ORGANISM: Artificial Sequence
<220> FEATURE:
<223> OTHER INFORMATION: B32oN-73 H-CDR1

<400> SEQUENCE: 154

Asp Tyr Ile Val His
1               5


<210> SEQ ID NO 155
<211> LENGTH: 17
<212> TYPE: PRT
<213> ORGANISM: Artificial Sequence
<220> FEATURE:
<223> OTHER INFORMATION: B32oN-73 H-CDR2

<400> SEQUENCE: 155

Tyr Ile Asn Pro Tyr Ser Gly Asp Thr Lys Phe Asn Glu Lys Phe Lys
1               5                   10                  15

Ser


<210> SEQ ID NO 156
<211> LENGTH: 10
<212> TYPE: PRT
<213> ORGANISM: Artificial Sequence
<220> FEATURE:
<223> OTHER INFORMATION: B32oN-73 H-CDR3

<400> SEQUENCE: 156

Ser Gly Leu Ile Ala Val Tyr Phe Asp Tyr
1               5                   10


<210> SEQ ID NO 157
<211> LENGTH: 107
<212> TYPE: PRT
<213> ORGANISM: Artificial Sequence
<220> FEATURE:
<223> OTHER INFORMATION: B32oN-73 VL

<400> SEQUENCE: 157

Glu Leu Val Leu Thr Gln Ser Pro Gly Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60
```

Thr Gly Ser Gly Thr Asp Phe Thr Leu Thr Ile Ser Ser Leu Gln Pro
65 70 75 80

Glu Asp Ile Ala Thr Tyr Tyr Cys Gln Gln Ser Tyr Ser Thr Pro Trp
85 90 95

Thr Phe Gly Gln Gly Thr Lys Leu Glu Ile Lys
100 105

<210> SEQ ID NO 158
<211> LENGTH: 11
<212> TYPE: PRT
<213> ORGANISM: Artificial Sequence
<220> FEATURE:
<223> OTHER INFORMATION: B32oN-73 L-CDR1

<400> SEQUENCE: 158

Arg Ala Ser Gln Ser Ile Gly Ser Ser Leu His
1 5 10

<210> SEQ ID NO 159
<211> LENGTH: 7
<212> TYPE: PRT
<213> ORGANISM: Artificial Sequence
<220> FEATURE:
<223> OTHER INFORMATION: B32oN-73 L-CDR2

<400> SEQUENCE: 159

Phe Ala Ser Gln Ser Ile Ser
1 5

<210> SEQ ID NO 160
<211> LENGTH: 9
<212> TYPE: PRT
<213> ORGANISM: Artificial Sequence
<220> FEATURE:
<223> OTHER INFORMATION: B32oN-73 L-CDR3

<400> SEQUENCE: 160

Gln Gln Ser Tyr Ser Thr Pro Trp Thr
1 5

<210> SEQ ID NO 161
<211> LENGTH: 726
<212> TYPE: PRT
<213> ORGANISM: Artificial Sequence
<220> FEATURE:
<223> OTHER INFORMATION: B33oN-21 complement n.t. sequence

<400> SEQUENCE: 161

Cys Thr Cys Gly Ala Cys Gly Thr Cys Gly Ala Cys Cys Ala Gly Cys
1 5 10 15

Thr Cys Gly Thr Cys Ala Gly Ala Cys Cys Thr Cys Gly Ala Cys Gly
20 25 30

Thr Gly Ala Cys Cys Ala Cys Thr Thr Cys Gly Gly Ala Cys Cys Cys
35 40 45

Cys Thr Gly Ala Gly Ala Cys Ala Cys Thr Thr Cys Thr Ala Cys Ala
50 55 60

Gly Ala Ala Cys Gly Thr Thr Thr Cys Gly Ala Ala Gly Ala Cys Cys
65 70 75 80

Ala Ala Thr Ala Gly Gly Thr Ala Ala Gly Thr Gly Ala Cys Thr Gly
85 90 95

Ala Thr Ala Thr Ala Ala Cys Ala Thr Gly Thr Gly Ala Cys Cys Cys
100 105 110

```
Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525
```

```
Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Gly Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Gly Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Cys Ala Thr Ala Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Cys Ala Cys Cys Thr Gly Cys Ala Ala Gly Cys Cys Gly Gly Thr
    690                 695                 700

Thr Cys Cys Cys Thr Gly Gly Thr Thr Cys Gly Ala Cys Cys Thr Cys
705                 710                 715                 720

Thr Ala Gly Thr Thr Thr
                725
```

<210> SEQ ID NO 162
<211> LENGTH: 121
<212> TYPE: PRT
<213> ORGANISM: Artificial Sequence
<220> FEATURE:
<223> OTHER INFORMATION: B33oN-21 VH

<400> SEQUENCE: 162

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly
        115                 120
```

<210> SEQ ID NO 163
<211> LENGTH: 5
<212> TYPE: PRT
<213> ORGANISM: Artificial Sequence
<220> FEATURE:

<223> OTHER INFORMATION: B33oN-21 H-CDR1

<400> SEQUENCE: 163

Asp Tyr Ile Val His
1 5

<210> SEQ ID NO 164
<211> LENGTH: 17
<212> TYPE: PRT
<213> ORGANISM: Artificial Sequence
<220> FEATURE:
<223> OTHER INFORMATION: B33oN-21 H-CDR2

<400> SEQUENCE: 164

Tyr Ile Asn Pro Tyr Ser Gly Asp Thr Lys Phe Asn Glu Lys Phe Lys
1 5 10 15

Ser

<210> SEQ ID NO 165
<211> LENGTH: 10
<212> TYPE: PRT
<213> ORGANISM: Artificial Sequence
<220> FEATURE:
<223> OTHER INFORMATION: B33oN-21 H-CDR3

<400> SEQUENCE: 165

Ser Gly Leu Ile Ala Val Tyr Phe Asp Tyr
1 5 10

<210> SEQ ID NO 166
<211> LENGTH: 107
<212> TYPE: PRT
<213> ORGANISM: Artificial Sequence
<220> FEATURE:
<223> OTHER INFORMATION: B33oN-21 VL

<400> SEQUENCE: 166

Glu Leu Val Leu Thr Gln Ser Pro Asp Phe Gln Ser Val Thr Pro Lys
1 5 10 15

Glu Lys Val Thr Ile Thr Cys Arg Ala Ser Gln Ser Ile Gly Ser Ser
20 25 30

Leu His Trp Tyr Gln Gln Lys Pro Asp Gln Ser Pro Lys Leu Leu Ile
35 40 45

Lys Phe Ala Ser Gln Ser Leu Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys Gln Gln Ser Tyr Ser Thr Pro Trp
85 90 95

Thr Phe Gly Gln Gly Thr Lys Leu Glu Ile Lys
100 105

<210> SEQ ID NO 167
<211> LENGTH: 11
<212> TYPE: PRT
<213> ORGANISM: Artificial Sequence
<220> FEATURE:
<223> OTHER INFORMATION: B33oN-21 L-CDR1

<400> SEQUENCE: 167

Arg Ala Ser Gln Ser Ile Gly Ser Ser Leu His
1 5 10

<210> SEQ ID NO 168
<211> LENGTH: 7
<212> TYPE: PRT
<213> ORGANISM: Artificial Sequence
<220> FEATURE:
<223> OTHER INFORMATION: B33oN-21 L-CDR2

<400> SEQUENCE: 168

Phe Ala Ser Gln Ser Leu Ser
1 5

<210> SEQ ID NO 169
<211> LENGTH: 9
<212> TYPE: PRT
<213> ORGANISM: Artificial Sequence
<220> FEATURE:
<223> OTHER INFORMATION: B33oN-21 L-CDR3

<400> SEQUENCE: 169

Gln Gln Ser Tyr Ser Thr Pro Trp Thr
1 5

<210> SEQ ID NO 170
<211> LENGTH: 726
<212> TYPE: PRT
<213> ORGANISM: Artificial Sequence
<220> FEATURE:
<223> OTHER INFORMATION: B33oN-22 complement n.t. sequence

<400> SEQUENCE: 170

Cys Thr Cys Gly Ala Cys Gly Thr Cys Gly Ala Cys Cys Ala Gly Cys
1 5 10 15

Thr Cys Gly Thr Cys Ala Gly Ala Cys Cys Thr Cys Gly Ala Cys Gly
20 25 30

Thr Gly Ala Cys Cys Ala Cys Thr Thr Cys Gly Gly Ala Cys Cys Cys
35 40 45

Cys Thr Gly Ala Gly Ala Cys Ala Cys Thr Thr Cys Thr Ala Cys Ala
50 55 60

Gly Ala Ala Cys Gly Thr Thr Thr Cys Gly Ala Ala Gly Ala Cys Cys
65 70 75 80

Ala Ala Thr Ala Gly Gly Thr Ala Ala Gly Thr Gly Ala Cys Thr Gly
85 90 95

Ala Thr Ala Thr Ala Ala Cys Ala Thr Gly Thr Gly Ala Cys Cys Cys
100 105 110

Ala Cys Thr Thr Cys Gly Thr Cys Thr Cys Ala Gly Thr Ala Cys Cys
115 120 125

Thr Thr Thr Cys Thr Cys Gly Gly Ala Ala Cys Thr Gly Ala Cys Cys
130 135 140

Thr Ala Ala Cys Cys Ala Ala Thr Ala Thr Ala Ala Thr Thr Ala Gly
145 150 155 160

Gly Ala Ala Thr Gly Thr Cys Ala Cys Cys Ala Cys Thr Ala Thr Gly
165 170 175

Ala Thr Thr Cys Ala Ala Gly Thr Thr Ala Cys Thr Thr Thr Thr Cys
180 185 190

Ala Ala Gly Thr Thr Cys Thr Cys Ala Thr Thr Cys Cys Gly Gly Thr
195 200 205

Gly Cys Ala Ala Cys Thr Gly Ala Cys Ala Ala Cys Thr Gly Thr Thr
210 215 220

Cys Ala Gly Gly Thr Cys Gly Thr Cys Gly Thr Gly Thr Cys Gly Gly

```
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Ala Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655
```

```
Thr Thr Gly Cys Ala Thr Ala Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Ala Gly Gly Cys Thr Gly Cys Ala Ala Gly Cys Cys Gly Gly Thr
    690                 695                 700

Thr Cys Cys Cys Thr Gly Gly Thr Thr Cys Cys Ala Cys Cys Thr Cys
705                 710                 715                 720

Thr Ala Gly Thr Thr Thr
                725
```

<210> SEQ ID NO 171
<211> LENGTH: 120
<212> TYPE: PRT
<213> ORGANISM: Artificial Sequence
<220> FEATURE:
<223> OTHER INFORMATION: B33oN-22 VH

<400> SEQUENCE: 171

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120
```

<210> SEQ ID NO 172
<211> LENGTH: 5
<212> TYPE: PRT
<213> ORGANISM: Artificial Sequence
<220> FEATURE:
<223> OTHER INFORMATION: B33oN-22 H-CDR1

<400> SEQUENCE: 172

```
Asp Tyr Ile Val His
1               5
```

<210> SEQ ID NO 173
<211> LENGTH: 17
<212> TYPE: PRT
<213> ORGANISM: Artificial Sequence
<220> FEATURE:
<223> OTHER INFORMATION: B33oN-22 H-CDR2

<400> SEQUENCE: 173

```
Tyr Ile Asn Pro Tyr Ser Gly Asp Thr Lys Phe Asn Glu Lys Phe Lys
1               5                   10                  15

Ser
```

```
<210> SEQ ID NO 174
<211> LENGTH: 10
<212> TYPE: PRT
<213> ORGANISM: Artificial Sequence
<220> FEATURE:
<223> OTHER INFORMATION: B33oN-22 H-CDR3

<400> SEQUENCE: 174

Ser Gly Leu Ile Ala Val Tyr Phe Asp Tyr
1               5                   10


<210> SEQ ID NO 175
<211> LENGTH: 107
<212> TYPE: PRT
<213> ORGANISM: Artificial Sequence
<220> FEATURE:
<223> OTHER INFORMATION: B33oN-22 VL

<400> SEQUENCE: 175

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105


<210> SEQ ID NO 176
<211> LENGTH: 11
<212> TYPE: PRT
<213> ORGANISM: Artificial Sequence
<220> FEATURE:
<223> OTHER INFORMATION: B33oN-22 L-CDR1

<400> SEQUENCE: 176

Arg Ala Ser Gln Ser Ile Gly Ser Ser Leu His
1               5                   10


<210> SEQ ID NO 177
<211> LENGTH: 7
<212> TYPE: PRT
<213> ORGANISM: Artificial Sequence
<220> FEATURE:
<223> OTHER INFORMATION: B33oN-22 L-CDR2

<400> SEQUENCE: 177

Phe Ala Ser Gln Ser Phe Ser
1               5


<210> SEQ ID NO 178
<211> LENGTH: 9
<212> TYPE: PRT
<213> ORGANISM: Artificial Sequence
<220> FEATURE:
<223> OTHER INFORMATION: B33oN-22 L-CDR3

<400> SEQUENCE: 178
```

```
Gln Gln Ser Tyr Ser Thr Pro Pro Thr
1               5


<210> SEQ ID NO 179
<211> LENGTH: 726
<212> TYPE: PRT
<213> ORGANISM: Artificial Sequence
<220> FEATURE:
<223> OTHER INFORMATION: B33oN-115 complement n.t. sequence

<400> SEQUENCE: 179

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350
```

```
Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Gly Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Ala Gly Ala Gly
    610                 615                 620

Thr Gly Gly Thr Ala Gly Thr Cys Gly Thr Cys Ala Gly Ala Cys Gly
625                 630                 635                 640

Thr Thr Gly Gly Ala Cys Thr Thr Cys Thr Ala Ala Ala Ala Cys Gly
                645                 650                 655

Thr Thr Gly Ala Ala Thr Gly Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Ala Thr Cys Ala Thr Gly Ala Ala Ala Gly Cys Cys Gly Gly Gly
    690                 695                 700

Ala Cys Cys Cys Thr Gly Gly Thr Thr Cys Cys Ala Cys Cys Thr Cys
705                 710                 715                 720

Thr Ala Gly Thr Thr Thr
                725
```

<210> SEQ ID NO 180
<211> LENGTH: 120
<212> TYPE: PRT
<213> ORGANISM: Artificial Sequence
<220> FEATURE:
<223> OTHER INFORMATION: B33oN-115 VH

<400> SEQUENCE: 180

Glu Leu Gln Leu Val Glu Gln Ser Gly Ala Ala Leu Val Lys Pro Gly
1 5 10 15

Asp Ser Val Lys Met Ser Cys Lys Ala Ser Gly Tyr Pro Phe Thr Asp
20 25 30

Tyr Ile Val His Trp Val Lys Gln Ser His Gly Lys Ser Leu Asp Trp
35 40 45

Ile Gly Tyr Ile Asn Pro Tyr Ser Gly Asp Thr Lys Phe Asn Glu Lys
50 55 60

Phe Lys Ser Lys Ala Thr Leu Thr Val Asp Lys Ser Ser Ser Thr Ala
65 70 75 80

Tyr Met Glu Phe Ser Arg Leu Thr Ser Glu Asp Ser Ala Ile Tyr Tyr
85 90 95

Cys Ala Arg Ser Gly Leu Ile Ala Val Tyr Phe Asp Tyr Trp Gly Gln
100 105 110

Gly Thr Thr Val Thr Val Ser Ser
115 120

<210> SEQ ID NO 181
<211> LENGTH: 5
<212> TYPE: PRT
<213> ORGANISM: Artificial Sequence
<220> FEATURE:
<223> OTHER INFORMATION: B33oN-115 H-CDR1

<400> SEQUENCE: 181

Asp Tyr Ile Val His
1 5

<210> SEQ ID NO 182
<211> LENGTH: 17
<212> TYPE: PRT
<213> ORGANISM: Artificial Sequence
<220> FEATURE:
<223> OTHER INFORMATION: B33oN-115 H-CDR2

<400> SEQUENCE: 182

Tyr Ile Asn Pro Tyr Ser Gly Asp Thr Lys Phe Asn Glu Lys Phe Lys
1 5 10 15

Ser

<210> SEQ ID NO 183
<211> LENGTH: 10
<212> TYPE: PRT
<213> ORGANISM: Artificial Sequence
<220> FEATURE:
<223> OTHER INFORMATION: B33oN-115 H-CDR3

<400> SEQUENCE: 183

Ser Gly Leu Ile Ala Val Tyr Phe Asp Tyr
1 5 10

<210> SEQ ID NO 184
<211> LENGTH: 107
<212> TYPE: PRT
<213> ORGANISM: Artificial Sequence
<220> FEATURE:
<223> OTHER INFORMATION: B33oN-115 VL

<400> SEQUENCE: 184

Glu Leu Val Leu Thr Gln Ser Pro Asp Phe Gln Ser Val Thr Pro Lys

```
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

Thr Phe Gly Pro Gly Thr Lys Val Glu Ile Lys
            100                 105


<210> SEQ ID NO 185
<211> LENGTH: 11
<212> TYPE: PRT
<213> ORGANISM: Artificial Sequence
<220> FEATURE:
<223> OTHER INFORMATION: B33oN-115 L-CDR1

<400> SEQUENCE: 185

Arg Ala Ser Gln Ser Ile Gly Ser Ser Leu His
1               5                   10


<210> SEQ ID NO 186
<211> LENGTH: 7
<212> TYPE: PRT
<213> ORGANISM: Artificial Sequence
<220> FEATURE:
<223> OTHER INFORMATION: B33oN-115 L-CDR2

<400> SEQUENCE: 186

Phe Ala Ser Gln Ser Leu Ser
1               5


<210> SEQ ID NO 187
<211> LENGTH: 9
<212> TYPE: PRT
<213> ORGANISM: Artificial Sequence
<220> FEATURE:
<223> OTHER INFORMATION: B33oN-115 L-CDR3

<400> SEQUENCE: 187

Gln Gln Ser Tyr Ser Thr Pro Ser Thr
1               5


<210> SEQ ID NO 188
<211> LENGTH: 726
<212> TYPE: PRT
<213> ORGANISM: Artificial Sequence
<220> FEATURE:
<223> OTHER INFORMATION: B33oN-35 complement n.t. sequence

<400> SEQUENCE: 188

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
```

```
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Gly Thr Cys Thr Ala
                405                 410                 415

Cys Thr Gly Gly Gly Thr Cys Ala Gly Ala Gly Gly Thr Ala Gly Gly
            420                 425                 430

Ala Gly Gly Gly Ala Cys Ala Gly Ala Cys Gly Thr Ala Gly Ala Cys
        435                 440                 445

Ala Thr Cys Cys Thr Cys Thr Gly Thr Cys Thr Cys Ala Gly Thr Gly
    450                 455                 460

Gly Thr Ala Gly Thr Gly Gly Ala Cys Gly Gly Cys Cys Cys Gly Gly
465                 470                 475                 480
```

Thr Cys Ala Gly Thr Cys Thr Cys Gly Thr Ala Ala Cys Cys Ala Thr
485 490 495

Cys Ala Thr Cys Gly Ala Ala Thr Gly Thr Gly Ala Cys Cys Ala Thr
500 505 510

Gly Gly Thr Cys Gly Thr Cys Thr Thr Thr Gly Gly Thr Cys Thr Ala
515 520 525

Gly Thr Cys Ala Gly Ala Gly Gly Thr Thr Thr Cys Gly Ala Gly Gly
530 535 540

Ala Gly Thr Ala Gly Thr Thr Cys Ala Ala Ala Cys Gly Ala Ala Gly
545 550 555 560

Gly Gly Thr Cys Ala Gly Gly Ala Ala Gly Ala Gly Thr Cys Cys Cys
565 570 575

Cys Ala Gly Gly Gly Gly Ala Gly Cys Thr Cys Cys Ala Ala Gly Cys
580 585 590

Cys Ala Cys Cys Gly Thr Cys Ala Cys Cys Thr Ala Gly Ala Cys Cys
595 600 605

Cys Thr Gly Thr Thr Thr Ala Ala Ala Gly Thr Gly Gly Gly Ala Gly
610 615 620

Thr Gly Gly Thr Ala Gly Thr Thr Ala Thr Cys Gly Gly Ala Cys Cys
625 630 635 640

Thr Thr Cys Gly Ala Cys Thr Thr Cys Thr Ala Cys Gly Ala Cys Gly
645 650 655

Thr Thr Gly Gly Ala Thr Ala Ala Thr Gly Ala Cys Ala Gly Thr Cys
660 665 670

Gly Thr Cys Thr Cys Ala Thr Cys Ala Thr Gly Ala Ala Ala Thr Gly
675 680 685

Gly Ala Gly Gly Gly Thr Gly Ala Ala Ala Ala Cys Cys Gly Gly Thr
690 695 700

Cys Cys Cys Cys Thr Gly Gly Thr Thr Cys Gly Ala Cys Cys Thr Cys
705 710 715 720

Thr Ala Gly Thr Thr Thr
725

<210> SEQ ID NO 189
<211> LENGTH: 120
<212> TYPE: PRT
<213> ORGANISM: Artificial Sequence
<220> FEATURE:
<223> OTHER INFORMATION: B33oN-35 VH

<400> SEQUENCE: 189

Glu Leu Gln Leu Val Glu Gln Ser Gly Ala Ala Leu Val Lys Pro Gly
1 5 10 15

Asp Ser Val Lys Met Ser Cys Lys Ala Ser Gly Tyr Pro Phe Thr Asp
20 25 30

Tyr Ile Val His Trp Val Lys Gln Ser His Gly Lys Ser Leu Asp Trp
35 40 45

Ile Gly Tyr Ile Asn Pro Tyr Ser Gly Asp Thr Lys Phe Asn Glu Lys
50 55 60

Phe Lys Ser Lys Ala Thr Leu Thr Val Asp Lys Ser Ser Ser Thr Ala
65 70 75 80

Tyr Met Glu Phe Ser Arg Leu Thr Ser Glu Asp Ser Ala Ile Tyr Tyr
85 90 95

Cys Ala Arg Ser Gly Leu Ile Ala Val Tyr Phe Asp Tyr Trp Gly Gln
100 105 110

```
Gly Thr Thr Val Thr Val Ser Ser
        115                 120


<210> SEQ ID NO 190
<211> LENGTH: 5
<212> TYPE: PRT
<213> ORGANISM: Artificial Sequence
<220> FEATURE:
<223> OTHER INFORMATION: B33oN-35 H-CDR1

<400> SEQUENCE: 190

Asp Tyr Ile Val His
1               5


<210> SEQ ID NO 191
<211> LENGTH: 17
<212> TYPE: PRT
<213> ORGANISM: Artificial Sequence
<220> FEATURE:
<223> OTHER INFORMATION: B33oN-35 H-CDR2

<400> SEQUENCE: 191

Tyr Ile Asn Pro Tyr Ser Gly Asp Thr Lys Phe Asn Glu Lys Phe Lys
1               5                   10                  15

Ser


<210> SEQ ID NO 192
<211> LENGTH: 10
<212> TYPE: PRT
<213> ORGANISM: Artificial Sequence
<220> FEATURE:
<223> OTHER INFORMATION: B33oN-35 H-CDR3

<400> SEQUENCE: 192

Ser Gly Leu Ile Ala Val Tyr Phe Asp Tyr
1               5                   10


<210> SEQ ID NO 193
<211> LENGTH: 107
<212> TYPE: PRT
<213> ORGANISM: Artificial Sequence
<220> FEATURE:
<223> OTHER INFORMATION: B33oN-35 VL

<400> SEQUENCE: 193

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Phe Ser Gly Val Pro Ser Arg Phe Gly Gly
    50                  55                  60

Ser Gly Ser Gly Thr Asn Phe Thr Leu Thr Ile Asn Ser Leu Glu Ala
65                  70                  75                  80

Glu Asp Ala Ala Thr Tyr Tyr Cys Gln Gln Ser Ser Thr Leu Pro Pro
                85                  90                  95

Thr Phe Gly Gln Gly Thr Lys Leu Glu Ile Lys
            100                 105


<210> SEQ ID NO 194
<211> LENGTH: 11
```

<212> TYPE: PRT
<213> ORGANISM: Artificial Sequence
<220> FEATURE:
<223> OTHER INFORMATION: B33oN-35 L-CDR1

<400> SEQUENCE: 194

Arg Ala Ser Gln Ser Ile Gly Ser Ser Leu His
1               5                   10

<210> SEQ ID NO 195
<211> LENGTH: 7
<212> TYPE: PRT
<213> ORGANISM: Artificial Sequence
<220> FEATURE:
<223> OTHER INFORMATION: B33oN-35 L-CDR2

<400> SEQUENCE: 195

Phe Ala Ser Gln Ser Phe Ser
1               5

<210> SEQ ID NO 196
<211> LENGTH: 9
<212> TYPE: PRT
<213> ORGANISM: Artificial Sequence
<220> FEATURE:
<223> OTHER INFORMATION: B33oN-35 L-CDR3

<400> SEQUENCE: 196

Gln Gln Ser Ser Thr Leu Pro Pro Thr
1               5

<210> SEQ ID NO 197
<211> LENGTH: 727
<212> TYPE: PRT
<213> ORGANISM: Artificial Sequence
<220> FEATURE:
<223> OTHER INFORMATION: B33oN-66 complement n.t. sequence

<400> SEQUENCE: 197

Val Cys Thr Cys Gly Ala Cys Gly Thr Cys Gly Ala Cys Cys Ala Gly
1               5                   10                  15

Cys Thr Cys Gly Thr Cys Ala Gly Ala Cys Cys Thr Cys Gly Ala Cys
            20                  25                  30

Gly Thr Gly Ala Cys Cys Ala Cys Thr Thr Cys Gly Gly Ala Cys Cys
        35                  40                  45

Cys Cys Thr Gly Ala Gly Ala Cys Ala Cys Thr Thr Cys Thr Ala Cys
    50                  55                  60

Ala Gly Ala Ala Cys Gly Thr Thr Thr Cys Gly Ala Ala Gly Ala Cys
65                  70                  75                  80

Cys Ala Ala Thr Ala Gly Gly Thr Ala Ala Gly Thr Gly Ala Cys Thr
                85                  90                  95

Gly Ala Thr Ala Thr Ala Ala Cys Ala Thr Gly Thr Gly Ala Cys Cys
            100                 105                 110

Cys Ala Cys Thr Thr Cys Gly Thr Cys Thr Cys Ala Gly Thr Ala Cys
        115                 120                 125

Cys Thr Thr Thr Cys Thr Cys Gly Gly Ala Ala Cys Thr Gly Ala Cys
    130                 135                 140

Cys Thr Ala Ala Cys Cys Ala Ala Thr Ala Thr Ala Ala Thr Thr Ala
145                 150                 155                 160

Gly Gly Ala Ala Thr Gly Thr Cys Ala Cys Cys Ala Cys Thr Ala Thr
                165                 170                 175

```
Gly Ala Thr Thr Cys Ala Ala Gly Thr Thr Ala Cys Thr Thr Thr Thr
            180                 185                 190

Cys Ala Ala Gly Thr Thr Cys Thr Cys Ala Thr Thr Cys Cys Gly Gly
        195                 200                 205

Thr Gly Cys Ala Ala Cys Thr Gly Ala Cys Ala Ala Cys Thr Gly Thr
    210                 215                 220

Thr Cys Ala Gly Gly Thr Cys Gly Thr Cys Gly Thr Gly Thr Cys Gly
225                 230                 235                 240

Gly Ala Thr Ala Thr Ala Cys Cys Thr Cys Ala Ala Ala Thr Cys Gly
                245                 250                 255

Gly Cys Thr Ala Ala Cys Thr Gly Thr Ala Gly Ala Cys Thr Cys Cys
            260                 265                 270

Thr Ala Ala Gly Ala Cys Gly Thr Thr Ala Gly Ala Thr Ala Ala Thr
        275                 280                 285

Gly Ala Cys Ala Cys Gly Thr Thr Cys Thr Ala Gly Cys Cys Cys Ala
    290                 295                 300

Gly Ala Cys Thr Ala Thr Cys Gly Thr Cys Ala Gly Ala Thr Gly Ala
305                 310                 315                 320

Ala Ala Cys Thr Ala Ala Thr Gly Ala Cys Cys Cys Cys Gly Gly Thr
                325                 330                 335

Thr Cys Cys Cys Thr Gly Gly Thr Gly Cys Cys Ala Gly Thr Gly Gly
            340                 345                 350

Cys Ala Gly Ala Gly Gly Ala Gly Thr Cys Cys Ala Cys Cys Ala Cys
        355                 360                 365

Cys Ala Cys Cys Ala Ala Gly Ala Cys Cys Gly Cys Cys Gly Cys Cys
    370                 375                 380

Gly Cys Cys Gly Ala Gly Gly Cys Cys Ala Cys Cys Ala Cys Cys Ala
385                 390                 395                 400

Cys Cys Ala Ala Gly Ala Cys Thr Cys Gly Ala Gly Cys Ala Cys Gly
                405                 410                 415

Ala Cys Thr Gly Ala Gly Thr Cys Ala Gly Ala Gly Gly Thr Cys Thr
            420                 425                 430

Gly Ala Ala Ala Gly Thr Cys Ala Gly Ala Cys Ala Cys Thr Gly Ala
        435                 440                 445

Gly Gly Thr Thr Thr Cys Cys Thr Cys Thr Thr Thr Cys Ala Gly Thr
    450                 455                 460

Gly Gly Thr Ala Gly Thr Gly Gly Ala Cys Gly Gly Cys Cys Cys Gly
465                 470                 475                 480

Gly Thr Cys Ala Gly Thr Cys Thr Cys Gly Thr Ala Ala Cys Cys Ala
                485                 490                 495

Thr Cys Ala Thr Thr Gly Ala Ala Thr Gly Thr Gly Ala Cys Cys Ala
            500                 505                 510

Thr Gly Gly Thr Cys Gly Thr Cys Thr Thr Thr Gly Gly Thr Cys Thr
        515                 520                 525

Ala Gly Thr Cys Ala Gly Ala Gly Gly Thr Thr Thr Cys Gly Ala Gly
    530                 535                 540

Gly Ala Gly Thr Ala Gly Thr Thr Cys Ala Ala Ala Cys Gly Ala Ala
545                 550                 555                 560

Gly Gly Gly Thr Cys Ala Gly Gly Ala Ala Gly Ala Gly Thr Cys Cys
                565                 570                 575

Cys Cys Ala Gly Gly Gly Gly Ala Gly Cys Thr Cys Cys Ala Ala Gly
            580                 585                 590

Thr Cys Ala Cys Cys Gly Thr Cys Ala Cys Cys Thr Ala Gly Ala Cys
```

595 600 605

Cys Cys Thr Gly Thr Cys Thr Ala Ala Ala Gly Thr Cys Gly Gly Ala
610 615 620

Gly Thr Gly Gly Thr Ala Gly Thr Thr Ala Thr Cys Gly Gly Ala Cys
625 630 635 640

Cys Thr Thr Cys Gly Ala Cys Thr Thr Cys Thr Ala Cys Gly Ala Cys
645 650 655

Gly Thr Thr Gly Ala Ala Thr Gly Ala Thr Gly Ala Cys Ala Gly Thr
660 665 670

Thr Gly Thr Cys Thr Cys Ala Ala Thr Gly Thr Cys Ala Thr Gly Gly
675 680 685

Gly Gly Ala Gly Gly Gly Thr Gly Gly Ala Ala Gly Cys Cys Gly Gly
690 695 700

Thr Thr Cys Cys Cys Thr Gly Thr Gly Cys Thr Gly Ala Cys Cys Thr
705 710 715 720

Cys Thr Ala Ala Thr Thr Thr
725

<210> SEQ ID NO 198
<211> LENGTH: 120
<212> TYPE: PRT
<213> ORGANISM: Artificial Sequence
<220> FEATURE:
<223> OTHER INFORMATION: B33oN-66 VH

<400> SEQUENCE: 198

Glu Leu Gln Leu Val Glu Gln Ser Gly Ala Ala Leu Val Lys Pro Gly
1 5 10 15

Asp Ser Val Lys Met Ser Cys Lys Ala Ser Gly Tyr Pro Phe Thr Asp
20 25 30

Tyr Ile Val His Trp Val Lys Gln Ser His Gly Lys Ser Leu Asp Trp
35 40 45

Ile Gly Tyr Ile Asn Pro Tyr Ser Gly Asp Thr Lys Phe Asn Glu Lys
50 55 60

Phe Lys Ser Lys Ala Thr Leu Thr Val Asp Lys Ser Ser Ser Thr Ala
65 70 75 80

Tyr Met Glu Phe Ser Arg Leu Thr Ser Glu Asp Ser Ala Ile Tyr Tyr
85 90 95

Cys Ala Arg Ser Gly Leu Ile Ala Val Tyr Phe Asp Tyr Trp Gly Gln
100 105 110

Gly Thr Thr Val Thr Val Ser Ser
115 120

<210> SEQ ID NO 199
<211> LENGTH: 5
<212> TYPE: PRT
<213> ORGANISM: Artificial Sequence
<220> FEATURE:
<223> OTHER INFORMATION: B33oN-66 H-CDR1

<400> SEQUENCE: 199

Asp Tyr Ile Val His
1 5

<210> SEQ ID NO 200
<211> LENGTH: 17
<212> TYPE: PRT
<213> ORGANISM: Artificial Sequence
<220> FEATURE:

<223> OTHER INFORMATION: B33oN-66 H-CDR2

<400> SEQUENCE: 200

```
Tyr Ile Asn Pro Tyr Ser Gly Asp Thr Lys Phe Asn Glu Lys Phe Lys
1               5                   10                  15

Ser
```

<210> SEQ ID NO 201
<211> LENGTH: 10
<212> TYPE: PRT
<213> ORGANISM: Artificial Sequence
<220> FEATURE:
<223> OTHER INFORMATION: B33oN-66 H-CDR3

<400> SEQUENCE: 201

```
Ser Gly Leu Ile Ala Val Tyr Phe Asp Tyr
1               5                   10
```

<210> SEQ ID NO 202
<211> LENGTH: 107
<212> TYPE: PRT
<213> ORGANISM: Artificial Sequence
<220> FEATURE:
<223> OTHER INFORMATION: B33oN-66 VL

<400> SEQUENCE: 202

```
Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Asn
            20                  25                  30

Leu His Trp Tyr Gln Gln Lys Pro Asp Gln Ser Pro Lys Leu Leu Ile
        35                  40                  45

Lys Phe Ala Ser Gln Ser Phe Ser Gly Val Pro Ser Arg Phe Ser Gly
    50                  55                  60

Ser Gly Ser Gly Thr Asp Phe Ser Leu Thr Ile Asn Ser Leu Glu Ala
65                  70                  75                  80

Glu Asp Ala Ala Thr Tyr Tyr Cys Gln Gln Ser Tyr Ser Thr Pro Pro
                85                  90                  95

Thr Phe Gly Gln Gly Thr Arg Leu Glu Ile Lys
            100                 105
```

<210> SEQ ID NO 203
<211> LENGTH: 11
<212> TYPE: PRT
<213> ORGANISM: Artificial Sequence
<220> FEATURE:
<223> OTHER INFORMATION: B33oN-66 L-CDR1

<400> SEQUENCE: 203

```
Arg Ala Ser Gln Ser Ile Gly Ser Asn Leu His
1               5                   10
```

<210> SEQ ID NO 204
<211> LENGTH: 7
<212> TYPE: PRT
<213> ORGANISM: Artificial Sequence
<220> FEATURE:
<223> OTHER INFORMATION: B33oN-66 L-CDR2

<400> SEQUENCE: 204

```
Phe Ala Ser Gln Ser Phe Ser
1               5
```

<210> SEQ ID NO 205
<211> LENGTH: 9
<212> TYPE: PRT
<213> ORGANISM: Artificial Sequence
<220> FEATURE:
<223> OTHER INFORMATION: B33oN-66 L-CDR3

<400> SEQUENCE: 205

Gln Gln Ser Tyr Ser Thr Pro Pro Thr
1 5

<210> SEQ ID NO 206
<211> LENGTH: 726
<212> TYPE: PRT
<213> ORGANISM: Artificial Sequence
<220> FEATURE:
<223> OTHER INFORMATION: B33oN-67 complement n.t. sequence

<400> SEQUENCE: 206

Cys Thr Cys Gly Ala Cys Gly Thr Cys Gly Ala Cys Cys Ala Gly Cys
1 5 10 15

Thr Cys Gly Thr Cys Ala Gly Ala Cys Cys Thr Cys Gly Ala Cys Gly
20 25 30

Thr Gly Ala Cys Cys Ala Cys Thr Thr Cys Gly Gly Ala Cys Cys Cys
35 40 45

Cys Thr Gly Ala Gly Ala Cys Ala Cys Thr Thr Cys Thr Ala Cys Ala
50 55 60

Gly Ala Ala Cys Gly Thr Thr Thr Cys Gly Ala Ala Gly Ala Cys Cys
65 70 75 80

Ala Ala Thr Ala Gly Gly Thr Ala Ala Gly Thr Gly Ala Cys Thr Gly
85 90 95

Ala Thr Ala Thr Ala Ala Cys Ala Thr Gly Thr Gly Ala Cys Cys Cys
100 105 110

Ala Cys Thr Thr Cys Gly Thr Cys Thr Cys Ala Gly Thr Ala Cys Cys
115 120 125

Thr Thr Thr Cys Thr Cys Gly Gly Ala Ala Cys Thr Gly Ala Cys Cys
130 135 140

Thr Ala Ala Cys Cys Ala Ala Thr Ala Thr Ala Ala Thr Thr Ala Gly
145 150 155 160

Gly Ala Ala Thr Gly Thr Cys Ala Cys Cys Ala Cys Thr Ala Thr Gly
165 170 175

Ala Thr Thr Cys Ala Ala Gly Thr Thr Ala Cys Thr Thr Thr Thr Cys
180 185 190

Ala Ala Gly Thr Thr Cys Thr Cys Ala Thr Thr Cys Cys Gly Gly Thr
195 200 205

Gly Cys Ala Ala Cys Thr Gly Ala Cys Ala Ala Cys Thr Gly Thr Thr
210 215 220

Cys Ala Gly Gly Thr Cys Gly Thr Cys Gly Thr Gly Thr Cys Gly Gly
225 230 235 240

Ala Thr Ala Thr Ala Cys Cys Thr Cys Ala Ala Ala Thr Cys Gly Gly
245 250 255

Cys Thr Ala Ala Cys Thr Gly Thr Ala Gly Ala Cys Thr Cys Cys Thr
260 265 270

Ala Ala Gly Ala Cys Gly Thr Thr Ala Gly Ala Thr Ala Ala Thr Gly
275 280 285

Ala Cys Ala Cys Gly Thr Thr Cys Thr Ala Gly Cys Cys Cys Ala Gly
290 295 300

```
Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Thr Ala Ala Ala Cys Gly Ala Ala Gly
545                 550                 555                 560

Gly Gly Thr Cys Ala Gly Gly Thr Ala Gly Ala Gly Thr Cys Cys Cys
                565                 570                 575

Cys Ala Gly Gly Gly Thr Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Ala Gly Ala Gly
    610                 615                 620

Thr Gly Gly Thr Ala Gly Thr Cys Gly Thr Cys Ala Gly Ala Cys Gly
625                 630                 635                 640

Thr Thr Gly Gly Ala Cys Thr Thr Cys Thr Ala Ala Ala Ala Cys Gly
                645                 650                 655

Thr Thr Gly Ala Ala Thr Gly Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Ala Gly Gly Gly Thr Gly Ala Ala Ala Gly Cys Cys Gly Gly Gly
    690                 695                 700

Ala Cys Cys Cys Thr Gly Gly Thr Thr Cys Gly Ala Cys Cys Thr Cys
705                 710                 715                 720
```

```
Thr Ala Gly Thr Thr Thr
                725


<210> SEQ ID NO 207
<211> LENGTH: 120
<212> TYPE: PRT
<213> ORGANISM: Artificial Sequence
<220> FEATURE:
<223> OTHER INFORMATION: B33oN-67 VH

<400> SEQUENCE: 207

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 208
<211> LENGTH: 5
<212> TYPE: PRT
<213> ORGANISM: Artificial Sequence
<220> FEATURE:
<223> OTHER INFORMATION: B33oN-67 H-CDR1

<400> SEQUENCE: 208

Asp Tyr Ile Val His
1               5


<210> SEQ ID NO 209
<211> LENGTH: 17
<212> TYPE: PRT
<213> ORGANISM: Artificial Sequence
<220> FEATURE:
<223> OTHER INFORMATION: B33oN-67 H-CDR2

<400> SEQUENCE: 209

Tyr Ile Asn Pro Tyr Ser Gly Asp Thr Lys Phe Asn Glu Lys Phe Lys
1               5                   10                  15

Ser


<210> SEQ ID NO 210
<211> LENGTH: 10
<212> TYPE: PRT
<213> ORGANISM: Artificial Sequence
<220> FEATURE:
<223> OTHER INFORMATION: B33oN-67 H-CDR3

<400> SEQUENCE: 210

Ser Gly Leu Ile Ala Val Tyr Phe Asp Tyr
1               5                   10
```

<210> SEQ ID NO 211
<211> LENGTH: 107
<212> TYPE: PRT
<213> ORGANISM: Artificial Sequence
<220> FEATURE:
<223> OTHER INFORMATION: B33oN-67 VL

<400> SEQUENCE: 211

```
Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Pro Gly Thr Lys Leu Glu Ile Lys
            100                 105
```

<210> SEQ ID NO 212
<211> LENGTH: 11
<212> TYPE: PRT
<213> ORGANISM: Artificial Sequence
<220> FEATURE:
<223> OTHER INFORMATION: B33oN-67 L-CDR1

<400> SEQUENCE: 212

```
Arg Ala Ser Gln Ser Ile Gly Ser Ser Leu His
1               5                   10
```

<210> SEQ ID NO 213
<211> LENGTH: 7
<212> TYPE: PRT
<213> ORGANISM: Artificial Sequence
<220> FEATURE:
<223> OTHER INFORMATION: B33oN-67 L-CDR2

<400> SEQUENCE: 213

```
Phe Ala Ser Gln Ser Ile Ser
1               5
```

<210> SEQ ID NO 214
<211> LENGTH: 9
<212> TYPE: PRT
<213> ORGANISM: Artificial Sequence
<220> FEATURE:
<223> OTHER INFORMATION: B33oN-67 L-CDR3

<400> SEQUENCE: 214

```
Gln Gln Ser Tyr Ser Thr Pro Pro Thr
1               5
```

<210> SEQ ID NO 215
<211> LENGTH: 726
<212> TYPE: PRT
<213> ORGANISM: Artificial Sequence
<220> FEATURE:
<223> OTHER INFORMATION: B33oN-69 complement n.t. sequence

<400> SEQUENCE: 215

-continued

```
Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
```

```
            420                 425                 430

Ala Ala Ala Gly Thr Thr Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Gly Ala Cys Cys Gly Ala Ala Thr Gly Thr Gly Ala Cys Cys Ala Thr
            500                 505                 510

Gly Gly Thr Cys Gly Thr Cys Thr Thr Thr Gly Gly Cys Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Thr Ala Ala Ala Cys Gly Ala Ala Gly
545                 550                 555                 560

Gly Gly Thr Cys Ala Gly Gly Ala Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Cys Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Cys Ala Thr Ala Ala Thr Gly Ala Cys Ala Gly Thr Cys
            660                 665                 670

Gly Thr Cys Thr Cys Ala Thr Cys Ala Thr Gly Ala Ala Ala Thr Gly
        675                 680                 685

Gly Ala Gly Gly Gly Thr Gly Ala Ala Ala Ala Cys Cys Gly Gly Thr
    690                 695                 700

Cys Cys Cys Cys Thr Gly Gly Thr Thr Cys Gly Ala Cys Cys Thr Cys
705                 710                 715                 720

Thr Ala Gly Thr Thr Thr
                725
```

<210> SEQ ID NO 216
<211> LENGTH: 120
<212> TYPE: PRT
<213> ORGANISM: Artificial Sequence
<220> FEATURE:
<223> OTHER INFORMATION: B33oN-69 VH

<400> SEQUENCE: 216

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
```

```
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 217
<211> LENGTH: 5
<212> TYPE: PRT
<213> ORGANISM: Artificial Sequence
<220> FEATURE:
<223> OTHER INFORMATION: B33oN-69 H-CDR1

<400> SEQUENCE: 217

Asp Tyr Ile Val His
1               5


<210> SEQ ID NO 218
<211> LENGTH: 17
<212> TYPE: PRT
<213> ORGANISM: Artificial Sequence
<220> FEATURE:
<223> OTHER INFORMATION: B33oN-69 H-CDR2

<400> SEQUENCE: 218

Tyr Ile Asn Pro Tyr Ser Gly Asp Thr Lys Phe Asn Glu Lys Phe Lys
1               5                   10                  15

Ser


<210> SEQ ID NO 219
<211> LENGTH: 10
<212> TYPE: PRT
<213> ORGANISM: Artificial Sequence
<220> FEATURE:
<223> OTHER INFORMATION: B33oN-69 H-CDR3

<400> SEQUENCE: 219

Ser Gly Leu Ile Ala Val Tyr Phe Asp Tyr
1               5                   10


<210> SEQ ID NO 220
<211> LENGTH: 107
<212> TYPE: PRT
<213> ORGANISM: Artificial Sequence
<220> FEATURE:
<223> OTHER INFORMATION: B33oN-69 VL

<400> SEQUENCE: 220

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Gly
            20                  25                  30

Leu His Trp Tyr Gln Gln Lys Pro Asp Gln Ser Pro Lys Leu Leu Ile
        35                  40                  45

Lys Phe Ala Ser Gln Ser Phe Ser Gly Val Pro Ser Arg Phe Ser Gly
    50                  55                  60

Ser Gly Ser Gly Thr Asp Phe Thr Leu Thr Ile Asn Gly Leu Glu Ala
65                  70                  75                  80
```

Glu Asp Ala Ala Thr Tyr Tyr Cys Gln Gln Ser Ser Thr Leu Pro Pro
85 90 95

Thr Phe Gly Gln Gly Thr Lys Leu Glu Ile Lys
100 105

<210> SEQ ID NO 221
<211> LENGTH: 11
<212> TYPE: PRT
<213> ORGANISM: Artificial Sequence
<220> FEATURE:
<223> OTHER INFORMATION: B33oN-69 L-CDR1

<400> SEQUENCE: 221

Arg Ala Ser Gln Ser Ile Gly Thr Gly Leu His
1 5 10

<210> SEQ ID NO 222
<211> LENGTH: 7
<212> TYPE: PRT
<213> ORGANISM: Artificial Sequence
<220> FEATURE:
<223> OTHER INFORMATION: B33oN-69 L-CDR2

<400> SEQUENCE: 222

Phe Ala Ser Gln Ser Phe Ser
1 5

<210> SEQ ID NO 223
<211> LENGTH: 9
<212> TYPE: PRT
<213> ORGANISM: Artificial Sequence
<220> FEATURE:
<223> OTHER INFORMATION: B33oN-69 L-CDR3

<400> SEQUENCE: 223

Gln Gln Ser Ser Thr Leu Pro Pro Thr
1 5

<210> SEQ ID NO 224
<211> LENGTH: 726
<212> TYPE: DNA
<213> ORGANISM: Artificial Sequence
<220> FEATURE:
<223> OTHER INFORMATION: B33oN-8 complement n.t. sequence

<400> SEQUENCE: 224
ctcgacgtcg accagctcgt cagacctcga cgtgaccact tcggacccct gagacacttc 60
tacagaacgt ttcgaagacc aataggtaag tgactgatat aacatgtgac ccacttcgtc 120
tcagtacctt tctcggaact gacctaacca atataattag gaatgtcacc actatgattc 180
aagttacttt tcaagttctc attccggtgc aactgacaac tgttcaggtc gtcgtgtcgg 240
atatacctca aatcggctaa ctgtagactc ctaagacgtt agataatgac acgttctagc 300
ccagactatc gtcagatgaa actaatgacc ccggttccct ggtgccagtg gcagaggagt 360
ccaccaccac caagaccgcc gccgccgagg ccaccaccac caagactcga gcacgactga 420
gtcagaggtc cgaaagtcag acactgaggt ttcctctttc agtggtagtg gacggcccgg 480
tcagtctcgt aaccatcatc gaatttgacc atggtcgtct ttggtctagt cggaggtttc 540
gaggagtagt ttaagcgaag cgtcaggtag agtccccaga gaagctccaa gtcaccgtga 600
cctagaccct gtctaaagtg ggagtgatag tcgtcggacg tcggacttct acaacgttga 660
ataatgacag ttgtctcaat gtcatgggga ggctgcaagc cggttccctg gttcgacctc 720

```
tagttt                                                           726


<210> SEQ ID NO 225
<211> LENGTH: 120
<212> TYPE: PRT
<213> ORGANISM: Artificial Sequence
<220> FEATURE:
<223> OTHER INFORMATION: B33oN-8 VH

<400> SEQUENCE: 225

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 226
<211> LENGTH: 5
<212> TYPE: PRT
<213> ORGANISM: Artificial Sequence
<220> FEATURE:
<223> OTHER INFORMATION: B33oN-8 H-CDR1

<400> SEQUENCE: 226

Asp Tyr Ile Val His
1               5


<210> SEQ ID NO 227
<211> LENGTH: 17
<212> TYPE: PRT
<213> ORGANISM: Artificial Sequence
<220> FEATURE:
<223> OTHER INFORMATION: B33oN-8 H-CDR2

<400> SEQUENCE: 227

Tyr Ile Asn Pro Tyr Ser Gly Asp Thr Lys Phe Asn Glu Lys Phe Lys
1               5                   10                  15

Ser


<210> SEQ ID NO 228
<211> LENGTH: 10
<212> TYPE: PRT
<213> ORGANISM: Artificial Sequence
<220> FEATURE:
<223> OTHER INFORMATION: B33oN-8 H-CDR3

<400> SEQUENCE: 228

Ser Gly Leu Ile Ala Val Tyr Phe Asp Tyr
1               5                   10
```

<210> SEQ ID NO 229
<211> LENGTH: 107
<212> TYPE: PRT
<213> ORGANISM: Artificial Sequence
<220> FEATURE:
<223> OTHER INFORMATION: B33oN-8 VL

<400> SEQUENCE: 229

```
Glu Leu Val Leu Thr Gln Ser Pro Gly Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu Asn Trp Tyr Gln Gln Lys Pro Asp Gln Pro Pro Lys Leu Leu Ile
        35                  40                  45

Lys Phe Ala Ser Gln Ser Ile Ser Gly Val Ser Ser Arg Phe Ser Gly
    50                  55                  60

Thr Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ser Tyr Ser Thr Pro Pro
                85                  90                  95

Thr Phe Gly Gln Gly Thr Lys Leu Glu Ile Lys
            100                 105
```

<210> SEQ ID NO 230
<211> LENGTH: 11
<212> TYPE: PRT
<213> ORGANISM: Artificial Sequence
<220> FEATURE:
<223> OTHER INFORMATION: B33oN-8 L-CDR1

<400> SEQUENCE: 230

```
Arg Ala Ser Gln Ser Ile Gly Ser Ser Leu Asn
1               5                   10
```

<210> SEQ ID NO 231
<211> LENGTH: 7
<212> TYPE: PRT
<213> ORGANISM: Artificial Sequence
<220> FEATURE:
<223> OTHER INFORMATION: B33oN-8 L-CDR2

<400> SEQUENCE: 231

```
Phe Ala Ser Gln Ser Ile Ser
1               5
```

<210> SEQ ID NO 232
<211> LENGTH: 9
<212> TYPE: PRT
<213> ORGANISM: Artificial Sequence
<220> FEATURE:
<223> OTHER INFORMATION: B33oN-8 L-CDR3

<400> SEQUENCE: 232

```
Gln Gln Ser Tyr Ser Thr Pro Pro Thr
1               5
```

<210> SEQ ID NO 233
<211> LENGTH: 726
<212> TYPE: PRT
<213> ORGANISM: Artificial Sequence
<220> FEATURE:
<223> OTHER INFORMATION: C32oN-10 complement n.t. sequence

<400> SEQUENCE: 233

-continued

```
Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
```

```
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Gly Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Ala Ala Ala Cys Gly
                645                 650                 655

Thr Thr Gly Ala Ala Thr Gly Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Ala Thr Cys Ala Thr Gly Ala Ala Ala Gly Cys Cys Gly Gly Gly
    690                 695                 700

Ala Cys Cys Cys Thr Gly Gly Thr Thr Cys Cys Ala Cys Cys Thr Cys
705                 710                 715                 720

Thr Ala Gly Thr Thr Thr
                725
```

<210> SEQ ID NO 234
<211> LENGTH: 120
<212> TYPE: PRT
<213> ORGANISM: Artificial Sequence
<220> FEATURE:
<223> OTHER INFORMATION: C32oN-10 VH

<400> SEQUENCE: 234

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
```

```
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 235
<211> LENGTH: 5
<212> TYPE: PRT
<213> ORGANISM: Artificial Sequence
<220> FEATURE:
<223> OTHER INFORMATION: C32oN-10 H-CDR1

<400> SEQUENCE: 235

Asp Tyr Ile Val His
1               5


<210> SEQ ID NO 236
<211> LENGTH: 17
<212> TYPE: PRT
<213> ORGANISM: Artificial Sequence
<220> FEATURE:
<223> OTHER INFORMATION: C32oN-10 H-CDR2

<400> SEQUENCE: 236

Tyr Ile Asn Pro Tyr Ser Gly Asp Thr Lys Phe Asn Glu Lys Phe Lys
1               5                   10                  15

Ser


<210> SEQ ID NO 237
<211> LENGTH: 10
<212> TYPE: PRT
<213> ORGANISM: Artificial Sequence
<220> FEATURE:
<223> OTHER INFORMATION: C32oN-10 H-CDR3

<400> SEQUENCE: 237

Ser Gly Leu Ile Ala Val Tyr Phe Asp Tyr
1               5                   10


<210> SEQ ID NO 238
<211> LENGTH: 107
<212> TYPE: PRT
<213> ORGANISM: Artificial Sequence
<220> FEATURE:
<223> OTHER INFORMATION: C32oN-10 VL

<400> SEQUENCE: 238

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Leu Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80
```

```
Glu Asp Phe Ala Thr Tyr Tyr Cys Gln Gln Ser Tyr Ser Thr Pro Ser
                85                  90                  95

Thr Phe Gly Pro Gly Thr Lys Val Glu Ile Lys
            100                 105


<210> SEQ ID NO 239
<211> LENGTH: 11
<212> TYPE: PRT
<213> ORGANISM: Artificial Sequence
<220> FEATURE:
<223> OTHER INFORMATION: C32oN-10 L-CDR1

<400> SEQUENCE: 239

Arg Ala Ser Gln Ser Ile Gly Ser Ser Leu His
1               5                   10


<210> SEQ ID NO 240
<211> LENGTH: 7
<212> TYPE: PRT
<213> ORGANISM: Artificial Sequence
<220> FEATURE:
<223> OTHER INFORMATION: C32oN-10 L-CDR2

<400> SEQUENCE: 240

Phe Ala Ser Gln Ser Leu Ser
1               5


<210> SEQ ID NO 241
<211> LENGTH: 9
<212> TYPE: PRT
<213> ORGANISM: Artificial Sequence
<220> FEATURE:
<223> OTHER INFORMATION: C32oN-10 L-CDR3

<400> SEQUENCE: 241

Gln Gln Ser Tyr Ser Thr Pro Ser Thr
1               5


<210> SEQ ID NO 242
<211> LENGTH: 726
<212> TYPE: PRT
<213> ORGANISM: Artificial Sequence
<220> FEATURE:
<223> OTHER INFORMATION: C32oN-21 complement n.t. sequence

<400> SEQUENCE: 242

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125
```

```
Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Gly Cys Cys Gly
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540
```

```
Ala Gly Thr Ala Gly Thr Thr Thr Ala Ala Ala Cys Gly Ala Ala Gly
545                 550                 555                 560

Gly Gly Thr Cys Ala Gly Gly Thr Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Gly Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Gly Ala Thr Ala Ala Thr Gly Ala Cys Ala Gly Thr Cys
            660                 665                 670

Gly Thr Cys Thr Cys Ala Thr Cys Ala Thr Gly Ala Ala Ala Thr Gly
        675                 680                 685

Gly Ala Gly Gly Gly Thr Gly Ala Ala Ala Ala Cys Cys Gly Gly Thr
    690                 695                 700

Cys Cys Cys Cys Thr Gly Gly Thr Thr Cys Gly Ala Cys Cys Thr Cys
705                 710                 715                 720

Thr Ala Gly Thr Thr Thr
                725
```

<210> SEQ ID NO 243
<211> LENGTH: 120
<212> TYPE: PRT
<213> ORGANISM: Artificial Sequence
<220> FEATURE:
<223> OTHER INFORMATION: C32oN-21 VH

<400> SEQUENCE: 243

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120
```

<210> SEQ ID NO 244
<211> LENGTH: 5
<212> TYPE: PRT
<213> ORGANISM: Artificial Sequence
<220> FEATURE:
<223> OTHER INFORMATION: C32oN-21 H-CDR1

<400> SEQUENCE: 244

```
Asp Tyr Ile Val His
1               5


<210> SEQ ID NO 245
<211> LENGTH: 17
<212> TYPE: PRT
<213> ORGANISM: Artificial Sequence
<220> FEATURE:
<223> OTHER INFORMATION: C32oN-21 H-CDR2

<400> SEQUENCE: 245

Tyr Ile Asn Pro Tyr Ser Gly Asp Thr Lys Phe Asn Glu Lys Phe Lys
1               5                   10                  15

Ser


<210> SEQ ID NO 246
<211> LENGTH: 10
<212> TYPE: PRT
<213> ORGANISM: Artificial Sequence
<220> FEATURE:
<223> OTHER INFORMATION: C32oN-21 H-CDR3

<400> SEQUENCE: 246

Ser Gly Leu Ile Ala Val Tyr Phe Asp Tyr
1               5                   10


<210> SEQ ID NO 247
<211> LENGTH: 107
<212> TYPE: PRT
<213> ORGANISM: Artificial Sequence
<220> FEATURE:
<223> OTHER INFORMATION: C32oN-21 VL

<400> SEQUENCE: 247

Glu Leu Val Leu Thr Gln Ser Pro Gly Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60

Thr Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Ser Thr Leu Pro Pro
                85                  90                  95

Thr Phe Gly Gln Gly Thr Lys Leu Glu Ile Lys
            100                 105


<210> SEQ ID NO 248
<211> LENGTH: 11
<212> TYPE: PRT
<213> ORGANISM: Artificial Sequence
<220> FEATURE:
<223> OTHER INFORMATION: C32oN-21 L-CDR1

<400> SEQUENCE: 248

Arg Ala Ser Gln Ser Ile Gly Ser Ser Leu His
1               5                   10


<210> SEQ ID NO 249
<211> LENGTH: 7
```

<212> TYPE: PRT
<213> ORGANISM: Artificial Sequence
<220> FEATURE:
<223> OTHER INFORMATION: C32oN-21 L-CDR2

<400> SEQUENCE: 249

Phe Ala Ser Gln Ser Ile Ser
1               5

<210> SEQ ID NO 250
<211> LENGTH: 9
<212> TYPE: PRT
<213> ORGANISM: Artificial Sequence
<220> FEATURE:
<223> OTHER INFORMATION: C32oN-21 L-CDR3

<400> SEQUENCE: 250

Gln Gln Ser Ser Thr Leu Pro Pro Thr
1               5

<210> SEQ ID NO 251
<211> LENGTH: 726
<212> TYPE: PRT
<213> ORGANISM: Artificial Sequence
<220> FEATURE:
<223> OTHER INFORMATION: C32oN-34 complement n.t. sequence

<400> SEQUENCE: 251

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly

```
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
            420                 425                 430

Ala Ala Ala Gly Thr Cys Ala Gly Ala Cys Ala Cys Thr Gly Ala Gly
        435                 440                 445

Gly Thr Thr Thr Cys Cys Thr Cys Thr Cys Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Gly Gly Thr Ala Ala Cys Cys Ala Thr
                485                 490                 495

Thr Ala Thr Thr Gly Ala Ala Thr Gly Thr Gly Ala Cys Cys Ala Thr
            500                 505                 510

Gly Gly Thr Cys Gly Thr Cys Thr Thr Thr Gly Gly Thr Cys Cys Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Ala Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Ala Ala Thr Ala Ala Thr Gly Ala Cys Ala Gly Thr Thr
            660                 665                 670
```

```
Gly Thr Cys Thr Cys Ala Ala Thr Gly Thr Cys Ala Thr Gly Gly Gly
        675                 680                 685

Gly Cys Ala Cys Cys Thr Gly Cys Ala Ala Gly Cys Cys Gly Gly Thr
    690                 695                 700

Thr Cys Cys Cys Thr Gly Gly Thr Thr Cys Cys Ala Cys Cys Thr Thr
705                 710                 715                 720

Thr Ala Gly Thr Thr Thr
                725
```

<210> SEQ ID NO 252
<211> LENGTH: 120
<212> TYPE: PRT
<213> ORGANISM: Artificial Sequence
<220> FEATURE:
<223> OTHER INFORMATION: C32oN-34 VH

<400> SEQUENCE: 252

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120
```

<210> SEQ ID NO 253
<211> LENGTH: 5
<212> TYPE: PRT
<213> ORGANISM: Artificial Sequence
<220> FEATURE:
<223> OTHER INFORMATION: C32oN-34 H-CDR1

<400> SEQUENCE: 253

```
Asp Tyr Ile Val His
1               5
```

<210> SEQ ID NO 254
<211> LENGTH: 17
<212> TYPE: PRT
<213> ORGANISM: Artificial Sequence
<220> FEATURE:
<223> OTHER INFORMATION: C32oN-34 H-CDR2

<400> SEQUENCE: 254

```
Tyr Ile Asn Pro Tyr Ser Gly Asp Thr Lys Phe Asn Glu Lys Phe Lys
1               5                   10                  15

Ser
```

<210> SEQ ID NO 255
<211> LENGTH: 10
<212> TYPE: PRT

<213> ORGANISM: Artificial Sequence
<220> FEATURE:
<223> OTHER INFORMATION: C32oN-34 H-CDR3

<400> SEQUENCE: 255

```
Ser Gly Leu Ile Ala Val Tyr Phe Asp Tyr
1               5                   10
```

<210> SEQ ID NO 256
<211> LENGTH: 107
<212> TYPE: PRT
<213> ORGANISM: Artificial Sequence
<220> FEATURE:
<223> OTHER INFORMATION: C32oN-34 VL

<400> SEQUENCE: 256

```
Glu Leu Val Leu Thr Gln Ser Pro Asp Phe Gln Ser Val Thr Pro Lys
1               5                   10                  15

Glu Arg Val Thr Ile Thr Cys Arg Ala Ser Gln Thr Ile Gly Asn Asn
            20                  25                  30

Leu His Trp Tyr Gln Gln Lys Pro Gly Gln Ser Pro Lys Leu Leu Ile
        35                  40                  45

Lys Phe Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105
```

<210> SEQ ID NO 257
<211> LENGTH: 11
<212> TYPE: PRT
<213> ORGANISM: Artificial Sequence
<220> FEATURE:
<223> OTHER INFORMATION: C32oN-34 L-CDR1

<400> SEQUENCE: 257

```
Arg Ala Ser Gln Thr Ile Gly Asn Asn Leu His
1               5                   10
```

<210> SEQ ID NO 258
<211> LENGTH: 7
<212> TYPE: PRT
<213> ORGANISM: Artificial Sequence
<220> FEATURE:
<223> OTHER INFORMATION: C32oN-34 L-CDR2

<400> SEQUENCE: 258

```
Phe Ala Ser Gln Ser Phe Ser
1               5
```

<210> SEQ ID NO 259
<211> LENGTH: 9
<212> TYPE: PRT
<213> ORGANISM: Artificial Sequence
<220> FEATURE:
<223> OTHER INFORMATION: C32oN-34 L-CDR3

<400> SEQUENCE: 259

```
Gln Gln Ser Tyr Ser Thr Pro Trp Thr
1               5
```

```
<210> SEQ ID NO 260
<211> LENGTH: 726
<212> TYPE: PRT
<213> ORGANISM: Artificial Sequence
<220> FEATURE:
<223> OTHER INFORMATION: C32oN-46 complement n.t. sequence

<400> SEQUENCE: 260

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365
```

Ala Cys Cys Ala Ala Gly Ala Cys Cys Gly Cys Cys Gly Cys Cys Gly
370 375 380

Cys Cys Gly Ala Gly Gly Cys Cys Ala Cys Cys Ala Cys Cys Ala Cys
385 390 395 400

Cys Ala Ala Gly Ala Cys Thr Cys Gly Ala Gly Cys Ala Cys Gly Ala
405 410 415

Cys Thr Gly Ala Gly Thr Cys Ala Gly Ala Gly Gly Thr Cys Thr Gly
420 425 430

Ala Ala Ala Gly Thr Cys Ala Gly Ala Cys Ala Cys Thr Gly Ala Gly
435 440 445

Gly Thr Thr Thr Cys Cys Thr Cys Thr Thr Thr Cys Ala Gly Thr Gly
450 455 460

Gly Thr Ala Gly Thr Gly Gly Ala Cys Gly Gly Cys Cys Cys Gly Gly
465 470 475 480

Thr Cys Ala Gly Thr Cys Thr Cys Ala Thr Ala Ala Cys Cys Ala Thr
485 490 495

Cys Ala Thr Cys Gly Ala Ala Thr Gly Thr Gly Ala Cys Cys Ala Thr
500 505 510

Gly Gly Thr Cys Gly Thr Cys Thr Thr Thr Gly Gly Thr Cys Thr Ala
515 520 525

Gly Thr Cys Ala Gly Ala Gly Gly Thr Thr Thr Cys Gly Ala Gly Gly
530 535 540

Ala Gly Thr Ala Gly Thr Thr Cys Ala Ala Ala Cys Gly Ala Ala Gly
545 550 555 560

Gly Gly Thr Cys Ala Gly Gly Gly Ala Gly Ala Gly Thr Cys Cys Cys
565 570 575

Cys Ala Gly Gly Thr Ala Gly Thr Thr Cys Cys Ala Ala Gly Thr
580 585 590

Cys Ala Cys Cys Gly Thr Cys Ala Cys Cys Thr Ala Gly Ala Cys Cys
595 600 605

Cys Thr Gly Thr Cys Thr Ala Ala Ala Gly Thr Gly Ala Gly Ala Gly
610 615 620

Thr Gly Gly Thr Ala Gly Thr Cys Gly Thr Cys Ala Gly Ala Cys Gly
625 630 635 640

Thr Thr Gly Gly Ala Cys Thr Thr Cys Thr Ala Ala Ala Ala Cys Gly
645 650 655

Thr Thr Gly Ala Ala Thr Gly Ala Thr Gly Ala Cys Ala Gly Thr Thr
660 665 670

Gly Thr Cys Thr Cys Ala Ala Thr Gly Thr Cys Ala Thr Gly Gly Gly
675 680 685

Gly Ala Gly Gly Thr Thr Gly Cys Ala Ala Gly Cys Cys Gly Gly Thr
690 695 700

Thr Cys Cys Cys Thr Gly Gly Thr Thr Cys Cys Ala Cys Cys Thr Thr
705 710 715 720

Thr Ala Gly Thr Thr Thr
725

<210> SEQ ID NO 261
<211> LENGTH: 120
<212> TYPE: PRT
<213> ORGANISM: Artificial Sequence
<220> FEATURE:
<223> OTHER INFORMATION: C32oN-46 VH

<400> SEQUENCE: 261

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 262
<211> LENGTH: 5
<212> TYPE: PRT
<213> ORGANISM: Artificial Sequence
<220> FEATURE:
<223> OTHER INFORMATION: C32oN-46 H-CDR1

<400> SEQUENCE: 262

Asp Tyr Ile Val His
1               5


<210> SEQ ID NO 263
<211> LENGTH: 17
<212> TYPE: PRT
<213> ORGANISM: Artificial Sequence
<220> FEATURE:
<223> OTHER INFORMATION: C32oN-46 H-CDR2

<400> SEQUENCE: 263

Tyr Ile Asn Pro Tyr Ser Gly Asp Thr Lys Phe Asn Glu Lys Phe Lys
1               5                   10                  15

Ser


<210> SEQ ID NO 264
<211> LENGTH: 10
<212> TYPE: PRT
<213> ORGANISM: Artificial Sequence
<220> FEATURE:
<223> OTHER INFORMATION: C32oN-46 H-CDR3

<400> SEQUENCE: 264

Ser Gly Leu Ile Ala Val Tyr Phe Asp Tyr
1               5                   10


<210> SEQ ID NO 265
<211> LENGTH: 107
<212> TYPE: PRT
<213> ORGANISM: Artificial Sequence
<220> FEATURE:
<223> OTHER INFORMATION: C32oN-46 VL

<400> SEQUENCE: 265

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
```

```
            20                  25                  30

Leu His Trp Tyr Gln Gln Lys Pro Asp Gln Ser Pro Lys Leu Leu Ile
        35                  40                  45

Lys Phe Ala Ser Gln Ser Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105


<210> SEQ ID NO 266
<211> LENGTH: 11
<212> TYPE: PRT
<213> ORGANISM: Artificial Sequence
<220> FEATURE:
<223> OTHER INFORMATION: C33oN-46 L-CDR1

<400> SEQUENCE: 266

Arg Ala Ser Gln Ser Ile Gly Ser Ser Leu His
1               5                   10


<210> SEQ ID NO 267
<211> LENGTH: 7
<212> TYPE: PRT
<213> ORGANISM: Artificial Sequence
<220> FEATURE:
<223> OTHER INFORMATION: C33oN-46 L-CDR2

<400> SEQUENCE: 267

Phe Ala Ser Gln Ser Leu Ser
1               5


<210> SEQ ID NO 268
<211> LENGTH: 9
<212> TYPE: PRT
<213> ORGANISM: Artificial Sequence
<220> FEATURE:
<223> OTHER INFORMATION: C33oN-46 L-CDR3

<400> SEQUENCE: 268

Gln Gln Ser Tyr Ser Thr Pro Pro Thr
1               5


<210> SEQ ID NO 269
<211> LENGTH: 726
<212> TYPE: PRT
<213> ORGANISM: Artificial Sequence
<220> FEATURE:
<223> OTHER INFORMATION: C32oN-89 complement n.t. sequence

<400> SEQUENCE: 269

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
```

```
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Ala Ala
                405                 410                 415

Cys Thr Gly Cys Gly Thr Cys Ala Gly Ala Gly Gly Thr Ala Gly Gly
            420                 425                 430

Ala Gly Gly Gly Ala Cys Ala Gly Ala Cys Gly Thr Ala Gly Ala Cys
        435                 440                 445

Ala Thr Cys Cys Thr Cys Thr Gly Thr Cys Thr Cys Ala Gly Thr Gly
    450                 455                 460

Gly Thr Ala Gly Thr Gly Ala Ala Cys Gly Gly Cys Cys Cys Gly Thr
465                 470                 475                 480

Thr Cys Ala Gly Thr Cys Thr Cys Gly Thr Ala Ala Thr Cys Gly Thr
                485                 490                 495
```

```
Cys Cys Ala Thr Ala Ala Ala Thr Thr Thr Ala Ala Cys Cys Ala Thr
            500                 505                 510

Ala Gly Thr Thr Gly Thr Thr Thr Thr Thr Gly Gly Thr Cys Cys Cys
        515                 520                 525

Thr Thr Thr Gly Gly Gly Gly Gly Ala Thr Thr Cys Gly Ala Gly Gly
    530                 535                 540

Ala Cys Thr Ala Gly Ala Ala Ala Cys Ala Ala Cys Gly Thr Ala Gly
545                 550                 555                 560

Gly Thr Thr Ala Ala Ala Cys Gly Thr Thr Thr Gly Ala Cys Cys Cys
                565                 570                 575

Cys Ala Gly Gly Gly Thr Ala Gly Thr Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Ala Gly Ala Gly
    610                 615                 620

Thr Gly Gly Thr Ala Gly Thr Cys Gly Thr Cys Gly Gly Ala Thr Cys
625                 630                 635                 640

Thr Cys Gly Gly Ala Cys Thr Thr Cys Thr Ala Ala Ala Ala Cys Gly
                645                 650                 655

Thr Cys Ala Ala Ala Thr Ala Ala Thr Gly Ala Cys Ala Gly Thr Cys
            660                 665                 670

Gly Thr Cys Gly Cys Ala Thr Cys Gly Thr Thr Gly Ala Cys Cys Gly
        675                 680                 685

Gly Gly Gly Ala Gly Thr Gly Ala Ala Ala Gly Cys Cys Gly Cys Cys
    690                 695                 700

Thr Cys Cys Cys Thr Gly Gly Thr Thr Thr Cys Ala Cys Cys Thr Ala
705                 710                 715                 720

Thr Ala Gly Thr Thr Thr
                725
```

<210> SEQ ID NO 270
<211> LENGTH: 120
<212> TYPE: PRT
<213> ORGANISM: Artificial Sequence
<220> FEATURE:
<223> OTHER INFORMATION: C32oN-89 VH

<400> SEQUENCE: 270

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120
```

<210> SEQ ID NO 271
<211> LENGTH: 5
<212> TYPE: PRT
<213> ORGANISM: Artificial Sequence
<220> FEATURE:
<223> OTHER INFORMATION: C32oN-89 H-CDR1

<400> SEQUENCE: 271

```
Asp Tyr Ile Val His
1               5
```

<210> SEQ ID NO 272
<211> LENGTH: 17
<212> TYPE: PRT
<213> ORGANISM: Artificial Sequence
<220> FEATURE:
<223> OTHER INFORMATION: C32oN-89 H-CDR2

<400> SEQUENCE: 272

```
Tyr Ile Asn Pro Tyr Ser Gly Asp Thr Lys Phe Asn Glu Lys Phe Lys
1               5                   10                  15

Ser
```

<210> SEQ ID NO 273
<211> LENGTH: 10
<212> TYPE: PRT
<213> ORGANISM: Artificial Sequence
<220> FEATURE:
<223> OTHER INFORMATION: C32oN-89 H-CDR3

<400> SEQUENCE: 273

```
Ser Gly Leu Ile Ala Val Tyr Phe Asp Tyr
1               5                   10
```

<210> SEQ ID NO 274
<211> LENGTH: 107
<212> TYPE: PRT
<213> ORGANISM: Artificial Sequence
<220> FEATURE:
<223> OTHER INFORMATION: C32oN-89 VL

<400> SEQUENCE: 274

```
Glu Leu Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Pro Pro Lys Leu Leu Ile
        35                  40                  45

Phe Val Ala Ser Asn Leu Gln Thr Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Asp Ile Lys
            100                 105
```

<210> SEQ ID NO 275
<211> LENGTH: 11
<212> TYPE: PRT
<213> ORGANISM: Artificial Sequence
<220> FEATURE:

<223> OTHER INFORMATION: C32oN-89 L-CDR1

<400> SEQUENCE: 275

```
Arg Ala Ser Gln Ser Ile Ser Arg Tyr Leu Asn
1               5                   10
```

<210> SEQ ID NO 276
<211> LENGTH: 7
<212> TYPE: PRT
<213> ORGANISM: Artificial Sequence
<220> FEATURE:
<223> OTHER INFORMATION: C32oN-89 L-CDR2

<400> SEQUENCE: 276

```
Val Ala Ser Asn Leu Gln Thr
1               5
```

<210> SEQ ID NO 277
<211> LENGTH: 9
<212> TYPE: PRT
<213> ORGANISM: Artificial Sequence
<220> FEATURE:
<223> OTHER INFORMATION: C32oN-89 L-CDR3

<400> SEQUENCE: 277

```
Gln Gln Arg Ser Asn Trp Pro Leu Thr
1               5
```

<210> SEQ ID NO 278
<211> LENGTH: 726
<212> TYPE: PRT
<213> ORGANISM: Artificial Sequence
<220> FEATURE:
<223> OTHER INFORMATION: C32oN-92 complement n.t. sequence

<400> SEQUENCE: 278

```
Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190
```

-continued

Ala Ala Gly Thr Thr Cys Thr Cys Ala Thr Thr Cys Cys Gly Gly Thr
195 200 205

Gly Cys Ala Ala Cys Thr Gly Ala Cys Ala Ala Cys Thr Gly Thr Thr
210 215 220

Cys Ala Gly Gly Thr Cys Gly Thr Cys Gly Thr Gly Thr Cys Gly Gly
225 230 235 240

Ala Thr Ala Thr Ala Cys Cys Thr Cys Ala Ala Ala Thr Cys Gly Gly
245 250 255

Cys Thr Ala Ala Cys Thr Gly Thr Ala Gly Ala Cys Thr Cys Cys Thr
260 265 270

Ala Ala Gly Ala Cys Gly Thr Thr Ala Gly Ala Thr Ala Ala Thr Gly
275 280 285

Ala Cys Ala Cys Gly Thr Thr Cys Thr Ala Gly Cys Cys Cys Ala Gly
290 295 300

Ala Cys Thr Ala Thr Cys Gly Thr Cys Ala Gly Ala Thr Gly Ala Ala
305 310 315 320

Ala Cys Thr Ala Ala Thr Gly Ala Cys Cys Cys Cys Gly Gly Thr Thr
325 330 335

Cys Cys Cys Thr Gly Gly Thr Gly Cys Cys Ala Gly Thr Gly Gly Cys
340 345 350

Ala Gly Ala Gly Gly Ala Gly Thr Cys Cys Ala Cys Cys Ala Cys Cys
355 360 365

Ala Cys Cys Ala Ala Gly Ala Cys Cys Gly Cys Cys Gly Cys Cys Gly
370 375 380

Cys Cys Gly Ala Gly Gly Cys Cys Ala Cys Cys Ala Cys Cys Ala Cys
385 390 395 400

Cys Ala Ala Gly Ala Cys Thr Cys Gly Ala Gly Cys Ala Cys Gly Ala
405 410 415

Cys Thr Gly Ala Gly Thr Cys Ala Gly Ala Gly Gly Thr Cys Thr Gly
420 425 430

Ala Ala Ala Gly Thr Cys Ala Gly Ala Cys Ala Cys Thr Gly Ala Gly
435 440 445

Gly Thr Thr Thr Cys Cys Thr Cys Thr Thr Thr Cys Ala Gly Thr Gly
450 455 460

Gly Thr Ala Gly Thr Gly Gly Ala Cys Gly Gly Cys Cys Cys Gly Gly
465 470 475 480

Thr Cys Ala Gly Thr Cys Thr Cys Gly Thr Ala Ala Cys Cys Ala Thr
485 490 495

Cys Ala Thr Cys Gly Ala Ala Thr Gly Thr Gly Ala Cys Cys Ala Thr
500 505 510

Gly Gly Thr Cys Gly Thr Cys Thr Thr Thr Gly Gly Thr Cys Thr Ala
515 520 525

Gly Thr Cys Ala Gly Ala Gly Gly Thr Thr Thr Cys Gly Ala Gly Gly
530 535 540

Ala Gly Thr Ala Gly Thr Thr Cys Ala Ala Ala Cys Gly Ala Ala Gly
545 550 555 560

Gly Gly Thr Cys Ala Gly Gly Gly Ala Gly Ala Gly Thr Cys Cys Cys
565 570 575

Cys Ala Gly Gly Gly Gly Ala Gly Cys Thr Cys Cys Ala Ala Gly Thr
580 585 590

Cys Ala Cys Cys Gly Thr Cys Ala Cys Cys Thr Ala Gly Ala Cys Cys
595 600 605

Cys Thr Gly Thr Cys Thr Ala Ala Ala Gly Cys Gly Gly Gly Ala Gly

```
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Gly Ala Thr Ala Ala Thr Gly Ala Cys Ala Gly Thr Cys
            660                 665                 670

Gly Thr Cys Thr Cys Ala Thr Cys Ala Thr Gly Ala Ala Ala Thr Gly
        675                 680                 685

Gly Ala Gly Gly Gly Thr Gly Ala Ala Ala Ala Cys Cys Gly Gly Thr
    690                 695                 700

Cys Cys Cys Cys Thr Gly Gly Thr Thr Cys Gly Ala Cys Cys Thr Cys
705                 710                 715                 720

Thr Ala Gly Thr Thr Thr
                725


<210> SEQ ID NO 279
<211> LENGTH: 120
<212> TYPE: PRT
<213> ORGANISM: Artificial Sequence
<220> FEATURE:
<223> OTHER INFORMATION: C32oN-92 VH

<400> SEQUENCE: 279

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 280
<211> LENGTH: 5
<212> TYPE: PRT
<213> ORGANISM: Artificial Sequence
<220> FEATURE:
<223> OTHER INFORMATION: C32oN-92 H-CDR1

<400> SEQUENCE: 280

Asp Tyr Ile Val His
1               5


<210> SEQ ID NO 281
<211> LENGTH: 17
<212> TYPE: PRT
<213> ORGANISM: Artificial Sequence
<220> FEATURE:
<223> OTHER INFORMATION: C32oN-92 H-CDR2

<400> SEQUENCE: 281
```

```
Tyr Ile Asn Pro Tyr Ser Gly Asp Thr Lys Phe Asn Glu Lys Phe Lys
1               5                   10                  15

Ser


<210> SEQ ID NO 282
<211> LENGTH: 10
<212> TYPE: PRT
<213> ORGANISM: Artificial Sequence
<220> FEATURE:
<223> OTHER INFORMATION: C32oN-92 H-CDR3

<400> SEQUENCE: 282

Ser Gly Leu Ile Ala Val Tyr Phe Asp Tyr
1               5                   10


<210> SEQ ID NO 283
<211> LENGTH: 107
<212> TYPE: PRT
<213> ORGANISM: Artificial Sequence
<220> FEATURE:
<223> OTHER INFORMATION: C32oN-92 VL

<400> SEQUENCE: 283

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Leu Ser Gly Val Pro Ser Arg Phe Ser Gly
    50                  55                  60

Ser Gly Ser Gly Thr Asp Phe Ala Leu Thr Ile Asn Ser Leu Glu Ala
65                  70                  75                  80

Glu Asp Ala Ala Thr Tyr Tyr Cys Gln Gln Ser Ser Thr Leu Pro Pro
                85                  90                  95

Thr Phe Gly Gln Gly Thr Lys Leu Glu Ile Lys
            100                 105


<210> SEQ ID NO 284
<211> LENGTH: 11
<212> TYPE: PRT
<213> ORGANISM: Artificial Sequence
<220> FEATURE:
<223> OTHER INFORMATION: C33oN-92 L-CDR1

<400> SEQUENCE: 284

Arg Ala Ser Gln Ser Ile Gly Ser Ser Leu His
1               5                   10


<210> SEQ ID NO 285
<211> LENGTH: 7
<212> TYPE: PRT
<213> ORGANISM: Artificial Sequence
<220> FEATURE:
<223> OTHER INFORMATION: C33oN-92 L-CDR2

<400> SEQUENCE: 285

Phe Ala Ser Gln Ser Leu Ser
1               5


<210> SEQ ID NO 286
<211> LENGTH: 9
```

```
<212> TYPE: PRT
<213> ORGANISM: Artificial Sequence
<220> FEATURE:
<223> OTHER INFORMATION: C33oN-92 L-CDR3

<400> SEQUENCE: 286

Gln Gln Ser Ser Thr Leu Pro Pro Thr
1               5


<210> SEQ ID NO 287
<211> LENGTH: 726
<212> TYPE: PRT
<213> ORGANISM: Artificial Sequence
<220> FEATURE:
<223> OTHER INFORMATION: C33oN-34 complement n.t. sequence

<400> SEQUENCE: 287

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320
```

```
Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Cys
            420                 425                 430

Ala Ala Ala Gly Thr Cys Ala Gly Ala Cys Ala Cys Cys Gly Ala Gly
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Ala Ala Gly Ala Gly Thr Cys Cys Cys
                565                 570                 575

Cys Ala Gly Gly Gly Gly Ala Gly Cys Thr Cys Cys Ala Ala Gly Cys
            580                 585                 590

Cys Ala Cys Cys Gly Thr Cys Ala Cys Cys Thr Ala Gly Ala Cys Cys
        595                 600                 605

Cys Thr Gly Thr Thr Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Gly Ala Thr Ala Ala Thr Gly Ala Cys Ala Gly Thr Cys
            660                 665                 670

Gly Thr Cys Thr Cys Ala Thr Cys Ala Thr Gly Gly Ala Ala Thr Gly
        675                 680                 685

Gly Ala Gly Gly Gly Thr Gly Ala Ala Ala Ala Cys Cys Gly Gly Thr
    690                 695                 700

Cys Cys Cys Cys Thr Gly Gly Thr Thr Cys Gly Ala Cys Cys Thr Cys
705                 710                 715                 720

Thr Ala Gly Thr Thr Thr
                725
```

<210> SEQ ID NO 288
<211> LENGTH: 120
<212> TYPE: PRT
<213> ORGANISM: Artificial Sequence
<220> FEATURE:
<223> OTHER INFORMATION: C33oN-32 VH

<400> SEQUENCE: 288

Glu Leu Gln Leu Val Glu Gln Ser Gly Ala Ala Leu Val Lys Pro Gly
1 5 10 15

Asp Ser Val Lys Met Ser Cys Lys Ala Ser Gly Tyr Pro Phe Thr Asp
20 25 30

Tyr Ile Val His Trp Val Lys Gln Ser His Gly Lys Ser Leu Asp Trp
35 40 45

Ile Gly Tyr Ile Asn Pro Tyr Ser Gly Asp Thr Lys Phe Asn Glu Lys
50 55 60

Phe Lys Ser Lys Ala Thr Leu Thr Val Asp Lys Ser Ser Ser Thr Ala
65 70 75 80

Tyr Met Glu Phe Ser Arg Leu Thr Ser Glu Asp Ser Ala Ile Tyr Tyr
85 90 95

Cys Ala Arg Ser Gly Leu Ile Ala Val Tyr Phe Asp Tyr Trp Gly Gln
100 105 110

Gly Thr Thr Val Thr Val Ser Ser
115 120

<210> SEQ ID NO 289
<211> LENGTH: 5
<212> TYPE: PRT
<213> ORGANISM: Artificial Sequence
<220> FEATURE:
<223> OTHER INFORMATION: C33oN-32 H-CDR1

<400> SEQUENCE: 289

Asp Tyr Ile Val His
1 5

<210> SEQ ID NO 290
<211> LENGTH: 17
<212> TYPE: PRT
<213> ORGANISM: Artificial Sequence
<220> FEATURE:
<223> OTHER INFORMATION: C33oN-32 H-CDR2

<400> SEQUENCE: 290

Tyr Ile Asn Pro Tyr Ser Gly Asp Thr Lys Phe Asn Glu Lys Phe Lys
1 5 10 15

Ser

<210> SEQ ID NO 291
<211> LENGTH: 10
<212> TYPE: PRT
<213> ORGANISM: Artificial Sequence
<220> FEATURE:
<223> OTHER INFORMATION: C33oN-32 H-CDR3

<400> SEQUENCE: 291

Ser Gly Leu Ile Ala Val Tyr Phe Asp Tyr
1 5 10

<210> SEQ ID NO 292
<211> LENGTH: 107
<212> TYPE: PRT

```
<213> ORGANISM: Artificial Sequence
<220> FEATURE:
<223> OTHER INFORMATION: C33oN-32 VL

<400> SEQUENCE: 292

Glu Leu Val Leu Thr Gln Ser Pro Glu Phe Gln Ser Val Ala Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Phe Ser Gly Val Pro Ser Arg Phe Gly Gly
    50                  55                  60

Ser Gly Ser Gly Thr Asn Phe Thr Leu Thr Ile Asn Ser Leu Glu Ala
65                  70                  75                  80

Glu Asp Ala Ala Thr Tyr Tyr Cys Gln Gln Ser Ser Thr Leu Pro Pro
                85                  90                  95

Thr Phe Gly Gln Gly Thr Lys Leu Glu Ile Lys
            100                 105


<210> SEQ ID NO 293
<211> LENGTH: 11
<212> TYPE: PRT
<213> ORGANISM: Artificial Sequence
<220> FEATURE:
<223> OTHER INFORMATION: C33oN-32 L-CDR1

<400> SEQUENCE: 293

Arg Ala Ser Gln Ser Ile Gly Ser Ser Leu His
1               5                   10


<210> SEQ ID NO 294
<211> LENGTH: 7
<212> TYPE: PRT
<213> ORGANISM: Artificial Sequence
<220> FEATURE:
<223> OTHER INFORMATION: C33oN-32 L-CDR2

<400> SEQUENCE: 294

Phe Ala Ser Gln Ser Phe Ser
1               5


<210> SEQ ID NO 295
<211> LENGTH: 9
<212> TYPE: PRT
<213> ORGANISM: Artificial Sequence
<220> FEATURE:
<223> OTHER INFORMATION: C33oN-32 L-CDR3

<400> SEQUENCE: 295

Gln Gln Ser Ser Thr Leu Pro Pro Thr
1               5


<210> SEQ ID NO 296
<211> LENGTH: 726
<212> TYPE: PRT
<213> ORGANISM: Artificial Sequence
<220> FEATURE:
<223> OTHER INFORMATION: C33oN-33 complement n.t. sequence

<400> SEQUENCE: 296

Cys Thr Cys Gly Ala Cys Gly Thr Cys Gly Ala Cys Cys Ala Gly Cys
1               5                   10                  15
```

```
Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140

Thr Ala Ala Cys Cys Ala Ala Thr Ala Thr Ala Ala Thr Thr Ala Gly
145                 150                 155                 160

Gly Ala Ala Thr Gly Thr Cys Ala Cys Cys Ala Cys Thr Ala Thr Gly
                165                 170                 175

Ala Thr Thr Cys Ala Ala Gly Thr Thr Ala Cys Thr Thr Thr Thr Cys
            180                 185                 190

Ala Ala Gly Thr Thr Cys Thr Cys Ala Thr Thr Cys Cys Gly Gly Thr
        195                 200                 205

Gly Cys Ala Ala Cys Thr Gly Ala Cys Ala Ala Cys Thr Gly Thr Thr
    210                 215                 220

Cys Ala Gly Gly Thr Cys Gly Thr Cys Gly Thr Gly Thr Cys Gly Gly
225                 230                 235                 240

Ala Thr Ala Thr Ala Cys Cys Thr Cys Ala Ala Ala Thr Cys Gly Gly
                245                 250                 255

Cys Thr Ala Ala Cys Thr Gly Thr Ala Gly Ala Cys Thr Cys Cys Thr
            260                 265                 270

Ala Ala Gly Ala Cys Gly Thr Thr Ala Gly Ala Thr Ala Ala Thr Gly
        275                 280                 285

Ala Cys Ala Cys Gly Thr Thr Cys Thr Ala Gly Cys Cys Cys Ala Gly
    290                 295                 300

Ala Cys Thr Ala Thr Cys Gly Thr Cys Ala Gly Ala Thr Gly Ala Ala
305                 310                 315                 320

Ala Cys Thr Ala Ala Thr Gly Ala Cys Cys Cys Cys Gly Gly Thr Thr
                325                 330                 335

Cys Cys Cys Thr Gly Gly Thr Gly Cys Cys Ala Gly Thr Gly Gly Cys
            340                 345                 350

Ala Gly Ala Gly Gly Ala Gly Thr Cys Cys Ala Cys Cys Ala Cys Cys
        355                 360                 365

Ala Cys Cys Ala Ala Gly Ala Cys Cys Gly Cys Cys Gly Cys Cys Gly
    370                 375                 380

Cys Cys Gly Ala Gly Gly Cys Cys Ala Cys Cys Ala Cys Cys Ala Cys
385                 390                 395                 400

Cys Ala Ala Gly Ala Cys Thr Cys Gly Ala Gly Cys Ala Cys Gly Ala
                405                 410                 415

Cys Thr Gly Ala Gly Thr Cys Ala Gly Ala Gly Gly Thr Cys Thr Gly
            420                 425                 430

Ala Ala Ala Gly Thr Cys Ala Gly Ala Cys Ala Cys Thr Gly Ala Gly
```

```
        435                 440                 445

Gly Thr Thr Thr Cys Cys Thr Cys Thr Thr Thr Cys Ala Gly Thr Gly
    450                 455                 460

Gly Thr Ala Gly Thr Gly Gly Ala Cys Gly Gly Cys Cys Cys Gly Gly
465                 470                 475                 480

Thr Cys Ala Gly Thr Cys Thr Cys Gly Thr Ala Ala Cys Cys Ala Thr
                485                 490                 495

Cys Ala Thr Cys Gly Ala Ala Thr Gly Thr Gly Ala Cys Cys Ala Thr
            500                 505                 510

Gly Gly Thr Cys Gly Thr Cys Thr Thr Thr Gly Gly Thr Cys Thr Ala
        515                 520                 525

Gly Thr Cys Ala Gly Ala Gly Gly Thr Thr Thr Cys Gly Ala Gly Gly
    530                 535                 540

Ala Gly Thr Ala Gly Thr Thr Cys Ala Ala Ala Cys Gly Ala Ala Gly
545                 550                 555                 560

Gly Gly Thr Cys Ala Gly Gly Gly Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Ala Ala Thr Gly Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Ala Thr Cys Ala Thr Gly Ala Ala Ala Gly Cys Cys Gly Gly Gly
    690                 695                 700

Ala Cys Cys Cys Thr Gly Gly Thr Thr Cys Cys Ala Cys Cys Thr Cys
705                 710                 715                 720

Thr Ala Gly Thr Thr Thr
                725
```

<210> SEQ ID NO 297
<211> LENGTH: 120
<212> TYPE: PRT
<213> ORGANISM: Artificial Sequence
<220> FEATURE:
<223> OTHER INFORMATION: C33oN-33 VH

<400> SEQUENCE: 297

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
```

```
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 298
<211> LENGTH: 5
<212> TYPE: PRT
<213> ORGANISM: Artificial Sequence
<220> FEATURE:
<223> OTHER INFORMATION: C33oN-33 H-CDR1

<400> SEQUENCE: 298

Asp Tyr Ile Val His
1               5


<210> SEQ ID NO 299
<211> LENGTH: 17
<212> TYPE: PRT
<213> ORGANISM: Artificial Sequence
<220> FEATURE:
<223> OTHER INFORMATION: C33oN-33 H-CDR2

<400> SEQUENCE: 299

Tyr Ile Asn Pro Tyr Ser Gly Asp Thr Lys Phe Asn Glu Lys Phe Lys
1               5                   10                  15

Ser


<210> SEQ ID NO 300
<211> LENGTH: 10
<212> TYPE: PRT
<213> ORGANISM: Artificial Sequence
<220> FEATURE:
<223> OTHER INFORMATION: C33oN-33 H-CDR3

<400> SEQUENCE: 300

Ser Gly Leu Ile Ala Val Tyr Phe Asp Tyr
1               5                   10


<210> SEQ ID NO 301
<211> LENGTH: 107
<212> TYPE: PRT
<213> ORGANISM: Artificial Sequence
<220> FEATURE:
<223> OTHER INFORMATION: C33oN-33 VL

<400> SEQUENCE: 301

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Leu Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Tyr Ser Thr Pro Ser
                85                  90                  95
```

```
Thr Phe Gly Pro Gly Thr Lys Val Glu Ile Lys
            100                 105


<210> SEQ ID NO 302
<211> LENGTH: 11
<212> TYPE: PRT
<213> ORGANISM: Artificial Sequence
<220> FEATURE:
<223> OTHER INFORMATION: C33oN-33 L-CDR1

<400> SEQUENCE: 302

Arg Ala Ser Gln Ser Ile Gly Ser Ser Leu His
1               5                   10


<210> SEQ ID NO 303
<211> LENGTH: 7
<212> TYPE: PRT
<213> ORGANISM: Artificial Sequence
<220> FEATURE:
<223> OTHER INFORMATION: C33oN-33 L-CDR2

<400> SEQUENCE: 303

Phe Ala Ser Gln Ser Leu Ser
1               5


<210> SEQ ID NO 304
<211> LENGTH: 9
<212> TYPE: PRT
<213> ORGANISM: Artificial Sequence
<220> FEATURE:
<223> OTHER INFORMATION: C33oN-33 L-CDR3

<400> SEQUENCE: 304

Gln Gln Ser Tyr Ser Thr Pro Ser Thr
1               5


<210> SEQ ID NO 305
<211> LENGTH: 726
<212> TYPE: PRT
<213> ORGANISM: Artificial Sequence
<220> FEATURE:
<223> OTHER INFORMATION: C33oN-49 complement n.t. sequence

<400> SEQUENCE: 305

Cys Thr Cys Gly Ala Cys Gly Thr Cys Gly Ala Cys Cys Ala Gly Cys
1               5                   10                  15

Thr Cys Gly Thr Cys Ala Gly Ala Cys Cys Thr Cys Gly Ala Cys Gly
            20                  25                  30

Thr Gly Ala Cys Cys Ala Cys Thr Thr Cys Gly Gly Ala Cys Cys Cys
        35                  40                  45

Cys Thr Gly Ala Gly Ala Cys Ala Cys Thr Thr Cys Thr Ala Cys Ala
    50                  55                  60

Gly Ala Ala Cys Gly Thr Thr Thr Cys Gly Ala Ala Gly Ala Cys Cys
65                  70                  75                  80

Ala Ala Thr Ala Gly Gly Thr Ala Ala Gly Thr Gly Ala Cys Thr Gly
                85                  90                  95

Ala Thr Ala Thr Ala Ala Cys Ala Thr Gly Thr Gly Ala Cys Cys Cys
            100                 105                 110

Ala Cys Thr Thr Cys Gly Thr Cys Thr Cys Ala Gly Thr Ala Cys Cys
        115                 120                 125

Thr Thr Thr Cys Thr Cys Gly Gly Ala Ala Cys Thr Gly Ala Cys Cys
    130                 135                 140
```

Thr Ala Ala Cys Cys Ala Ala Thr Ala Thr Ala Ala Thr Thr Ala Gly
145 150 155 160

Gly Ala Ala Thr Gly Thr Cys Ala Cys Cys Ala Cys Thr Ala Thr Gly
165 170 175

Ala Thr Thr Cys Ala Ala Gly Thr Thr Ala Cys Thr Thr Thr Thr Cys
180 185 190

Ala Ala Gly Thr Thr Cys Thr Cys Ala Thr Thr Cys Cys Gly Gly Thr
195 200 205

Gly Cys Ala Ala Cys Thr Gly Ala Cys Ala Ala Cys Thr Gly Thr Thr
210 215 220

Cys Ala Gly Gly Thr Cys Gly Thr Cys Gly Thr Gly Thr Cys Gly Gly
225 230 235 240

Ala Thr Ala Thr Ala Cys Cys Thr Cys Ala Ala Ala Thr Cys Gly Gly
245 250 255

Cys Thr Ala Ala Cys Thr Gly Thr Ala Gly Ala Cys Thr Cys Cys Thr
260 265 270

Ala Ala Gly Ala Cys Gly Thr Thr Ala Gly Ala Thr Ala Ala Thr Gly
275 280 285

Ala Cys Ala Cys Gly Thr Thr Cys Thr Ala Gly Cys Cys Cys Ala Gly
290 295 300

Ala Cys Thr Ala Thr Cys Gly Thr Cys Ala Gly Ala Thr Gly Ala Ala
305 310 315 320

Ala Cys Thr Ala Ala Thr Gly Ala Cys Cys Cys Cys Gly Gly Thr Thr
325 330 335

Cys Cys Cys Thr Gly Gly Thr Gly Cys Cys Ala Gly Thr Gly Gly Cys
340 345 350

Ala Gly Ala Gly Gly Ala Gly Thr Cys Cys Ala Cys Cys Ala Cys Cys
355 360 365

Ala Cys Cys Ala Ala Gly Ala Cys Cys Gly Cys Cys Gly Cys Cys Gly
370 375 380

Cys Cys Gly Ala Gly Gly Cys Cys Ala Cys Cys Ala Cys Cys Ala Cys
385 390 395 400

Cys Ala Ala Gly Ala Cys Thr Cys Gly Ala Gly Cys Ala Cys Gly Ala
405 410 415

Cys Thr Gly Ala Gly Thr Cys Ala Gly Ala Gly Gly Thr Cys Thr Gly
420 425 430

Ala Ala Ala Gly Thr Cys Ala Gly Ala Cys Ala Cys Thr Gly Ala Gly
435 440 445

Gly Thr Thr Thr Cys Cys Thr Cys Thr Thr Thr Cys Ala Gly Thr Gly
450 455 460

Gly Thr Ala Gly Thr Gly Gly Ala Cys Gly Gly Cys Cys Cys Gly Gly
465 470 475 480

Thr Cys Ala Gly Thr Cys Thr Cys Gly Thr Ala Ala Cys Cys Ala Thr
485 490 495

Cys Ala Thr Cys Gly Ala Ala Thr Gly Thr Gly Ala Cys Cys Ala Thr
500 505 510

Gly Gly Thr Cys Gly Thr Cys Thr Thr Thr Gly Gly Thr Cys Thr Ala
515 520 525

Gly Thr Cys Ala Gly Ala Gly Gly Thr Thr Thr Cys Gly Ala Gly Gly
530 535 540

Ala Gly Thr Ala Gly Thr Thr Cys Ala Ala Ala Cys Gly Ala Ala Gly
545 550 555 560

```
Gly Gly Thr Cys Ala Gly Gly Ala Ala Gly Ala Gly Thr Cys Cys Cys
                565                 570                 575

Cys Ala Gly Gly Gly Gly Ala Gly Cys Thr Cys Cys Ala Ala Gly Thr
            580                 585                 590

Cys Ala Cys Cys Gly Thr Cys Ala Cys Cys Thr Ala Gly Ala Cys Cys
        595                 600                 605

Cys Thr Gly Thr Cys Thr Ala Ala Ala Gly Thr Gly Gly Gly Ala Gly
    610                 615                 620

Thr Gly Gly Thr Ala Gly Thr Thr Ala Thr Cys Gly Gly Ala Cys Cys
625                 630                 635                 640

Thr Thr Cys Gly Ala Cys Thr Thr Cys Thr Ala Cys Gly Ala Cys Gly
                645                 650                 655

Thr Thr Gly Cys Ala Thr Ala Ala Thr Gly Ala Cys Ala Gly Thr Thr
            660                 665                 670

Gly Thr Cys Thr Cys Ala Ala Thr Gly Thr Cys Ala Thr Gly Gly Gly
        675                 680                 685

Gly Cys Ala Cys Cys Thr Gly Cys Ala Ala Gly Cys Cys Gly Gly Thr
    690                 695                 700

Thr Cys Cys Cys Thr Gly Gly Thr Thr Cys Gly Ala Cys Cys Thr Cys
705                 710                 715                 720

Thr Ala Gly Thr Thr Thr
                725


<210> SEQ ID NO 306
<211> LENGTH: 120
<212> TYPE: PRT
<213> ORGANISM: Artificial Sequence
<220> FEATURE:
<223> OTHER INFORMATION: C32oN-49 VH

<400> SEQUENCE: 306

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120


<210> SEQ ID NO 307
<211> LENGTH: 5
<212> TYPE: PRT
<213> ORGANISM: Artificial Sequence
<220> FEATURE:
<223> OTHER INFORMATION: C32oN-49 H-CDR1

<400> SEQUENCE: 307

Asp Tyr Ile Val His
1               5
```

<210> SEQ ID NO 308
<211> LENGTH: 17
<212> TYPE: PRT
<213> ORGANISM: Artificial Sequence
<220> FEATURE:
<223> OTHER INFORMATION: C32oN-49 H-CDR2

<400> SEQUENCE: 308

Tyr Ile Asn Pro Tyr Ser Gly Asp Thr Lys Phe Asn Glu Lys Phe Lys
1               5                   10                  15

Ser

<210> SEQ ID NO 309
<211> LENGTH: 10
<212> TYPE: PRT
<213> ORGANISM: Artificial Sequence
<220> FEATURE:
<223> OTHER INFORMATION: C32oN-49 H-CDR3

<400> SEQUENCE: 309

Ser Gly Leu Ile Ala Val Tyr Phe Asp Tyr
1               5                   10

<210> SEQ ID NO 310
<211> LENGTH: 107
<212> TYPE: PRT
<213> ORGANISM: Artificial Sequence
<220> FEATURE:
<223> OTHER INFORMATION: C32oN-49 VL

<400> SEQUENCE: 310

Glu Leu Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105

<210> SEQ ID NO 311
<211> LENGTH: 11
<212> TYPE: PRT
<213> ORGANISM: Artificial Sequence
<220> FEATURE:
<223> OTHER INFORMATION: C32oN-49 L-CDR1

<400> SEQUENCE: 311

Arg Ala Ser Gln Ser Ile Gly Ser Ser Leu His
1               5                   10

<210> SEQ ID NO 312
<211> LENGTH: 7
<212> TYPE: PRT
<213> ORGANISM: Artificial Sequence
<220> FEATURE:

```
<223> OTHER INFORMATION: C32oN-49 L-CDR2

<400> SEQUENCE: 312

Phe Ala Ser Gln Ser Phe Ser
1               5


<210> SEQ ID NO 313
<211> LENGTH: 9
<212> TYPE: PRT
<213> ORGANISM: Artificial Sequence
<220> FEATURE:
<223> OTHER INFORMATION: C32oN-49 L-CDR3

<400> SEQUENCE: 313

Gln Gln Ser Tyr Ser Thr Pro Trp Thr
1               5
```